US012458740B2

(12) United States Patent
Hake et al.

(10) Patent No.: US 12,458,740 B2
(45) Date of Patent: Nov. 4, 2025

(54) MODULAR SERVICEABILITY SLEDS AND INTERCONNECTIONS

(71) Applicant: Terumo BCT, Inc., Lakewood, CO (US)

(72) Inventors: Charles L. Hake, Arvada, CO (US); Mark E. Hillam, Wheat Ridge, CO (US); Dave Gibbons, Littleton, CO (US); Bruce Ellingboe, Littleton, CO (US); Anne Baker Oram, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 437 days.

(21) Appl. No.: 18/117,007

(22) Filed: Mar. 3, 2023

(65) Prior Publication Data

US 2023/0285656 A1 Sep. 14, 2023

Related U.S. Application Data

(60) Provisional application No. 63/318,692, filed on Mar. 10, 2022.

(51) Int. Cl.
*A61M 1/38* (2006.01)

(52) U.S. Cl.
CPC .................................... *A61M 1/38* (2013.01)

(58) Field of Classification Search
CPC .......... A61M 1/36222; A61M 1/36224; A61M 1/362262; A61M 1/3696; A61M 1/38; B04B 5/0442

(Continued)

(56) References Cited

U.S. PATENT DOCUMENTS

| | | |
|---|---|---|
| 4,753,697 A | 6/1988 | Shaposka et al. |
| 4,770,735 A | 9/1988 | Shaposka et al. |

(Continued)

FOREIGN PATENT DOCUMENTS

| | | |
|---|---|---|
| AU | 2003200372 B2 | 9/2008 |
| AU | 2003202448 B2 | 11/2008 |

(Continued)

OTHER PUBLICATIONS

International Search Report and Written Opinion issued in the corresponding International Application No. PCT/US2023/014549; mailed on Jun. 6, 2023 (total 16 pages).

(Continued)

*Primary Examiner* — Kevin J Comber
(74) *Attorney, Agent, or Firm* — Harness, Dickey & Pierce, P.L.C.

(57) ABSTRACT

A modular serviceability sled includes a frame, subassembly, interconnection, gasket, and shielding component. The interconnection is operatively connected to the subassembly and includes an electrical, pneumatic, and/or hydraulic connection. The gasket can engage the frame and a base assembly of an apparatus. The shielding component can contact the frame and the base assembly and includes an electromagnetic interference and/or radio frequency shielding component. The sled is movable between an engaged state and a disengaged state. In the engaged state, the sled is at least partially within a receiving space of the apparatus, the gasket engages the frame and the base assembly, the shielding component contacts the frame and the base assembly, and the interconnection is operatively connected to a machine interconnection of the apparatus. In the disengaged state, the interconnection is disconnected from the machine interconnection and the sled is configured to freely move with respect to the base assembly.

23 Claims, 94 Drawing Sheets

(58) Field of Classification Search
USPC ........................................................ 361/126
See application file for complete search history.

(56) References Cited

U.S. PATENT DOCUMENTS

| | | | |
|---|---|---|---|
| 4,793,880 | A | 12/1988 | Shaposka et al. |
| 4,832,773 | A | 5/1989 | Shaposka et al. |
| 4,864,101 | A | 9/1989 | Shaposka et al. |
| 4,897,138 | A | 1/1990 | Shaposka et al. |
| 4,913,756 | A | 4/1990 | Shaposka et al. |
| 4,933,036 | A | 6/1990 | Shaposka et al. |
| 5,141,592 | A | 8/1992 | Shaposka et al. |
| 5,156,701 | A | 10/1992 | Spencer et al. |
| 5,158,630 | A | 10/1992 | Shaposka et al. |
| 5,209,800 | A | 5/1993 | Spencer et al. |
| 5,244,522 | A | 9/1993 | Spencer et al. |
| 5,248,359 | A | 9/1993 | Shaposka et al. |
| 5,279,685 | A | 1/1994 | Ivansons et al. |
| D355,848 | S | 2/1995 | Ivansons et al. |
| 5,397,425 | A | 3/1995 | Ivansons et al. |
| D357,926 | S | 5/1995 | Ivansons et al. |
| 5,525,186 | A | 6/1996 | Ivansons et al. |
| 5,632,852 | A | 5/1997 | Ivansons et al. |
| 5,674,333 | A | 10/1997 | Spencer |
| 5,855,731 | A | 1/1999 | Spencer |
| 5,871,612 | A | 2/1999 | Spencer |
| 6,132,833 | A | 10/2000 | Spencer |
| 6,177,652 | B1 | 1/2001 | Ivansons |
| 6,460,592 | B1 | 10/2002 | Sano et al. |
| 6,637,489 | B1 | 10/2003 | Spencer |
| 6,730,055 | B2 | 5/2004 | Bainbridge et al. |
| 7,060,183 | B1 | 6/2006 | Goudaliez et al. |
| 7,427,278 | B2 | 9/2008 | Goudaliez et al. |
| 7,718,430 | B2 | 5/2010 | Antwiler |
| 7,879,000 | B2 | 2/2011 | Behague et al. |
| 8,066,269 | B2 | 11/2011 | Ivansons et al. |
| 8,163,555 | B2 | 4/2012 | Antwiler |
| 8,383,406 | B2 | 2/2013 | Bratosin et al. |
| 8,508,956 | B2 | 8/2013 | Nicol et al. |
| 8,815,350 | B2 | 8/2014 | Marmey et al. |
| 8,986,237 | B2 | 3/2015 | Goudaliez et al. |
| 9,095,663 | B2 | 8/2015 | Duhaut et al. |
| 9,950,469 | B2 | 4/2018 | Ivansons et al. |
| 10,052,641 | B2 | 8/2018 | Letourneur et al. |
| 10,058,646 | B2 | 8/2018 | Walker et al. |
| 10,085,712 | B2 | 10/2018 | Miyagi et al. |
| 10,507,231 | B2 | 12/2019 | Bouckenooghe et al. |
| 10,624,227 | B1 * | 4/2020 | Ni .......................... G06F 1/181 |
| 10,932,383 | B2 | 2/2021 | Ehlen |
| 2002/0033370 | A1 * | 3/2002 | Bainbridge ........... A61M 1/303 604/6.11 |
| 2003/0078559 | A1 | 4/2003 | Goudaliez et al. |
| 2012/0281368 | A1 * | 11/2012 | Nicol .................. H05K 9/0054 361/728 |
| 2013/0292320 | A1 | 11/2013 | Verpoort et al. |
| 2015/0320389 | A1 * | 11/2015 | Miyagi ............... A61B 8/4427 600/459 |
| 2019/0075666 | A1 * | 3/2019 | Ehlen .................. H05K 7/1487 |
| 2019/0310185 | A1 | 10/2019 | Helfmann et al. |
| 2022/0167890 | A1 | 6/2022 | Unal et al. |
| 2022/0288288 | A1 | 9/2022 | Robiquet et al. |
| 2022/0378997 | A1 | 12/2022 | Coddeville |
| 2023/0040306 | A1 | 2/2023 | Brebant et al. |

FOREIGN PATENT DOCUMENTS

| | | | |
|---|---|---|---|
| AU | 2003252890 | B2 | 4/2010 |
| AU | 2005203406 | B2 | 3/2011 |
| AU | 2003270995 | B2 | 9/2011 |
| AU | 2011218711 | A1 | 9/2011 |
| AU | 2007231706 | B2 | 6/2012 |
| AU | 2011218658 | B2 | 12/2013 |
| AU | 2010316952 | B2 | 8/2015 |
| AU | 2016269730 | B2 | 7/2022 |
| BR | 112015000080 | B1 | 2/2021 |
| BR | 112016029976 | B1 | 8/2022 |
| CA | 2114878 | C | 4/2005 |
| CA | 2457364 | C | 9/2012 |
| CA | 2625439 | C | 4/2013 |
| CA | 2458128 | C | 5/2013 |
| CA | 2659195 | C | 11/2015 |
| CA | 2688586 | C | 8/2016 |
| CA | 2841030 | C | 8/2019 |
| CA | 2887583 | C | 3/2021 |
| CN | 101157277 | A | 4/2008 |
| CN | 201132383 | Y | 10/2008 |
| CN | 201133750 | Y | 10/2008 |
| CN | 101313880 | A | 12/2008 |
| CN | 101314150 | A | 12/2008 |
| CN | 201177433 | Y | 1/2009 |
| CN | 203662813 | U | 6/2014 |
| CN | 203663097 | U | 6/2014 |
| CN | 302858415 | S | 6/2014 |
| CN | 302896624 | S | 7/2014 |
| CN | 302896625 | S | 7/2014 |
| CN | 203810844 | U | 9/2014 |
| CN | 203810845 | U | 9/2014 |
| CN | 302931892 | S | 9/2014 |
| CN | 203953670 | U | 11/2014 |
| CN | 302995195 | S | 11/2014 |
| CN | 302998997 | S | 11/2014 |
| CN | 303012497 | S | 11/2014 |
| CN | 104188667 | A | 12/2014 |
| CN | 104248511 | A | 12/2014 |
| CN | 204072108 | U | 1/2015 |
| CN | 204072768 | U | 1/2015 |
| CN | 204085054 | U | 1/2015 |
| CN | 204100706 | U | 1/2015 |
| CN | 303065939 | S | 1/2015 |
| CN | 204150302 | U | 2/2015 |
| CN | 204161680 | U | 2/2015 |
| CN | 303095750 | S | 2/2015 |
| CN | 303107432 | S | 2/2015 |
| CN | 303396051 | S | 9/2015 |
| CN | 204688521 | U | 10/2015 |
| CN | 204814863 | U | 12/2015 |
| CN | 204815041 | U | 12/2015 |
| CN | 204840279 | U | 12/2015 |
| CN | 104027117 | B | 5/2016 |
| CN | 105561411 | A | 5/2016 |
| CN | 105619792 | A | 6/2016 |
| CN | 205380885 | U | 7/2016 |
| CN | 104296498 | B | 8/2016 |
| CN | 104340422 | B | 8/2016 |
| CN | 104369919 | B | 8/2016 |
| CN | 105844375 | A | 8/2016 |
| CN | 205514625 | U | 8/2016 |
| CN | 205515719 | U | 8/2016 |
| CN | 104236251 | B | 11/2016 |
| CN | 205885443 | U | 1/2017 |
| CN | 304082783 | S | 3/2017 |
| CN | 106620911 | A | 5/2017 |
| CN | 106621027 | A | 5/2017 |
| CN | 106730075 | A | 5/2017 |
| CN | 106731016 | A | 5/2017 |
| CN | 106823536 | A | 6/2017 |
| CN | 106861242 | A | 6/2017 |
| CN | 106902403 | A | 6/2017 |
| CN | 206326681 | U | 7/2017 |
| CN | 107031053 | A | 8/2017 |
| CN | 206381683 | U | 8/2017 |
| CN | 107116800 | A | 9/2017 |
| CN | 107126585 | A | 9/2017 |
| CN | 107297904 | A | 10/2017 |
| CN | 107297905 | A | 10/2017 |
| CN | 107320790 | A | 11/2017 |
| CN | 107443487 | A | 12/2017 |
| CN | 206748613 | U | 12/2017 |
| CN | 206749079 | U | 12/2017 |
| CN | 206979779 | U | 2/2018 |
| CN | 107753966 | A | 3/2018 |
| CN | 107753967 | A | 3/2018 |
| CN | 107754031 | A | 3/2018 |
| CN | 107802901 | A | 3/2018 |

(56) References Cited

FOREIGN PATENT DOCUMENTS

| | | | |
|---|---|---|---|
| CN | 107812258 | A | 3/2018 |
| CN | 107812259 | A | 3/2018 |
| CN | 107823658 | A | 3/2018 |
| CN | 107823735 | A | 3/2018 |
| CN | 107827025 | A | 3/2018 |
| CN | 107875463 | A | 4/2018 |
| CN | 207224612 | U | 4/2018 |
| CN | 207224613 | U | 4/2018 |
| CN | 207240897 | U | 4/2018 |
| CN | 108042858 | A | 5/2018 |
| CN | 108042859 | A | 5/2018 |
| CN | 108042860 | A | 5/2018 |
| CN | 108057136 | A | 5/2018 |
| CN | 108057142 | A | 5/2018 |
| CN | 108113877 | A | 6/2018 |
| CN | 108114373 | A | 6/2018 |
| CN | 108126252 | A | 6/2018 |
| CN | 108143575 | A | 6/2018 |
| CN | 108143623 | A | 6/2018 |
| CN | 108144140 | A | 6/2018 |
| CN | 108144141 | A | 6/2018 |
| CN | 108145321 | A | 6/2018 |
| CN | 108158796 | A | 6/2018 |
| CN | 108186329 | A | 6/2018 |
| CN | 108186333 | A | 6/2018 |
| CN | 207545982 | U | 6/2018 |
| CN | 108261239 | A | 7/2018 |
| CN | 108310489 | A | 7/2018 |
| CN | 108310490 | A | 7/2018 |
| CN | 108310806 | A | 7/2018 |
| CN | 108310810 | A | 7/2018 |
| CN | 108311796 | A | 7/2018 |
| CN | 108451633 | A | 8/2018 |
| CN | 207890977 | U | 9/2018 |
| CN | 106625881 | B | 11/2018 |
| CN | 108846465 | A | 11/2018 |
| CN | 108898204 | A | 11/2018 |
| CN | 108962370 | A | 12/2018 |
| CN | 109051005 | A | 12/2018 |
| CN | 109125821 | A | 1/2019 |
| CN | 109178518 | A | 1/2019 |
| CN | 305161996 | S | 5/2019 |
| CN | 305362979 | S | 9/2019 |
| CN | 305431737 | S | 11/2019 |
| CN | 210205465 | U | 3/2020 |
| CN | 210205466 | U | 3/2020 |
| CN | 107198821 | B | 5/2020 |
| CN | 212605945 | U | 2/2021 |
| CN | 113104331 | A | 7/2021 |
| CN | 113318287 | A | 8/2021 |
| CN | 306826991 | S | 9/2021 |
| CN | 306848919 | S | 9/2021 |
| CN | 306848920 | S | 9/2021 |
| CN | 306848929 | S | 9/2021 |
| CN | 113588345 | A | 11/2021 |
| CN | 113736655 | A | 12/2021 |
| CN | 215308954 | U | 12/2021 |
| CN | 215607667 | U | 1/2022 |
| CN | 307084614 | S | 1/2022 |
| CN | 307084615 | S | 1/2022 |
| CN | 215882627 | U | 2/2022 |
| CN | 215887060 | U | 2/2022 |
| CN | 307102428 | S | 2/2022 |
| CN | 114410468 | A | 4/2022 |
| CN | 216319494 | U | 4/2022 |
| CN | 216396711 | U | 4/2022 |
| CN | 216410070 | U | 4/2022 |
| CN | 216410411 | U | 4/2022 |
| CN | 307283201 | S | 4/2022 |
| CN | 307303695 | S | 4/2022 |
| CN | 114485402 | A | 5/2022 |
| CN | 216496773 | U | 5/2022 |
| CN | 216550372 | U | 5/2022 |
| CN | 216550374 | U | 5/2022 |
| CN | 216550485 | U | 5/2022 |
| CN | 216556517 | U | 5/2022 |
| CN | 216639492 | U | 5/2022 |
| CN | 216806081 | U | 6/2022 |
| CN | 216826706 | U | 6/2022 |
| CN | 216841114 | U | 6/2022 |
| CN | 216890911 | U | 7/2022 |
| CN | 216899873 | U | 7/2022 |
| CN | 307471980 | S | 7/2022 |
| CN | 217310308 | U | 8/2022 |
| CN | 307491408 | S | 8/2022 |
| CN | 217594869 | U | 10/2022 |
| CN | 217600744 | U | 10/2022 |
| CN | 217602892 | U | 10/2022 |
| CN | 217605105 | U | 10/2022 |
| CN | 307600731 | S | 10/2022 |
| CN | 307625906 | S | 10/2022 |
| CN | 217786697 | U | 11/2022 |
| CN | 307759010 | S | 12/2022 |
| CN | 218421177 | U | 2/2023 |
| CN | 218422377 | U | 2/2023 |
| CN | 218459561 | U | 2/2023 |
| CN | 307831980 | S | 2/2023 |
| DE | 29603873 | U1 | 5/1996 |
| DE | 20218624 | U1 | 4/2003 |
| DE | 60022126 | T2 | 3/2006 |
| DE | 60208647 | T2 | 11/2006 |
| DE | 69932151 | T2 | 4/2007 |
| DE | 60129333 | T2 | 4/2008 |
| DE | 60315386 | T2 | 5/2008 |
| DE | 69938576 | T2 | 5/2009 |
| EM | 0009082230001 | | 9/2004 |
| EM | 0001939580001 | | 4/2008 |
| EM | 0016674110001 | | 3/2010 |
| EM | 0022415700001 | | 6/2013 |
| EM | 0022415880001 | | 5/2023 |
| EP | 0084512 | B1 | 1/1988 |
| EP | 0526678 | B2 | 3/2000 |
| EP | 1034772 | A1 | 9/2000 |
| EP | 1309364 | A1 | 5/2003 |
| EP | 1389473 | A1 | 2/2004 |
| EP | 1498148 | A2 | 1/2005 |
| EP | 1048315 | B1 | 6/2005 |
| EP | 1743535 | A2 | 1/2007 |
| EP | 1903101 | A1 | 3/2008 |
| EP | 1438981 | B1 | 2/2009 |
| EP | 1044670 | B1 | 6/2010 |
| EP | 1438982 | B1 | 3/2011 |
| EP | 1867359 | B1 | 2/2012 |
| EP | 1064959 | B1 | 5/2012 |
| EP | 1894000 | B1 | 6/2012 |
| EP | 2075018 | B1 | 2/2013 |
| EP | 1953218 | B1 | 3/2014 |
| EP | 1262202 | B1 | 4/2014 |
| EP | 1757986 | B1 | 5/2014 |
| EP | 2783717 | A1 | 10/2014 |
| EP | 2179648 | B1 | 12/2014 |
| EP | 2007869 | B1 | 4/2015 |
| EP | 2385106 | B1 | 9/2015 |
| EP | 2999449 | A1 | 3/2016 |
| EP | 2816991 | B1 | 5/2016 |
| EP | 1997374 | B1 | 11/2016 |
| EP | 2119352 | B1 | 4/2017 |
| EP | 1798614 | A3 | 11/2017 |
| EP | 2934626 | B1 | 7/2018 |
| EP | 2393521 | B1 | 9/2018 |
| EP | 2999450 | B1 | 10/2018 |
| EP | 3509660 | A1 | 7/2019 |
| EP | 2921496 | B1 | 10/2019 |
| EP | 2999513 | B1 | 12/2019 |
| EP | 3060292 | B1 | 12/2019 |
| EP | 3509659 | B1 | 7/2020 |
| EP | 2889049 | B1 | 8/2020 |
| EP | 3085409 | B1 | 8/2020 |
| EP | 3278106 | B1 | 10/2020 |
| EP | 2482851 | B1 | 11/2020 |
| EP | 3233280 | B1 | 3/2021 |
| EP | 2889048 | B1 | 11/2021 |
| ES | 2270543 | T3 | 4/2007 |
| ES | 2282873 | T3 | 10/2007 |

(56) References Cited

FOREIGN PATENT DOCUMENTS

| | | | |
|---|---|---|---|
| ES | 2333707 | T3 | 2/2010 |
| ES | 2379279 | T3 | 4/2012 |
| ES | 2404284 | T3 | 5/2013 |
| ES | 2467941 | T3 | 6/2014 |
| ES | 2558137 | T3 | 2/2016 |
| ES | 2612782 | T3 | 5/2017 |
| ES | 2795675 | T3 | 11/2020 |
| FR | 2743300 | B1 | 2/1998 |
| FR | 2781680 | B1 | 11/2000 |
| FR | 2793417 | B1 | 9/2001 |
| FR | 2797403 | B1 | 3/2002 |
| FR | 2814080 | B1 | 2/2003 |
| FR | 2817152 | B1 | 5/2003 |
| FR | 2821762 | B1 | 11/2003 |
| FR | 2856004 | B1 | 8/2005 |
| FR | 2846005 | B1 | 6/2006 |
| FR | 2862880 | B1 | 10/2006 |
| FR | 2880261 | B1 | 2/2007 |
| FR | 2868946 | B1 | 5/2007 |
| FR | 2892949 | B1 | 5/2008 |
| FR | 2932989 | B1 | 8/2011 |
| FR | 2943532 | B1 | 10/2012 |
| FR | 2970845 | B1 | 2/2013 |
| FR | 2962901 | B1 | 8/2013 |
| FR | 2954085 | B1 | 8/2014 |
| FR | 2991886 | B1 | 8/2014 |
| FR | 3015902 | B1 | 3/2017 |
| FR | 3043918 | B1 | 1/2018 |
| FR | 3028863 | B1 | 6/2018 |
| FR | 2983735 | B1 | 12/2019 |
| FR | 3052864 | B1 | 8/2020 |
| FR | 3093928 | B1 | 2/2021 |
| FR | 3047181 | B1 | 4/2021 |
| FR | B083121 | B1 | 10/2021 |
| FR | 3061436 | B1 | 1/2022 |
| FR | 3068611 | B1 | 1/2022 |
| FR | 3077823 | B1 | 1/2022 |
| FR | 3077824 | B1 | 1/2022 |
| FR | 20215186001 | S1 | 4/2022 |
| FR | 3096265 | B1 | 6/2022 |
| FR | 3094643 | B1 | 9/2022 |
| FR | 3120795 | A1 | 9/2022 |
| FR | 3117871 | B1 | 11/2022 |
| FR | 3117039 | B1 | 2/2023 |
| FR | 20225362002 | S1 | 2/2023 |
| FR | 20225364001 | S1 | 2/2023 |
| FR | 20225365001 | S1 | 2/2023 |
| FR | 3126337 | A1 | 3/2023 |
| JP | 5075405 | B2 | 11/2012 |
| WO | 2005004862 | A2 | 1/2005 |
| WO | 2005030444 | A2 | 4/2005 |
| WO | 2005087294 | A1 | 9/2005 |
| WO | 2006016021 | A1 | 2/2006 |
| WO | 2006136698 | A2 | 12/2006 |
| WO | 2007042644 | A1 | 4/2007 |
| WO | 2007122299 | A1 | 11/2007 |
| WO | 2008016777 | A2 | 2/2008 |
| WO | 2008034476 | A1 | 3/2008 |
| WO | 2009000445 | A1 | 12/2008 |
| WO | 2009080914 | A2 | 7/2009 |
| WO | 2010004104 | A2 | 1/2010 |
| WO | 2010089485 | A1 | 8/2010 |
| WO | 2011036357 | A2 | 3/2011 |
| WO | 2012080664 | A2 | 6/2012 |
| WO | 2013007921 | A1 | 1/2013 |
| WO | 2013088070 | A1 | 6/2013 |
| WO | 2013124599 | A1 | 8/2013 |
| WO | 2013156135 | A1 | 10/2013 |
| WO | 2014006339 | A1 | 1/2014 |
| WO | 2014057220 | A1 | 4/2014 |
| WO | 2014096643 | A1 | 6/2014 |
| WO | 2014188128 | A1 | 11/2014 |
| WO | 2014189446 | A1 | 11/2014 |
| WO | 2015060774 | A1 | 4/2015 |
| WO | 2015090222 | A1 | 6/2015 |
| WO | 2015197955 | A1 | 12/2015 |
| WO | 2016124569 | A1 | 8/2016 |
| WO | 2016193591 | A1 | 12/2016 |
| WO | 2018046842 | A1 | 3/2018 |
| WO | 2022029040 | A1 | 2/2022 |
| WO | 2022198908 | A1 | 9/2022 |
| WO | 2022136084 | A3 | 10/2022 |
| WO | 2022252910 | A1 | 12/2022 |

OTHER PUBLICATIONS

U.S. Appl. No. 60/750,511, filed Dec. 15, 2005, 40 pages.

* cited by examiner

MODULAR SERVICEABILITY SLEDS AND INTERCONNECTIONS

CROSS-REFERENCE TO RELATED APPLICATION

This application claims the benefit of U.S. Provisional Application No. 63/318,692 filed on Mar. 10, 2022. The entire disclosure of the above application is incorporated herein by reference.

FIELD

The present disclosure relates to modular serviceability sleds and interconnections.

BACKGROUND

This section provides background information related to the present disclosure which is not necessarily prior art.

There are two common methods for blood donation/collection. A first common method includes obtaining whole blood donation from a donor. Once the whole blood is obtained a centrifugal process may be used to separate blood components from the whole blood, for example, based on the density of different the blood component. The desired components can be manually, semi-automatically, or automatically moved to a collection container during and/or after application of the centrifugal forces. A second common method may be referred to as an apheresis collection, which requires a specialized machine. For example, the apheresis method may extract whole blood from a donor while the donor is connected to the specialized apheresis machine. The whole blood may then be centrifuged to collect only the desired blood component(s) (e.g., plasma) returning all other blood components to the donor during the same donation connection or cycle. The donor is connected to the apheresis machine during the separation and collection of the blood component. Unfortunately, however, the apheresis process can be lengthy and uncomfortable for the donor. For example, often the donor must remain connected to the specialized apheresis machine for an hour or more to obtain the blood component donation. Accordingly, it would be desirable to develop processes, and also to enhance the specialized apheresis machine, to improve the comfort and efficiency of the blood component donation procedure.

SUMMARY

This section provides a general summary of the disclosure and is not a comprehensive disclosure of its full scope or all of its features.

There is a need for a plasma or other blood component system that can reduce the donation time and increase the comfort of the donor. Embodiments presented herein can increase the efficiency of the donation process by using the separated blood component to push or drive the non-desired blood components back to the donor without stopping and restarting the centrifuge. For example, in at least one example embodiment, the present disclosure provides methods and apparatuses for positioning portions, including, for example, loops, of disposables in medical devices. In at least one example embodiment, the present disclosure provides systems, including, for example, surfaces, for automatically guiding loops. In at least one example embodiment, the present disclosure provides medical devices, including, for example, blood separation machines, such as apheresis machines.

In at least one example embodiment, the present disclosure provides an assembly for separating a component from a multi-component fluid. The assembly may include a filler and a loop rotational position guide. The filler may include a channel for holding a separation bladder of a disposable. The channel may include two opposing walls. The loop rotational position guide may include a plurality of bearings. The loop rotational position guide may hold a flexible loop of the disposable when the separation bladder is loaded in the channel. In at least one example embodiment, the loop rotational position guide may include a stop plate. In at least one example embodiment, the flexible loop may contact the stop plate when held in the loop rotational position guide. In at least one example embodiment, the assembly may be part of an apheresis machine. In at least one example embodiment, the assembly may be connected to a rotor that rotates the loop rotational position guide around an axis of rotation. In at least one example embodiment, the plurality of bearings may include a plurality of pairs of roller bearings.

In at least one example embodiment, the present disclosure provides a centrifuge assembly. The centrifuge assembly may include a centrifuge housing having an outer surface and an internal cavity. The centrifuge housing may rotate about a rotation axis of the centrifuge assembly. The centrifuge assembly may include a fluid separating body disposed at least partially within an internal cavity of the centrifuge housing. The fluid separating body may be configured to rotate relative to the centrifuge housing about the rotation axis of the centrifuge assembly. The centrifuge assembly may include a fluid line loop arm attached to a portion of the centrifuge housing and running along a length of the outer surface of the centrifuge housing. The fluid line loop arm may include a bearing set disposed at a point along the length of the outer surface, where the bearing set is configured to contact a tubing portion of an interconnected fluid line loop and maintain the fluid line loop in an engaged position relative to the centrifuge housing while allowing the fluid line loop to rotate in the engaged position. In at least one example embodiment the bearing set may include a pair of roller bearings. In at least one example embodiment, the bearing set may include a plurality of pairs of roller bearings. In at least one example embodiment, the centrifuge assembly may be part of an apheresis machine. In at least one example embodiment, the fluid line loop may be affixed to a static nonrotating portion of the apheresis machine at a first end of the fluid line loop via a first positively-located connector, and the fluid line loop may be interconnected to the fluid separating body within the internal cavity at a second end of the fluid line loop via a second positively-located connector. In at least one example embodiment, the second end of the fluid line loop nay rotate with the fluid separating body. In at least one example embodiment, the fluid line loop may be physically and fluidly attached to a disposable fluid separation bladder at the second positively-located connector. In at least one example embodiment, the fluid line loop may include a plurality of lumens. In at least one example embodiment, the fluid separation bladder may include a first flexible sheet attached to a second flexible sheet forming a fluid pathway, where a first portion of the fluid pathway may be narrow compared to a second portion of the fluid pathway.

In at least one example embodiment, the present disclosure provides a method for automatically loading a fluid line loop into a centrifuge assembly. The method may include attaching the fluid line loop at a first end to a fluid separating body of the centrifuge assembly and rotating the fluid separating body in a first rotational direction relative to a housing of the centrifuge assembly, where rotating the fluid separating body may cause the fluid line loop to rotate relative to the housing and to guide into a channel of a loop arm attached to a portion of the housing. The channel may include bearings disposed in a bearing set attached to the loop arm. The bearings may hold the fluid line loop in a position relative to the housing as the centrifuge assembly rotates. In at least one example embodiment, the bearings may contact a portion of the fluid line loop as the fluid line loop rotates inside the channel in the position relative to the housing. In at least one example embodiment, the centrifuge housing may rotates in the first rotational direction at a first angular velocity about a rotation axis and the fluid separating body may rotate at a different second angular velocity about the rotation axis via a twisting force provided by the fluid line loop. In at least one example embodiment, the second angular velocity may be substantially two times the first angular velocity. In at least one example embodiment, the fluid line loop may be physically and fluidly attached to a disposable fluid separation bladder disposed at least partially within the fluid separating body. In at least one example embodiment, the method may further include attaching a second end of the fluid line loop to a rotationally fixed point of an apheresis machine and rotating (for example, via a rotor and motor assembly of the apheresis machine) the centrifuge assembly about the rotation axis relative to the rotationally fixed point of the apheresis machine.

In at least one example embodiment, the present disclosure provides a method for collecting a blood component through apheresis. The method may include drawing whole blood into a centrifuge from a donor; spinning the centrifuge to cause centrifugal force to act on the whole blood to separate the whole blood into a least a first blood component and a third blood component; separating a first blood component from the whole blood; extracting the first blood component into a container; detecting when a second blood component is being extracted; and after the second blood component is detected and while the centrifuge continues to spin, forcing the separated first blood component back towards the centrifuge to move at least the third blood component from the centrifuge and back into the donor. In at least one example embodiment, the first blood component may include one or more of plasma, platelets, red blood cells and/or high hematocrit blood. In at least one example embodiment, the second blood component may include one or more of plasma, platelets, red blood cells and/or high hematocrit blood. In at least one example embodiment, the third blood component may include one or more of plasma, platelets, red blood cells and/or high hematocrit blood. In at least one example embodiment, the first blood component may include two or more of plasma, platelets, red blood cells and/or high hematocrit blood. In at least one example embodiment, the centrifuge may spin at a first speed when separating the first blood component from the whole blood. In at least one example embodiment, the centrifuge may continue to spin at the first speed when forcing the separated first blood component back towards the centrifuge. In at least one example embodiment, the centrifuge may spin at a second speed when drawing whole blood into the centrifuge from the donor. In at least one example embodiment, the second speed may include slower than the first speed. In at least one example embodiment, the first blood component may include separated from the whole blood in a blood component collection set that is inserted into the centrifuge. In at least one example embodiment, the centrifuge may include a filler that spins a blood component collection bladder associated with the blood component collection set. In at least one example embodiment, the blood component collection bladder may be inserted into a collection insert channel formed in the filler to hold the blood component collection bladder.

In at least one example embodiment, the present disclosure provides an apheresis system. The apheresis system may include a first tube having a lumen, fluidly associated with the needle, that moves whole blood from a donor through the lumen; a draw pump engaged with the first tube that draws the whole blood into a centrifuge from the donor; the centrifuge that spins to cause centrifugal force to act on the whole blood to separate the whole blood into a least a first blood component and a third blood component; a blood component collection bladder, inserted into the centrifuge and fluidly associated with the first tube, that separates the first blood component from the whole blood; a second tube, fluidly associated the blood collection bladder, that moves the first blood component from the blood component collection bladder; a collection container, fluidly associated with the second tube, that extracts the first blood component from the apheresis system; a sensor positioned in physical proximity to the second tube to detect when a second blood component is being extracted from the whole blood; and after the second blood component is detected by the sensor and while the centrifuge continues to spin, a return pump, engaged with the second tube, that forces the separated first blood component back towards the blood component collection bladder through the second tube to move at least the third blood component from the blood component collection bladder and back into the donor. In at least one example embodiment, the first blood component may include plasma and the second blood component may include platelets, red blood cells, and/or high hematocrit blood. In at least one example embodiment, the apheresis system may further include an anticoagulant pump configured to draw anticoagulant from an anticoagulant bag and mix the anticoagulant with whole blood at a manifold or junction fluidly associated with the first tube. In at least one example embodiment, the centrifuge may include a filler that spins the blood component collection bladder. In at least one example embodiment, the blood component collection bladder may be inserted into a collection insert channel formed in the filler to hold the blood component collection bladder.

In at least one example embodiment, the present disclosure provides a blood component collection set associated with an apheresis system. The blood component collection set may include a needle inserted into a blood vessel of a donor to draw whole blood from a donor; a first tube having a lumen, fluidly associated with the needle, that moves the whole blood through the lumen, where a draw pump engaged with the first tube draws the whole blood from the donor; a blood component collection bladder, inserted into a centrifuge and fluidly associated with the first tube, that separates the first blood component and a third component from the whole blood; a second tube, fluidly associated with the blood collection bladder, that moves the first blood component from the blood component collection bladder; and a collection container fluidly associated with the second tube that extracts the first blood component from the apheresis system, where a sensor is positioned in physical proximity to the second tube to detect when a second blood component is being extracted from the whole blood; and where, after the second blood component is detected by the sensor and while the centrifuge continues to spin, a return pump engaged with the second tube forces the separated first blood component back towards the blood component collection bladder through the second tube to move at least the third blood component from the blood component collection bladder and back into the donor. In at least one example embodiment, the first blood component may include plasma and the second blood component may include platelets. In at least one example embodiment, the draw pump may be disengaged when the return pump forces the separated first blood component back towards the blood component collection bladder through the second tube to move at least the third blood component from the blood component collection bladder and back into the donor. In at least one example embodiment, the blood component collection bladder may be inserted and held in a filler, in the centrifuge, that spins the blood component collection bladder. In at least one example embodiment, the blood component collection bladder may be inserted into a collection insert channel formed in the filler to hold the blood component collection bladder.

In at least one example embodiment, the present disclosure provides filler configured for holding a separation bladder in which a component is separated from a composite fluid. The filler may include a channel for holding a separation bladder during separation of the component from the composite fluid. The channel may include a first wall and a second wall opposite the first wall. A first end of the channel may be adjacent to a central portion of the filler and the channel spirals toward an outside perimeter of the filler. In at least one example embodiment, a top portion of the channel may be narrower than a middle portion of the channel. In at least one example embodiment, at least a portion of the second wall may have a concave surface. In at least one example embodiment, the second end of the channel may be located so that it experiences a higher gravitational force during separation than the first end. In at least one example embodiment, the top portion of the channel may provide reinforcement to the separation bladder during separation.

In at least one example embodiment, the present disclosure provides a fluid separation filler. The fluid separation filler may include a body having a rotation axis substantially disposed at a mass center of the body and a fluid collection insert channel disposed in the body and following a substantially spiral path running from a first point adjacent to the rotation axis spirally outward to a second point disposed adjacent to a periphery of the body. The fluid collection insert channel may jog outwardly toward the periphery of the body near an end of the substantially spiral path defining a third point of the fluid collection insert channel disposed furthest from the rotation axis. In at least one example embodiment, the fluid separation filler may further include a fluid collection chamber disposed within the body and following a portion of the substantially spiral path, where the fluid collection insert channel connects to the fluid collection chamber defining access area between an interior of the fluid collection chamber and an exterior of the body. In at least one example embodiment, the fluid collection chamber may be configured to receive a disposable fluid collection bladder. In at least one example embodiment, a dimension from the rotation axis to the third point of the substantially spiral path may be greater than a dimension from the rotation axis to the second point of the substantially spiral path. In at least one example embodiment, a width of the fluid collection chamber at a point along the substantially spiral path may be greater than a width of the fluid collection insert channel at the point along the substantially spiral path. In at least one example embodiment the fluid collection chamber may further include a first wall following an innermost portion of the substantially spiral path and a second wall substantially parallel to the first wall and following an outermost portion of the substantially spiral path. In at least one example embodiment, the fluid collection chamber may further include one or more tapered walls disposed between the first wall and the second wall, and the one or more tapered walls may be configured to guide the disposable fluid collection bladder into a seated position within the fluid collection chamber. In at least one example embodiment, a fluid inlet for the disposable fluid collection bladder when installed in the fluid collection chamber may be disposed adjacent to the rotation axis and a first fluid path in the disposable fluid collection bladder may follow the substantially spiral path outwardly toward an end of the disposable fluid collection bladder disposed adjacent to the third point of the fluid collection insert channel disposed furthest from the rotation axis, and may fluidly interconnects with a second fluid path separated from the first fluid path in the disposable fluid collection bladder running in a direction from the third point following the substantially spiral path inwardly toward a fluid outlet for the disposable fluid collection bladder disposed adjacent to the rotation axis. In at least one example embodiment, the fluid inlet and the fluid outlet may be part of a connector attached to the disposable fluid collection bladder, and the body of the fluid separation filler may include a connection point that engages with the connector. In at least one example embodiment, the connector may include at least one key feature, where the connection point may include at least one mating key feature, and the key features may positively locate the connector relative to the connection point.

In at least one example embodiment, the present disclosure provides a centrifuge assembly. The centrifuge assembly may include a centrifuge housing having an internal cavity, where the centrifuge housing rotates about a rotation axis of the centrifuge assembly, and a fluid separating body disposed at least partially within the internal cavity of the centrifuge housing and configured to rotate relative to the centrifuge housing about the rotation axis. The fluid separating body may include a fluid collection insert channel disposed in the fluid separating body following a substantially spiral path running from a first point adjacent to the rotation axis spirally outward to a second point disposed adjacent to a periphery of the fluid separating body. The fluid collection insert channel may In at least one example embodiment, the fluid separating body may further include a fluid collection chamber disposed within the body and following a portion of the substantially spiral path, where the fluid collection insert channel may connect to the fluid collection chamber to define an access area between an interior of the fluid collection chamber and an exterior of the fluid separating body. In at least one example embodiment, the centrifuge assembly may further include a disposable fluid collection bladder disposed within the fluid collection chamber following the substantially spiral path. The disposable fluid collection bladder may include a fluid inlet disposed adjacent to the rotation axis and a first fluid path in the disposable fluid collection bladder may follow the substantially spiral path outwardly toward an end of the disposable fluid collection bladder disposed adjacent to the third point of the fluid collection insert channel disposed furthest from the rotation axis and may fluidly interconnect with a second fluid path separated from the first fluid path in the disposable fluid collection bladder running in a direction from the third point following the substantially spiral path inwardly toward a fluid outlet for the disposable fluid collection bladder disposed adjacent to the rotation axis. In at least one example embodiment, the centrifuge assembly may be part of an apheresis machine. In at least one example embodiment, the centrifuge housing may be split into an upper housing and a lower housing, where the upper housing may include the internal cavity, the upper housing may be rotatable between an open state and a closed state about a pivot axis that is offset and substantially perpendicular to the rotation axis, and the fluid collection insert channel of the fluid separating body may be accessible in the open state and inaccessible in the closed state.

In at least one example embodiment, the present disclosure provides a blood component collection loop. The blood component collection loop may include a flexible loop; a system static loop connector disposed at a first end of the flexible loop, where the system static loop connector is connected to the fixed loop connection of a centrifuge to fix the first end of the flexible loop to rotate in unison with the centrifuge; and a filler loop connector disposed at a second end, opposite the first end, of the flexible loop, where the filler loop connector is connected to a loop connection area of a filler, where torsional forces based on twist in the flexible loop are imparted to the filler through the filler loop connector, and where the flexible loop is rotationally moved to be captured by a loop rotational position guide positioned on the centrifuge. In at least one example embodiment, the blood component collection loop may be part of a blood component collection set, and the blood component collection set may be associated with an apheresis system. In at least one example embodiment, the loop rotational position guide may be attached to a rotor that rotates the loop rotational position guide and the flexible loop around an axis of rotation. In at least one example embodiment, the blood component collection loop may be at least partially positioned by a loop position stop plate. In at least one example embodiment, the flexible loop may be curved around the centrifuge. In at least one example embodiment, the flexible loops may be also held in position by a loop containment bracket. In at least one example embodiment, at least a portion of the loop rotational position guide may include a loop twist support bearing. In at least one example embodiment, the loop twist support bearing may include a pair of roller bearings. In at least one example embodiment, the loop twist support bearing may allow the flexible loop to twist. In at least one example embodiment, the twist may cause the filler to rotate at a greater angular velocity than the centrifuge. In at least one example embodiment, the flexible loop may include two or more lumens to move whole blood and/or blood components within the flexible loop.

In at least one example embodiment, the present disclosure provides an assembly for loading a flexible loop. The assembly may include a loop rotation position guide that includes a channel for holding a flexible loop of a blood component collection set; a loop twist support bearing, disposed in the channel and on a portion of the loop rotation position guide, to support the flexible loop; and a loop capture arm, where the loop capture arm may be positioned adjacent the channel and connected to the loop rotation position guide, to guide the flexible loop into the channel and in contact with the loop twist support bearing. In at least one example embodiment, the assembly may be part of an apheresis machine, and the loop rotation position guide may be attached to centrifuge that rotates the loop rotation position guide and the flexible loop around an axis of rotation. In at least one example embodiment the loop rotation position guide may further include a loop position stop plate to further position the flexible loop. In at least one example embodiment, the assembly may further include a loop containment bracket, positioned in a plane with the loop rotation position guide and disposed on the centrifuge, to further capture the flexible loop.

In at least one example embodiment, the present disclosure provides a method for automatically loading a flexible loop into an assembly. The method may include connecting a system static loop connector, disposed at a first end of the flexible loop, to a fixed loop connection of a centrifuge to fix the first end of the flexible loop to rotate in unison with the centrifuge; connecting a filler loop connector, disposed at a second end, opposite the first end, of the flexible loop, to a loop connection area of a filler, where torsional forces based on twist in the flexible loop are imparted to the filler through the filler loop connector; and rotationally moving the flexible loop into a loop rotational position guide positioned on the centrifuge. In at least one example embodiment, the flexible loop may engage a loop twist support bearing, disposed in a channel formed by the loop rotation position guide, where the loop twist support bearing supports the flexible loop. In at least one example embodiment, a loop capture arm may contact the flexible loop when rotating to guide the flexible loop into the channel and in contact with the loop twist support bearing. In at least one example embodiment, the loop rotation position guide may further include a loop position stop plate to prevent over-rotation of the flexible loop past the channel. In at least one example embodiment, a loop containment bracket, positioned in a plane with the loop rotation position guide and disposed on the centrifuge, may further capture and holds the flexible loop.

In at least one example embodiment, the present disclosure provides a soft cassette. The soft cassette may include a first cassette port, a second cassette port, a direct flow lumen fluidly connected to the first cassette port and the second cassette port, a drip chamber inter-disposed in the direct flow lumen such that the fluid passing through the direct flow lumen passes through the drip chamber, and a fluid flow bypass path both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber. In at least one example embodiment, the fluid flow bypass path may include a first bypass branch fluidly connected to the direct flow lumen adjacent the first cassette port and a second bypass branch fluidly connected to the direct flow lumen adjacent the second cassette port. In at least one example embodiment, the fluid flow bypass path may further include a fluid pressure annulus disposed between and fluidly connected to the first bypass branch and the second bypass branch. In at least one example embodiment, the direct flow lumen may include a first compliant region, disposed between a first connection with the first bypass branch and the drip chamber, that allows a first fluid control valve to occlude the direct flow lumen. In at least one example embodiment, the direct flow lumen may include a second compliant region, disposed between a second connection with the second bypass branch and the drip chamber, that allows a second fluid control valve to occlude the direct flow lumen. In at least one example embodiment the direct flow lumen may include a third compliant region, disposed in the first bypass branch, that allows a draw fluid control valve to occlude the first bypass branch. In at least one example embodiment, the first cassette port may be fluidly connected to a cassette inlet tubing that moves fluid from a donor into the soft cassette or fluid from the soft cassette to the donor, and the second cassette port may be fluidly connected to a loop inlet tubing that moves fluid from a soft cassette into the centrifuge or fluid from the centrifuge to the soft cassette. In at least one example embodiment, when drawing fluid from the donor, the fluid may pass through the fluid flow bypass path. In at least one example embodiment, when sending fluid to the donor, the fluid may pass through the direct flow lumen. In at least one example embodiment, when drawing fluid from the donor in a subsequent draw, a portion of the fluid previously sent to the donor through the direct flow lumen may be maintained in the drip chamber when the fluid passes through the fluid flow bypass path. In at least one example embodiment, the soft cassette may be part of a blood component collection set. In at least one example embodiment, the blood component collection set may be part of an apheresis system.

In at least one example embodiment, the present disclosure provides a blood component collection set. The blood component collection set may include a centrifuge to separate blood components from whole blood; a cassette inlet tubing fluidly connected to a donor; a loop inlet tubing fluidly connected to the centrifuge; a soft cassette that includes a first cassette port fluidly connected to the cassette inlet tubing; a second cassette port fluidly connected to the loop inlet tubing; a direct flow lumen fluidly connected to the first cassette port and the second cassette port; a drip chamber inter-disposed in the direct flow lumen such that the fluid passing through the direct flow lumen passes through the drip chamber; and a fluid flow bypass path both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber. In at least one example embodiment, the fluid flow bypass path may include a first bypass branch fluidly connected to the direct flow lumen adjacent the first cassette port, a second bypass branch fluidly connected to the direct flow lumen adjacent the second cassette port, and a fluid pressure annulus disposed between and fluidly connected to the first bypass branch and the second bypass branch. In at least one example embodiment, the direct flow lumen may include a first compliant region, disposed between a first connection with the first bypass branch and the drip chamber, that allows a first fluid control valve to occlude the direct flow lumen, where the direct flow lumen includes a second compliant region, disposed between a second connection with the second bypass branch and the drip chamber, that allows a second fluid control valve to occlude the direct flow lumen, and where the direct flow lumen includes a third compliant region, disposed in the first bypass branch, that allows a draw fluid control valve to occlude the first bypass branch. In at least one example embodiment, when drawing fluid from the donor, the first fluid control valve and the second fluid flow control valve may be closed and occlude the direct flow lumen, and the draw fluid control valve may be open and allows whole blood to pass through the fluid flow bypass path. In at least one example embodiment, when sending fluid to the donor, the first fluid control valve and the second fluid flow control valve may be open and allow fluid to pass through the direct flow lumen, and the draw fluid control valve may be closed and occludes the fluid flow bypass path. In at least one example embodiment, when drawing fluid from the donor in a subsequent draw, a portion of the fluid previously sent to the donor through the direct flow lumen may be maintained in the drip chamber when the fluid passes through the fluid flow bypass path.

In at least one example embodiment, the present disclosure provides a method for moving fluids through a soft cassette. The method may include providing a soft cassette, where the soft cassette includes a first cassette port fluidly connected to a cassette inlet tubing, a second cassette port fluidly connected to a loop inlet tubing, a direct flow lumen fluidly connected to the first cassette port and the second cassette port, a drip chamber inter-disposed in the direct flow lumen such that the fluid passing through the direct flow lumen passes through the drip chamber, and a fluid flow bypass path both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber. In at least one example embodiment, the method may include, when drawing whole blood from a donor, receiving whole blood from the cassette inlet tubing at a first cassette port fluidly connected to the cassette inlet tubing, moving the whole blood through the fluid flow bypass path to the second cassette port, and preventing whole blood from moving through the direct lumen. In at least one example embodiment, the method may include, when returning red blood cells to the donor, receiving red blood cells from the loop inlet tubing at a second cassette port fluidly connected to the loop inlet tubing, moving the red blood cells through the direct flow lumen and the drip chamber to the first cassette port, and preventing red blood cells from moving through the fluid flow bypass path. In at least one example embodiment, when drawing fluid from the donor in a subsequent draw, a portion of the fluid previously may be sent to the donor through the direct flow lumen, and when returning red blood cells to the donor.

At least one example embodiment relates to a modular serviceability sled for an apparatus.

In at least one example embodiment, the modular serviceability sled includes a frame, a first subassembly, a first sled interconnection, a gasket, and a shielding component. The first sled interconnection is operatively connected to the first subassembly. The first sled interconnection includes an electrical connection, a pneumatic connection, a hydraulic connection, or any combination thereof. The gasket is configured to engage the frame and a base assembly of the apparatus. The shielding component is configured to contact the frame and the base assembly of the apparatus. The shielding component includes an electromagnetic interference shielding component, a radio frequency interference shielding component, or both the electromagnetic interference shielding component and the radio frequency interference shielding component. The modular serviceability sled is configured to be moved between an engaged state and a disengaged state. Tn the engaged state, the modular serviceability sled is at least partially within a receiving space of the apparatus, the gasket engages the frame and the base assembly, the shielding component contacts the frame and the base assembly, and the first sled interconnection is operatively connected to a first machine interconnection of the apparatus. In the disengaged state, the first sled interconnection is disconnected from the first machine interconnection and the modular serviceability sled is configured to be freely moved with respect to the base assembly.

In at least one example embodiment, the first subassembly includes an electrical component, a pneumatic component, a mechanical component, or any combination thereof.

In at least one example embodiment, the first subassembly includes the electrical component. The electrical component includes a microcontroller. Sensor, a relay, a printed circuit board, a transformer, or any combination thereof.

In at least one example embodiment, the first subassembly includes the pneumatic component. The pneumatic component includes a fluid reservoir, a compressor, a solenoid valve, an air valve, a plenum, a manifold, or any combination thereof.

In at least one example embodiment, the first subassembly includes the mechanical component. The mechanical component includes a linear actuator, a load cell, a strain gauge, a pneumatic cylinder, a bladder, a balloon. an air cylinder, a motor, or any combination thereof.

In at least one example embodiment, the first subassembly includes a pump.

In at least one example embodiment, the modular serviceability sled further includes a plurality of sled interconnections including the first sled interconnection. Each of the plurality of sled interconnections is independently selected from an electrical connection, a pneumatic connection, a hydraulic connection, or any combination thereof.

In at least one example embodiment, the first sled interconnection includes the electrical connection. The first sled interconnection includes a power connection, a communications connection, or both a power connection and a communications connection.

In at least one example embodiment, the modular serviceability sled further includes a second subassembly and a second sled interconnection. The second subassembly is attached to the frame. The second sled interconnection is operatively connected to the second subassembly. The first sled interconnection includes an electrical connection, a pneumatic connection, a hydraulic connection, or any combination thereof.

In at least one example embodiment, the shielding component includes a conductive gasket.

In at least one example embodiment, the gasket includes an O-ring.

In at least one example embodiment, the frame defines a junction. A communication path operatively connects the first subassembly to the first sled interconnection via the junction.

In at least one example embodiment, the junction includes an aperture, an electrical via, or both an aperture and an electrical via.

In at least one example embodiment, the junction is hermetically sealed.

At least one example embodiment relates to an apheresis system. The apheresis system includes a base assembly and a first modular serviceability sled. The base assembly defines a first receiving space. The first modular serviceability sled includes a sled frame, a subassembly, a sled interconnection, a gasket, and a shielding component. The subassembly is attached to the sled frame. The sled interconnection is operatively connected to the subassembly. The sled interconnection includes an electrical connection, a pneumatic connection, a hydraulic connection, or any combination thereof. The gasket is configured to engage the sled frame and a base assembly. The shielding component is configured to contact the sled frame and the base assembly. The shielding component includes an electromagnetic interference shielding component, a radio frequency interference shielding component, or both the electromagnetic interference shielding component and the radio frequency interference shielding component. The first modular serviceability sled is configured to be moved between an engaged state and a disengaged state. Tn the engaged state, the first modular serviceability sled is at least partially within the first receiving space, the gasket engages the sled frame and the base assembly, the shielding component contacts the sled frame and the base assembly, and the sled interconnection is operatively connected to a machine interconnection of the apheresis system. In the disengaged state, the sled interconnection is disconnected from the machine interconnection and the first modular serviceability sled is configured to be freely moved with respect to the base assembly.

In at least one example embodiment, the apheresis system further includes a plurality of modular serviceability sleds including the first modular serviceability sled. The base assembly defines a plurality of receiving spaces including the first receiving space. Each of the plurality of modular serviceability sleds is configured to be at least partially in a respective one of the plurality of receiving spaces.

In at least one example embodiment, each of the plurality of modular serviceability sleds is configured operate independently of the other of the modular serviceability sleds.

In at least one example embodiment, each of the plurality of modular serviceability sleds includes a respective memory including a unique identifier. The apheresis system is configured to identify each of the modular serviceability sleds based on the unique identifier.

In at least one example embodiment, the base assembly includes a base frame and a base housing. The base frame includes a metal. The base housing includes a plastic. In the engaged state, the gasket engages the sled frame and the base housing and the shielding component engages the sled frame and the base frame.

In at least one example embodiment, the base housing defines a sloped region adjacent to a periphery of the first receiving space.

At least one example embodiment relates to a method of servicing a modular serviceability sled of an apheresis system.

In at least one example embodiment, the method includes detaching the modular serviceability sled from a base assembly of the apheresis system. The modular serviceability sled includes a frame, a subassembly attached to the frame, a sled interconnection operatively connected to the subassembly, a gasket, and a shielding component configured to contact the frame and the base assembly. The shielding component includes an electromagnetic interference shielding component, a radio frequency interference shielding component, or both the electromagnetic interference shielding component and the radio frequency interference shielding component. The sled interconnection includes an electrical connection, a pneumatic connection, a hydraulic connection, or any combination thereof. The method further includes disconnecting the sled interconnection from a machine interconnection. The method further includes at least partially removing the modular serviceability sled from a receiving space defined in the base assembly. The method further includes servicing the modular serviceability sled.

In at least one example embodiment, the servicing includes maintaining the modular serviceability sled, repairing the modular serviceability sled, replacing the modular serviceability sled, or any combination thereof.

In at least one example embodiment, the method further includes after the servicing, connecting the sled interconnection with the machine interconnection. The method further includes attaching the modular serviceability sled to the base assembly such that the gasket engages the base assembly and the housing and the shielding component contacts the frame and the base assembly.

The present disclosure provides a number of advantages depending on the particular aspect, embodiment, and/or configuration. For example, in at least one example embodiment, the speed of rotation of the centrifuge while moving the unneeded blood components back to the donor, the apheresis procedure may be reduced in time, for example, by about 30% or more. This increase in efficiency may allow for faster and more comfortable donations. With faster donation times, a donation center may obtain more donations in a typical day, which may increase productivity and revenue. Further, donors are more likely to return to donate again if the donation is faster. Having faster donations may also allow donation centers to attract donors using other donation centers with slower donation speeds.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Corresponding reference numerals indicate corresponding parts throughout the several views of the drawings.

DETAILED DESCRIPTION

Figure 1:
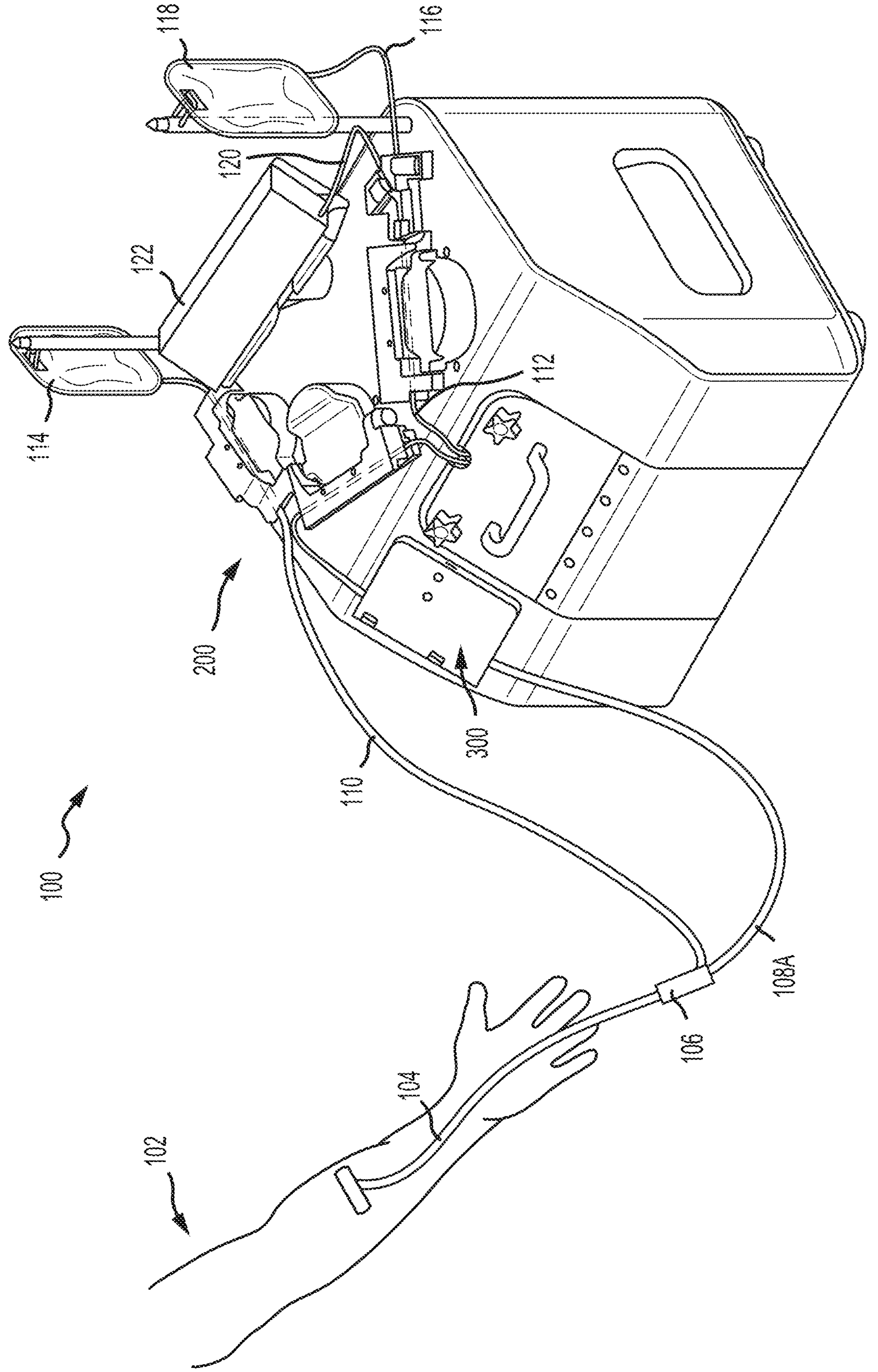
FIG. 1 shows a perspective view of an operating environment of an apheresis system in accordance with at least one example embodiment of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Various components are referred to herein as "operably associated." As used herein, "operably associated" refers to components that are linked together in operable fashion and encompasses embodiments in which components are linked directly, as well as embodiments in which additional components are placed between the linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g., a peristaltic pump that pumps fluids through flexible tubing by compressing the exterior of the tube).

The term "donor," as used herein, can mean any person providing a fluid (e.g., whole blood) to the apheresis system. A donor can also be a patient that also provides a fluid to the apheresis system temporarily while the fluid is processed, treated, manipulated, etc. before being provided back to the patient.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any tangible storage and/or transmission medium that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

The term "module" as used herein refers to any known or later developed hardware, software, firmware, artificial intelligence, fuzzy logic, or combination of hardware and software that is capable of performing the functionality associated with that element.

The terms "determine", "calculate" and "compute," and variations thereof, as used herein, are used interchangeably and include any type of methodology, process, mathematical operation or technique.

Embodiments of the present disclosure will be described more fully with reference to the accompanying drawings and in connection with apheresis methods and systems. Embodiments below may be described with respect to separating blood components from whole blood. However, the example procedures are provided simply for illustrative purposes. It is noted that the embodiments are not limited to the description below. The embodiments are intended for use in products, processes, devices, and systems for separating any composite liquid. Accordingly, the present disclosure is not limited to separation of blood components from whole blood.

Referring to FIG. 1, a perspective view of an operating environment 100 of an apheresis system 200 is shown in accordance with at least one example embodiment of the present disclosure. The operating environment 100 may include an apheresis system 200, a donor 102, and one or more connections (e.g., donor feed tubing 104, cassette inlet tubing 108A, anticoagulant tubing 110, etc.) running from the donor 102 to the apheresis system 200, and/or vice versa. As shown in FIG. 1, the donor feed tubing 104 may be fluidly connected with at least one blood vessel, for example, a vein, of the donor 102 via venipuncture. For example, a cannula connected to an end of the donor feed tubing 104 may be inserted through the skin of the donor 102 and into a target site, or vein. This connection may provide an intravenous path for blood to flow from the donor 102 to the apheresis system 200, and/or for blood components to flow back to the donor 102. In at least one example embodiment, the fluid paths and connections may form an extracorporeal tubing circuit of the apheresis system 200.

Blood supplied from the donor 102 may flow along the donor feed tubing 104 through a tubing connector 106 and along the cassette inlet tubing 108A into a soft cassette assembly 300. The soft cassette assembly 300 may include one or more fluid control paths and valves for selectively controlling the flow of blood to and/or from the donor 102. The apheresis system 200 may include an anticoagulant supply contained in an anticoagulant (AC) bag 114. The anticoagulant may be pumped at least through the anticoagulant tubing 110 and the tubing connector 106 preventing the coagulation of blood in the apheresis system 200.

Anticoagulants can include one or more of, but are not limited to, citrate and/or unfractionated heparin. The AC bag 114 and other bags or bottles described herein can be made from, for example, one or more of, but not limited to: polyvinyl chloride (PVC), plasticized-PVC, polyethylene, ethylene with vinyl acetate (EVA), rubber, silicone, thermoplastics, thermoplastic elastomer, polymers, copolymers, and/or combinations thereof. The volume of AC in the AC bag 114 may vary based on the various factors, including the mass of the donor 102, the volumetric flow of blood from the donor, etc. In one example, the volume in the AC bag 114 may be 250 to 500 mL, although the volume in the AC bag 114 may be more or less than this volume.

Figure 2A:
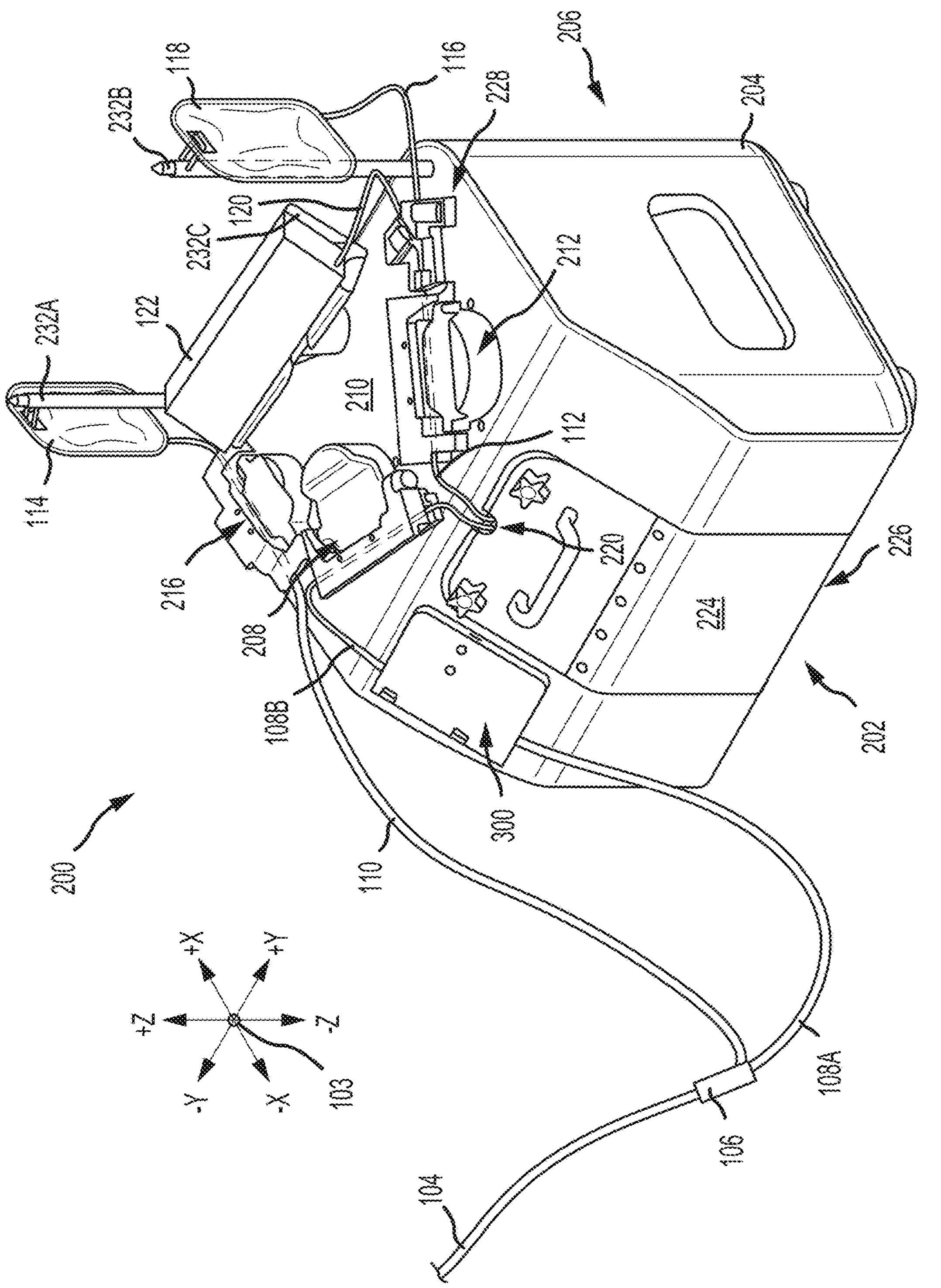
FIG. 2A is a perspective view of the apheresis system shown in FIG. 1.

In at least one example embodiment, the apheresis system 200 may include a plasma collection bottle 122, or container, a saline fluid contained in a saline bag 118, and one or more lines or tubes such as saline tubing 116 and plasma tubing 120 (e.g., fluid conveying tubing, etc.) connecting the saline bag 118 and the plasma collection bottle 122 with the extracorporeal tubing circuit of the apheresis system 200. The amount of saline provided in the saline bag 118 can be 500 to 800 mL, although the volume in the saline bag 118 may be more or less than this volume. An example donation of a blood component (e.g., plasma) may be 880 mL. Thus, the plasma collection bottle 122 may hold at least this amount of plasma. In at least one example embodiment, the plasma collection bottle 122 may include a connection point disposed at, adjacent to, or in physical proximity to, a substantially bottommost portion of the plasma collection bottle 122 (e.g., when the plasma collection bottle 122 is installed in a plasma collection cradle 232C, as shown in FIG. 2A). The connection point may include one or more connectors that are configured to interconnect with the plasma tubing 120 to receive and/or convey plasma. The disposition of the connection point at the bottom of the plasma collection bottle 122 can allow plasma contained in the plasma collection bottle 122 to move out of the plasma tubing 120 back through the lines, as described herein, without trapping air bubbles, etc. In at least one example embodiment, the plasma collection bottle 122 may be configured as a flexible bag, rigid container, and/or other container, and thus, the plasma collection bottle 122 is not limited to bottles or bottle-like containers.

FIG. 2A shows a perspective view of the apheresis system 200 described in FIG. 1. The apheresis system 200 may provide for a continuous whole blood separation process. In at least one example embodiment, whole blood may be withdrawn from a donor 102 and substantially continuously provided to a blood component separation device of the apheresis system 200 where the blood may be separated into various components and at least one of these blood components may be collected from the apheresis system 200. In at least one example embodiment, one or more of the separated blood components may be either collected, for subsequent use, or returned to the donor 102. The blood may be withdrawn from the donor 102 and directed into a centrifuge of the apheresis system 200 through an opening 220 in an access panel 224 of the apheresis system 200. In at least one example embodiment, the tubing the donor feed tubing 104, the cassette inlet tubing 108A, inlet tubing 108B (also referred to herein as loop inlet tubing 108B), exit tubing 112 (also referred to herein as loop exit tubing 112), the saline tubing 116, and the plasma tubing 120, used in the extracorporeal tubing circuit may together define a closed, sterile, and disposable system, or blood component collection set, which may be further described hereinafter.

Examples of apheresis, plasmapheresis, and other separation systems that may be used with embodiments of the present disclosure (e.g., as apheresis system 200) include, but are not limited to, the SPECTRA OPTIA® apheresis system, COBE® spectra apheresis system, and the TRIMA ACCEL® automated blood collection system, all manufactured by Terumo BCT, of Lakewood, Colo.

Operation of the various pumps, valves, and blood component separation device, or centrifuge, may be controlled by one or more processors included in the apheresis system 200, and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory, etc.); communication/networking devices (e.g., wired such as modems/network cards, or wireless such as Wi-Fi); input devices such as keyboard(s), touch screen(s), camera(s), and/or microphone(s); and output device(s) such as display(s), and audio system(s), etc. To assist the operator of the apheresis system 200 with various aspects of its operation, in at least one example embodiment the blood component separation device, or centrifuge, may include a graphical user interface with a display that includes an interactive touch screen.

The apheresis system 200 may include a housing 204 and/or structural frame, a cover 210, an access panel 224 disposed at a front 202 and/or rear 206 of the apheresis system 200, and one or more supports 232A-232C including hooks, rests, cradles, arms, protrusions, plates, and/or other support features for holding, cradling, and/or otherwise supporting a container or the AC bag 114, the saline bag 118, or the plasma collection bottle 122. In at least one example embodiment, the features of the apheresis system 200 may be described with reference to a coordinate system 103 and/or one or more axes thereof. The housing 204 may include a machine frame (e.g., made of welded, bolted, and/or connected structural elements, extruded material, beams, etc.) to which one or more panels, such as the cover 210, doors, subassemblies, and/or components are attached. In at least one example embodiment, at least one panel of the apheresis system 200 may include a mounting surface for the soft cassette assembly 300, one or more pumps such as a draw pump 208, a return pump 212, or an anticoagulant (AC) pump 216, and/or a fluid valve control system 228 (e.g., plasma and saline valve control, etc.).

The access panel 224 may include one or more handles, locks, and a pivoting or hinged axis 226 (e.g., a door hinge, piano hinge, continuous hinge, cleanroom hinge, etc.). In any event, the access panel 224 may be selectively opened to provide access to an interior of the apheresis system 200, and more specifically to a blood separation assembly, or centrifuge. In at least one example embodiment, the access panel 224 may provide access to load and/or unload the centrifuge with one or more components in the blood component collection set. Details of the centrifuge are described in greater detail at least with respect to FIGS. 4A-4L below.

The inside of the apheresis system 200 may be separated into at least a centrifuge portion and a controls portion. For instance, the centrifuge portion may include a cavity configured to receive the centrifuge, rotation motor, and associated hardware. This area may be physically separated from the controls portion via one or more walls of the cavity. In at least one example embodiment, access to the controls portion (e.g., configured to house or otherwise contain the motor controller, CPU or processor(s), electronics, wiring, etc.) may be provided via a securely fastened panel of the housing 204, and/or panel separate from the access panel 224.

In at least one example embodiment, the apheresis system 200 may include a number of pumps, such as the draw pump 208, the return pump 212, or the AC pump 216, configured to control the flow of fluid (e.g., blood and/or blood components, anticoagulant, saline, etc.) through the apheresis system 200. For instance, the apheresis system 200 may include the draw pump 208 that controls blood flow to and/or from the donor 102 into the centrifuge of the apheresis system 200. The draw pump 208 may engage with a portion of the inlet tubing 108B disposed between the soft cassette assembly 300 and the centrifuge of the apheresis system 200. In at least one example embodiment, the apheresis system 200 may include the return pump 212 configured to control a flow of separated blood components (e.g., plasma, etc.) from the centrifuge to a plasma collection bottle 122 and/or vice versa. Additionally or alternatively, the return pump 212 may control a flow of saline (e.g., supplied from the saline bag 118) throughout the blood component collection set and/or apheresis system 200. The AC pump 216 may engage with a portion of the anticoagulant tubing 110 to selectively control the flow of anticoagulant throughout the blood component collection set of the apheresis system 200. As shown in FIG. 2A, the draw pump 208, the return pump 212, and the AC pump 216 can be disposed at least partially on a top portion of the cover 210 of the apheresis system 200.

Figure 2C:
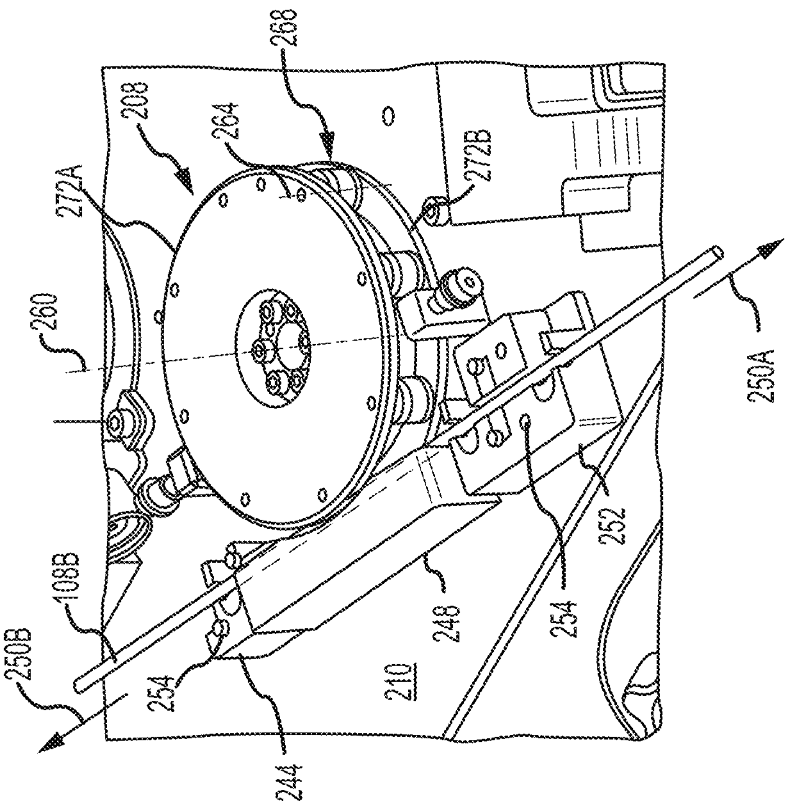
FIG. 2C is a second detail perspective view of a pump of an apheresis system in accordance with at least one example embodiment of the present disclosure.
Figure 2B:
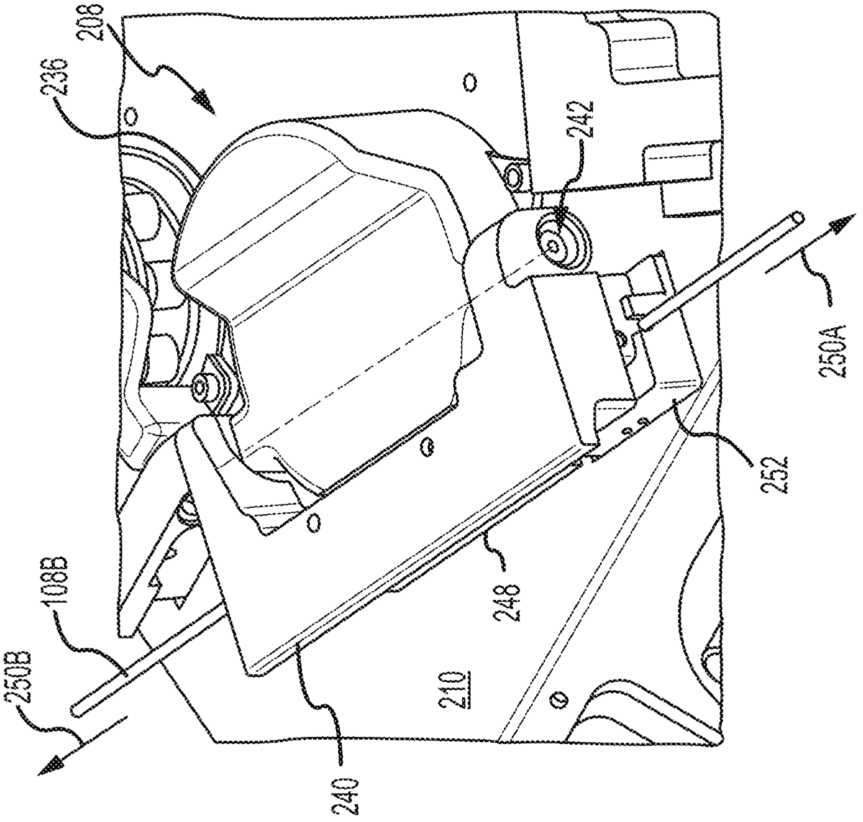
FIG. 2B is a first detail perspective view of a pump of an apheresis system in accordance with at least one example embodiment of the present disclosure.

FIGS. 2B and 2C show various perspective views of the draw pump 208, the return pump 212, or the AC pump 216 of the apheresis system 200 in accordance with at least one example embodiment of the present disclosure. Although the draw pump 208 is shown and described in conjunction with FIGS. 2B and 2C, it should be appreciated that the other pump assemblies of the apheresis system 200, i.e., the return pump 212 and the AC pump 216, may be different and operate differently in some particulars; however, in many instances the return pump 212 and/or the AC pump 216 may be or may include a substantially similar, if not identical, construction to the draw pump 208 described.

The draw pump 208 may include a pump cover 236 or housing configured to at least partially enclose the moving elements of the draw pump 208. In at least one example embodiment, the pump cover 236 may include a hinged tubing guard door sub-assembly or a tubing guard 240 that is configured to open and close about a tubing guard pivot axis 242. In at least one example embodiment, the tubing guard 240 may be attached to the pump cover 236 via one or more fasteners disposed along the tubing guard pivot axis 242. As shown in FIGS. 2B and 2C, blood provided by the donor 102 may be conveyed, or drawn, by the draw pump 208 into a centrifuge in a first draw or centrifuge direction 250A. Additionally or alternatively, blood or other fluid may be conveyed, or drawn, by the draw pump 208 toward the donor 102 in a donor direction 250B, opposite the centrifuge direction 250A.

In at least one example embodiment, the draw pump 208 and/or the return pump 212 and the AC pump 216 may be a tubing pump, peristaltic pump, diaphragm pump, and/or other pump configured to manipulate the flow of fluid (e.g., blood, blood components, anticoagulant, saline, etc.) in at least a portion of tubing. For example, the draw pump 208, the return pump 212, or the AC pump 216 may include a motor operatively interconnected with a rotating tubing contact assembly. In operation, the tubing (e.g., the inlet tubing 108B, the exit tubing 112, the anticoagulant tubing 110, etc.) may be inserted into a lead tubing guide 244, a tubing pressure block 248, and an end tubing guide 252 adjacent to a rotating tubing contact head. In at least one example embodiment, the tubing pressure block 248 may be moved in a direction away from the rotating tubing contact head of the draw pump 208, the return pump 212, or the AC pump 216 providing a loading clearance area, or vice versa. The rotating tubing contact head may comprise a number of rotary pressure rollers 268 configured to rotate about respective pressure roller rotation axes 264. Each of the rotary pressure rollers 268 may be disposed between a first rotary pump plate 272A and a second rotary pump plate 272B, where the first rotary pump plate 272A and the second rotary pump plate 272B are configured to rotate about a pump rotation axis 260. In at least one example embodiment, the rotary pressure rollers 268 may be disposed at a periphery of the first rotary pump plate 272A and the second rotary pump plate 272B.

The one or more of the draw pump 208, the return pump 212, or the AC pump 216 may include, or operate similarly to, the Pulsafeeder® model UX-74130 peristaltic pump, Pulsafeeder® MEC-O-MATIC series of pumps, all manufactured by Pulsafeeder Inc., of Punta Gorda, Fla., without limitation. Other examples of the draw pump 208, the return pump 212, or the AC pump 216 may include, but are in no way limited to, the INTEGRA DOSE IT laboratory peristaltic pump manufactured by INTEGRA Biosciences AG, of Switzerland, and WELCO WP1200, WP1100, WP1000, WPX1, and/or WPM series of peristaltic pumps all manufactured by WELCO Co., Ltd., of Tokyo, Japan.

Once the tubing is loaded into the lead tubing guide 244, the tubing pressure block 248, and/or the end tubing guide 252, at least some of the rotary pressure rollers 268 may be caused to engage with, contact, or otherwise compress the tubing disposed between the rotating tubing contact head and the tubing pressure block 248. As the first rotary pump plate 272A and the second rotary pump plate 272B rotate about the pump rotation axis 260 the rotary pressure rollers 268 may compress a portion of the tubing between the draw pump 208, the return pump 212, or the AC pump 216 and the tubing pressure block 248 positively displacing fluid inside the portion of the tubing in a particular direction such as the centrifuge direction 250A or the donor direction 250B as the rotary pressure rollers 268 move. For instance, as the first rotary pump plate 272A and the second rotary pump plate 272B rotate in a counterclockwise direction about the pump rotation axis 260, the rotation of the rotary pressure rollers 268 compressing the tubing between the rotary pressure rollers 268 and the tubing pressure block 248 may displace, or pump, fluid in the centrifuge direction 250A. As another example, as the first rotary pump plate 272A and the second rotary pump plate 272B rotate in a clockwise direction about the pump rotation axis 260, the rotation of the rotary pressure rollers 268 compressing the tubing between the rotary pressure rollers 268 and the tubing pressure block 248 may displace, or pump, fluid in the donor direction 250B. When not actively pumping, the pump 208 can be maintained in a state where at least one of the rotary pressure rollers 268 continues to occlude the inlet tubing 108B (normally closed or NC) or in a state where none of the rotary pressure rollers 268 occludes the inlet tubing 108B (normally open or NO). Thus, the draw pump 208, based on the state when motionless, can also act as a "valve" to prevent or allow fluid movement. This ability may also be available with the return pump 212 and/or the AC pump 216.

The tubing guard 240 and the pump cover 236 may serve to protect an operator (e.g., phlebotomist, apheresis technician, etc.) and/or the donor 102 from incidental contact with one or more moving parts of the draw pump 208, the return pump 212, or the AC pump 216. In at least one example embodiment, the tubing guard 240 may be held in a closed position via one or more guard closure features 254 disposed in or in operative relation to the tubing guard 240, the lead tubing guide 244, the tubing pressure block 248, and/or the end tubing guide 252. In some cases, these guard closure features 254 may be magnets contained in the tubing guard 240, the lead tubing guide 244, tubing pressure block 248, and/or the end tubing guide 252. In at least one example embodiment, the draw pump 208, the return pump 212, or the AC pump 216 may be stopped or prevented from moving/operating when the tubing guard 240 is open. In at least one example embodiment, a door closure sensor may be included in the guard closure features 254, the lead tubing guide 244, the end tubing guide 252, and/or the tubing pressure block 248.

One or more fluid control valves may be used to control the routing or flow direction of fluid conveyed throughout the tubing of the apheresis system 200. In at least one example embodiment, the apheresis system 200 may include a plasma and saline valve control system such as the fluid valve control system 228 disposed adjacent to the saline bag 118 and/or the plasma collection bottle 122. The fluid valve control system 228 is shown in the detailed perspective view of FIG. 2D.

Figure 2D:
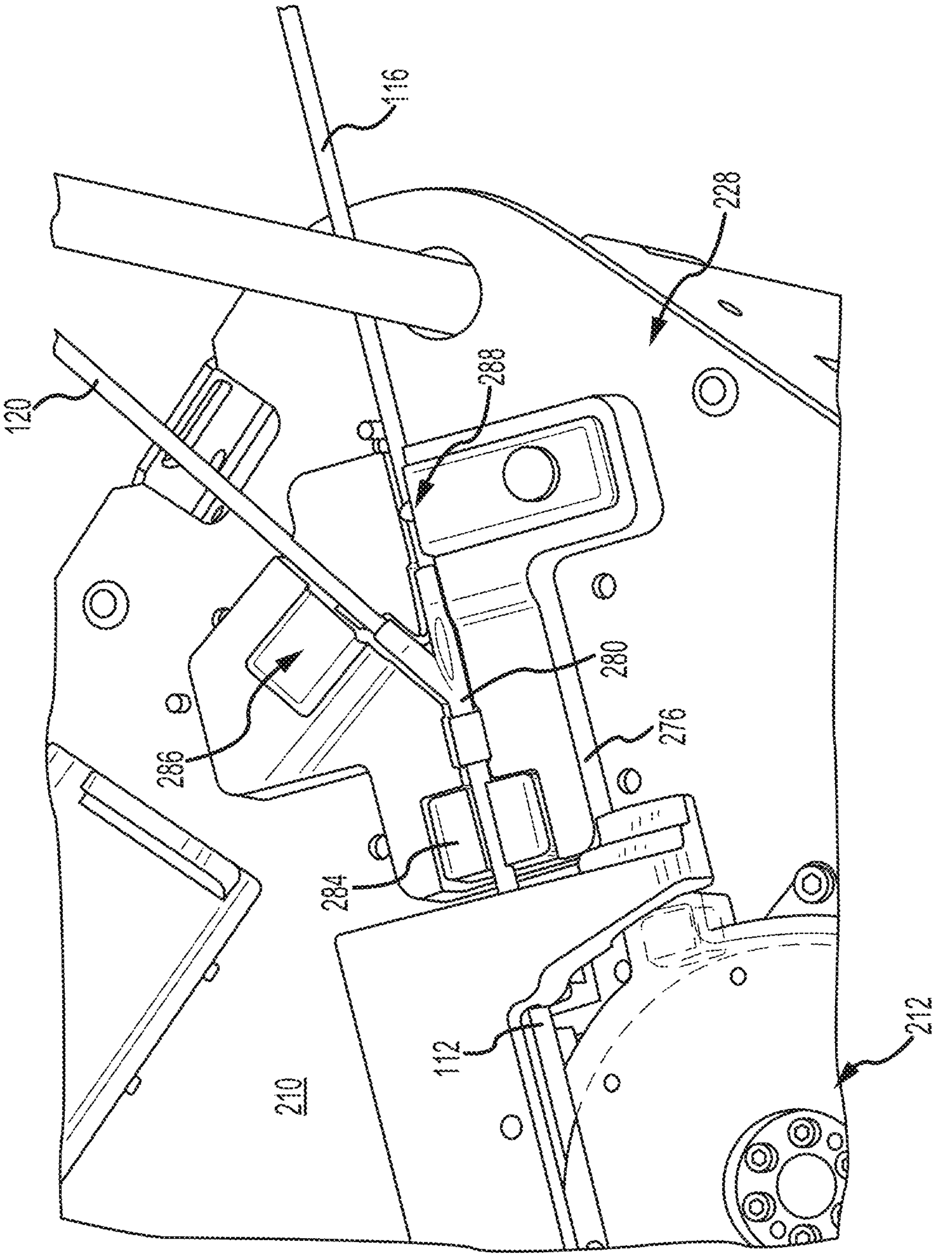
FIG. 2D is a detail perspective view of a fluid valve control system in accordance with at least one example embodiment of the present disclosure.

As shown in FIG. 2D, the exit tubing 112 may pass through the return pump 212 and interconnect with a saline and plasma tubing y-connector 280. The saline and plasma tubing y-connector 280 may allow connection of the exit tubing 112 to a saline tubing 116 line and a plasma tubing 120 line. The fluid valve control system 228 may include an air detection sensor 284 disposed at a first end of the saline and plasma valve housing 276 and surrounding a portion of the exit tubing 112. The air detection sensor 284 can be any light, ultrasonic, or other type of sensor that can detect the presence of fluid or air in the exit tubing 112 and provide that signal to a controller of the apheresis system 200. Types of air detection sensors 284 may include, for example, the SONOCHECK ABD05, made by SONOTEC US Inc., or another similar sensor.

The saline and plasma valve housing 276 may include a number of receiving features (e.g., grooves, channels, receptacles, etc.) that receive a portion of the exit tubing 112, the saline tubing 116, the plasma tubing 120, and/or the saline and plasma tubing y-connector 280. Upon detecting air in the exit tubing 112, the fluid valve control system 228 may selectively actuate one or more of the fluid control valves such as a plasma flow control valve 286 and a saline flow control valve 288. In at least one example embodiment, the detection of air via the air detection sensor 284 may be used to signal an operation step and/or trigger a step in a control method as described herein.

The plasma flow control valve 286 and/or the saline flow control valve 288 may be a solenoid valve, linear actuator, pinch valve, clamp valve, tubing valve, and/or other actuatable valve configured to selectively alter (e.g., occlude) a fluid passage associated with a particular portion of the exit tubing 112, the saline tubing 116, or the plasma tubing 120. As shown in FIG. 2D, the plasma flow control valve 286 may be configured to pinch a portion of the plasma tubing 120 at least partially contained in a receiving feature of the saline and plasma valve housing 276. The saline flow control valve 288 may be configured to pinch a portion of the saline tubing 116 at least partially contained in a receiving feature of the saline and plasma valve housing 276. In any event, the plasma flow control valve 286 and the saline flow control valve 288 may include an actuatable extendable finger that moves from a retracted, or partially retracted, position to an extended, or partially extended, position to pinch the portion of tubing contained in the saline and plasma valve housing 276. While the plasma flow control valve 286 and the saline flow control valve 288 may completely pinch the tubing (e.g., completely restricting fluid flow therethrough), it should be appreciated that the plasma flow control valve 286 and the saline flow control valve 288 may be partially actuated to a position that partially restricts fluid flow through a portion of the tubing.

As should be understood, the draw pump 208, the return pump 212, and the AC pump 216 include additional components such as described in entitled "FLUID CONTROL AND BYPASS FEATURES FOR AN APHERESIS SYSTEM", filed on Mar. 2, 2023 and assigned application Ser. No. 18/116,527, the entire contents of which are herein incorporated by reference.

First Example of Soft Cassettes with Integrated Features

Figure 3A:
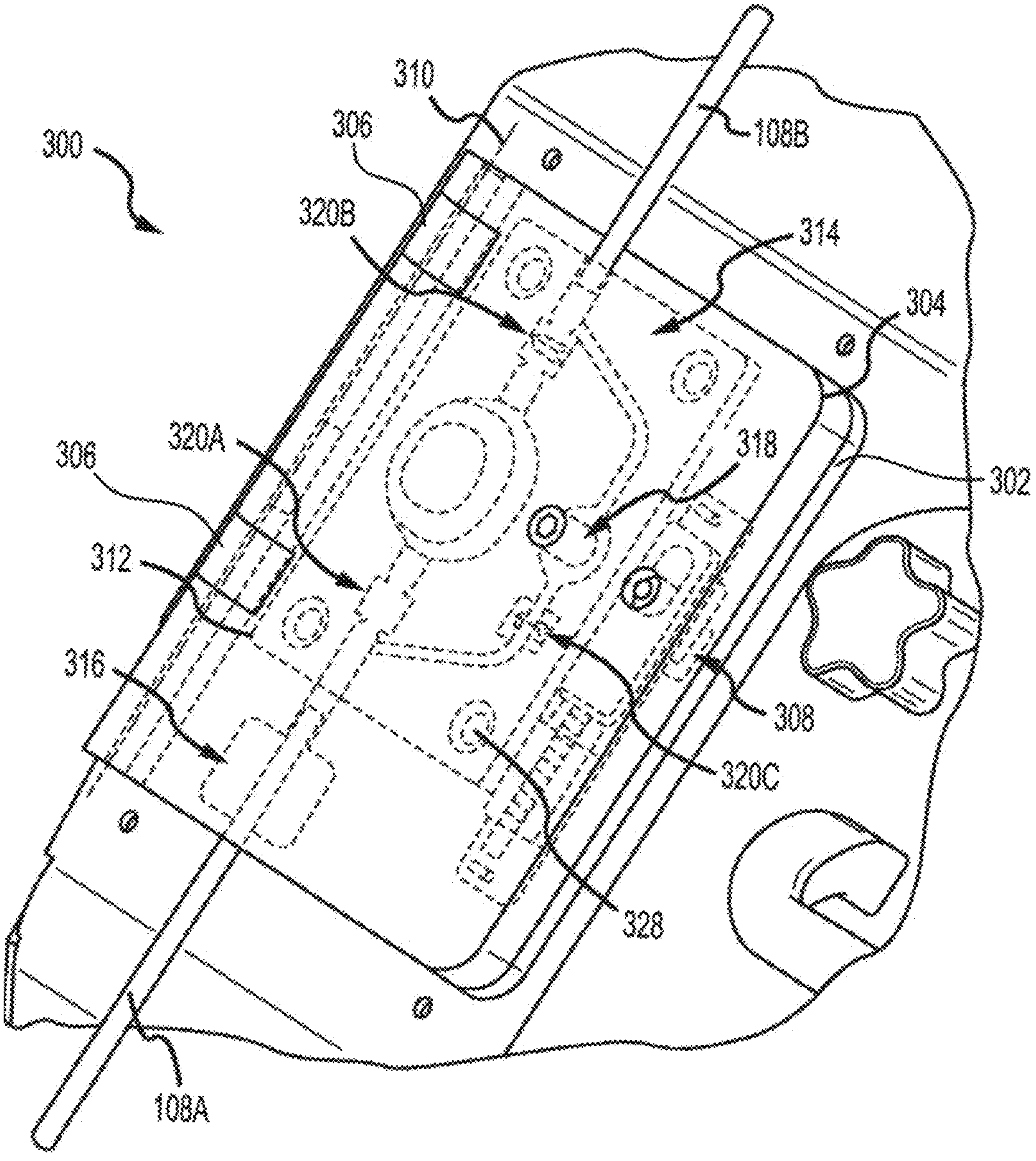
FIG. 3A is a detail perspective view of a disposable soft cassette assembly in accordance with at least one embodiment of the present disclosure.

FIG. 3A is a partial perspective view of a soft cassette assembly according to at least one example embodiment.

In at least one example embodiment, as shown in FIG. 3A, a detailed perspective view of a disposable soft cassette assembly 300 is shown in accordance with embodiments of the present disclosure. The soft cassette assembly 300 may include a baseplate 302 and a cassette access door 304 that is attached to the baseplate 302 via at least one hinge 306 and/or cassette access door latch 308. In at least one example embodiment, the cassette access door 304 may be unlocked via actuating a cassette access door latch 308 and pivoting the cassette access door 304 about a cassette access door hinge axis 310.

In at least one example embodiment, the soft cassette assembly 300 may be configured with one or more soft cassette receiving features 312 for at least partially containing and/or locating a soft cassette 314 therein. The soft cassette 314 may be a part of the blood component collection set described herein. For instance, the soft cassette 314 may be disposed between the cassette inlet tubing 108A and the loop inlet tubing 108B of the extracorporeal tubing circuit (shown in FIG. 5A). In at least one example embodiment, the soft cassette 314 may provide one or more features for controlling the flow of blood and/or blood components from a donor 102 (shown in FIG. 1A) to the apheresis system 200 (shown in FIG. 1A), and/or vice versa.

In at least one example embodiment, the soft cassette assembly 300 includes an air detection sensor 316, a fluid sensor 318, and one or more fluid control valves 320A, 320B, 320C configured to control a routing or flow direction of fluid through the soft cassette 314. In at least one example embodiment, these components may be independently embedded in the cassette access door 304, the baseplate 302, and/or a portion of the housing 204 of the apheresis system 200 (shown in FIG. 1A). Similar to the guard closure feature 254 described in conjunction with FIGS. 2B-2C, the soft cassette assembly 300 may include one or more door closure features 328. The door closure features 328 may include, but are not limited to, magnetic catches, protrusions, tabs and slots, and/or other connections. In at least one example embodiment, the door closure features 328 may include pressure contact surfaces configured to hold or at least partially position a soft cassette 314 inside the soft cassette assembly 300.

In at least one example embodiment, the valves 320A, 320B, 320C may include, but are not limited to, solenoid valves, linear actuators, pinch valves, clamp valves, tubing valves, and/or other actuatable valve configured to selectively alter, for example, occlude, a fluid passage (e.g., cross-sectional area, etc.) associated with a particular portion of the soft cassette 314.

In at least one example embodiment, the soft cassette assembly 300 may include a first fluid control valve 320A configured to pinch a portion of the soft cassette 314 adjacent to a cassette inlet tubing 108A. The second fluid control valve 320B may be configured to pinch a portion of the soft cassette 314 adjacent to the loop inlet tubing 108B. A draw fluid control valve 320C may be configured to pinch a portion of the soft cassette 314 along a branch tubing extending from a point adjacent to the cassette inlet tubing 108A to a point adjacent to the loop inlet tubing 108B. In at least one example embodiment, each of the valves 320A, 320B, 320C may include an actuatable extendable finger that moves from a retracted, or partially retracted, position to an extended, or partially extended, position to pinch the portion of the soft cassette 314 contained in the soft cassette assembly 300. While the valves 320A, 320B, 320C may completely pinch flow paths in the soft cassette 314 (e.g., completely restricting fluid flow therethrough), it should be appreciated that the valves 320A, 320B, 320C may be partially actuated to a position that partially restricts fluid flow through a portion of the soft cassette 314.

In at least one example embodiment, the sensors 316, 318 may be one or more of an ultrasonic detector, pressure sensor, magnetic position sensor, and/or the like. In some cases, the fluid sensor 318 may be configured to determine whether fluid is present in the soft cassette 314 based on a position of a magnet relative to a portion of the soft cassette 314. For instance, when the portion of the soft cassette 314 is filled with a fluid, the magnet may be disposed at a first position from a surface of the soft cassette 314. On the other hand, when the portion of the soft cassette 314 is filled with air, the force from the magnet may compress the portion of the soft cassette 314 to a second position closer to the surface of the soft cassette 314 than the first position. In at least one example embodiment, the detection of air or fluid via the air detection sensor 316 and the fluid sensor 318, respectively, may be used to signal an operation step and/or trigger a step in a control method as described herein.

Figure 3B:
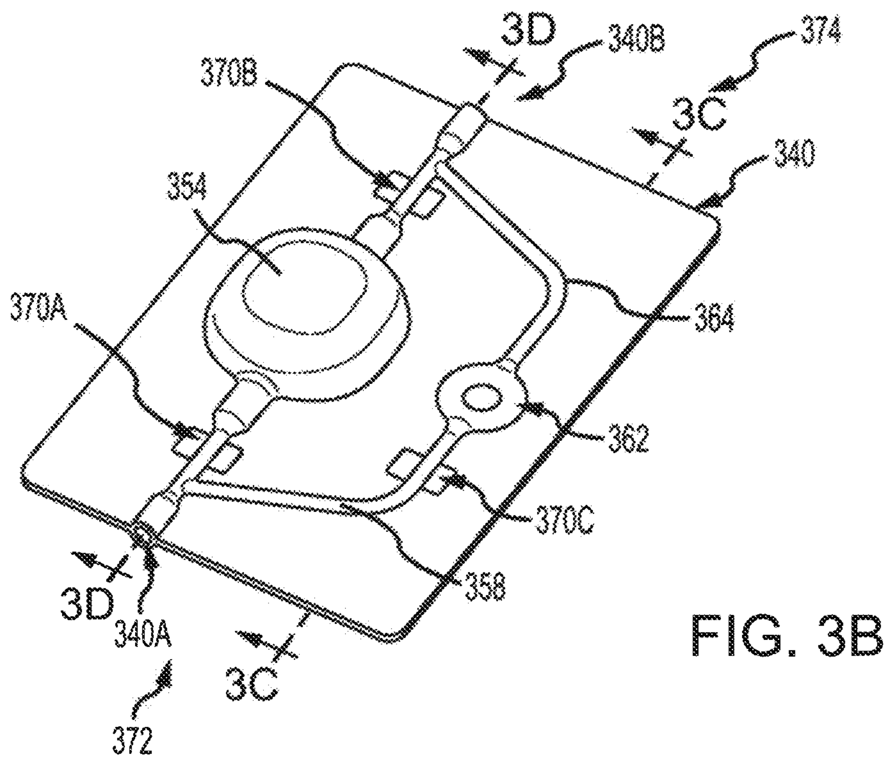
FIG. 3B is a perspective view of a disposable soft cassette in accordance with at least one embodiment of the present disclosure.
Figure 3C:
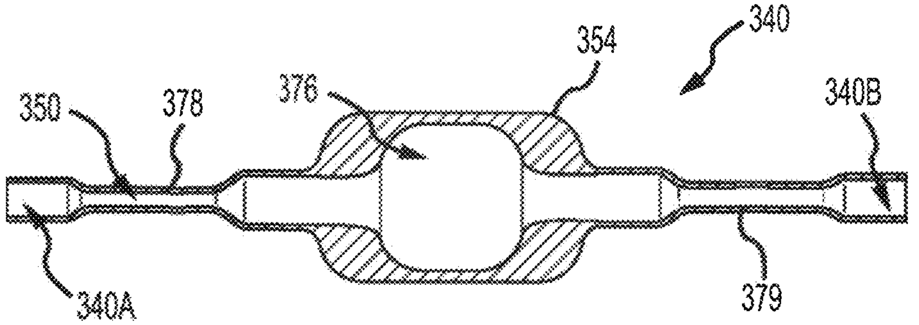
FIG. 3C is an elevation section view taken through line 3C of FIG. 3B in accordance with at least one example embodiment of the present disclosure.
Figure 3D:
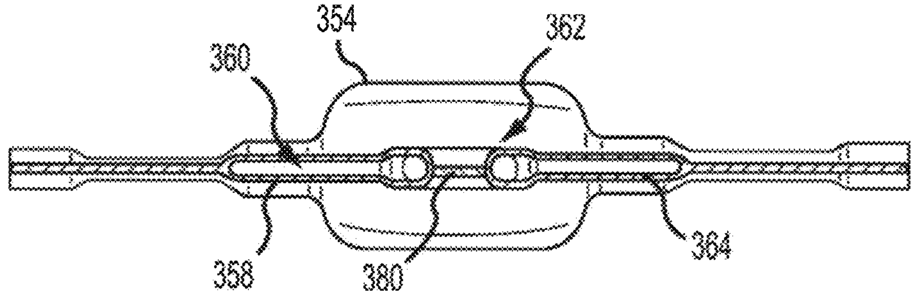
FIG. 3D is an elevation section view taken through line 3D of FIG. 3B in accordance with at least one example embodiment of the present disclosure.

FIG. 3B is a perspective view of a soft cassette of the soft cassette assembly of FIG. 3A according to at least one example embodiment. FIG. 3C is a sectional view of the soft cassette of FIG. 3B taken along line 3C-3C of FIG. 3A according to at least one example embodiment. FIG. 3D is a sectional view of the soft cassette of FIG. 3A taken along line 3D-3D of FIG. 3A according to at least one example embodiment.

In at least one example embodiment, the soft cassette 314 may be part of the blood component collection set. For instance, the soft cassette 314 may be a disposable component used in the blood separation methods described herein. In at least one example embodiment, the soft cassette 314 may be made from a substantially compliant and/or flexible material. The compliant material may be chemically inert and/or be capable of withstanding sterilization and cleaning operations, temperatures, and/or treatments. The soft cassette 314 may be formed from a thermoplastic material. In at least one example embodiment, the soft cassette 314 includes polyvinyl chloride (PVC), plasticized-PVC, polyethylene, ethylene with vinyl acetate (EVA), rubber, silicone, thermoplastic elastomer, copolymers thereof, and/or combinations thereof. In at least one example embodiment, the soft cassette 314 is molded, rotomolded, cast, injection molded, or otherwise formed from one or more of the materials described above.

In at least one example embodiment, the soft cassette 314 may include and/or define a first cassette port 340A (shown in FIGS. 3B-3C), a second cassette port 340B (shown in FIGS. 3B-3C), and a direct flow lumen 350 (shown in FIG. 3C) running between the first and second cassette ports 340A, 340B. In at least one example embodiment, the first and/or second cassette ports 340A, 340B may be configured to receive and/or fluidly couple with one or more tubes of the blood component collection set. In at least one example embodiment, the first cassette port 340A may couple with the cassette inlet tubing 108A and the second cassette port 340B may couple with the loop inlet tubing 108B. These couplings may be air tight and/or fluid tight. In at least one example embodiment, the first and/or second cassette ports 340A, 340B may be or include an aperture disposed within the soft cassette 314 that is configured to elastically stretch around an end of the tubing (e.g., cassette inlet tubing 108A, loop inlet tubing 108B, etc.).

In at least one example embodiment, blood supplied by the donor 102 (shown in FIG. 1A) may be directed along one or more fluid paths disposed within the soft cassette 314. In one embodiment, the blood may be directed along the direct flow lumen 350 from the first cassette port 340A to the second cassette port 340B. In some embodiments, this flow path may direct the blood through a first or drip chamber 354 of the soft cassette 314. In some embodiments, blood and/or other fluids returned to the donor 102 may be directed along the direct flow lumen 350 from the second cassette port 340B to the first cassette port 340A.

In at least one example embodiment, the soft cassette 314 includes a fluid flow bypass path provided by a first bypass branch 358 (shown in FIGS. 3B, 3D) having a bypass flow lumen 360 (shown in FIG. 3D) that is fluidly connected to a portion of the direct flow lumen 350 adjacent to the first cassette port 340A or as part of the first cassette port 340A. In some embodiments, the bypass flow lumen 360 may run from a point of the direct flow lumen 350 adjacent to the first cassette port 340A, along the first bypass branch 358, through a second chamber or fluid pressure annulus 362 (shown in FIGS. 3B, 3D) to a second bypass branch 364 (shown in FIGS. 3B, 3D), and then reconnect to the direct flow lumen 350 at a point adjacent to the second cassette port 340B or as part of the second cassette port 340B. As the name suggests, the bypass flow lumen 364 provides a flow path within the soft cassette 314 that bypasses the drip chamber 354.

In at least one example embodiment, controlling the flow path, or directing fluid, within the soft cassette 314 may include actuating the fluid control valves 320A, 320B, 320C (shown in FIG. 3A) of the soft cassette assembly 300 to interact with various compliant regions 370A, 370B, 370C (shown in FIG. 3B) blocking and/or opening portions of the direct flow lumen 350 and/or bypass flow lumen 360. The first compliant region 370A provides a pinch valve area at a point along the direct flow lumen 350 between the first cassette port 340A and the drip chamber 354 near a first cassette end 372 of the soft cassette 314. When the first fluid control valve 320A is actuated, the valve 320A may pinch the direct flow lumen 350 closed at this first compliant region 370A, restricting or completely preventing the flow of fluid at this point in the soft cassette 314. The second compliant region 370B provides a pinch valve area at a point along the direct flow lumen 370 between the second cassette port 340B and the drip chamber 354 near a second cassette end 374 (e.g., opposite the first cassette end 372). When the second fluid control valve 320B is actuated, the valve 320B may pinch the direct flow lumen 370 closed at this second compliant region 370B, restricting or completely preventing the flow of fluid at this point in the soft cassette 314. As can be appreciated, the third compliant region 370C disposed along the first bypass branch 358 adjacent to the fluid pressure annulus 362 may provide a pinch valve area at a point along the bypass flow lumen 360. When the draw fluid control valve 320C is actuated, the valve 320C may pinch the bypass flow lumen 360 closed at this third compliant region 370C, restricting or completely preventing the flow of fluid through the bypass flow lumen 360.

In at least one example embodiment, as shown in the elevation section view of FIG. 3C, taken through a plane running through the direct flow lumen 350 and drip chamber 354, the direct flow lumen 350 runs from the first cassette port 340A through an inner chamber volume 376 of the drip chamber 354 to the second cassette port 340B. The direct flow lumen 350 may be formed as a fluid passage running inside a first tubing section 378, the inner chamber volume 376, and a second tubing section 379 of the soft cassette 314.

In at least one example embodiment, the bypass path of the soft cassette 314 may include the fluid pressure annulus 362 through which fluid can flow from the first bypass branch 358 to the second bypass branch 364, and/or vice versa. In at least one example embodiment, a pressure diaphragm 380 (shown in FIG. 3D) may be formed in the material of the soft cassette 314 an area within, or adjacent to, the fluid pressure annulus 362. The fluid pressure annulus 362 and pressure diaphragm 380 are illustrated in the elevation section view of FIG. 3D taken through a plane running through the fluid pressure annulus 362 and a portion of the first and second bypass branches 358, 364.

In at least one example embodiment, the pressure diaphragm 380 may provide a contact, or measurement, surface for the fluid sensor 318 to detect whether the fluid pressure annulus 362 and/or the bypass flow lumen 360 includes an amount of fluid, air, and/or combinations thereof. As provided above, as fluid fills a portion of the fluid pressure annulus 362, the fluid may provide greater resistance to movement than when the fluid pressure annulus 362 is filled with air. This difference in resistance may be measured via the fluid sensor 316 to determine, among other things, an amount and/or type of fluid (e.g., air, blood, etc.) in the bypass flow lumen 360 and/or the fluid pressure annulus 362.

Example Centrifuge Assembly

Figure 4A:
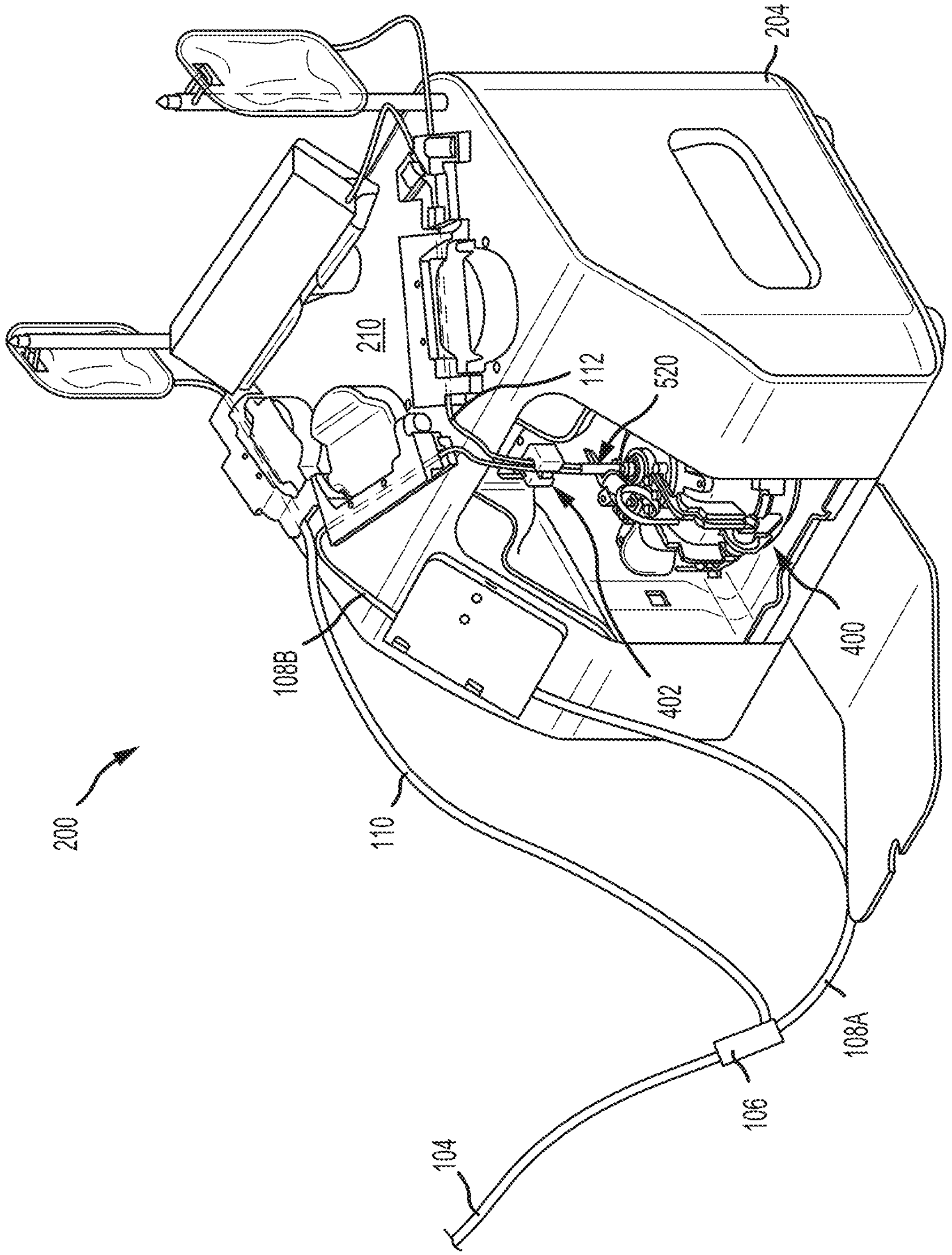
FIG. 4A shows a perspective view of a centrifuge assembly in an apheresis system in accordance with at least one example embodiment of the present disclosure.

FIG. 4A is a perspective view of an example centrifuge assembly 400 for use in the apheresis system 200 in accordance with at least one example embodiment of the present disclosure. The centrifuge assembly 400 may be disposed in an interior space of the apheresis system 200. The interior space may be at least partially enclosed with one or more elements of the housing 204 and/or centrifuge chamber. Access to the interior space and the centrifuge assembly 400 may be provided via the access panel 224 disposed at the front 202 of the apheresis system 200. For example, in FIG. 4A, the access panel 224 is shown in an open position, opened along the hinged axis 226. The hinged axis 226 may correspond to a door hinge, continuous hinge, cleanroom hinge, and/or other panel hinges.

The centrifuge assembly 400 may be operatively mounted inside the apheresis system 200 such that the assembly 400 is capable of rotating relative to the housing 204 and/or other elements of the apheresis system 200. The centrifuge assembly 400 may be loaded with one or more portions of the blood component collection set (for example, the blood component collection set 500 illustrated in FIGS. 5A-5H) by routing tubing (e.g., the inlet tubing 108B and the exit tubing 112, etc.) into the interior space of the apheresis system 200 (e.g., via the opening 220 shown in FIG. 2A), connecting a portion of the blood component collection loop 520 to the fixed loop connection 402 and inserting the blood component collection bladder 536 into a filler 460. The fixed loop connection 402 maintains the inlet tubing 108B and the exit tubing 112 in a fixed position and may prevent twisting of the tubing 108B, 112 outside of the apheresis system 200. In at least one example embodiment, the blood component collection loop 520 may be interconnected to the fixed loop connection 402 via one or more keyed features or positive location features.

Figure 4B:
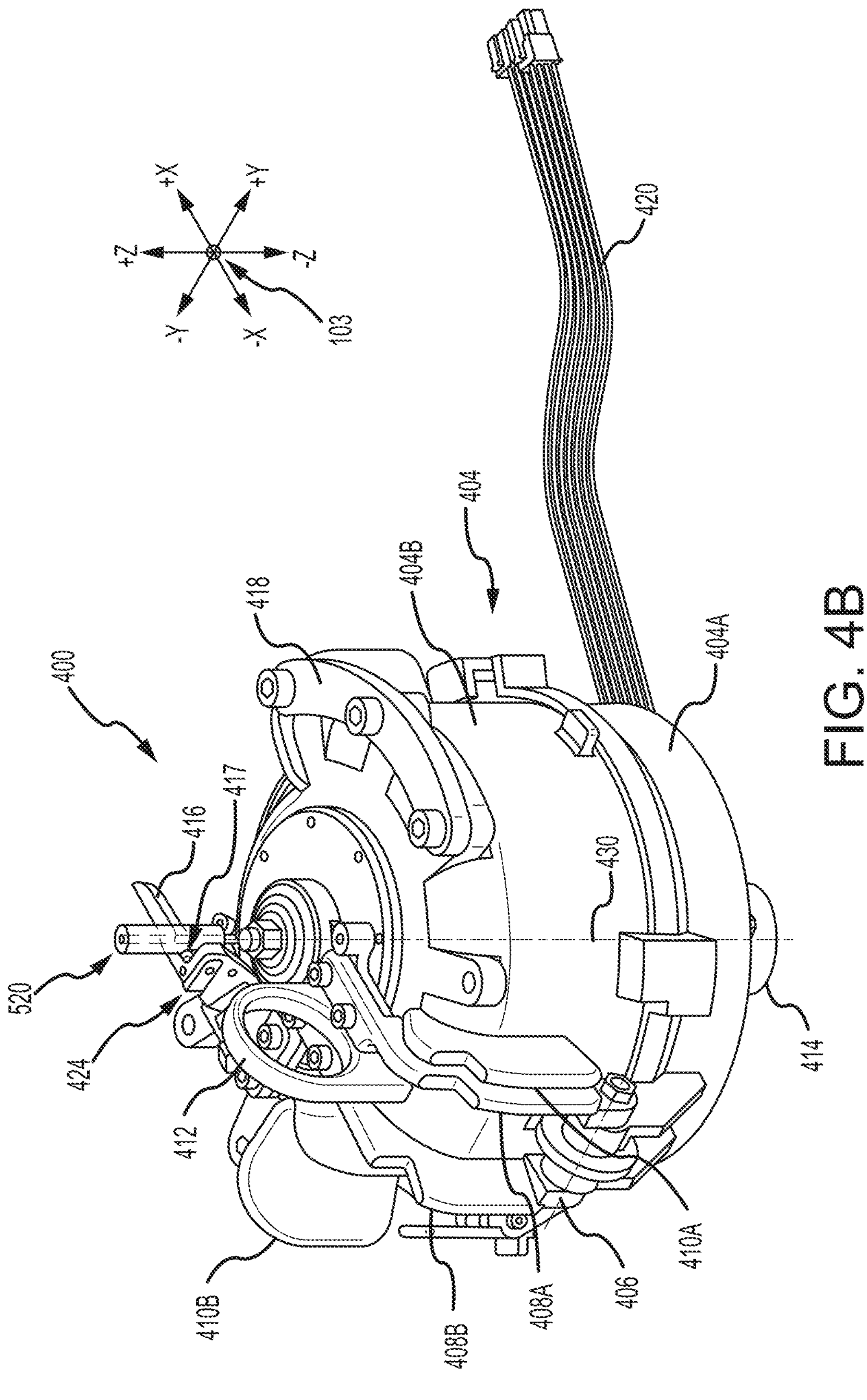
FIG. 4B shows a front perspective view of the centrifuge assembly shown in FIG. 4A.
Figure 4C:
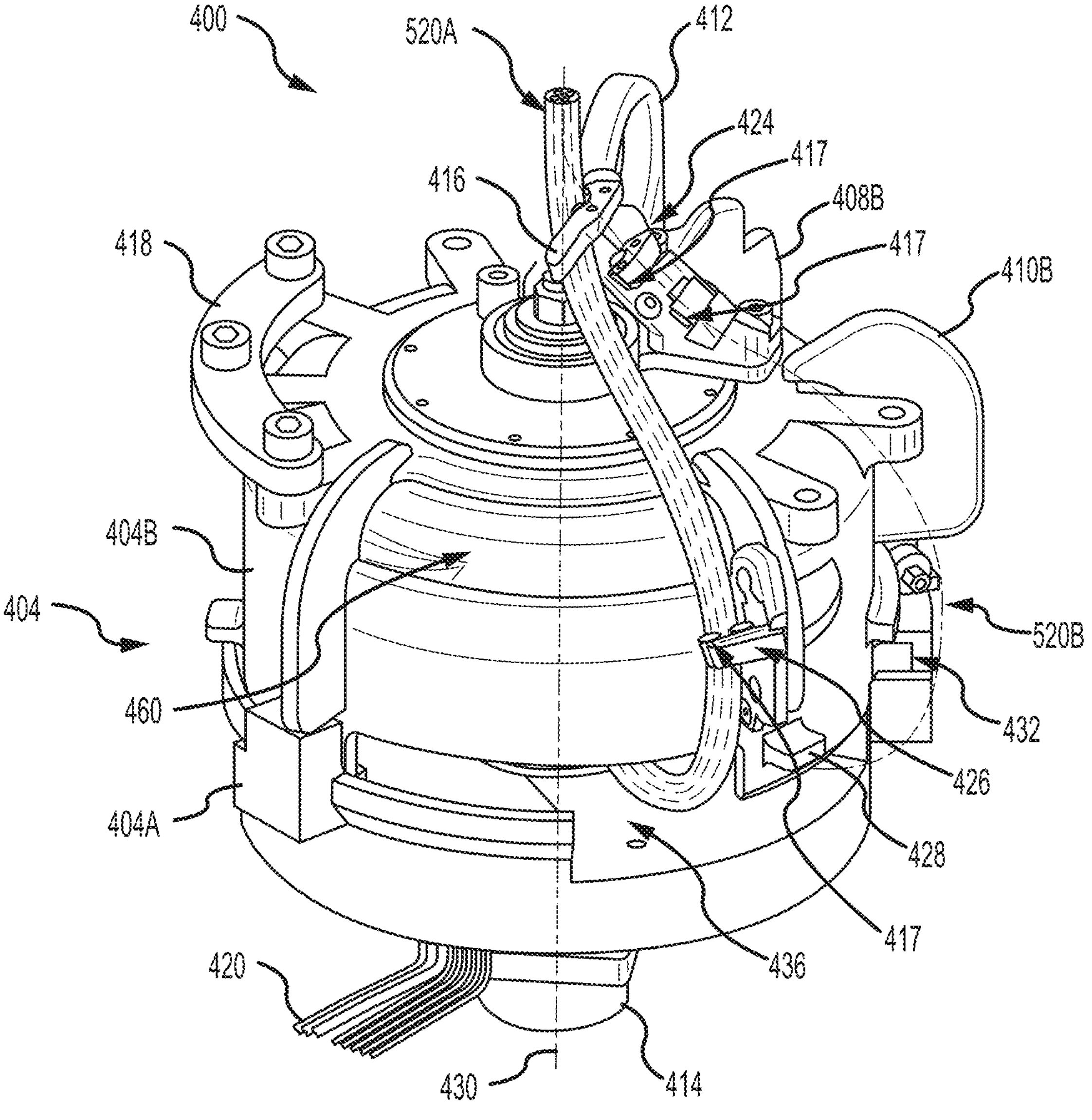
FIG. 4C shows a rear perspective view of the centrifuge assembly shown in FIG. 4A.

For illustrative purposes, FIGS. 4B-4C show the centrifuge assembly 400 separated from the apheresis system 200. The centrifuge assembly 400 may include a centrifuge split-housing 404 comprising a lower housing 404A pivotally connected to an upper housing 404B. The upper housing 404B may open to provide access for loading a blood component collection bladder (for example, the blood component collection set 500 illustrated in FIGS. 5A-5H) into the centrifuge assembly 400. In at least one example embodiment, the upper housing 404B may pivot about the split-housing pivot axis 406 (e.g., configured as a hinge, pin, fastener, shoulder bolt, etc.).

The different halves (e.g., the lower housing 404A and upper housing 404B) of the centrifuge split-housing 404 may be configured to lock and/or unlock together. Unlocking the upper housing 404B from the lower housing 404A may provide access to an interior of the centrifuge assembly 400. This selective locking may be achieved by rotating the upper housing 404B relative to the lower housing 404A about the centrifuge rotation axis 430. Although the centrifuge split-housing 404 is shown in FIGS. 4B-4C in an unlocked state, it should be appreciated that the upper housing 404B can be rotated (e.g., in a counterclockwise direction) about the centrifuge rotation axis 430 to engage one or more locking tabs 428 or elements of the upper housing 404B with locking slots 432 disposed in the lower housing 404A (as shown, for example, in FIG. 4C). When in the unlocked position, the upper housing 404B may be opened, or pivoted, about the split-housing pivot axis 406 to load the centrifuge assembly 400 with a blood component collection loop 520 and/or a blood component collection bladder 536. When in the locked position, the upper housing 404B is rotationally locked relative to the lower housing 404A, and the two halves of the centrifuge split-housing 404 may spin together, locked in unison, during a centrifuge or blood separation operation.

The centrifuge assembly 400 may include at least one clockwise rotation stop 408A, counterclockwise rotation stop 408B, upper housing clockwise rotation flag 410A, and/or upper housing counterclockwise rotation flag 410B. In at least one example embodiment, the rotation stops 408A, 408B may be rotationally fixed relative to the centrifuge rotation axis 430 of the lower housing 404A. The rotation flags 410A, 410B may be attached, or formed in, the upper housing 404B and configured to contact respective rotation stops 408A, 408B to prevent over-rotation of the upper housing 404B relative to the lower housing 404A when locking and/or unlocking the two halves of the centrifuge split-housing 404 together. For instance, upon rotating the upper housing 404B in a clockwise, or unlocking, direction about the centrifuge rotation axis 430, a portion of the upper housing clockwise rotation flag 410A may contact the clockwise rotation stop 408A preventing further rotation in the clockwise direction. Additionally or alternatively, upon rotating the upper housing 404B in a counterclockwise, or locking, direction about the centrifuge rotation axis 430, a portion of the upper housing counterclockwise rotation flag 410B may contact the counterclockwise rotation stop 408B preventing further rotation in the counterclockwise direction. In at least one example embodiment, the centrifuge split-housing 404 may include one or more locking elements configured to maintain the halves of the centrifuge split-housing 404 in a locked state, while the locking elements are engaged.

In at least one example embodiment, the centrifuge split-housing 404 may include a pull ring 412 attached to a portion of the upper housing 404B to pivot the upper housing 404B relative to the lower housing 404A about the split-housing pivot axis 406. The pull ring 412 may provide an aperture, through which a user may insert a finger and apply a pull force to a rotationally unlocked upper housing 404B.

The centrifuge assembly 400 may include a rotor and motor assembly 414 that is controlled and/or powered via electrically interconnected electrical cabling 420. The electrical cabling 420 may include a connector that attaches to a controller, processor, and/or power supply. This electrical cabling 420 may convey power and/or data signals between the rotor and motor assembly 414 and one or more controllers/processors of the apheresis system 200. The rotor and motor assembly 414 may be configured as an electric motor and/or portions of an electric motor that rotate the complete centrifuge assembly 400 relative to the apheresis system 200 (e.g., relative to a portion of the housing 204 and/or base of the apheresis system 200). In other words, the rotor and motor assembly 414 may include one or more components that cause the centrifuge assembly 400 (e.g., both halves of the centrifuge split-housing 404 together) to rotate inside the apheresis system 200.

As described herein, the centrifuge assembly 400 may include one or more features to guide, contain, and/or position elements of the blood component collection set relative to the centrifuge split-housing 404. For example, in FIG. 4B, the blood component collection loop 520 is shown captured in an operational position in a loop rotational position guide 424 comprising a loop capture arm 416. The loop rotational position guide 424 may include a number of bearings 417, and/or bearing surfaces, arranged to at least partially support the blood component collection loop 520 in an operational position. In the operational position, the blood component collection loop 520 may twist along its length within the support provided by the bearings 417 of the loop rotational position guide 424. For example, the blood component collection loop 520 may be fixedly attached at one end to the fixed loop connection 402 of the apheresis system 200 while the other end of the blood component collection loop 520 may be attached to a filler 460 (e.g., the inner rotating component of the centrifuge assembly 400. As the centrifuge assembly 400 spins during a centrifuge operation, the twisting of the blood component collection loop 520 between the fixed loop connection 402 and the connection at the filler 460 may cause the filler 460 to rotate relative to the centrifuge split-housing 404 of the centrifuge assembly 400. In at least one example embodiment, the low inertia of the filler 460 coupled with the twisting of the blood component collection loop 520 as the centrifuge assembly 400 rotates in the apheresis system 200, may cause the filler 460 to rotate at two times the angular velocity of the centrifuge split-housing 404 in the same direction of spin. In this example, when the centrifuge split-housing 404 spins in a counterclockwise direction about the centrifuge rotation axis 430 at a first angular velocity, 1ω, the filler 460 may spin inside the centrifuge split-housing 404 in the counterclockwise direction at a second angular velocity, 2ω (e.g., substantially two times the first angular velocity, etc.).

The centrifuge assembly 400 may include one or more balancing features, elements, and/or structures disposed about the centrifuge rotation axis 430 of the centrifuge assembly 400. These balancing features may provide an axially balanced centrifuge assembly 400, such that when spun on the centrifuge rotation axis 430, the centrifuge assembly 400 may impart substantially no vibration to the apheresis system 200. In at least one example embodiment, a centrifuge balance weight 418 may be attached to a portion of the centrifuge split-housing 404 (e.g., the lower housing 404A and/or the upper housing 404B, etc.). This centrifuge balance weight 418 may be custom tuned for the centrifuge assembly 400 and as such may be selectively attached and removed from the centrifuge assembly 400. The tuning of the centrifuge balance weight 418 may be calculated and/or empirically derived to produce a completely balanced centrifuge assembly 400, especially when loaded with one or more elements of the blood component collection set.

FIG. 4C shows a rear perspective view of the centrifuge assembly 400 in accordance with at least one example embodiment of the present disclosure. A portion of the filler 460 is visible through an aperture in the upper housing 404B. The blood component collection loop 520 is shown in an initial loop loading position 520A, where a first end is interconnected with the filler 460 and a second end is fixedly attached to the fixed loop connection 402 (not shown). The blood component collection loop 520 is shown passing through a loop access clearance 436 in the centrifuge split-housing 404. When the blood component collection loop 520 is loaded in the loop loading position 520A a portion of the blood component collection loop 520 may be partially contained, held, and/or supported by a loop containment bracket 426. The loop containment bracket 426 may include one or more bearings 417 (e.g., roller bearings, ball bearings, needle bearings, etc., and/or assemblies thereof, etc.), or bearing surfaces, arranged to at least partially support the blood component collection loop 520 as it twists relative to the centrifuge assembly 400. In at least one example embodiment, the blood component collection loop 520 may rotate about an axis running along the length of the flexible loop 524 (e.g., in an installed or mounted condition and/or state, etc.) allowing for relative rotational motion of the flexible loop 524 to the loop rotational position guide 424. For instance, the loop does not "twist up" but actually rotates, or rolls, relative to the loop rotational position guide 424 (e.g., support structure) in between one or more bearings 417. This rotation or torsion, without binding or twisting up the flexible loop 524, may be referred to herein as a twist. The twist allows the flexible loop 524 to transmit rotational force to the filler 460 without a substantial reduction in the inside diameter of the lumen of the flexible loop 524. In some cases, there is no reduction in the inside diameter of the lumen of the flexible loop 524.

As described above, when the upper housing 404B is rotated from the rotationally unlocked position shown in FIGS. 4B-4C, to a rotationally locked position, the locking tab 428 of the upper housing 404B may engage with the locking slot 432 in the lower housing 404A. Additionally or alternatively, when moved into the rotationally locked position, the loop containment bracket 426 may rotate, along with the blood component collection loop 520 and the upper housing 404B, to a position in-line with the loop rotational position guide 424 along the loop engaged position 520B. In at least one example embodiment, the loop capture arm 416 may guide the blood component collection loop 520 into the bearings 417 and/or bearing surfaces of the loop rotational position guide 424 as the upper housing 404B and the blood component collection loop 520 rotate into the loop engaged position 520B. Further details regarding the loading of the blood component collection loop 520 are described in conjunction with FIGS. 6A-7B below.

Figure 4D:
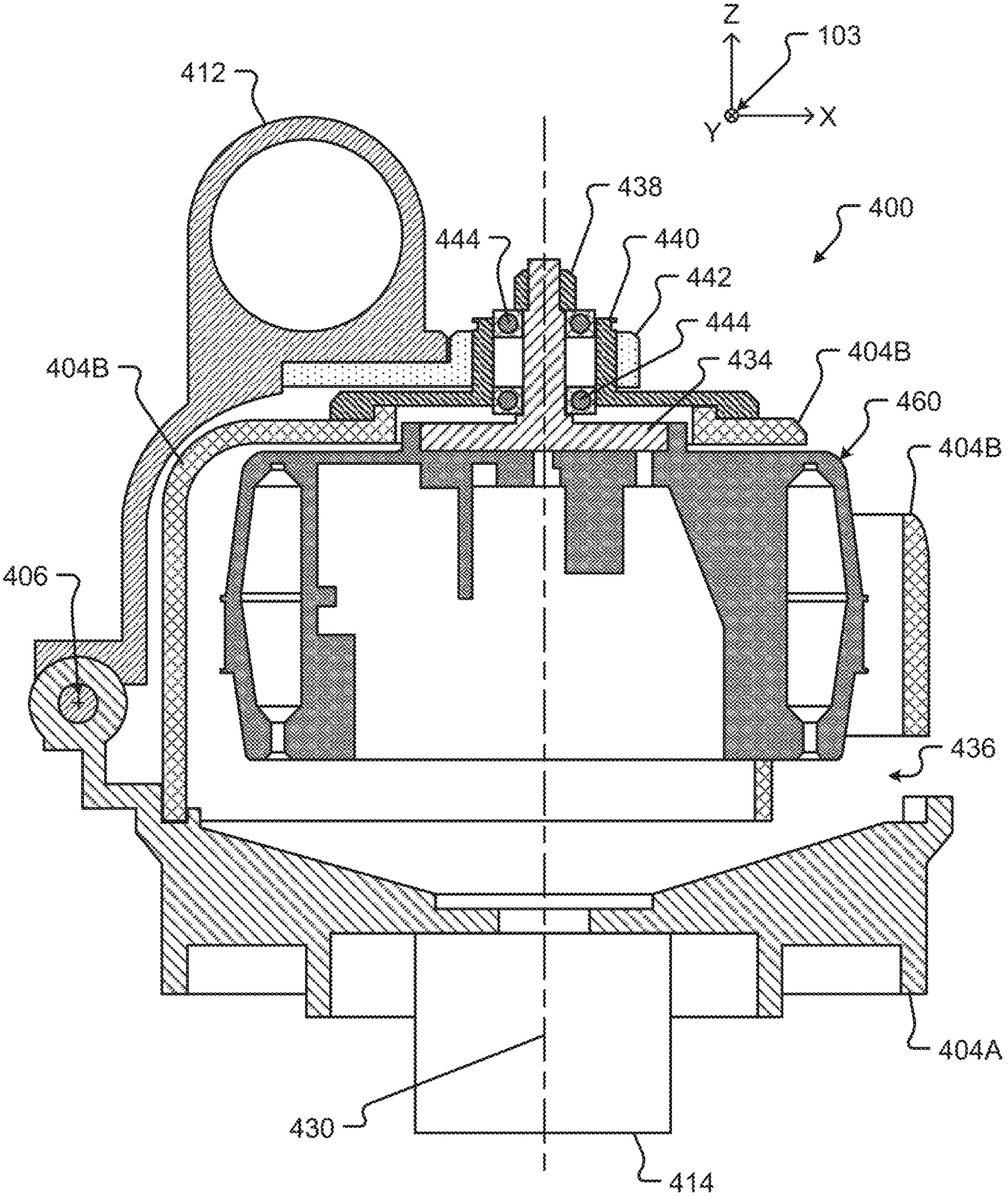
FIG. 4D is a schematic section view of a centrifuge assembly in a closed state in accordance with at least one example embodiment of the present disclosure.
Figure 4E:
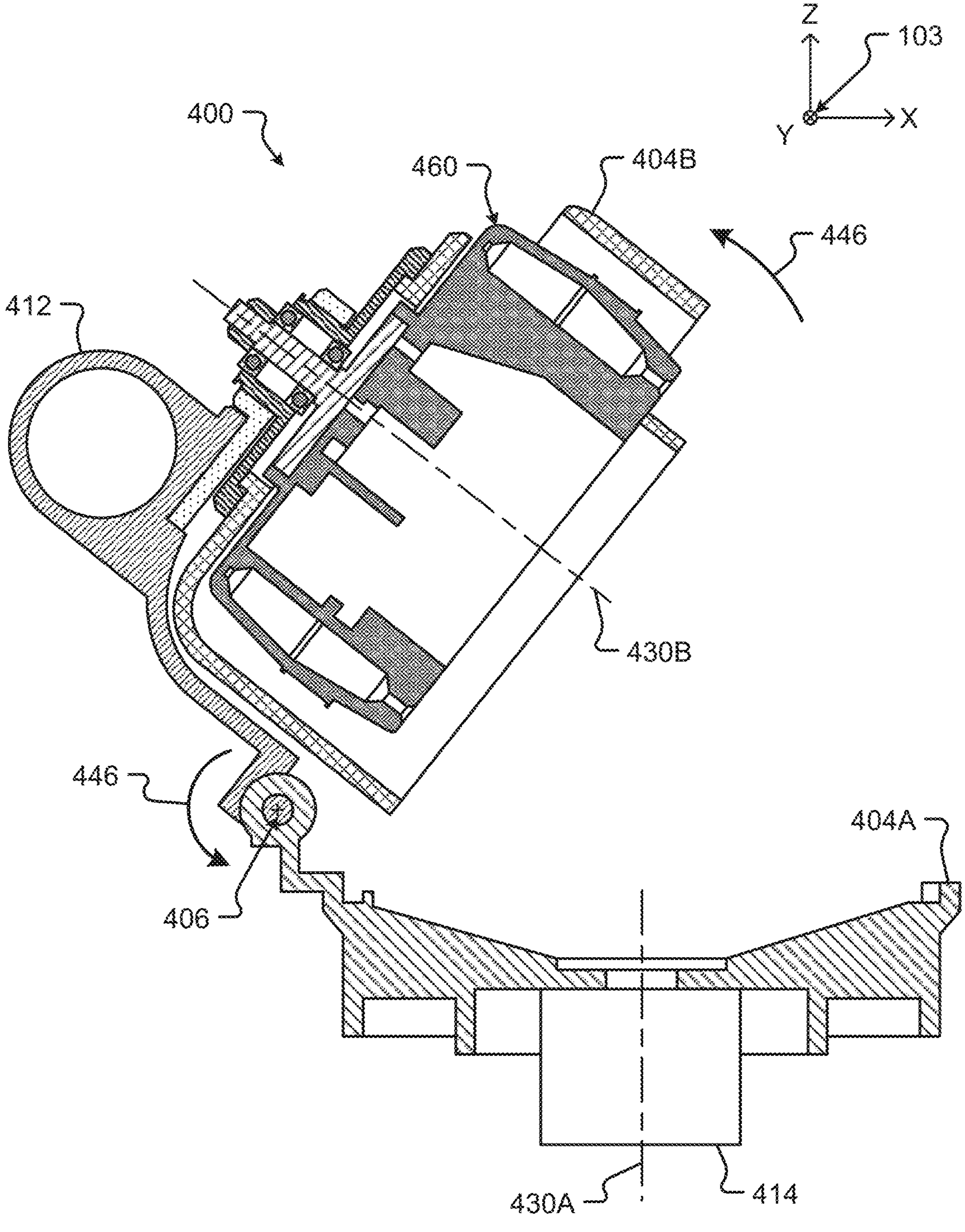
FIG. 4E is a schematic section view of a centrifuge assembly in a partially open state in accordance with at least one example embodiment of the present disclosure.
Figure 4F:
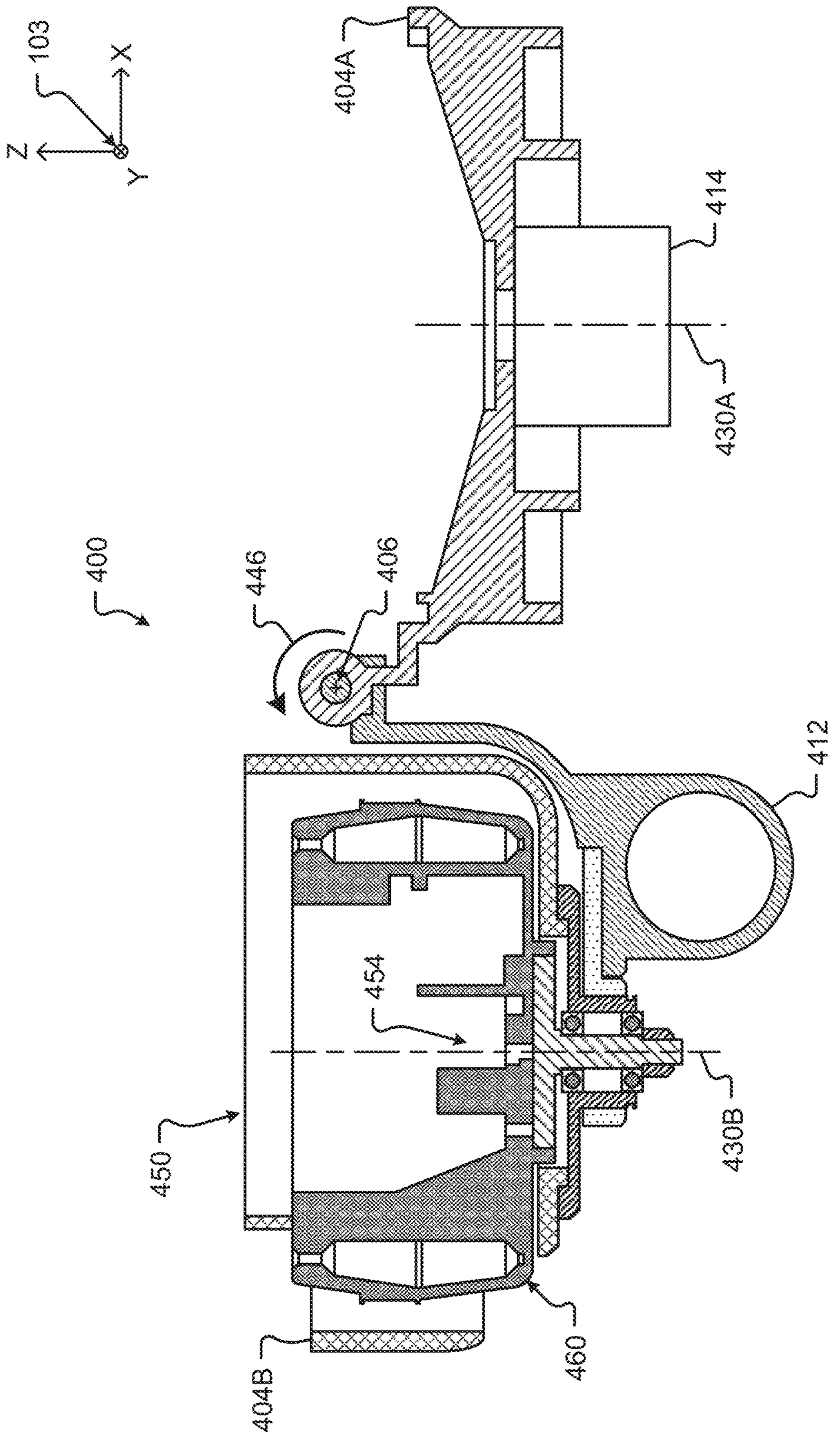
FIG. 4F is a schematic section view of a centrifuge assembly in an open state in accordance with at least one example embodiment of the present disclosure.

FIGS. 4D-4F show various schematic section views taken through the center of the centrifuge assembly 400 (e.g., bisecting the centrifuge assembly 400 through the centrifuge rotation axis 430, etc.). As described above, the centrifuge assembly 400 may include a lower housing 404A that is pivotally attached to an upper housing 404B by a split-housing pivot axis 406, or hinge. The upper housing 404B may be attached to an upper housing adapter 440 that is rotationally interconnected to the upper housing bushing block 442 attached to the pull ring 412. In at least one example embodiment, a bearing 417, bushing, or bearing surface may be disposed between the upper housing adapter 440 and the upper housing bushing block 442 allowing the upper housing 404B to rotate along centrifuge rotation axis 430 from a locked position into an unlocked position, and vice versa. The pull ring 412 may be rotationally fixed about centrifuge rotation axis 430 relative to the lower housing 404A. In at least one example embodiment, the upper housing adapter 440 and the upper housing 404B may be formed from an integral structure.

The filler 460 may be fixedly attached to a filler mandrel 434 that is configured to rotate relative to the upper housing 404B about centrifuge rotation axis 430. In at least one example embodiment, the filler mandrel 434 may be formed from a portion of the filler 460. In any event, one or more mandrel support bearings 444 may be disposed between the filler mandrel 434 and the upper housing adapter 440 allowing the filler 460 to rotate inside the centrifuge split-housing 404 and centrifuge assembly 400 about the centrifuge rotation axis 430. In at least one example embodiment, the filler mandrel 434 may be retained in an operative position via at least one retaining nut 438. The filler 460 and filler mandrel 434 may spin together relative to the centrifuge split-housing 404

FIG. 4D shows a schematic section view of the centrifuge assembly 400 in a closed state (e.g., prior to loading the blood component collection loop 520). Upon unlocking the upper housing 404B relative to the lower housing 404A, an operator may pull on the pull ring 412 to pivot the entire upper housing 404B and filler 460 about the split-housing pivot axis 406. In at least one example embodiment, the upper housing 404B and the filler 460 may be partially opened by pivoting the components about the split-housing pivot axis 406 in an opening direction 446. For example, as illustrated, in FIG. 4E, where the centrifuge assembly 400 is shown in a partially opened state, the upper housing 404B and filler 460 are rotated out of axis from the lower housing rotation axis 430A. In this position, the filler 460 may be allowed to rotate about the filler rotation axis 430B. When the lower housing 404A and upper housing 404B are in a closed state, the lower housing rotation axis 430A and the filler rotation axis 430B align (coincidentally, or substantially coincidentally) to form the centrifuge rotation axis 430.

Continuing to rotate the upper housing 404B and the filler 460 about the y-axis of the split-housing pivot axis 406 in the opening direction 446 (e.g., by continuing to pull the pull ring 412) may cause the upper housing 404B and the filler 460 to pivot substantially 180 degrees from the closed position shown in FIG. 4D. As shown in FIG. 4F, the centrifuge assembly 400 is in an open, or loading, state. In this position, the upper housing 404B and the filler 460 may be pivoted outside of the interior space of the apheresis system 200. For example, at least a portion of the upper housing 404B and/or the filler 460 may be positioned through an open space of the opened access panel 224. In this position, a loading access area 450 may be provided to the loop connection area 454 of the filler 460. As can be appreciated, orienting the upper housing 404B in the open position provides easy access to the interior of the upper housing 404B and the filler 460. Among other things, this arrangement may provide ample clearance for an operator to attach the blood component collection loop 520 to the filler 460 at the loop connection area 454.

Figure 4G:
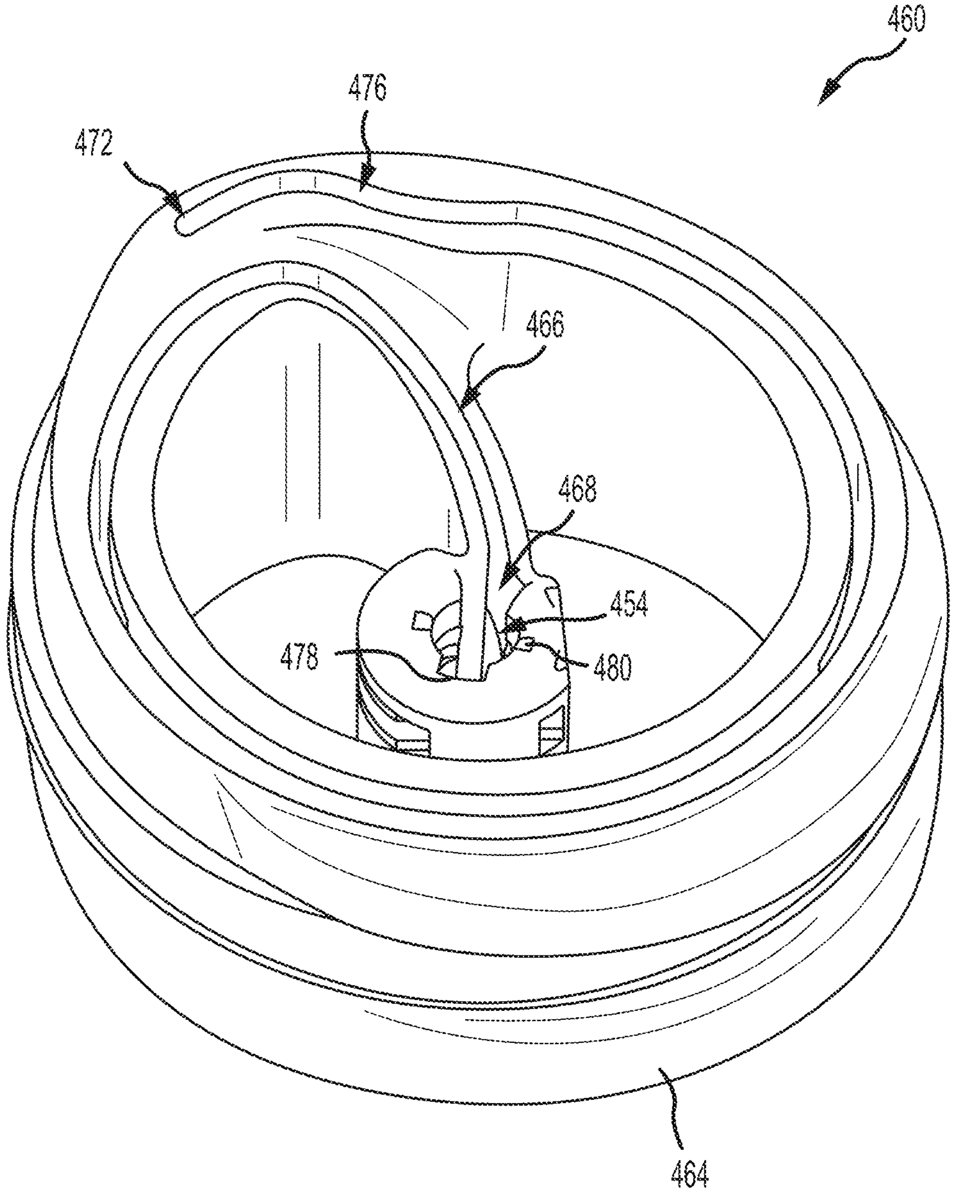
FIG. 4G shows a perspective view of a filler for a centrifuge in accordance with at least one example embodiment of the present disclosure.

Referring to FIG. 4G, a perspective view of a filler 460 for the centrifuge assembly 400 is shown in accordance with at least one example embodiment of the present disclosure. In at least one example embodiment, the filler 460 may be made from a lightweight material such as plastic, carbon fiber, aluminum, etc. In at least one example embodiment, the filler 460 may be three-dimensionally (3D) printed via a 3D printing machine. For instance, the filler 460 may be produced via an additive manufacturing technique or system such as fused deposition modeling (FDM), selective laser sintering (SLS), stereolithography (SLA), and/or other additive manufacturing machines. Among other things, these additive rapid prototyping manufacturing techniques can allow for more complex geometries of the filler 460 that may not be possible through the use of conventional machining or manufacturing processes. In at least one example embodiment, the material of the filler 460 may be selected based on a desired mass of the filler 460, the desired physical strength of the manufactured filler 460, and/or suitable material for use in manufacturing.

The filler 460 may include a loop connection area 454 disposed substantially at the center of the filler 460. The loop connection area 454 may include one or more keying, or positive location, features for a portion of the blood component collection loop 520 to engage. As shown in FIG. 4G, the loop connection area 454 includes a first positive location feature 478 disposed along a portion of the center axis of the filler 460. The first positive location feature 478 may be a keyway, groove, slot, or other feature for engaging with a mating feature disposed on the blood component collection loop 520. In at least one example embodiment, the filler 460 may include a second positive location feature 480 in the loop connection area 454. The location features 478, 480 may prevent rotation of the blood component collection loop 520 at the loop connection area 454 and/or prevent the blood component collection loop 520 from disengaging from the loop connection area 454 of the filler 460.

Figure 4H:
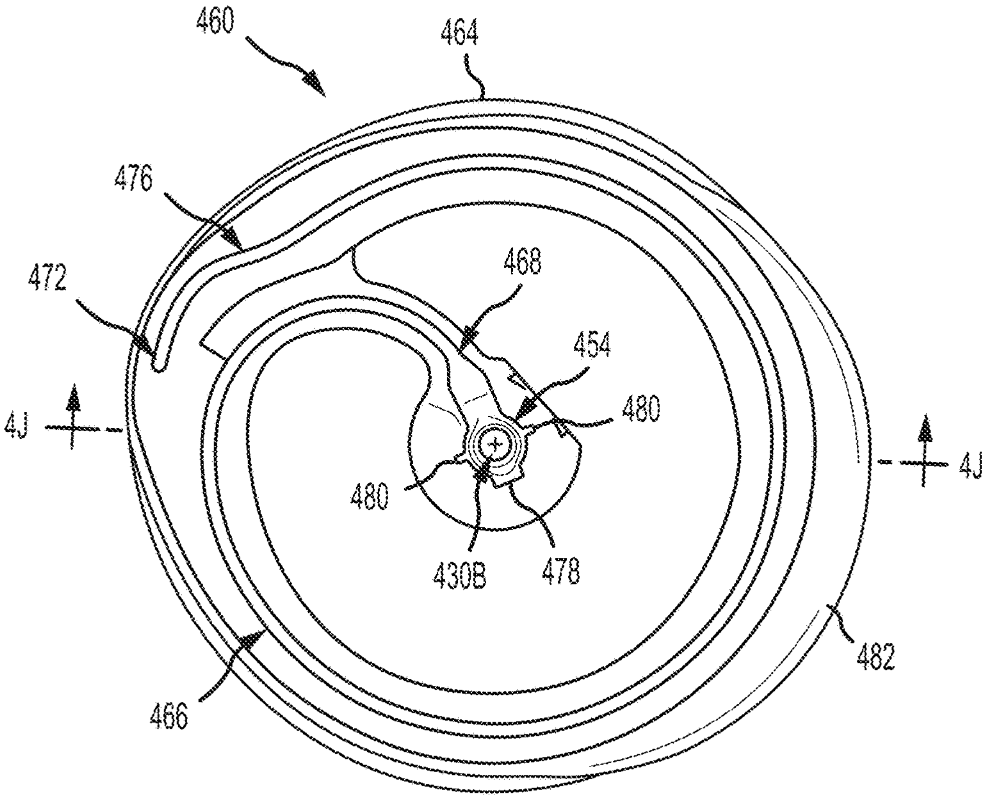
FIG. 4H is a plan view of a filler for a centrifuge in accordance with at least one example embodiment of the present disclosure.
Figure 4I:
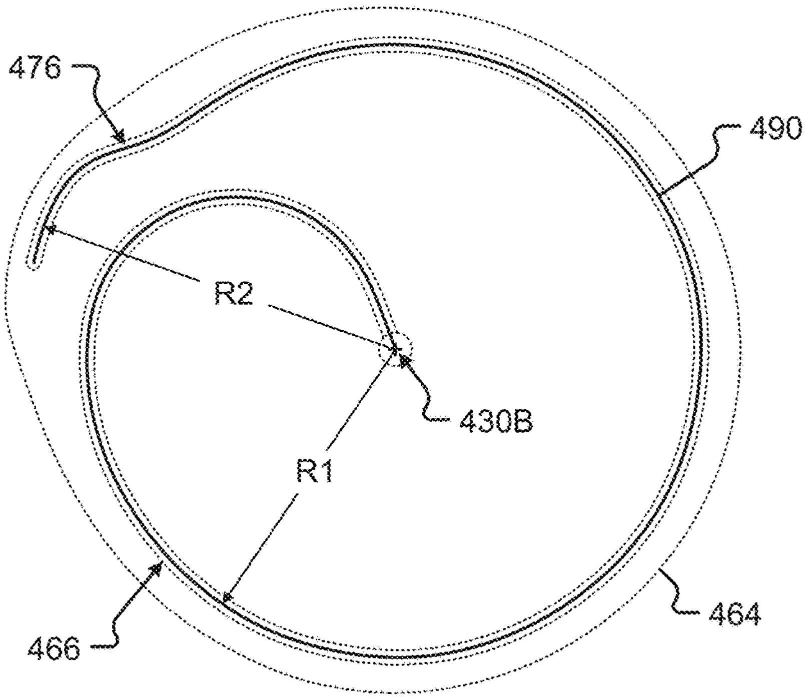
FIG. 4I is a schematic plan view of a substantially spiral-shaped receiving channel for a filler in accordance with at least one example embodiment of the present disclosure.

In at least one example embodiment, the filler 460 may include a collection insert channel 466 configured to receive, and at least partially contain, a blood component collection bladder of the blood component collection set and, more specifically, the blood component collection loop 520. The collection insert channel 466 may be configured as a groove, slot, extending outwardly, in a substantially spiral fashion, from a center of the filler 460. In at least one example embodiment, the collection insert channel 466 may follow a substantially spiral shaped path that may include a first spiral path portion extending outwardly from the center of the filler 460 to a substantially constant radius (e.g., about the center of the filler 460) along a length of the collection insert channel 466 periphery. In any event, the path may be referred to herein as a spiral path or a substantially spiral path. The collection insert channel 466 may start at a channel entrance 468 adjacent to the center of the filler body 464 and terminate at a channel end 472 adjacent at a point furthest from the center of the filler body 464. As shown in FIGS. 4G-4I, the collection insert channel 466 may extend along a substantially spiral path 490 running from a point adjacent to the filler rotation axis 430B to the channel end 472. The substantially spiral path 490 may include a channel path jog 476 at a point near, or adjacent to, the channel end 472. This channel path jog 476 may extend the distance of the collection insert channel 466 from the center of the filler body 464 thereby increasing the centripetal and centrifugal forces at the channel end 472 of the collection insert channel 466. In at least one example embodiment, this channel path jog 476 may correspond to a critical inlet and exit port at a radial maximum within a blood component collection bladder 536 that is inserted or disposed, at least partially, within the collection insert channel 466 of the filler 460. In at least one example embodiment, the filler 460 may include one or more filler balance protrusions 482 disposed on, in, or about a portion of the filler body 464. These filler balance protrusions 482 may provide an axially balanced (e.g., about the filler rotation axis 430B) filler 460, especially when the collection insert channel 466 includes a blood component collection bladder and fluid (e.g., blood, blood components, etc.).

FIG. 4I is a schematic plan view of a substantially spiral-shaped receiving channel, or collection insert channel 466, for a filler 460 in accordance with at least one example embodiment of the present disclosure. The schematic plan view shows a first distance, R1, of the collection insert channel 466 from a center of the filler body 464 (e.g., adjacent to the filler rotation axis 430B, etc.) at a first point along the substantially spiral path 490 and a second distance, R2, of the collection insert channel 466 from the center of the filler body 464 past a point adjacent to the channel path jog 476. As illustrated in FIG. 4I, the second distance, R2, is further from the center of the filler body 464 than the first distance, R1. This increase in distance may provide higher centripetal and centrifugal forces in the channel at a point near, or at, the channel end 472 than at any other point along the substantially spiral path 490. In at least one example embodiment, the end of the blood collection bladder may substantially coincide with the channel end 472, providing the greatest blood separation forces at the end of the bladder.

Figure 4J:
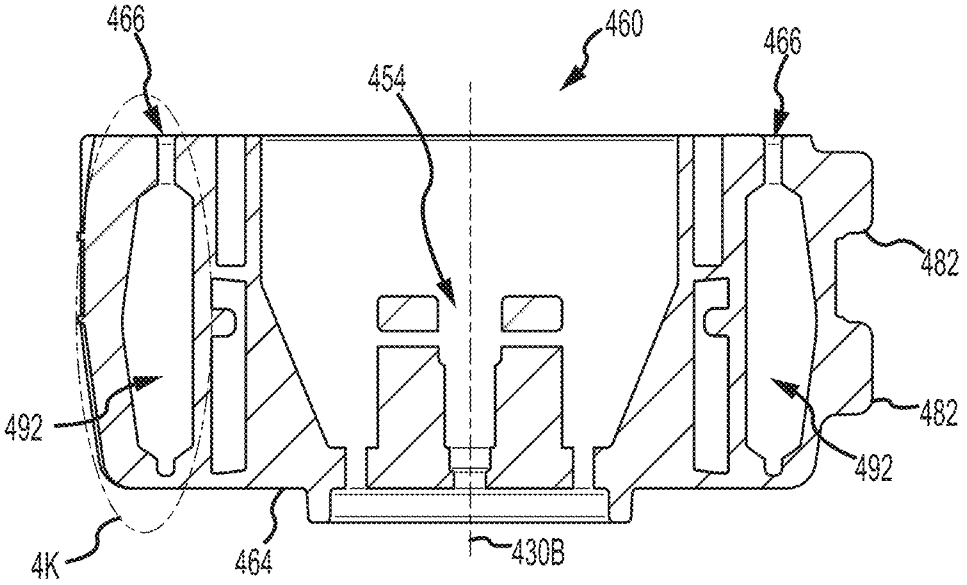
FIG. 4J is an elevation section view taken through line 4J of FIG. 4H.
Figure 4K:
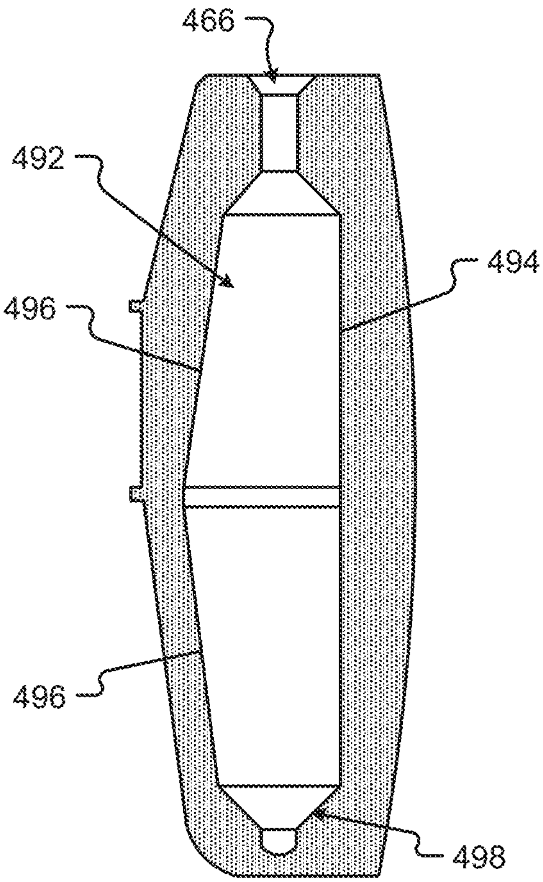
FIG. 4K is a detail section view of a portion of a channel in the filler in accordance with at least one example embodiment of the present disclosure.
Figure 4L:
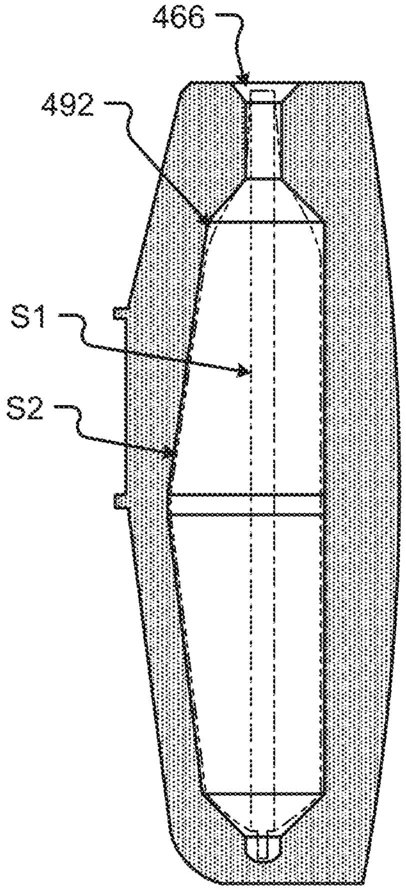
FIG. 4L shows different states of fluid collection bladders disposed inside the channel in the filler of FIG. 4K.

FIGS. 4J-4L show various elevation sections of the filler 460 and, more specifically of, the collection insert channel 466 and filler insert chamber 492 disposed inside the filler body 464. In at least one example embodiment, the collection insert channel 466 may include a cross-section, or shape, that substantially follows the substantially spiral path 490 in the filler body 464. The collection insert channel 466 may include an insert groove configured to receive a substantially flat, or unfilled, blood component collection bladder. The blood component collection bladder may be inserted into the collection insert channel 466 and a filler insert chamber 492 formed in the filler body 464 along the substantially spiral path 490. The filler insert chamber 492 may be defined by one or more sidewalls 494, 496 forming a cavity that follows the substantially spiral path 490. As shown in FIG. 4K, the filler insert chamber 492 includes an inner chamber wall 494 separated a distance from at least one outer chamber wall 496. The filler insert chamber 492 may be formed in the filler 460 by 3D printing the filler 460 and/or by some other metal or plastic forming operation, or operations (e.g., casting, molding, forming, etc.). In at least one example embodiment, the filler insert chamber 492 may include one or more insert guide features 498. These insert guide features 498 may be configured to guide, locate, and/or seat a blood component collection bladder inside the filler insert chamber 492 of the filler 460. Although shown as a chamfered, or lead-in, feature of the filler insert chamber 492, the insert guide feature 498 may include one or more radius, chamfer, slope, taper, draft angle, receptacle, groove, and/or other shaped material configured to direct and/or orient a portion of an inserted blood component collection bladder.

FIG. 4L shows different states of fluid collection bladders (e.g., blood component collection bladders, etc.) disposed inside the collection insert channel 466 and the filler insert chamber 492 of the filler 460. As described above, a blood component collection bladder may be inserted into the collection insert channel 466 in a substantially flat, or unfilled, state, S1. In the substantially flat state, S1, the blood component collection bladder may be sized to enter the upper opening of the collection insert channel 466 and be maintained in a pre-fill condition inside the filler insert chamber 492. When the filler 460 begins to spin and separate blood components from blood provided by a donor 102, the blood component collection bladder may expand from the substantially flat first state, S1, to an expanded, or filled, state, S2. In at least one example embodiment, the blood component collection bladder may expand with blood and/or blood components until the walls of the blood component collection bladder contact the walls 494, 496 of the filler insert chamber 492. In at least one example embodiment, the shape of the filler insert chamber 492 may be designed to optimize the amount of fluid (e.g., maximize the volume of fluid while minimizing the amount of material for the filler 460) capable of being collected and/or separated in the filler insert chamber 492.

Example Blood Component Collection Set

FIGS. 5A-5H illustrate a blood component collection set 500 prepared in accordance with at least one example embodiment of the present disclosure. The blood component collection set 500 includes various connections that include, for example, tubes and connectors. For example, as illustrated, the blood component collection set 500 may include one or more tubes, such as the cassette inlet tubing 108A, the loop inlet tubing 108B, the anticoagulant tubing 110, the loop exit tubing 112, the saline tubing 116, and/or the plasma tubing 120, and also one or more connectors, such as the tubing connector 106 and/or the saline and plasma tubing y-connector 280. The blood component collection set 500 may also include one or more other connectors, such as a first tubing fitting 504, a second tubing fitting 508, a bag fitting 512, a system static loop connector 528, and/or a filler loop connector 532. The various connections may fluidly connect the soft cassette 340 and the blood component collection loop 520.

The one or more tubes, including the cassette inlet tubing 108A, the loop inlet tubing 108B, the anticoagulant tubing 110, the loop exit tubing 112, the saline tubing 116, and/or the plasma tubing 120 (collectively referred to as "the tubing"), each have a central lumen configured to convey fluid therethrough. The tubing may include one or more polymeric materials, including, for example, polyvinyl chloride (PVC), plasticized-polyvinyl chloride, polyethylene, ethylene vinyl acetate (EVA), rubbers, copolymers and combinations thereof.

The one or more connectors, including the tubing connector 106, the saline and plasma tubing y-connector 280, the first tubing fittings 504, the second tubing fitting 508, the bag fitting 512, the system static loop connector 528, and/or the filler loop connector 532 (collectively referred to as "the connectors"), may be each configured to fluidly interconnect the tubing and/or to fluidly interconnect the tubing and other medical accessories and/or to fluidly interconnect the tubing and needles or spikes. For example, the connectors may insert into the central lumen of the respective tube and/or attach to an outside of the respective tube and/or the bag fitting 512 may be configured to be inserted into a receiving bag, like the saline bag 118. In at least one example embodiment, the connectors may include various fittings, including, for example, Luer fittings, twist-to-connect fittings, and/or other small-bore couplings, to provide universal and/or reliable interconnections for establishing fluid connections.

As illustrated, the blood component collection loop 520 may include a flexible loop 524 disposed between the system static loop connector 528 and the filler loop connector 532. The static loop connector 528 may be attached to the flexible loop 524 and/or a blood component collection bladder 536, as further discussed below, by a mechanical lock, which can be formed with a photo curable adhesive. The flexible loop 524 may be configured as a hollow flexible tube configured to receive and/or contain at least a portion of the loop inlet tubing 108B and the loop exit tubing 112. In at least one example embodiment, the flexible loop 524 may include a thermoplastic elastomer having enhanced flexibility for transmitting twist from a first end of the flexible loop 524 towards and to a second distal end. Such thermoplastic elastomers may provide the flexibility of rubber while maintaining the strength and torque characteristics of plastics. Examples of the thermoplastic elastomer may include, for example, copolyester, DUPONT™ HYTRE1® thermoplastic elastomers, EASTMAN NEOSTAR™ elastomers, CELANESE RITEFLEX® elastomers, TOYOBO PELPRENE®, and/or other similar brand elastomers offering high flexibility and strength characteristics.

In at least one example embodiment, the blood component collection loop 520 may include a blood component collection bladder 536. The blood component collection bladder 536 may have a first or bladder loop end 540A and a second or bladder free end 540B. The blood component collection bladder 536 may include a first collection flow chamber 544 extending between the bladder loop end 540A and the bladder free end 540B and connected to the flexible loop 524 via the filler loop connector 532. For example, in at least one example embodiment, fluid may flow between the loop inlet tubing 108B and the first collection flow chamber 544 via the flowpath defined by the flexible loop 524, the system static loop connector 528, and the filler loop connector 532. The bladder free end 540B of the first collection flow chamber 544 may include a flow chamber transition 548 and fluid flowing from the bladder loop end 540A to the bladder free end 540B via first collection flow chamber 544 may enter a second collection flow chamber 552 via the flow chamber transition 548. The second collection flow chamber 552 may be connected to the flexible loop 524 via the filler loop connector 532. For example, in at least one example embodiment, fluid may flow between the loop exit tubing 112 and the second collection flow chamber 552 via a flowpath defined by the flexible loop 524, the system static loop connector 528, and the filler loop connector 532.

Figure 5A:
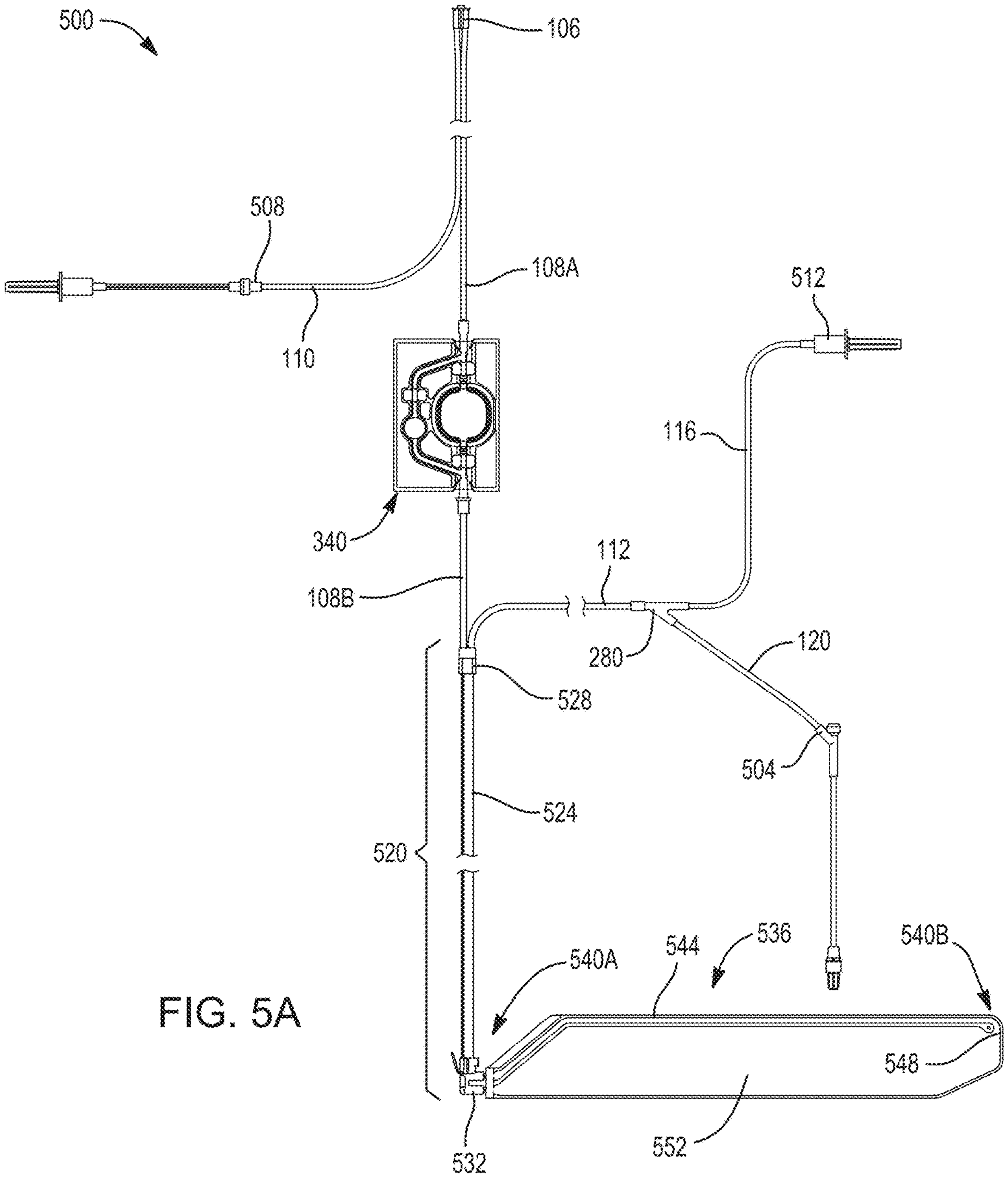
FIG. 5A is an illustration of a fluid component collection set including a fluid component collection loop in accordance with at least one example embodiment of the present disclosure.
Figure 5B:
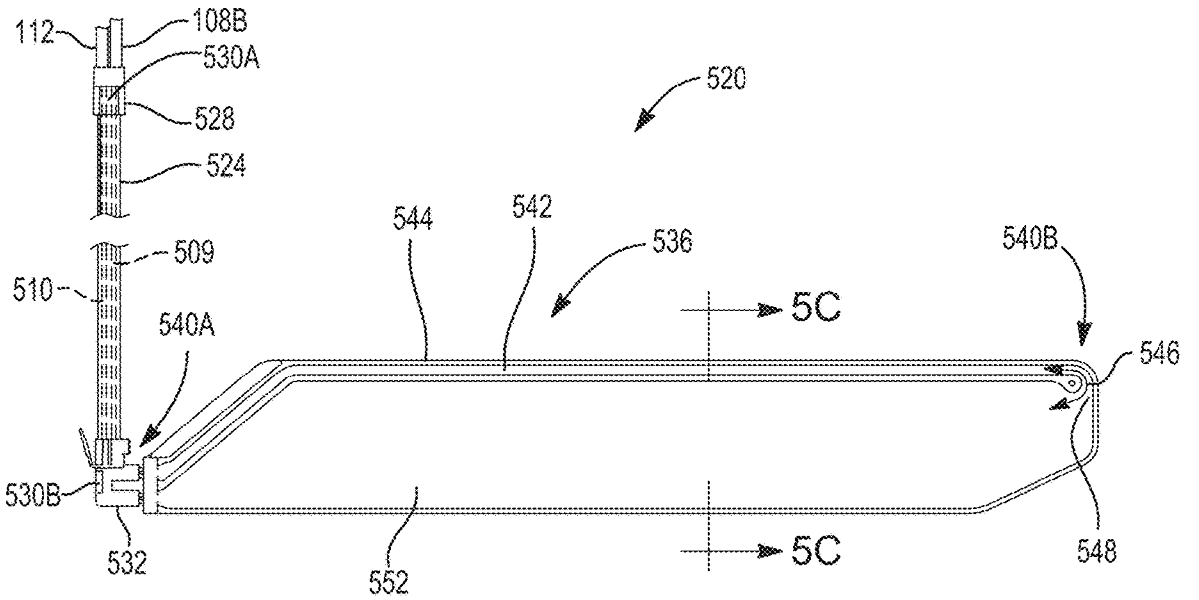
FIG. 5B is an illustration of the fluid component collection loop which includes a fluid component collection bladder in accordance with at least one example embodiment of the present disclosure.

In at least one example embodiment, as illustrated in FIG. 5B, the flexible loop 524 may include a first distinct pathway 509 that is configured to receive the loop inlet tubing 108B and a second distinct pathway 510 that is configured to receive the loop exit tubing 112. For example, in at least some example embodiment, at least a portion of the loop inlet tubing 108B may be held within the first pathway 509 of the flexible loop 524 and connected with the first collection flow chamber 544 at the bladder loop end 540A via the filler loop connector 532. Additionally, or alternatively, at least a portion of the loop exit tubing 112 may be held within the second pathway 510 of the flexible loop 524 and connect with the second collection flow chamber 552 at the bladder loop end 540A via the filler loop connector 532. In this manner, fluid enters the blood component bladder 536 via the first collection flow chamber 544, where the fluid can be separated (e.g., into one or more blood components) and conveyed along the second collection flow chamber 552 to the loop exit tubing 112 held within the second pathway 510 of the flexible loop 524.

As illustrated, the first collection flow chamber 544 may be separated from the second collection flow chamber 552 via a flow chamber separator 542. In at least one example embodiment, the flow chamber separator 542 may be a sealed portion (e.g., heat sealed) of the blood component collection bladder 536. For example, in at least one example embodiment, the blood component collection bladder 536 may include, and may be prepared from, one or more overlapping and sealed material layers. The material layers may include one or more polymeric materials. For example, in at least one example embodiment, the material layers may include polyvinyl chloride (PVC), plasticized-polyvinyl chloride, polyethylene, ethylene vinyl acetate (EVA), thermoplastics, thermoplastic elastomer, copolymers and combinations thereof.

Figure 5C:
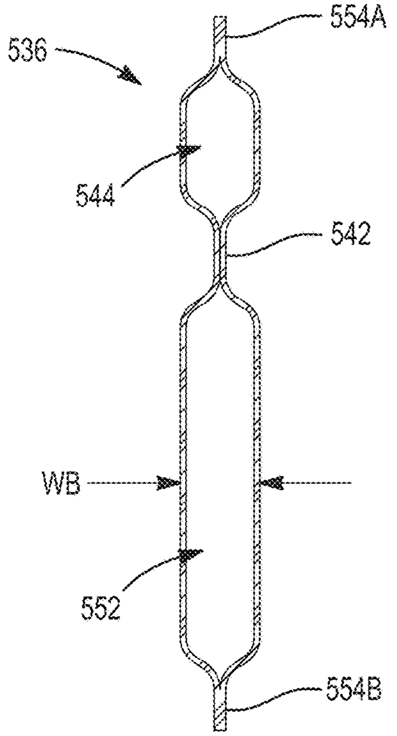
FIG. 5C is a cross-section illustration of the fluid component collection bladder in accordance with at least one example embodiment of the present disclosure.
Figure 5D:
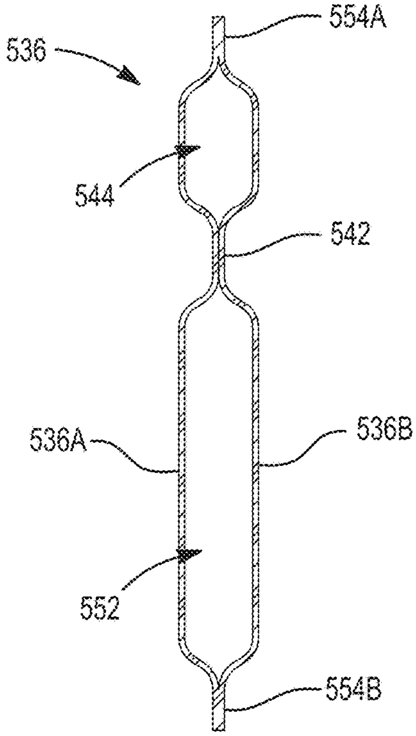
FIG. 5D is another cross-section illustration of the fluid component collection bladder in accordance with at least one example embodiment of the present disclosure.

The material layers may be shaped (e.g., cut or otherwise shaped, etc.) and sealed along one or more edges to form the blood component collection bladder 536. As illustrated in FIGS. 5C and 5D, the flow chamber separator 542 may be formed in the blood component collection bladder 536 by sealing the one or more material layers to one or more other material layers, and/or one or more first portions of a single material layer to one or more second portions of the single material layer, along one or more preselected path. For example, as illustrated in FIG. 5D, which shows the blood component collection bladder 536 prior to the sealing, the flow chamber separator 542 may be formed as a sealed region of material by joining a bladder first side material 536A to a bladder second side material 536B. The bladder first side material 536A and the bladder second side material 536B may also be sealed at one or more ends 554A, 554B to form a top and bottom of the blood component collection bladder 536. By way of comparison, FIG. 5C shows the blood component collection bladder 536 after the sealing. As illustrated in FIGS. 5A and 5B, the seal defining the flow chamber separator 542 does not extend the entire length of the blood component collection bladder 536 and thereby defines the flow chamber transition 548 such that fluid can pass between the first collection flow chamber 544 and the second collection flow chamber 552.

Once formed, the width of the bladder (WB) may correspond to the width of the first collection flow chamber 544 and/or the second collection flow chamber 552 in an unexpanded state (S1) (see, FIG. 4L). During operation, as fluid fills at least a portion of the blood component collection bladder 536, the width of the bladder (WB) may increase in dimension from the resting dimension illustrated in FIG. 5C. For example, in at least one example embodiment, the width of the bladder (WB) may increase substantially to the size of the filler insert chamber 492 of the filler 460. In at least one example embodiment, the sealed to welded portions of the blood component collection bladder 536 may be supported in the filler 460. For example, as illustrated in FIGS. 5G and 5H, a top of the filler 460 may support the top two seals 554A, 542 and the bottom of the filler 460 may support the bottom seal 554B.

In at least one example embodiment, the blood component collection loop 520 may include one or more location features (also referred to as key features) 530A, 530B that are configured to help positively locate portions of the blood component collection loop 520 relative to the apheresis system 200, and more specifically, the filler 460 of the centrifuge assembly 400. For example, as illustrated, the blood component collection loop 520 may include a first connector location feature 530A on or near the system static loop connector 528 and/or a second connector location feature 530B on or near the filler loop connector 532. The location features 530A, 530B may be configured as a key, a tab, and/or other material protrusion that extends from the respective connector 528, 532. In at least one example embodiment, the second connector location feature 530B may include features that interconnect (e.g., mate) with the first positive location feature 478 and/or the second positive location feature 480 of the loop connection area 454 in the filler 460.

FIGS. 5E-5H are various perspective views of the blood component collection loop 520 in a flexed state and also illustrate the flexed blood component collection bladder 536 of the blood component collection loop 520 as inserted into the filler 460 of the centrifuge assembly 400. The various components of the blood component collection loop 520 may be flexible and/or capable of being formed or shaped by the application of force. In at least one example embodiment, this flexibility may be elastic such that forming the various parts of the blood component collection loop 520 does not permanently deform the components.

Figure 5E:
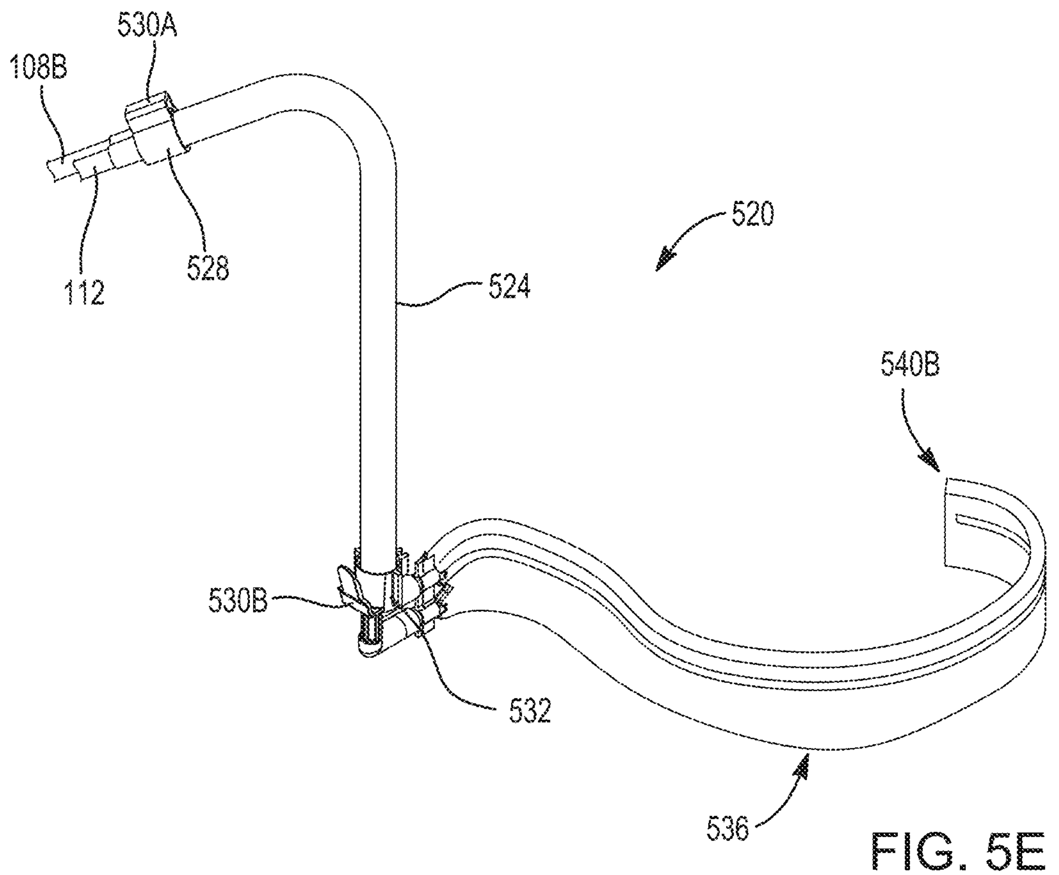
FIG. 5E shows a perspective view of a fluid component collection loop in a flexed state in accordance with at least one example embodiment of the present disclosure.

FIG. 5E illustrates the blood component collection loop 520 in a flexed state. For example, in FIG. 5E, the flexible loop 524 is shown elastically bent along its length and the blood component collection bladder 536 is shown following a number of bends or curves along its length. The flexible loop 524 nonetheless provides fluids to the blood component collection bladder 536, for example, via the loop inlet tubing 108B, and/or takes fluids away from the blood component collection bladder 536, for example, via the loop exit tubing 112, while one or more of the various components of the blood component collection loop 520 are in a flexed state.

Figure 5F:
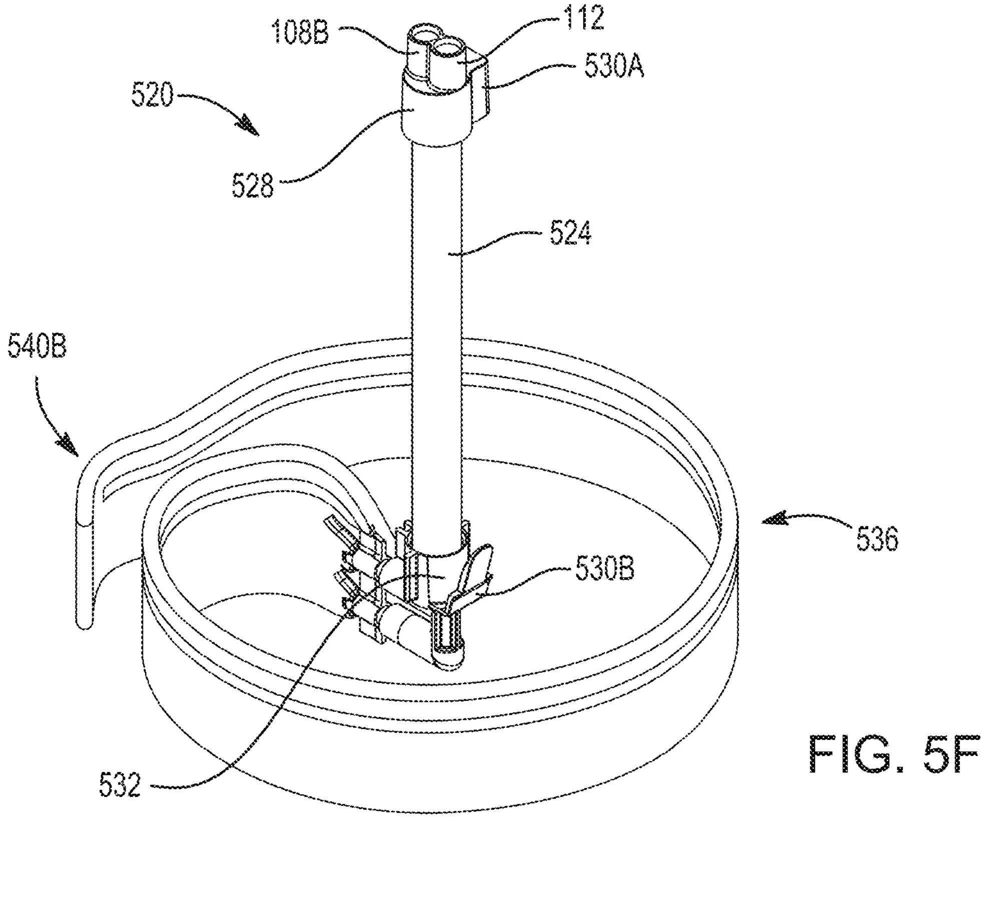
FIG. 5F shows a perspective view of a fluid component collection loop in a loading state in accordance with at least one example embodiment of the present disclosure.
Figure 5G:
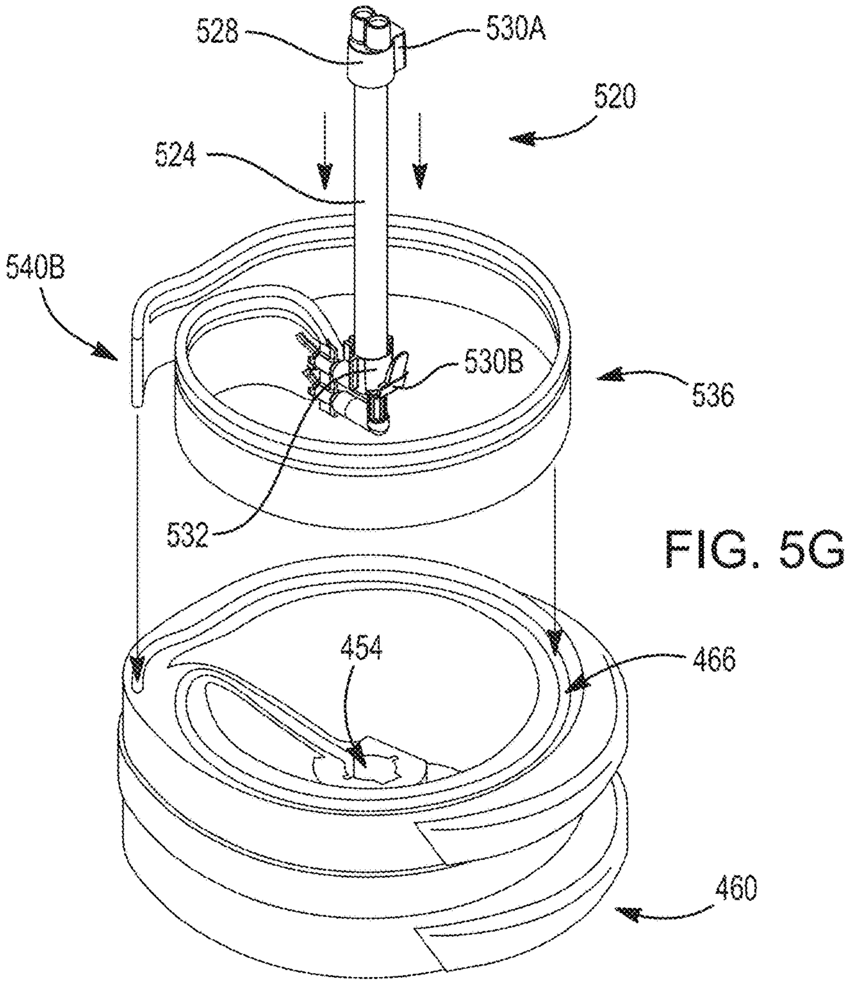
FIG. 5G shows a perspective view of a fluid component collection loop loaded into a filler in accordance with at least one example embodiment of the present disclosure.
Figure 5H:
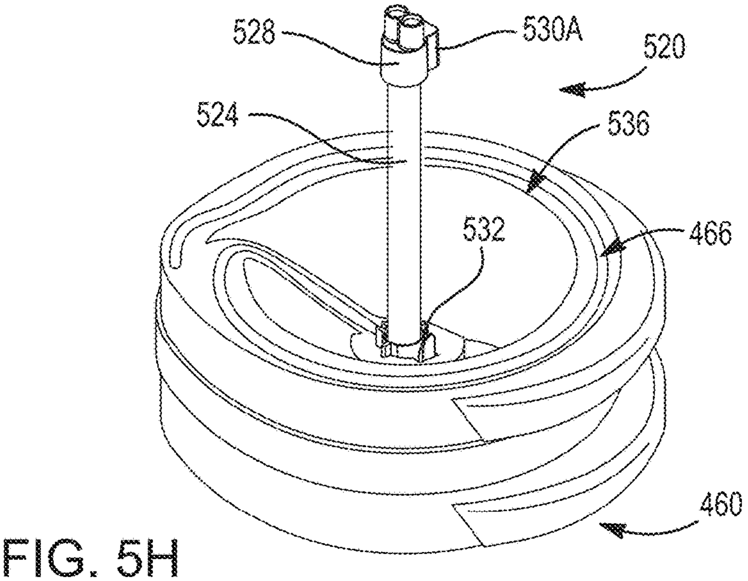
FIG. 5H shows a perspective view of a fluid component collection loop loaded in a filler in accordance with at least one example embodiment of the present disclosure.

In at least one example embodiment, the blood component collection loop 520 may be pre-formed, for example, as illustrated in FIG. 5F, to fit within the collection insert channel 466 of the filler 460 of the centrifuge assembly 400. The pre-forming may include twisting the blood component collection bladder 536 of the blood component collection loop 520 so as to match the substantially spiral path 490 of the collection insert channel 466. Once pre-formed, the features of the blood component collection loop 520 may be aligned with one or more features of the filler 460, as illustrated in FIG. 5G. For example, in one at least one example embodiment, the filler loop connector 532 of the blood component collection loop 520 may be aligned with the loop connection area 454 of the filler 460 such that the second connector location feature 530B is aligned to engage with the first positive location feature 478. Additionally, or alternatively, the blood component collection bladder 536 may be shaped, or formed (e.g., manually or automatically), to match the substantially spiral path 490 of the collection insert channel 466 in the filler 460. In at least one example embodiment, this shaping or forming may include aligning the bladder free end 540B of the blood component collection bladder 536 with the channel end 472 of the collection insert channel 466 in the filler 460. When the components are generally aligned with one another, the blood component collection loop 520 may be moved in a direction toward the collection insert channel 466 and the loop connection area 454, as shown in FIG. 5G. In at least one example embodiment, when the filler loop connector 532 is moved toward and into the loop connection area 454 of the filler 460, the first positive location feature 478 may interconnect and/or retain the second connector location feature 530B of the filler loop connector 532 of the blood component collection loop 520. This interconnection may prevent the filler loop connector 532 from rotating relative to the filler 460. In at least one example embodiment, the interconnection may maintain the filler loop connector 532 of the blood component collection loop 520 inside the loop connection area 454 of the filler 460. FIG. 5H illustrates the blood component collection loop 520 as loaded in the filler 460. The system static loop connector 528 and the filler loop connector 532 can work together to transfer torque as applied to the flexible loop 524 to the blood component collection bladder 536 and the filler 460.

In at least one example embodiment, fluid (e.g., blood and/or blood components, etc.) in the blood component collection bladder 536 contained in the filler insert chamber 492 of the filler 460 may travel in a direction toward the bladder free end 540B along the first collection flow chamber 544 around an end of the flow chamber separator 542 (e.g., following blood component movement direction 546) and into the second collection flow chamber 552. In this example, blood components (e.g., plasma, etc.) may be forced back along the substantially spiral path 490 toward the center of the filler body 464 along the second collection flow chamber 552 and through the loop exit tubing 112 (e.g., to a plasma collection bottle 122).

Example Centrifuge Assembly in Loop-Loading State

Figures 6A, 6B, 6C:
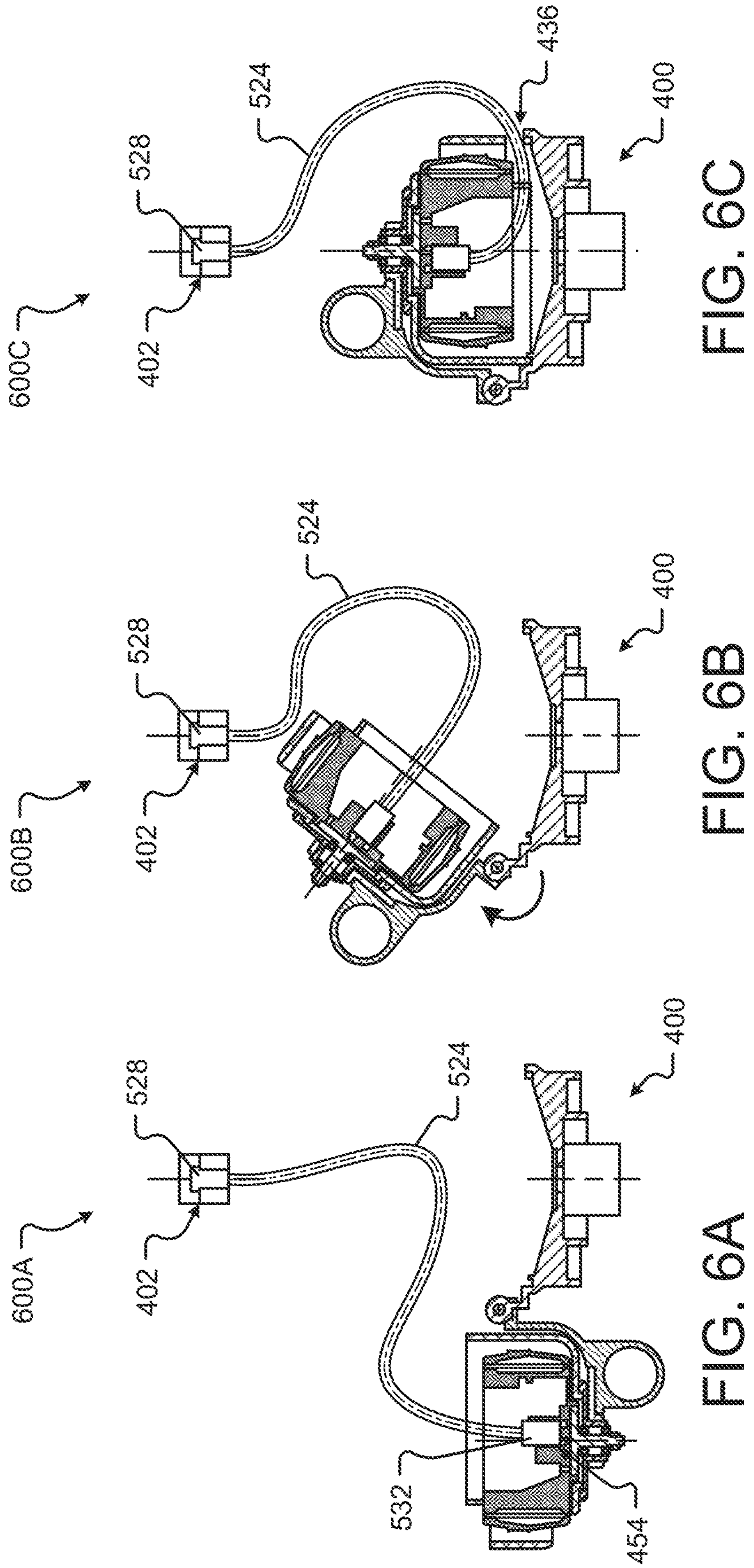
FIG. 6A shows a schematic section view of a centrifuge assembly in a first loop-loading state in accordance with at least one example embodiment of the present disclosure.
FIG. 6B shows a schematic section view of a centrifuge assembly in a second loop-loading state in accordance with at least one example embodiment of the present disclosure.
FIG. 6C shows a schematic section view of a centrifuge assembly in a third loop-loading state in accordance with at least one example embodiment of the present disclosure.

FIGS. 6A-6C are schematic section views of a centrifuge assembly 400 in various loop-loading states in accordance with at least one example embodiment of the present disclosure. The centrifuge assembly 400 as illustrated in FIGS. 6A-6C may correspond to the centrifuge assembly 400 described above and especially in conjunction with FIGS. 4D-4F. In particular, FIG. 6A shows a schematic section view of a first loop-loading state, FIG. 6B shows a schematic section view of a second loop-loading state, and FIG. 6C shows a schematic section view of a second loop-loading state for the centrifuge assembly 400.

In FIG. 6A, the centrifuge assembly 400 is shown in an open, loop-loading, position where the upper housing 404B has been pivoted 180 degrees from a closed, or operational, position. This open position may correspond to the position of the centrifuge assembly 400 shown in FIG. 4F. However, in FIG. 6A, a blood component collection loop 520 has been inserted into the filler 460 and the filler loop connector 532 is interconnected to the loop connection area 454 of the filler body 464. The other end of the blood component collection loop 520 is connected to the fixed loop connection 402 via the system static loop connector 528. In this first loop-loading state, the flexible loop 524 is fixed from rotating at the fixed loop connection 402 but rotates, in unison, with the filler 460 at the loop connection area 454.

In FIG. 6B, the centrifuge assembly 400 is shown in a partially closed position where the upper housing 404B is being moved from the open position to a closed, or operational, position. As the upper housing 404B pivots, the flexible loop 524 may move to a resting position relative to the centrifuge assembly 400. Although the flexible loop 524 is rotationally fixed at the fixed loop connection 402, the filler 460 may be free to rotate about the filler rotation axis 430B (e.g., restricted only by the rotationally fixed flexible loop 524).

In FIG. 6C, the centrifuge assembly 400 is shown in a closed, or operational, position where the upper housing 404B may be locked to the lower housing 404A (such that the lower housing 404A and the upper housing 404B may rotate in unison about the centrifuge rotation axis 430). In this position, the flexible loop 524 may pass from the loop connection area 454 of the filler 460 through the loop access clearance 436 of the centrifuge split-housing 404 to the fixed loop connection 402. In at least one example embodiment, the flexible loop 524 may be free to move within the loop access clearance 436 with or without contacting one or more portions of the centrifuge split-housing 404. In this position, as the centrifuge assembly 400 may rotate about the centrifuge rotation axis 430, the flexible loop 524 rotationally fixed at the fixed loop connection 402 may twist along the length of the flexible loop 524 thereby rotating the filler 460 inside the centrifuge assembly 400 (e.g., along the centrifuge rotation axis 430). As provided above, the rotation of the filler 460 relative to the centrifuge assembly 400 may be at a 2:1 ratio. For instance, as the centrifuge assembly 400 rotates one revolution, the rotationally fixed flexible loop 524 (e.g., fixed at the fixed loop connection 402) twists at the loop connection area 454 (e.g., trying to unravel from being twisted by the rotation of the centrifuge assembly 400, etc.) thereby rotating the filler 460 in the same rotational direction as the centrifuge assembly 400 but at substantially two revolutions. This rotation of the filler 460, by the twisting of the flexible loop 524 along its length, requires no gearing between the centrifuge assembly 400 and the filler 460.

Example Centrifuge Assembly in Loop-Loaded State

Figure 7A:
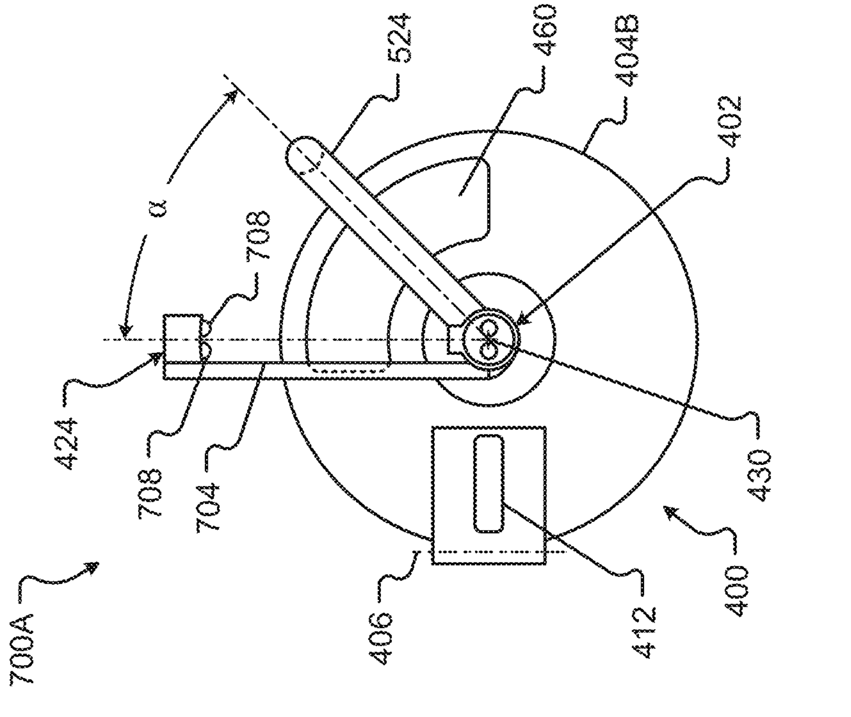
FIG. 7A shows a schematic plan view of a centrifuge assembly in a loop-loaded state in accordance with at least one example embodiment of the present disclosure.
Figure 7B:
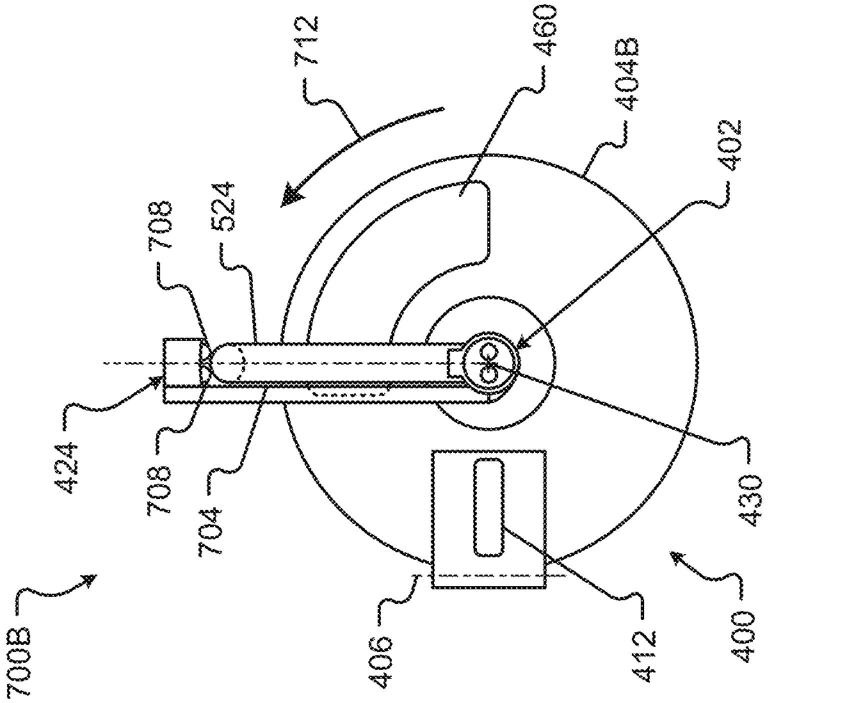
FIG. 7B shows a schematic plan view of a centrifuge assembly in an operational state in accordance with at least one example embodiment of the present disclosure.

FIGS. 7A-7B show schematic plan views of the centrifuge assembly 400 automatically loading a loop into an operational position (e.g., blood separation) for centrifuging. The centrifuge assembly 400 shown in FIGS. 7A-7B may correspond to the centrifuge assembly 400 as previously discussed and/or as described in conjunction with FIGS. 4A-4F and/or FIGS. 6A-6C. Once the blood component collection loop 520 has been loaded into the centrifuge assembly 400, as illustrated in FIG. 6C, the flexible loop 524 may be automatically loaded into a loop engaged position 520B as shown in FIGS. 7A-7B.

In at least one example embodiment, when the upper housing 404B is locked to the lower housing 404A, the flexible loop 524 may run from the loop connection area 454 of the filler 460 to the fixed loop connection 402 of the apheresis system 200. Although the flexible loop 524 may be rotationally fixed to the fixed loop connection 402 at the system static loop connector 528, the flexible loop 524 passing through the loop access clearance 436 in the centrifuge split-housing 404 may not initially be held, or at least partially captured, by the loop rotational position guide 424 and/or other features of the centrifuge assembly 400. This state of the flexible loop 524 relative to the loop rotational position guide 424, or loop arm, may correspond to an uncaptured loop state 700A. In other words, the flexible loop 524 may be oriented at some angle (a) relative to the loop rotational position guide 424, loop position stop plate 704, and/or one or more loop twist support bearings 708, or bearing sets. In at least one example embodiment, the loop twist support bearing 708 may correspond to the bearings 417 described in conjunction with FIGS. 4B-4C. A loop containment area, or channel, may be formed by the loop position stop plate 704, and/or one or more loop twist support bearings 708 disposed along a length of the upper housing 404B. In at least one example embodiment, this orientation may be engineered to allow access and/or ease of loading during the loop-loading described in conjunction with FIGS. 6A-6C.

As the centrifuge assembly 400 is rotated in a loop and filler rotation direction 712 about centrifuge rotation axis 430, the flexible loop 524 may move from the uncaptured loop state 700A to the captured loop state 700B shown in FIG. 7B. This rotation may be caused by an operator rotating the centrifuge assembly 400 and/or the filler 460 in the loop and filler rotation direction 712 and/or by the rotor and motor assembly 414 causing the centrifuge assembly 400 to rotate about the centrifuge rotation axis 430. In at least one example embodiment, as the flexible loop 524 rotates in the loop and filler rotation direction 712, an outer portion of the flexible loop 524 may contact a loop position stop plate 704, or other rotational stop surface, of the loop rotational position guide 424.

While the flexible loop 524 is held, or at least partially contained, in the loop rotational position guide 424, a portion of the flexible loop 524 may move within one or more of the loop twist support bearings 708. As described above, the flexible loop 524 may be rotationally fixed to the fixed loop connection 402 via the first connector location feature 530A of the system static loop connector 528 associated with the blood component collection loop 520. This rotationally fixed connection prevents the flexible loop 524 from rotating relative to the apheresis system 200 at the fixed loop connection 402. The other end of the flexible loop 524 may be interconnected at the loop connection area 454 of the filler 460 where the end can move with the filler 460 and/or centrifuge assembly 400. As the centrifuge assembly 400 continues to rotate in the loop and filler rotation direction 712, the forces from the flexible loop 524 attempting to unravel, or keep from binding, rotate the filler 460 and the end of the flexible loop 524 attached thereto.

In any event, once the fluid separation methods described herein are completed, the centrifuge assembly 400 may be stopped from rotating and the centrifuge split-housing 404 can be opened to remove the disposable elements of the blood component collection set 500 from the centrifuge assembly 400. In some cases, the flexible loop 524 may be moved from the captured loop state 700B shown in FIG. 7B to the uncaptured loop state 700A shown in FIG. 7A by rotating the centrifuge assembly 400 and/or the filler 460 in a direction opposite the loop and filler rotation direction 712.

Example Functional Diagram of an Example Apheresis System

Figure 8:
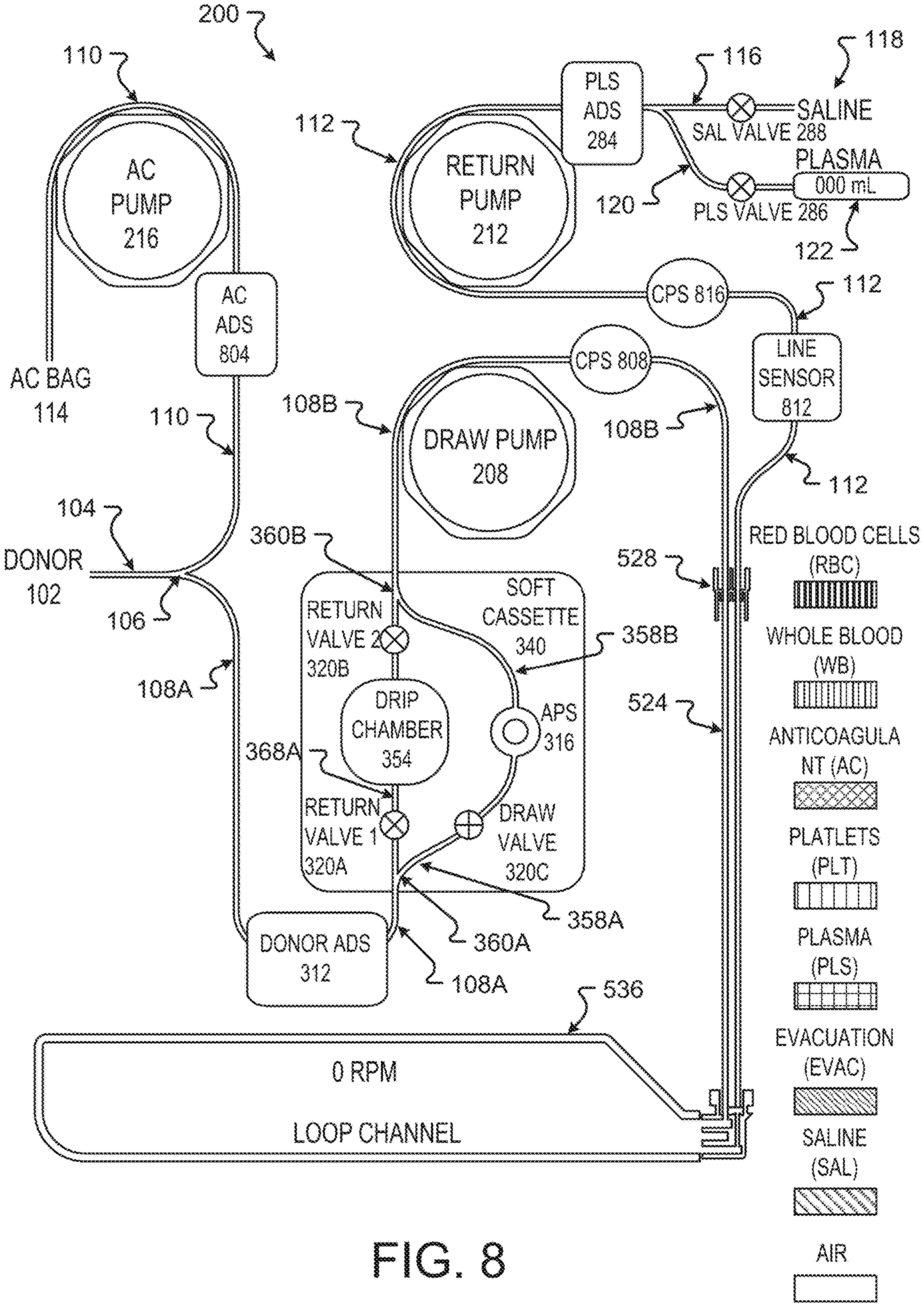
FIG. 8 is a functional diagram of an embodiment of the apheresis system in accordance with at least one example embodiment of the present disclosure.

A functional diagram of the apheresis system 200 may be as shown in FIG. 8 in accordance with at least one example embodiment of the present disclosure. The description herein shows the components previously described, in FIGS. 1-7B, in a functional diagram to describe the operation of the system 200 for extracting plasma or other blood components from the whole blood of a donor 102 during an apheresis procedure or process.

The system 200 can include an anticoagulant (AC) pump 216. The AC pump 216 pumps fluid in AC tubing 110 from the AC bag 114. The AC pump 216, the AC tubing 110, and/or the AC bag 114 may be as described previously. The AC tubing 110 may also include an AC air detection sensor (ADS) 804 to detect air or fluid within the AC tubing 110.

The AC ADS 804 may be the same or similar in type and/or function to sensor 284 and/or sensor 312, described previously. AC tubing 110 can intersect with and be fluidly associated with the donor feed tubing 104 and the cassette inlet tubing 108A at tubing connector 106. The tubing connector 106 can be any type of connection between tubing 110, 104, and/or 108A, as described previously.

The donor feed tubing 104 proceeds from the donor 102, where the donor 102 may be stuck with a lumen needle or other device, allowing whole blood to flow from the donor 102 into the apheresis system 200 and allowing blood components to flow back to the donor 102. Tubing 108A may proceed to the soft cassette 340. Further, a donor air detection sensor 312 can be placed on or in tubing 108A to detect the presence of fluid and/or air within tubing 108A.

As explained previously, the soft cassette 340 can include the first cassette port 360A, which can function as, include, and/or be substantially proximate to a “Y” connector or section, or branches, that separates the tubing 108A into the first bypass branch 358A and the first tubing section 368A (the “Y” section will be designated by reference character 360A). The two tubing sections 358 and 368 can reconnect at the second cassette port 360B, which can also function as, include, and/or be substantially proximate to a second “Y” connector or section (the second “Y” section will be designated by reference character 360B). Tubing 358 is bisected by the fluid sensor 316, which separates the tubing 358 into the first bypass branch 358A and the second bypass branch 358B. Likewise, tubing 368 is bisected by the drip chamber 354 that separates tubing 368 into a first tubing section 368A and a second tubing section 368B.

The first tubing section 368A can include a first fluid control valve 320A. The second tubing second 368B can likewise include a second fluid control valve 320B. The first bypass branch 358A can similarly include a draw fluid control valve 320C. As such, the various sections of tubing 368A, 358A, 358B, and 368B can be isolated by the valves 320A, 320B, and/or 320C based on the configuration of the system 200 and depending on the operation of the system 200.

A drip chamber 354 may be disposed between the first tubing section 368A and the second tubing section 368B. The drip chamber 354 can collect a volume of whole blood and/or high hematocrit blood (blood with a high percentage of red blood cells) depending on the operation of the system 200, as described hereinafter. The fluid sensor 316, as described previously, may be disposed between the first bypass branch 358A and the second bypass branch 358B.

The inlet tubing 108B can connect to the second cassette port 360B and can connect the soft cassette 340 to the flexible loop 524. The inlet tubing 108B may also include a sensor 808, disposed on or in the tubing 108B, placed with the tubing 108B before connecting with the system static loop connector 528 of the flexible loop 524. The pressure sensor (CPS) 808 may detect one or more of, but not limited to: pressure, presence of fluid or air, and/or possibly another characteristic of the fluid in tube 108B. Further, a draw pump 208 can cause fluid to be pumped through tubing 108B either away from the soft cassette 340 or to the soft cassette 340.

Two or more different tubes can be connected to the flexible loop 524 through the system static loop connector 528 and provide fluid to, or receive fluid from, the blood component collection bladder 536. A exit tubing 112 exits the system static loop connector 528 from flexible loop 524. This exit tubing 112 can also include another line sensor 812 disposed thereon or therein to detect fluid, air, cellular concentration, color, and/or color change in the fluid coming from the flexible loop 524; the line sensor 812 can be the same or similar in type and/or function to sensors 804, 312, 320, 808, and/or 284 previously described. A second CPS sensor 816 or fluid sensor may also be disposed in or on line 112. Sensor 816 may detect one or more of, but not limited to: the presence or absence of fluid, pressure within tubing 112, and/or other characteristic of the fluid in tubing 112. Similarly, sensor 816 can be the same or similar in type and/or function to sensors 804, 312, 320, 808, 812 and/or 284 previously described.

The exit tubing 112 may then flow into a plasma air detection sensor 284 before the saline and plasma tubing y-connector 280 separates the exit tubing 112 into saline tubing 116 and plasma tubing 120. The return pump 212 may interact with the exit tubing 112 and can cause fluid or air to flow through the exit tubing 112 from either the flexible loop 524 or from a saline bag 118 and/or a plasma collection bottle 122.

The saline bag 118 and associated tubing can be as previously described and can provide saline through the system 200 back to the donor 102. A saline flow control valve 288 can isolate the saline bag 118 from the rest of the system 200. Further, a plasma collection bottle 122 can receive plasma from the flexible loop 524 when processed or separated from the whole blood. The plasma collection bottle 122 can be selectively isolated from the system by the plasma flow control valve 286.

Electrical and Control System

Figure 9:
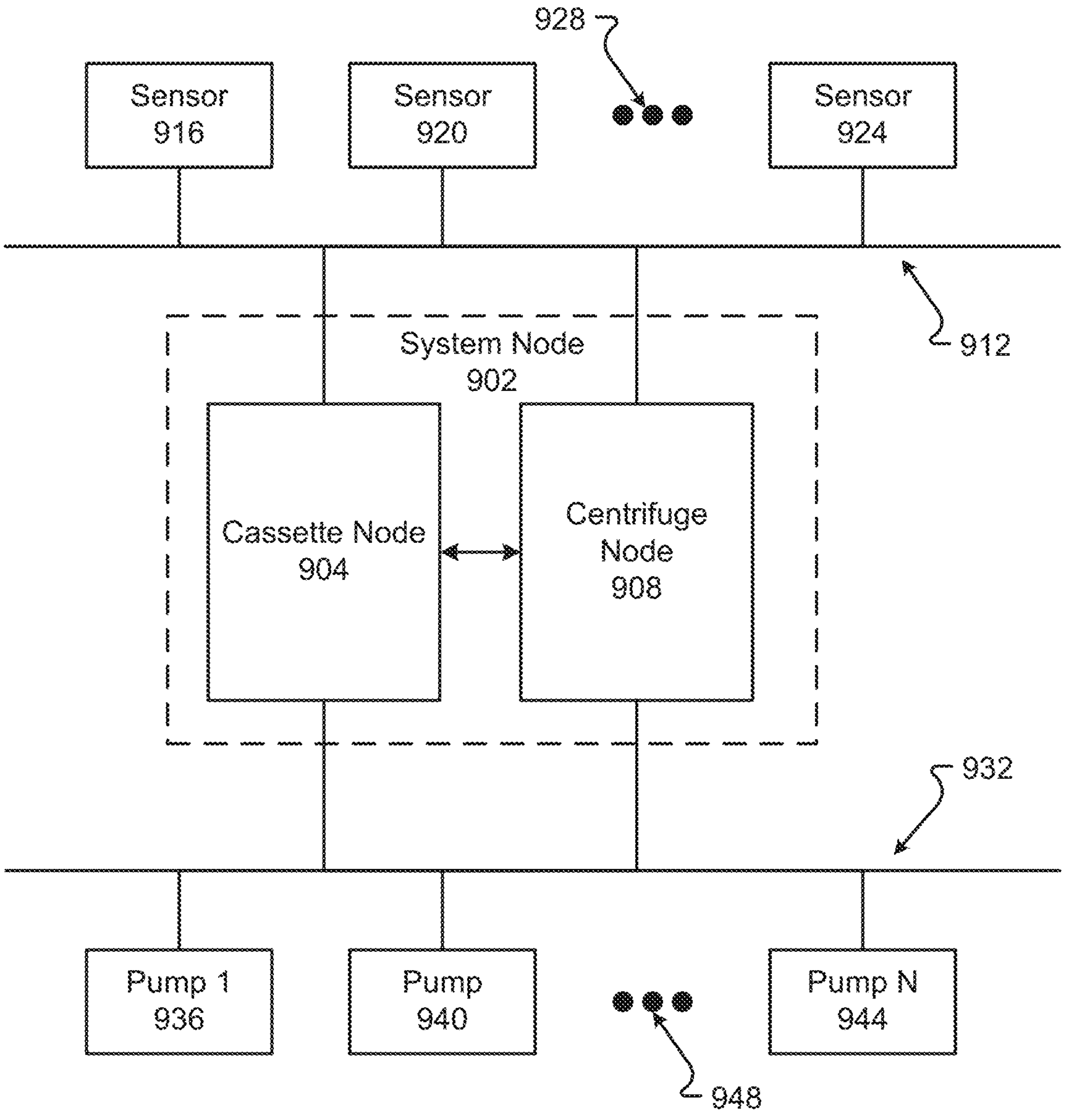
FIG. 9 is a block diagram of the electrical system of the apheresis system in accordance with at least one example embodiment of the present disclosure.

An embodiment of the electrical and control system 900 controlling the functions of the apheresis system 200 may be as shown in FIG. 9 in accordance with embodiments of the present disclosure. The control system 900 can include one or more nodes, which can include various hardware, firmware, and/or software configured to control and/or communicate with the mechanical, electromechanical, and electrical components of the apheresis system 200.

Each node may function to control a different part of the apheresis system 200. For example, the control system 900 can include a cassette node 904 which may be a soft cassette assembly system and a centrifuge node 908 that may be a centrifuge system, which may control or communicate with the components of the blood component collection set 500 (and the associated hardware or mechanical components interfacing with the soft cassette assembly 300) and the centrifuge assembly 400 (and the associated hardware or mechanical components associated therewith), respectively. The cassette node 904 and centrifuge node 908 may be in communication either wirelessly or through some other electrical or data connection. In some configurations, the cassette node 904 and the centrifuge node 908 may be separate nodes that may be two portions of a single node 902 or system. As such, each of the cassette node 904 and the centrifuge node 908 may have the same physical hardware operating to control different functions. In at least one example embodiment, the single node 902 may include physical hardware for both the cassette node 904 and the centrifuge node 908 or the cassette node 904 may include physical hardware separate from physical hardware of the centrifuge node 908. An example of the cassette node 904 may be as described in conjunction with FIG. 10; a centrifuge node 908 may be as described in conjunction with FIG. 11.

Each of the cassette node 904 and the centrifuge node 908 may be in communication with one or more sensors 916, 920, and/or 924. There may be more or fewer sensors than those shown in FIG. 9, as represented by ellipsis 928. Each of the cassette node 904 and the centrifuge node 908 can communicate directly to each sensor 916-924 or may communicate with the several sensors 916-924 via a bus 912. The bus 912 may communicate by any type of communication protocol, such as universal serial bus (USB), a universal asynchronous receive/transmit (UART), or other types of bus systems or parallel communication connections. Thus, the bus 912 may be optional, but is shown as a possible communication platform to communicate with the various sensors 916-924. The sensors 916-924 can be any type of sensor that can communicate information about light, fluid, the presence of air, color, pressure, etc., as described herein. Some of the sensors 916-924 can include sensors such as the air detection sensor 312, the fluid sensor 316, the AC ADS 804, the pressure sensor 808, the line sensor 812, the second CPS sensor 816, and/or the air detection sensor 284. The function of these sensors 912-924 may be as described hereinafter.

The cassette node 904 and the centrifuge node 908 may also communicate with one or more pump drives, pump motors, etc. 936, 940, 944, simply referred to as "pumps." There may be more or fewer pumps than are shown in FIG. 9, as represented by ellipsis 948. The cassette node 904 and the centrifuge node 908 can communicate with the pumps 936-944 through direct wired or wireless communication or through a bus 932. The bus 932 can be a control area network (CAN) bus, USB, or other type of bus architecture to communicate with the pumps 936-944. The pumps 936-944 can include or be a part of at least one of the draw pump 208, the return pump 212, and/or the AC pump 216, as previously described. The function of the pumps 936-944 may be described as herein.

Figure 10:
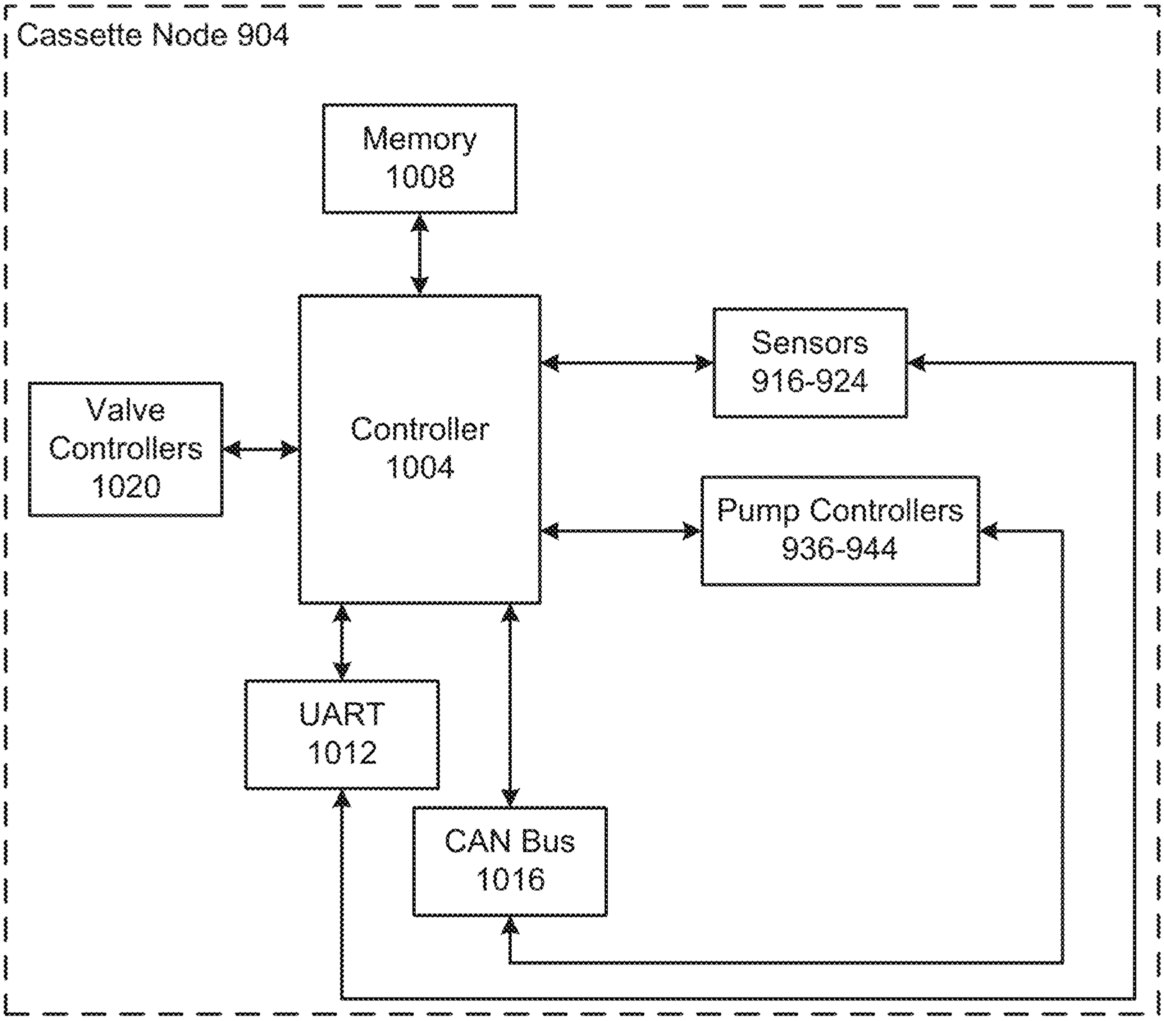
FIG. 10 is a further block diagram of the electrical system of the apheresis system in accordance with at least one example embodiment of the present disclosure.

An embodiment of the cassette node 904 may be as shown in FIG. 10 in accordance with embodiments of the present disclosure. The cassette node 904 can include one or more of a controller 1004, a memory 1008, a valve controller 1020, and/or communication interfaces for a CAN bus 1016, a UART 1012, or other types of buses. The cassette node 904 can include other hardware, firmware, and/or software that are not shown for clarity.

The controller 1004, also referred to herein as a processor, can be any type of microcontroller, microprocessor, Field Programmable Gate Array (FPGA), Application Specific Integrated Circuit (ASIC), etc. An example controller 1004 may be the NK10DN512VOK10 microcontroller, made and sold by N9P USA, Incorporated, which is a microcontroller unit with a 32-bit architecture. Other types of controllers are possible. The controller 1004 can control other types of devices or direct the functions of other types of devices, such as valves such as the first fluid control valve 320A, the second fluid control valve 320B, the draw fluid control valve 320C, the plasma flow control valve 286, the saline flow control valve 288, and the pumps 936-944, etc. Further, the controller 1004 can communicate with various sensors 916-924 or other devices to receive or send information regarding the function of the apheresis system 200.

Other examples of the processors or microcontrollers 1004, as described herein, may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, ARM® Cortex™-M processors, ARM® Cortex-A and ARM926EJ-S™ processors, other industry-equivalent processors, and may perform computational functions using any known or future-developed standard, instruction set, libraries, and/or architecture.

The memory 1008 can be any type of memory including random access memory (RAM), read only memory (ROM), electrically erasable programmable ROM (EEPROM), a portable compact disc read-only memory (CD-ROM), an optical storage device, a magnetic storage device, any suitable combination of the foregoing, or other type of storage or memory device that stores and provides instructions to program and control the controller 1004. The memory 1008 may provide all types of software or firmware that programs the functions of the controller 1004, as described hereinafter.

The controller 1004 can communicate with one or more valve controllers 1020. Each valve such as such as the first fluid control valve 320A, the second fluid control valve 320B, the draw fluid control valve 320C, the plasma flow control valve 286, the saline flow control valve 288, as described herein, may be controlled by a valve controller 1020 and may be associated with a component of the system 200, as described herein. The valve controller 1020 can provide the electrical signal, operational directive, or power to close or open any one of the valves described herein, for example, the saline and plasma valve housing 276, the plasma flow control valve 286, the saline flow control valve 288, the first fluid control valve 320A, the second fluid control valve 320B, and/or the draw fluid control valve 320C, etc.

The controller 1004 can also be connected to a bus 912, 932 (e.g., UART bus, CAN bus), or other busses through transceivers 1012, 1016 provided outside of the controller 1004 or integral to the controller 1004. The UART transceiver 1012 may communicate with one or more of the sensors 916-924 or other devices. Likewise, the CAN bus transceiver 1016 can communicate with one or more of the pump controllers 936-944 or other devices. UART transceivers 1012 and busses and CAN bus transceivers 1016 and busses are well known in the art and need not be explained further herein.

Figure 11:
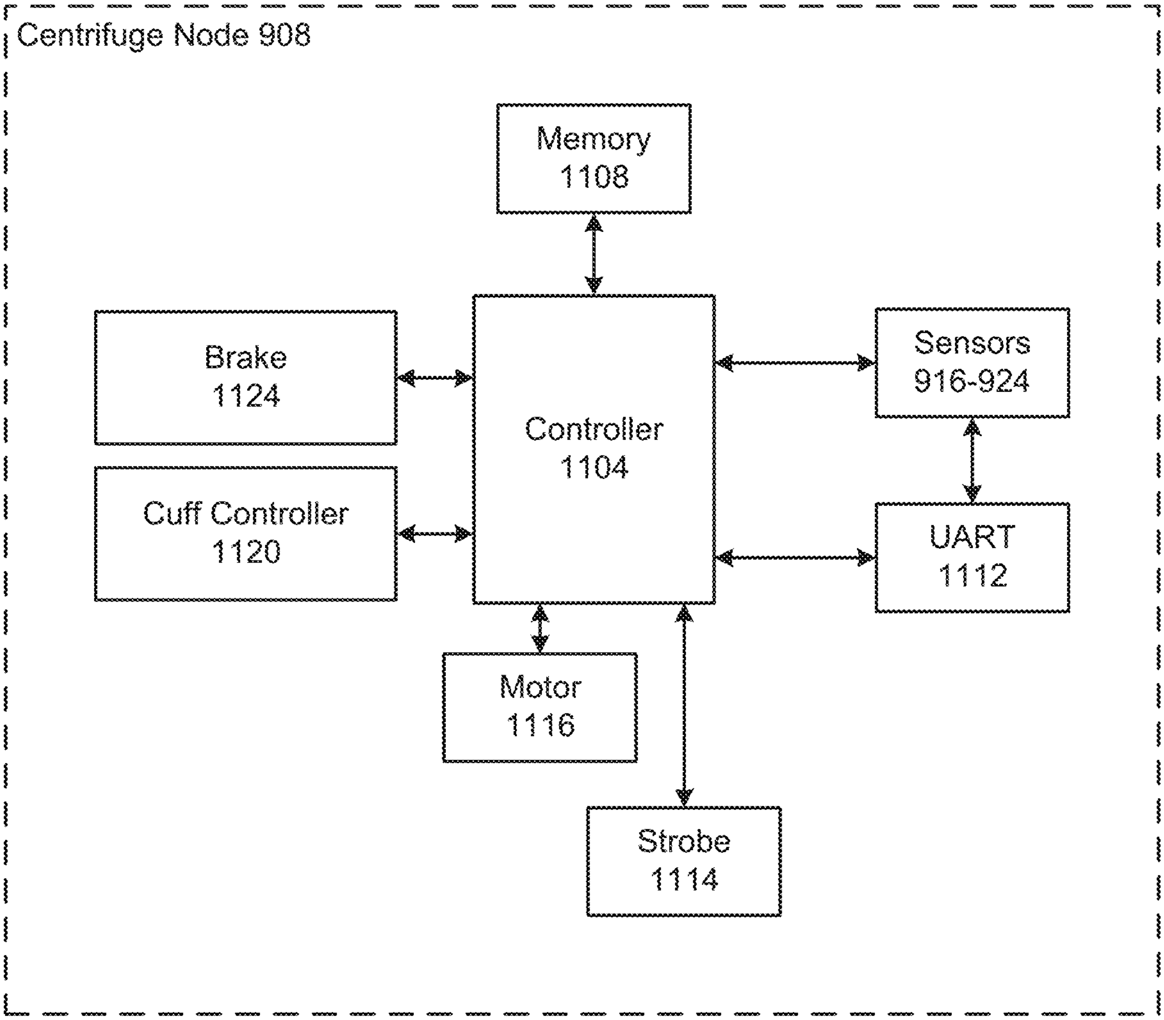
FIG. 11 is a further block diagram of the electrical system of the apheresis system in accordance with at least one example embodiment of the present disclosure.

An embodiment of the centrifuge node 908 may be as shown in FIG. 11, in accordance with embodiments of the present disclosure. The centrifuge node 908, can include the same or similar types of components as the cassette node 904. For example, the centrifuge node 908 can include a controller 1104, a UART transceiver 1112, etc. Similar to the controller 1004, the controller 1104 can be any type of processor or microcontroller, for example the NK10DN512VOK10 microcontroller unit with 32-bit architecture from N9P USA, Incorporated, as mentioned previously, or other controllers, processors, etc., for example, the devices mentioned previously.

The controller 1104 can communicate with the sensors 916-924 directly, through the UART transceiver 1112, or through other busses or systems. The controller 1104 can also communicate with a brake controller 1124 that can brake or slow and stop the centrifuge 400. Likewise, a controller 1104 can communicate with a motor transceiver 1116 that communicates with a motor power system or a motor controller that functions to spin up or rotate the centrifuge 400 or control the speed setting or other function of the centrifuge 400.

In some configurations, the controller 1104 can also communicate with a cuff controller 1120 that can change or set the pressure of a pressure cuff on a donor's arm during the apheresis process. Further, the controller 1104 can communicate with and/or control a strobe light 1114, which can be any light that flashes at a periodicity in synchronicity with the rate of spin of the motor, such that an operator of the apheresis system 200 can see the operation of the filler 460, as described previously. Thus, the controller 1104 can communicate with the strobe light 1114 to change the frequency of the flashing of the strobe light 1114, the intensity of the strobe light 1114, etc.

As should be understood the cassette node 904 and the centrifuge node 908 include additional components such as described in titled "METHODS AND SYSTEMS FOR HIGH-THROUGHPUT BLOOD COMPONENT COLLECTION", filed on Aug. 3, 2021 and assigned application Ser. No. 17/392,804, the entire contents of which are herein incorporated by reference.

Example Code Scanning and Data Control Methods

Figure 12A:
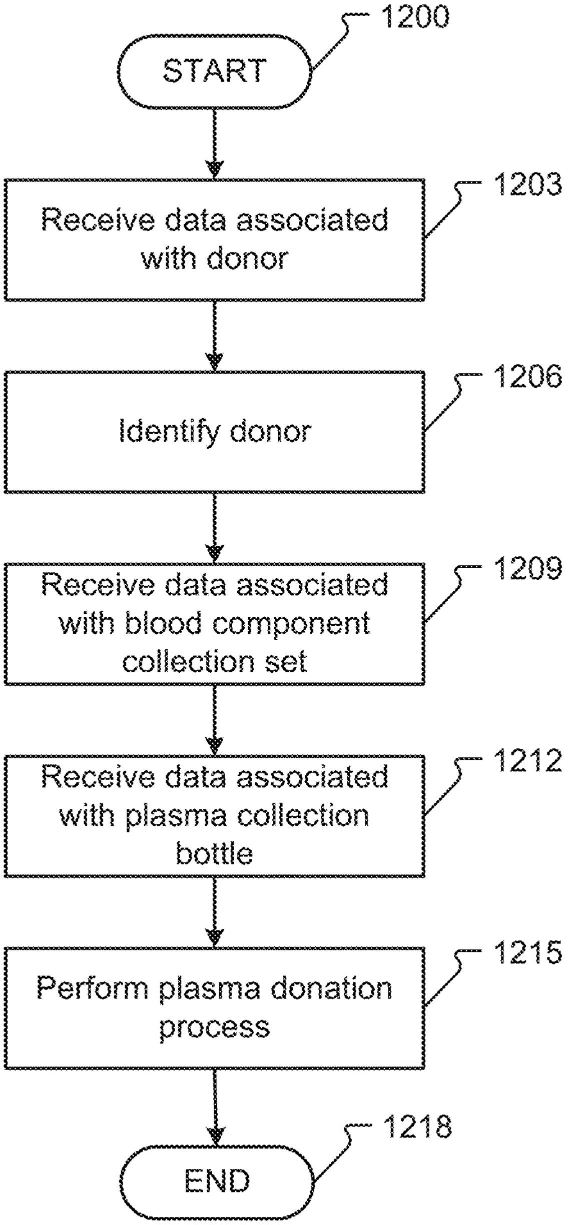
FIG. 12A is a flowchart of a method in accordance with at least one example embodiment of the present disclosure.

In at least one example embodiment, a data entry process, as illustrated in FIG. 12A, may be used to initialize an apheresis system 200 for each new donor 102. The data entry process may ensure a target amount or volume of plasma based on donor weight or other donor information is obtained. Also, information such as bottle identification may be entered through the data entry process such that the apheresis system may be capable of recording in memory an indication as to which bottle was used for which donor.

Figure 12B:
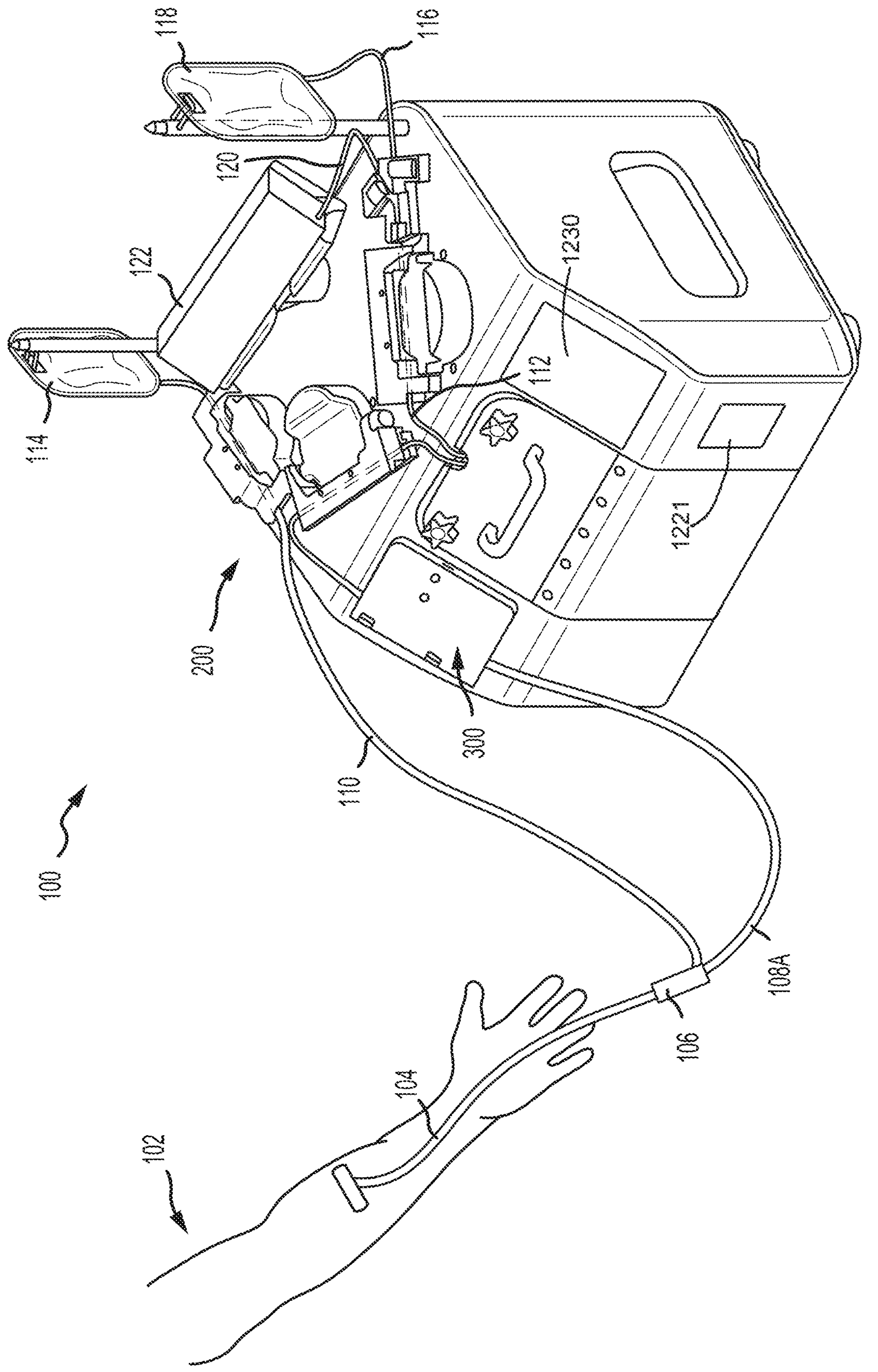
FIG. 12B shows an apheresis system with a scanner in accordance with at least one example embodiment of the present disclosure.
Figure 12C:
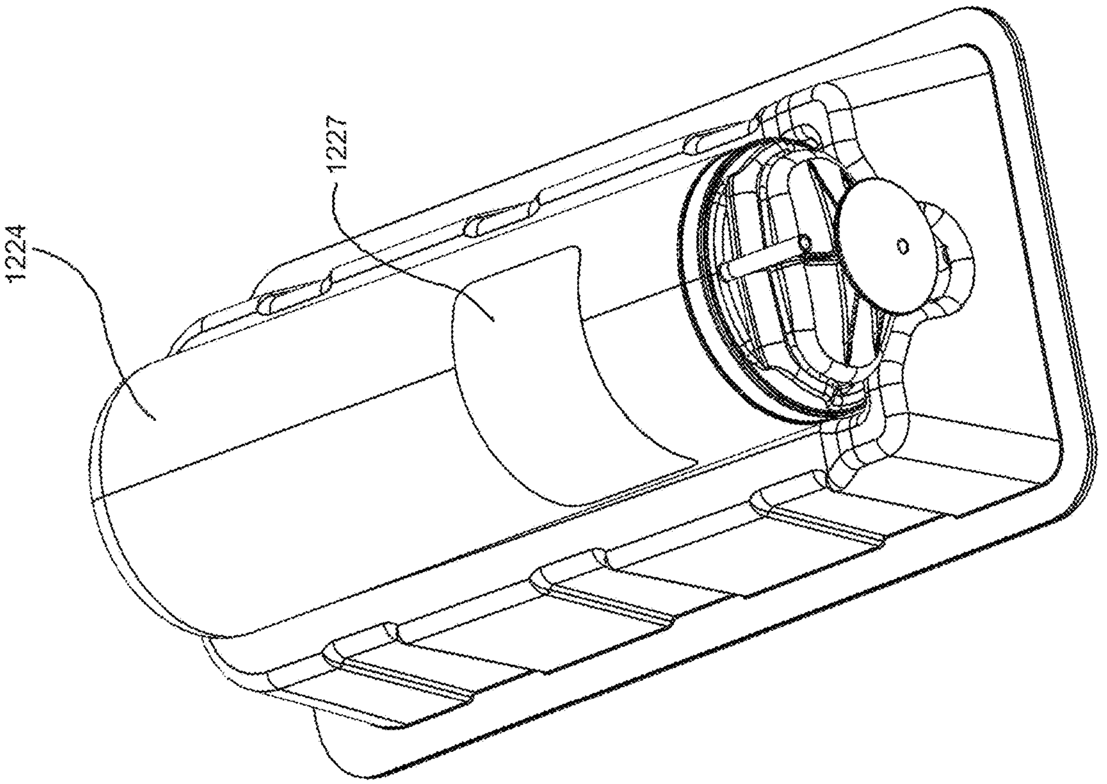
FIG. 12C shows a bottle in accordance with at least one example embodiment of the present disclosure.

In at least one example embodiment, the process of FIG. 12A may begin at 1200 in which the apheresis system 200 may be powered on and waiting for a new donor. The apheresis system 200 may include an integrated identification reader (e.g., RFID reader, barcode reader, etc.) 1221, as illustrated in FIG. 12B, configured to read a code (e.g., RFID tag, barcode, etc.) associated with a particular donor 102 and control operations of the apheresis system 200 based on the information read by the identification reader. The information may include but is in no way limited to individual donor data (e.g., body mass index (BMI), 1st time donor, weight, height, etc.). This information may be used for faster and higher quality donor experiences. Codes may also be used to label other equipment used during the donation process, such as a label 1227 on a bottle 1224 used for plasma collection as illustrated in FIG. 12C.

At 1203, the reader 1221 of the apheresis system 200 may be used to scan a barcode, QR code, or other type of image to receive data associated with a donor. In at least one example embodiment, the reader 1221 may be configured to read input from an RFID. For example, the donor may use an ID card or other type of object which may comprise one or more of a barcode, QR code, RFID, etc. By scanning the ID card or other type of object, the apheresis system 200 may be enabled to receive data relating to the donor.

Barcodes (e.g., 1D, 2D, etc.) may be read by an integrated barcode scanner disposed on a front of the apheresis system. For example, when starting the apheresis procedure, a user may scan a donor ID (e.g., from a PDA, phone, tablet, etc.), a blood component collection set (e.g., separation set), and/or a plasma collection bottle, sequentially and without requiring further input from the user via the user interface. The system may be enabled to receive the information and confirm entry of the data automatically and without human input. As can be appreciated, this automatic sequential intake of data increases the speed of the operation compared to conventional nonsequential inputting.

Data received from the donor may comprise biological information such as age, weight, height, donor history, or other information which may be relevant to the donation process. The data received from the donor may be used to determine whether the donor qualifies for the donation procedure and to determine particular settings which may be required for the donation procedure, such as a total expected amount of plasma or other information. For example, the height and weight of the donor may be used to determine a body mass of the donor. The body mass of the donor may then be used to determine the target amount or volume of plasma to be collected.

In at least one example embodiment, the information may be portable between donation sites, apheresis systems 200, locations, etc. The information may be stored in the form of a nomogram, for example, in a 2D barcode. In this way, a donor may be enabled to carry a single form of identification between donation sites and each donation site may be enabled to collect information about the donor, such as time since the last visit.

The information stored in the nomogram, and that is capable of being read by the integrated identification reader, may be limited to information that the apheresis system 200 is allowed to collect (e.g., by privacy laws, health laws, etc.). In at least one example embodiment, other private information may be stored in the 2D barcode, but may be encrypted, or locked, from being read by the integrated identification reader of the apheresis system 200.

The apheresis system 200 may scan, or read, the barcode and then determine what operations to perform. For example, the barcode may contain information regarding the weight and the height of the donor 102, which may be used to define the amount or volume of plasma the donor 102 can provide or donate. As can be appreciated, a donor 102 having a first weight may be allowed to donate a first amount of plasma while a donor 102 having a heavier second weight may be allowed to donate a second amount of plasma that is greater than the first amount. Additionally, the body mass of the donor 102 may be used to define the amount or volume of plasma the donor 102 can provide or donate. Once the apheresis system 200 reads the barcode, the apheresis system 200 can adjust the settings based on the information, and cease operations when the requisite amount of plasma, etc., is collected.

The apheresis system 200 may also be enabled to write information which may be read by other apheresis systems in the same or other donation sites. For example, donor data may be stored at a network location. The apheresis system 200 may be enabled to send data such as donation results, a current weight of the donor, a date and/or time of the donation, or other information.

In at least one example embodiment, the apheresis system 200 may comprise one or more computer systems. For example, as will be discussed in greater detail below with respect to FIG. 16D, the apheresis system 200 may include one or more computer systems 1627 which may comprise a processor 1630, memory 1633, input/output devices 1636, one or more pump control systems 1639, one or more sensors 1642, and/or other elements as can be appreciated.

In at least one example embodiment, as will be discussed in greater detail below with respect to FIG. 16B, the apheresis system 200 may be enabled to communicate with a server 1621 via a network 1618, such as the Internet. In at least one example embodiment, the apheresis system 200 may communicate with a local computer system, such as a computer on location at a donation site, which may be configured to communicate with the server.

Figure 12D:
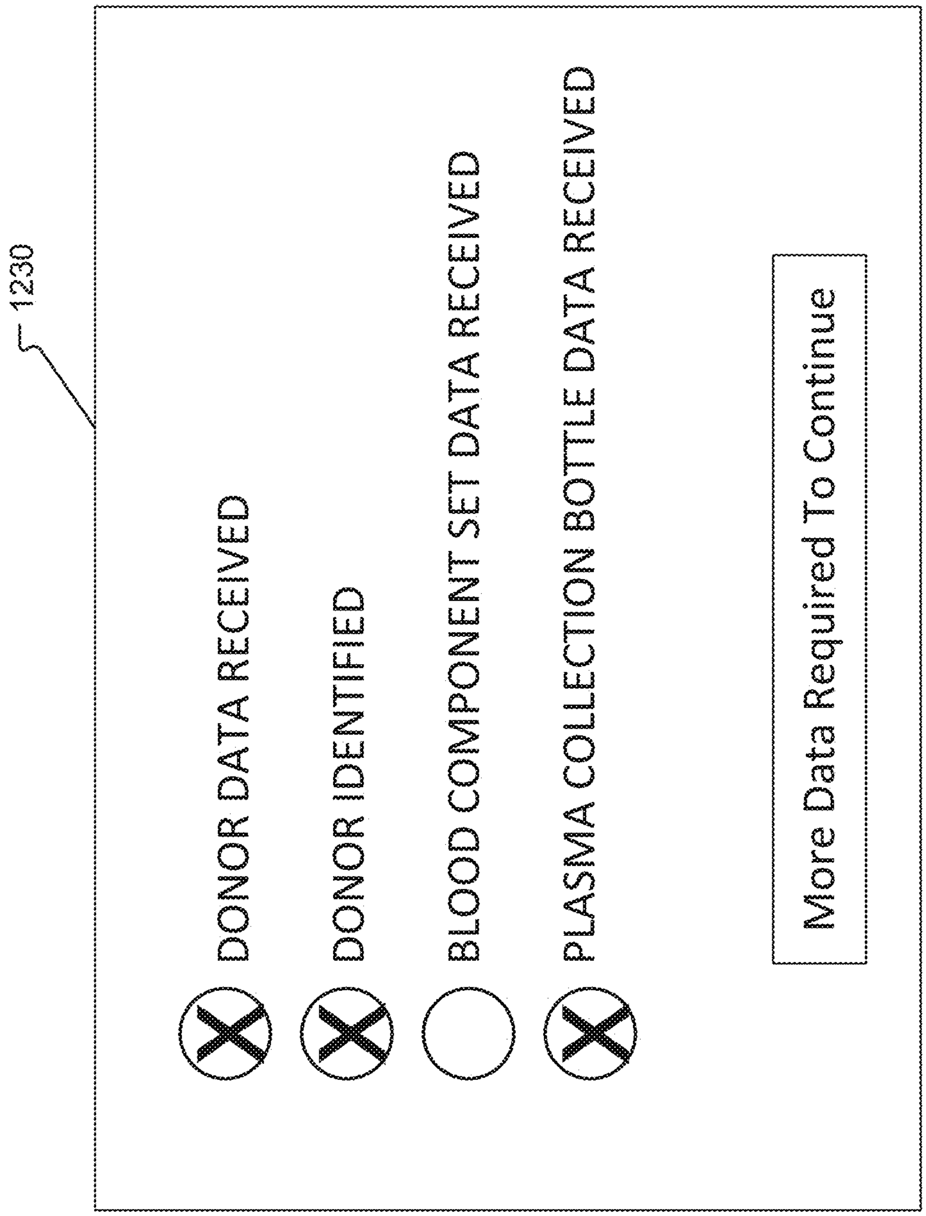
FIG. 12D shows a graphical user interface in accordance with at least one example embodiment of the present disclosure.

In at least one example embodiment, after receiving the data associated with the donor, the apheresis system 200 may confirm receipt of the data associated with the donor through a feedback system such as a graphical user interface (GUI) 1230, as illustrated in FIGS. 12B and 12D. In this way, a nurse, practitioner, or other user of the apheresis system 200 may be enabled to quickly ascertain whether the donor information has been properly inputted into the apheresis system 200. In at least one example embodiment, the feedback system may also or alternatively comprise a speaker which may be configured to provide audible feedback.

At 1206, the apheresis system 200 may be configured to determine, based on the data associated with a donor, an identification of the donor. For example, the apheresis system 200 may be configured to identify, using the data received via the scanner 1221, whether the donor is associated with any donor ID information in a database or whether the donor is a new donor. In at least one example embodiment, the scanner 1221 may access donor information from a server or other computer system either locally or via a network connection.

Donor ID information accessed via a database may comprise information such as age, body mass, weight, height, and/or a target volume, i.e., an expected amount of plasma, or other donation fluid, to be received from the donor.

At 1209, the apheresis system 200 may receive data associated with a blood component collection set. The blood component collection set may comprise, for example, a soft cassette assembly, such as the soft cassette assembly 300, to be used during the donation process. The data associated with the blood component collection set may be received by the apheresis system 200 via a barcode, a QR code, an RFID chip, or other type of scannable object which may be placed on the blood component collection set. For example, each blood component collection set may be affixed with a label or sticker which may include a distinct barcode, QR code, RFID chip, or other type of scannable object. By scanning the label or sticker on the blood component collection set, the apheresis system 200 may be enabled to record into memory which blood component collection set is being used for the current donation process. In this way, the apheresis system 200 may be enabled to associate donor with a blood component collection set. Any data received during the scanning process may be recorded into memory and shared with a server or other type of computing system.

The data associated with the blood component collection set may comprise a date of manufacture, an identity of manufacturer, for other information which may be useful for data processing purposes after the donation is complete. In at least one example embodiment, data associated with the blood component collection set received through scanning may be used to determine a type of blood component collection set. The type of blood component collection set may be used by the apheresis system to adjust one or more settings such as flow rate or other information during the donation process.

In at least one example embodiment, after scanning the blood component collection set, a user of the apheresis system 200 may be enabled to receive confirmation of the receipt of the information from the blood component collection set. For example, a graphical user interface 1230, as illustrated in FIG. 12D, may display an indication as to whether data from a blood component collection set has been received. Such a graphical user interface 1230 may be used by an operator of the apheresis system during the process of initializing the apheresis system for a new donor.

In at least one example embodiment, instead of or in addition to displaying through a graphical user interface, the apheresis system may play an audible sound through one or more speakers or display lights of various colors to indicate the data has been received.

At 1212, the method may comprise receiving, with the apheresis system 200, data associated with a plasma collection bottle. For example, to initialize the apheresis system 200 for a new donor, a plasma collection bottle may be required. After donation, the plasma collection bottle may be filled with the donated plasma. For data tracking purposes, the plasma collection bottle may be required to be associated with the donor. For example, information linking the donor to the plasma collection bottle may be stored in memory. For this reason, it may be necessary for an identity of the plasma collection bottle to be recorded. As such, a user of the apheresis system 200 may be enabled to scan a label, sticker, or other object on or printed on the plasma collection bottle using the apheresis system 200. For example, as illustrated in FIG. 12C, a plasma collection bottle 1224 may be affixed with a sticker or label 1227. In some example embodiments, the sticker or label 1227 includes a QR code.

As with other steps, upon receiving data from a plasma collection bottle, the apheresis system 200 may acknowledge receipt of the data via a graphical user interface, speaker, white, or other feedback system.

At 1215, the apheresis system may perform a plasma donation process based on the information received in the above steps. For example, the apheresis system 200 may perform the plasma donation process using information about the identity of the donor. Data received from the plasma collection bottle and/or the blood components may also be used during the plasma donation process.

For example, a rate of flow during the plasma donation process may be controlled based on one or more of a body mass and a weight of the donor determined based on the received data associated with the donor. A volume of plasma collected may also be controlled based on one or more of a body mass and a weight of the donor determined based on the received data associated with the donor.

At 1218, the process may end, at which point the donation process may continue with the extraction of fluids from the donor being completed. Any data received through the steps discussed above may be recorded into memory and/or shared with one or more computer systems. For example, a database entry may be created for the particular donation, including information such as an amount or volume of plasma extracted from the donor, a current weight of the donor, a time and/or date of the donation, and/or other information.

At least one example embodiment of the present disclosure includes a method comprising: receiving, with an apheresis system, data associated with a donor; determining, based on the data associated with a donor, an identification of the donor; receiving, with the apheresis system, data associated with a blood component collection set; receiving, with the apheresis system, data associated with a plasma collection bottle; and performing, with the apheresis system, a plasma donation process based on the identification of the donor, the data associated with the blood component set, and the data associated with the plasma collection bottle.

Aspects of the above embodiment include wherein receiving the data associated with the donor comprises scanning, with a scanner, an image. Aspects of the above embodiment include wherein the scanner is disposed on the apheresis system. Aspects of the above embodiment include wherein the image is one of a one-dimensional barcode and a two-dimensional barcode. Aspects of the above embodiment include wherein the image is displayed on a user device. Aspects of the above embodiment include wherein receiving the data associated with the donor comprises scanning an RFID. Aspects of the above embodiment include, after receiving the data associated with the donor, confirming receipt of the data associated with the donor through a feedback system. Aspects of the above embodiment include wherein the feedback system comprises one or more of a speaker and a graphical user interface. Aspects of the above embodiment include determining, based on the data associated with the donor, the donor is a new donor Aspects of the above embodiment include determining, based on the data associated with the donor, one or more of a body mass and a weight of the donor Aspects of the above embodiment include wherein receiving the data associated with the blood component collection set comprises scanning, with a scanner, one or an image and an RFID attached to the blood component collection set. Aspects of the above embodiment include, after receiving the data associated with the blood component collection set, confirming receipt of the data associated with the blood component collection set through a feedback system. Aspects of the above embodiment include wherein the feedback system comprises one or more of a speaker and a graphical user interface. Aspects of the above embodiment include wherein receiving the data associated with the plasma collection bottle comprises scanning, with a scanner, one or an image and an RFID attached to the plasma collection bottle. Aspects of the above embodiment include, after receiving the data associated with the plasma collection bottle, confirming receipt of the data associated with the plasma collection bottle through a feedback system. Aspects of the above embodiment include wherein the feedback system comprises one or more of a speaker and a graphical user interface. Aspects of the above embodiment include wherein a rate of flow during the plasma donation process is controlled based on one or more of a body mass and a weight of the donor determined based on the received data associated with the donor.

Example Calibration, Maintenance, and Service of Apheresis Systems

The apheresis system 200 may comprise one or more devices, systems, and/or features that are configured to allow the apheresis system 200 to be calibrated in the field. For example, the apheresis system 200 may comprise one or more devices, systems, and/or features that are configured to allow the apheresis system 200 to be calibrated in the field. Stated another way, the apheresis system 200 may be calibrated after manufacturing and after being installed in a donor processing location. Conventional systems provide no way of being calibrated while in the field.

In at least one embodiment, the apheresis system 200 may be self-calibrating. The apheresis system 200 may comprise a pump and syringe that utilizes pressure supplied from a compressor integrated with the apheresis system 200, for example, to set a calibration pressure. In other embodiments, the compressor may not be integrated with the apheresis system 200 and may be a component separate from the apheresis system 200. The apheresis system 200 may also include a test port that is configured to generate a known or calibration pressure using, for example, the pump and the compressor. In at least one example embodiment, the test port is positioned on a back side of the apheresis system 200 adjacent other ports, such as a pressure cuff connection that can change or set the pressure of a pressure cuff on a donor's arm during the apheresis process, as set forth above with respect to FIG. 11. Tubing of a blood component collection loop 520, calibration tube set, etc., may be attached or otherwise interconnected to the test port for testing and/or calibration. When interconnected with the test port, the compressor generates the known calibration pressure, and a pressure sensor in the apheresis system 200 may calibrate based on the detected pressure by the pressure sensor. For example, the known calibration pressure may be compared to the detected pressure and the difference may be used to calibrate the pressure sensor. The pressure sensor may be located at, for example, the test port, or may be located anywhere in the apheresis system 200.

Figure 13A:
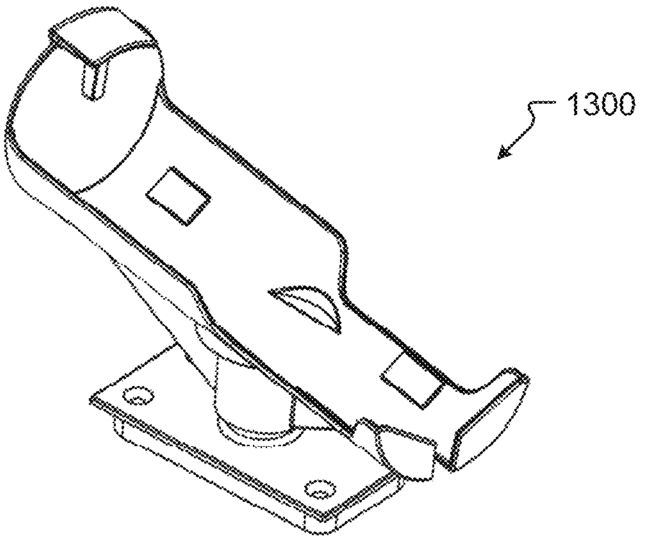
FIG. 13A is an isometric view of a plasma collection bottle holder according to at least one example embodiment of the present disclosure.
Figure 14A:
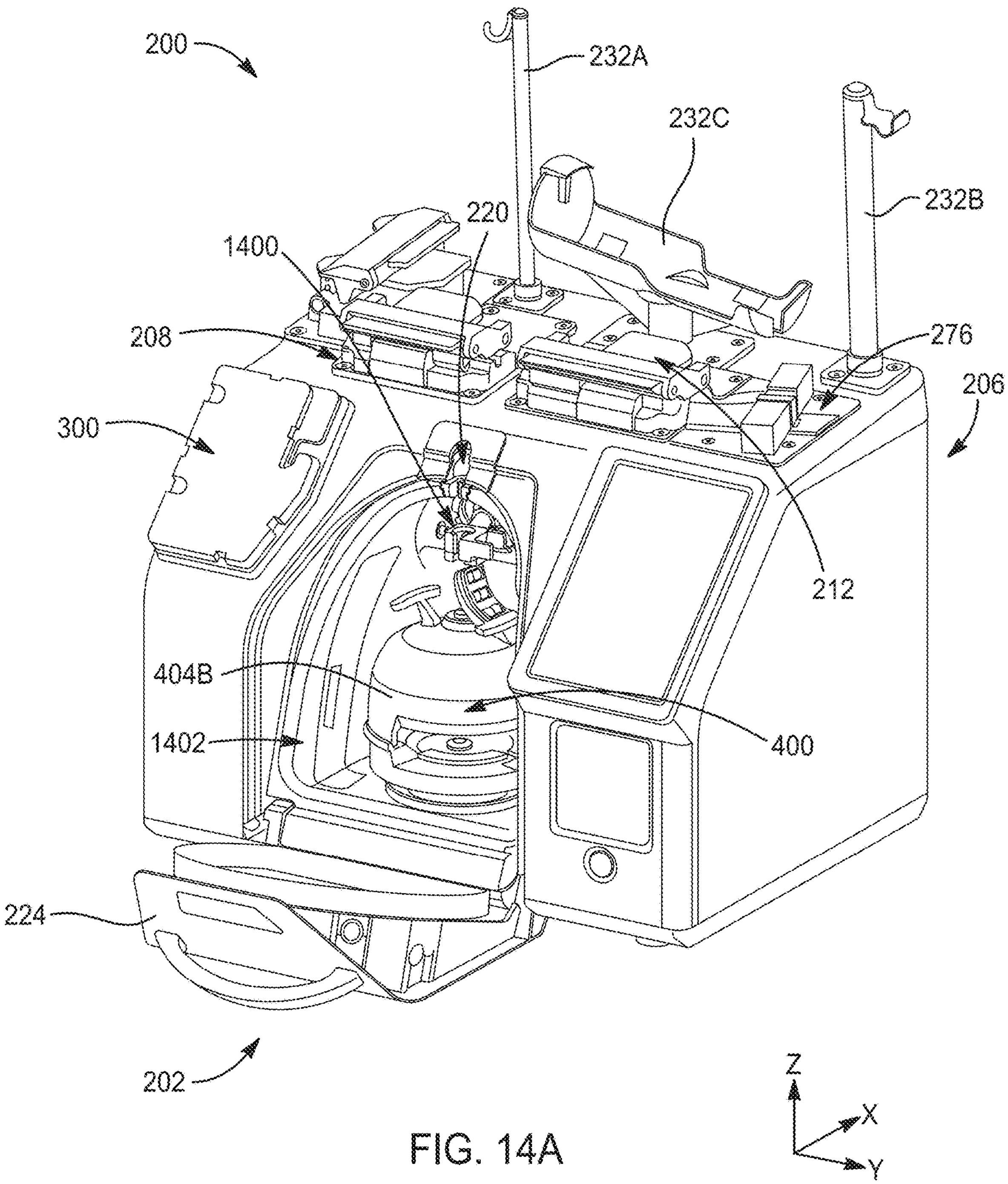
FIG. 14A is a perspective view of a moving loop holder of an apheresis system in accordance with at least one example embodiment of the present disclosure.

Calibration may also comprise using a calibration object with a known weight (such as, for example, a NIST weight) to check and/or calibrate a holder, such as the holder 1300 shown in FIG. 13A and/or the bottle tray load cell assembly shown in FIGS. 15A-15C, which will be discussed in greater detail below. In at least one example embodiment, the holder 1300 may be configured to receive the plasma collection bottle 122. The holder 1300 may be disposed on the top cover 210 of the housing 204 and may be may be similar to the plasma collection cradle 232C, as shown in FIG. 14A. The holder 1300 may comprise a weight sensor configured to sense a weight of an object placed on the holder 1300. As such, during a calibration, the calibration object may be placed on the holder 1300 and the weight sensor may detect the weight of the calibration object. A difference in the known weight of the calibration object and the detected weight as detected by the weight sensor may indicate that the weight sensor may need calibration (which may be automatically triggered by the difference) or service. In at least one example embodiment, if the difference is greater than a predetermined threshold, then the apheresis system 200 may automatically trigger calibration of the weight sensor. In other embodiments, a notification may be generated to alert a user to calibrate the weight sensor if the difference is greater than the predetermined threshold.

Calibration test(s) and/or calibration may be performed when one or more components are exchanged or swapped on the apheresis system 200. For example, exchanging or replacing one or more pumps (e.g., pumps 208, 212, 216) may trigger the calibration test(s). Calibration (whether of the pressure, sensors, weight, etc.) may be automatically performed if one or more components of the apheresis system 200 does not pass the calibration test(s). If the calibration of one or more components is unsuccessful, the apheresis system 200 may be locked and may not be used until each component passes its respective calibration test.

Figure 13B:
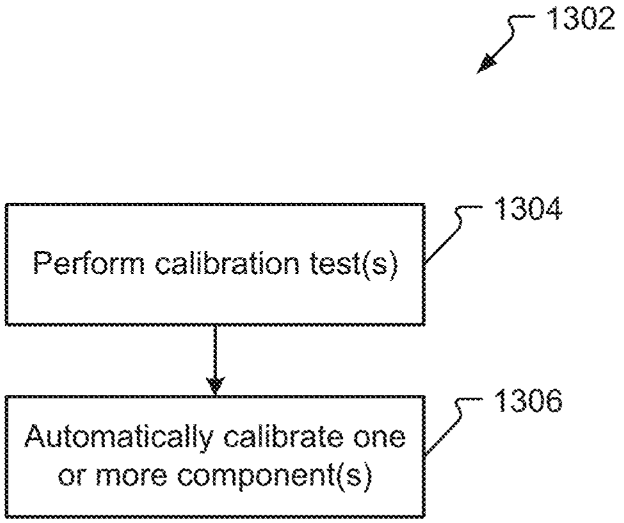
FIG. 13B is a flow chart according to at least one example embodiment of the present disclosure.

The method 1302 for performing a calibration test and calibration illustrated by the flowchart of FIG. 13B may begin at 1304. At the beginning of the method 1302, one or more calibration test(s) may be performed or executed. The calibration test(s) may be automatically triggered by exchanging or replacing one or more components (e.g., one or more sleds, sensors, pumps, etc.) of an apheresis system, such as the apheresis system 200. In other example embodiments, the calibration test(s) may be triggered by user input. In still other example embodiments, the calibration tests may be performed prior to use of the apheresis system 200.

At 1306, one or more components of the system (e.g., calibration tubing, sensors, pumps, etc.) may be automatically calibrated. The calibration may be triggered by, for example, failure of at least one test of the one or more tests executed in the step 1304. In other example embodiments, the calibration may be triggered by user input. The calibration may be executed using one or more calibration tools such as, for example, a pump, a test port, a calibration object, or the like. The calibration may cause a user interface such as a graphical user interface (GUI) to alert a user to connect one or more calibration tooling(s) or components to run the calibration.

It will be appreciated that the step 1304 and 1306 may be repeated (whether separately or together). For example, a component may fail a calibration test in step 1304, the component may be automatically calibrated in the step 1306, and the component may be retested in the step 1304 to test whether the component was properly calibrated.

The apheresis system 200 may also include one or more protocols to service the device. These protocols may include Calibrate (described above), Auto-Test (e.g., testing limits and full range), Fluid Run (with actual parameters), and/or the like. In at least one example embodiment, a saline check may be executed. In such embodiments, the apheresis system 200 may comprise a weight sensor configured to sense a weight of the plasma collection bottle 122. Saline may be moved from the saline bag 118 to the plasma collection bottle 122 and a change in the weight of the plasma collection bottle 122 may be detected by the weight sensor. Such a change in weight indicates that saline is properly flowing from the saline bag 118, through the saline tubing 116, and to the plasma collection bottle 112. In at least one example embodiment, a disposable test may be executed to check the blood component collection set 500 for leaks. In such embodiments, the apheresis system 200 may include a pump configured to form a vacuum in the blood component collection set 500. The apheresis system 200 may also include a sensor for detecting such leaks in the blood component collection set 500. In at least one example embodiment, a centrifuge test may be executed to test the centrifuge assembly 400. In such embodiments, a motor of the rotor and motor assembly 414 may be activated to validate proper rotation of the centrifuge assembly 400.

Example Moving Loop Holder

Figure 14B:
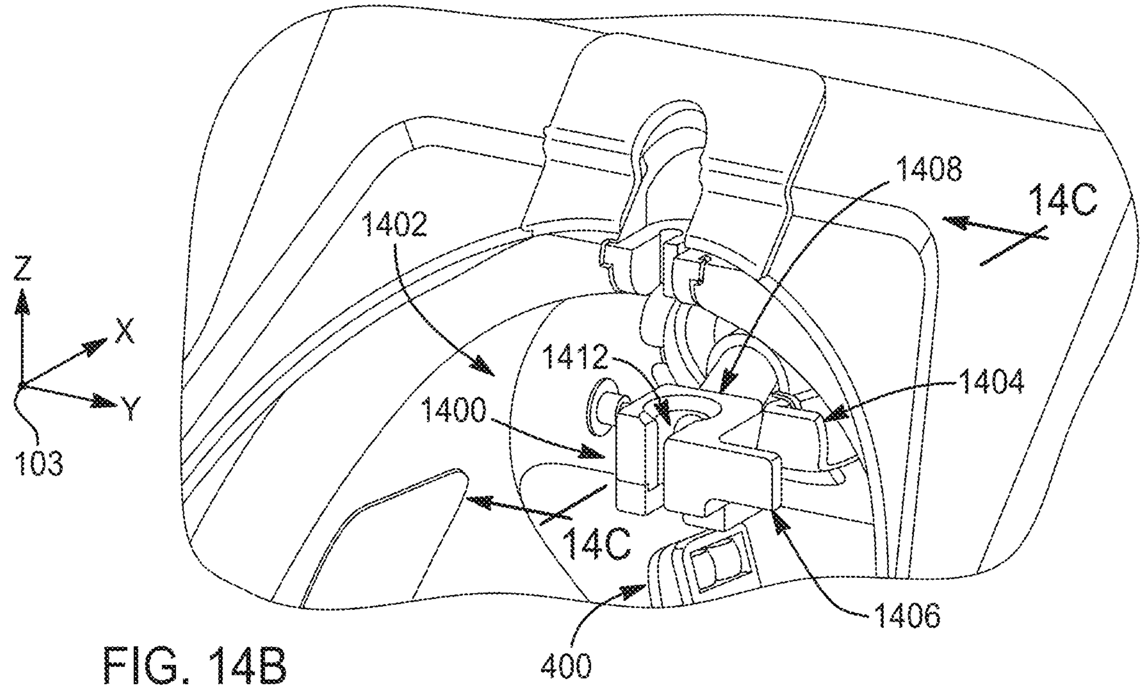
FIG. 14B is a partial view of the moving loop holder illustrated in FIG. 14A.

FIGS. 14A-14F illustrate a moving loop holder 1400 as included in the apheresis system 200. As illustrated, the moving loop holder 1400 may be at least partially disposed within the centrifuge chamber 1402 of the apheresis system 200. The centrifuge chamber 1402 is defined as the interior space of the apheresis system 200 where the centrifuge assembly 400 is housed and, for example, as located behind the access panel 224. As illustrated in FIG. 14B, the moving loop holder 1400 may be arranged above the centrifuge assembly 400 (e.g., offset from the centrifuge assembly 400 in the positive z-axis direction). The moving loop holder 1400 may correspond to the fixed loop connection 402, or a portion of the fixed loop connection 402, as described above.

The moving loop holder 1400 may include a loop holder body (also referred to as a loop holder) 1408 having a loop connection space (also referred to as a loop connection) 1412. A portion of the blood component collection set 500 may be held by the loop connection space 1412. For example, as illustrated for example in FIG. 14C, the loop connection space 1412 may be configured to receive or capture a portion of the flexible loop 524, the system static loop connector 528, or a combination thereof. In at least one example embodiment, a connector lock wheel 1424 and flange 1428 may work to lock (positively) the system static loop connector 528 within the loop connection space 1412. For example, as illustrated, the system static loop connector 528 and/or the flexible loop 524 may be disposed between the connector lock upper wheel 1424 and the flange 1428 and the connector lock upper wheel 1424 may be moved relative to the flange 1428 to apply a holding pressure to the system static loop connector 528 and/or the flexible loop 524. In at least one example embodiment, the moving loop holder 1400 may allow for a shorter distance of the flexible loop 524 to be used in the blood component collection set 500 than would be required absent the moving loop holder 1400. In certain variations, the shorter distance may lower an effective circulating volume of the blood component collection set 500. The shorter distance may reduce waste, for example, from materials used to make the blood component collection set 500, blood components remaining in the blood component collection set 500 after use, and the like. The shorter distance may provide a controlled length of the flexible loop 524 such that the flexible loop 544 resists tangling, catching, and/or ensures proper loading in the apheresis system 200.

The moving loop holder 1400 may be movable (using an automated process or a manual process) between a first or operational or extended state (see, e.g., FIGS. 14A-14B and 14D) and a second or load or restricted state (see, e.g., 14E). For example, the moving loop holder 1400 may be moveable (along the x-axis) from an extended position near a first or front side 202 of the apheresis system 200 to or towards a second or rear side 206 of the apheresis system 200. While in the extended position, the moving loop holder 1400 may be fixedly coupled to the blood component collection loop 520. While in the retracted position, the blood component collection loop 520 may be detached or disconnected from the loop holder body 1408. For example, the moving loop holder 1400 may include a release latch 1404 may be actuated (e.g., pulled, unlatched, etc.) unlocking the moving loop holder 1400 from a first or locked state to a second or unlocked state. In the unlocked state, the loop holder body 1408 may be moved in a retraction direction 1420 (e.g., away from the front 202 and toward a rear 206 of the apheresis system 200 and/or housing 204). The retraction direction 1420 may be defined along both the x-axis and the z-axis in the XZ-plane.

Figure 14C:
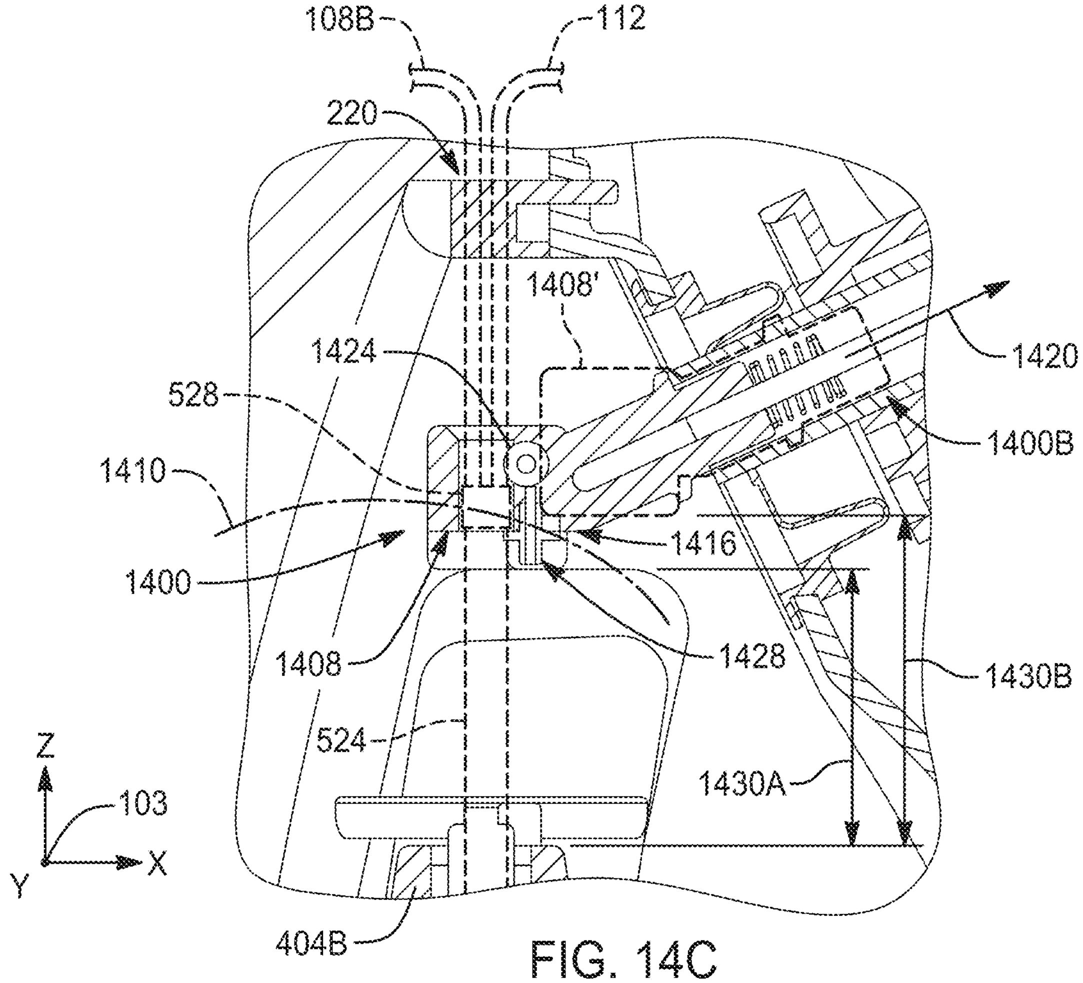
FIG. 14C is an elevation cross-sectional view along line 14C illustrated in FIG. 14B.
Figure 14D:
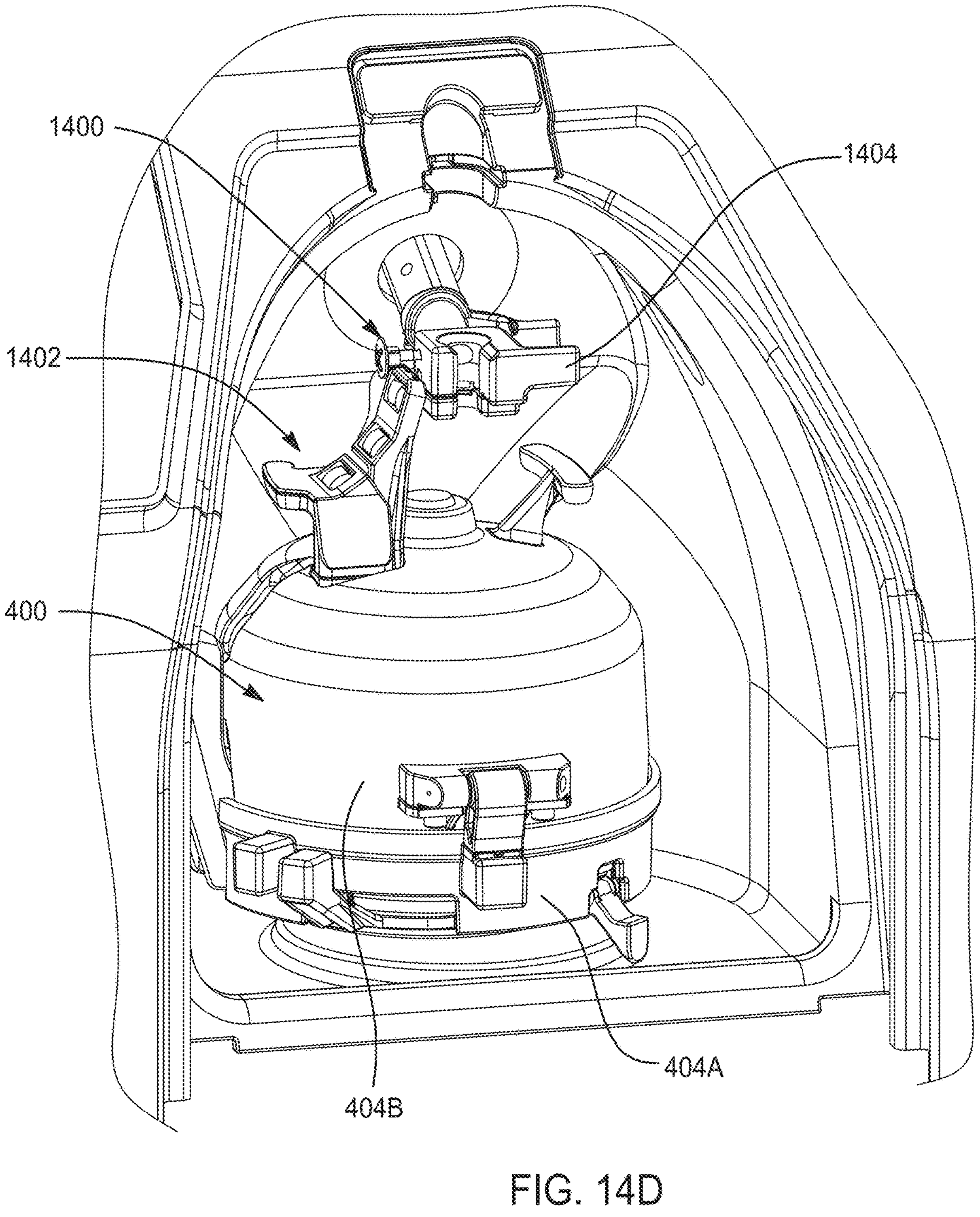
FIG. 14D is a partial view of the moving loop holder in an extended position in accordance with at least one example embodiment of the present disclosure.
Figure 14E:
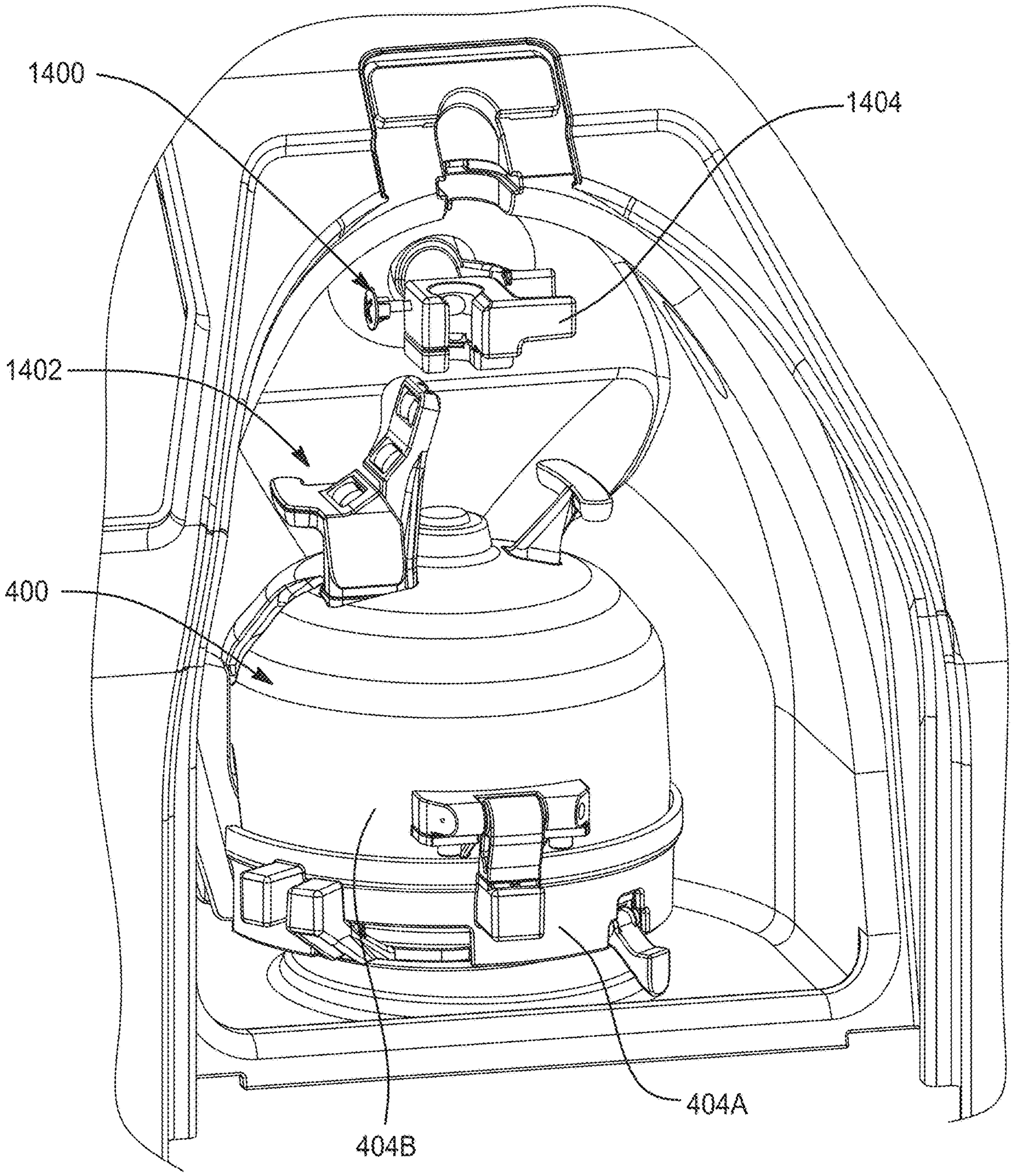
FIG. 14E is a partial view of the moving loop holder in a retracted position in accordance with at least one example embodiment of the present disclosure.
Figure 14F:
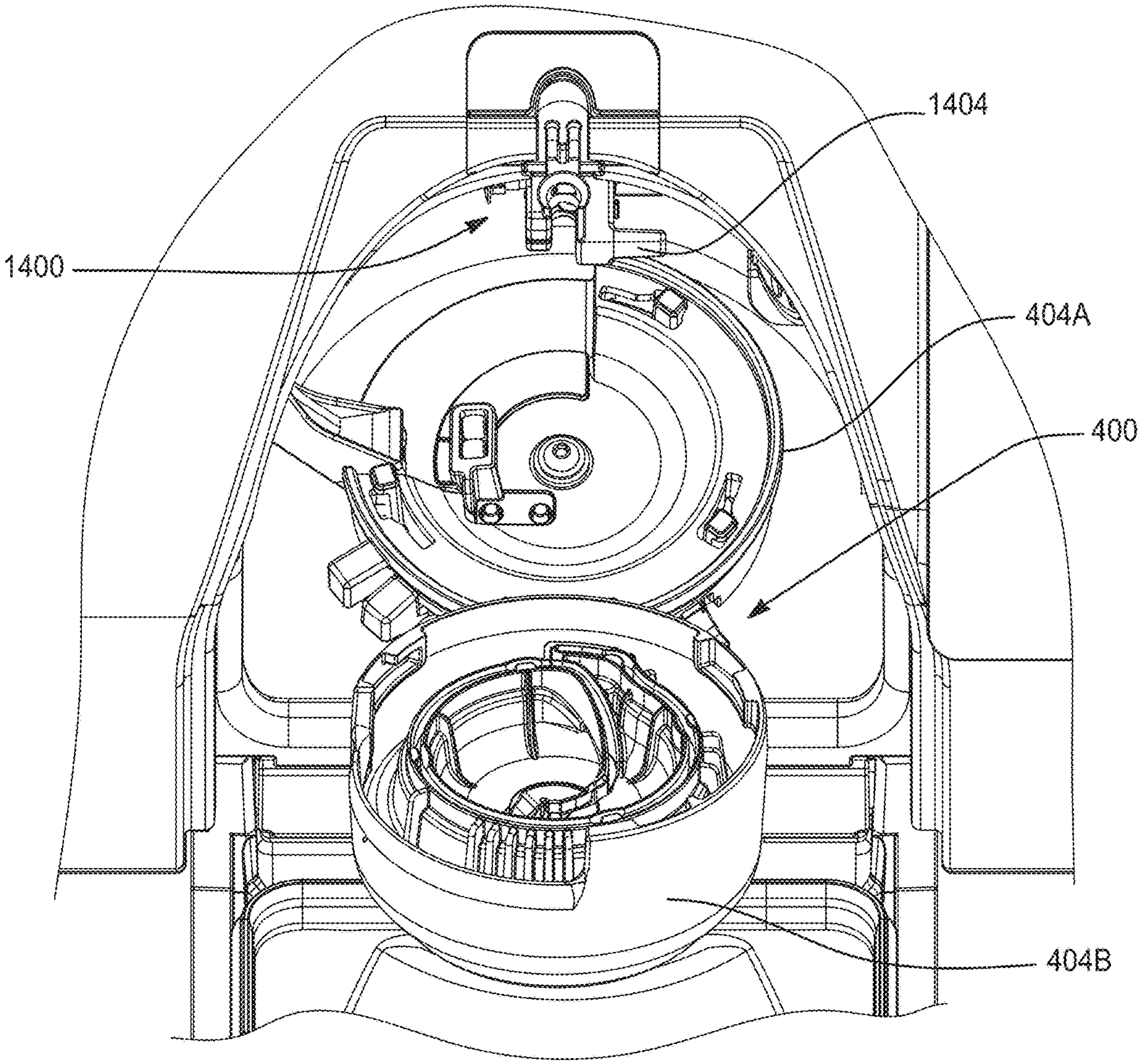
FIG. 14F is a partial view of the moving loop holder in the retracted position and the lid of a centrifuge assembly in the apheresis system is in an open position in accordance with at least one example embodiment of the present disclosure.

In at least one example embodiment, as illustrated for example in FIG. 14E, the retraction of the moving loop holder 1400 may provide clearance for the upper housing 404B to pivot from an interior of the centrifuge chamber 1402 to a position outside of the centrifuge chamber 1402 (compare, e.g., FIGS. 4D and 4E and 4F). For example, when the loop holder body 1408 is moves in the retraction direction 1420, the loop holder body 1408 may be positioned outside of a filler opening pivot arc 1410, which is illustrated in FIG. 14C as an arcuate centerline that pivots, for example, about the y-axis). A pivot clearance space 1416 may be disposed between the loop holder body 1408 and the filler opening pivot arc 1410. The pivot clearance space 1416 may allow the upper housing 404B to pivot relative to the lower housing 404A as the centrifuge split-housing 404 moves between an operating state and a loading state and vice versa (e.g., without the upper housing 404B contacting the loop holder body 1408, etc.). For example, when the moving loop holder 1400 is in a retracted position, the upper housing 404B may hinge and invert to allow the filler 460 to be loaded, for example, with a blood component collection loop 520 and blood component collection bladder 536. Once loaded, the upper housing 404B may be closed and secured in an operational state. When the upper housing 404B is secured in the operational state (e.g., the upper housing 404B and the lower housing 404A are connected), the moving loop holder 1400 may be extended (e.g., moved to the extended state) to hold the blood component collection loop 520, for example, in a fixed position relative to the centrifuge assembly 400.

In at least one example embodiment, when the moving loop holder 1400 is arranged in the extended state, the loop holder body 1408 may be offset a first distance 1430A from the centrifuge assembly 400 including the upper housing 404B preventing the upper housing 404B from moving between an operating state and a loading state and or vice versa. For example, when the loop holder body 1408 is offset the first distance 1430A in the extended state, the upper housing 404B would contact the loop holder body 1408 if the upper housing 404B hinges relative to the lower housing 404A. To move the centrifuge assembly 400 between the operating state and the loading state, the moving loop holder 1400 needs to be first moved to the retracted state 1400B. When the moving loop holder 1400 is in the retracted state 1400B, for example, as illustrated in FIG. 14C, the retracted loop holder body 1408' may be offset a second distance 1430B from the centrifuge assembly 400. The second distance 1430B may be greater than the first distance 1430A and may define the pivot clearance space 1416 between the loop holder body 1408 and the filler opening pivot arc 1410. The filler opening pivot arc 1410 may correspond to a path associated with an outermost portion of the upper housing 404B as the upper housing 404B hinges about the split-housing pivot axis 406 (e.g., relative to the lower housing 404A, etc.). While the moving loop holder 1400 is in the retracted state 1400B, the upper housing 404B may be hinged relative to the lower housing 404A without contacting the loop holder body 1408.

In at least one example embodiment, when the moving loop holder 1400 is in the retracted state 1400B, the apheresis system 200 may be unable to operate. The apheresis system 200 may only be allowed to operate when the moving loop holder 1400 is in the extended state. For instance, the apheresis system 200 may include one or more sensors configured to detect a position of the moving loop holder 1400 and, based on the detected position, provide an input including information about the position of the moving loop holder 1400 to the controller of the apheresis system 200. In response, the controller may restrict operation of the apheresis system 200 when the moving loop holder 1400 is in the retracted state while allowing operation of the apheresis system 200 when the moving loop holder 1400 is in the extended state.

The apheresis system 200 may be loaded with a portion of a blood component collection set 500 by moving the moving loop holder 1400 to the retracted state 1400B and hinging the upper housing 404B to the loading position (see, e.g., FIGS. 4F and 6A). In at least one example embodiment, when the upper housing 404B is opened and in the loading state, at least a portion of the upper housing 404B may extend outside of the centrifuge chamber 1402. In this "flipped" loading state the inverted upper housing 404B may provide clearance and accessibility for loading the blood component collection bladder 536 in the filler 460 (e.g., disposed in the upper housing 404B), as described above. When the blood component collection loop 520 is connected, or otherwise coupled, to the filler 460, the upper housing 404B may be hinged from the loading state to the operating state (see, e.g., FIG. 6C). In this position the moving loop holder 1400 may be moved from the retracted state 1400B to the extended state (see, e.g., FIG. 14C) and the system static loop connector 528 of the blood component collection loop 520 may be interconnected with the loop connection space 1412 of the loop holder body 1408. Unloading the filler 460 may be performed by reversing the order of above-described operations. For example, unloading the filler 460 and/or the centrifuge assembly 400 may include uncoupling the system static loop connector 528 from the loop connection space 1412 and moving the loop holder 1400 from the extended state to the retracted state 1400B. Once in the retracted state 1400B, the upper housing 404B may be rotated, or hinged, from the operating position to the open loading position. In the open position, the blood component collection loop 520 may be disconnected and removed from the filler 460. The process of loading and unloading may repeat to reload the filler 460 and/or the centrifuge assembly 400 between uses, or operations, of the apheresis system 200.

In at least one example embodiment, the present disclosure provides an apheresis system. The apheresis system may include a housing having a front side and a rear side, a centrifuge chamber disposed in the housing, a centrifuge assembly disposed in the centrifuge chamber, and a moving loop holder disposed in the centrifuge chamber, where the moving loop holder includes a loop holder body and a loop connection space disposed in the loop holder body. The loop connection space may be sized to receive a connector of a flexible loop. The moving loop holder may be moveable between an extended state inside the centrifuge chamber and a retracted state inside the centrifuge chamber, where in the extended state, the loop holder body is arranged offset a first distance from the centrifuge assembly, and in the retracted state, the loop holder body is arranged offset a second distance from the centrifuge assembly and the second distance is larger than the first distance. In at least one example embodiment, the centrifuge assembly may include a centrifuge housing, and the centrifuge housing may include a loading state and an operating state. The centrifuge housing may be prevented from moving from the operating state to the loading state when the moving loop holder is in the extended state, and the centrifuge housing may be allowed to move from the operating state to the loading state when the moving loop holder is in the retracted state. In at least one example embodiment, the centrifuge housing may include a split housing that includes a lower housing portion and an upper housing portion, where the upper housing portion hinges relative to the lower housing portion, and the upper housing portion hinges along an arc when moving between the operating state and the loading state. In at least one example embodiment, when the moving loop holder is in the retracted state, a clearance space may be disposed between the loop holder body and the arc so as to provide a movement path along the arc for the upper housing portion to hinge relative to the lower housing portion between the operating state and the loading state clear of the loop holder body. In at least one example embodiment, when the moving loop holder is in the extended state, the clearance space may be removed between the loop holder body and the arc may prevent the upper housing portion from hinging relative to the lower housing portion between the operating state and the loading state. In at least one example embodiment, when the moving loop holder is in the retracted state, the loop holder body may be disposed closer to the rear side of the housing than when the moving loop holder is in the extended state. In at least one example embodiment, the loop holder body may include a connector lock that engages with the connector of a flexible loop locking the flexible loop relative to the loop holder body and the loop connection space. In at least one example embodiment, the moveable loop holder may include a loop holder body and a loop connection space disposed in the loop holder body. The loop connection space may be sized to receive a connector of a flexible loop of a blood component collection set. The moveable loop holder may be moveable between an extended state inside a centrifuge chamber of an apheresis system and a retracted state inside the centrifuge chamber, where in the extended state, the loop holder body is arranged offset a first distance from a centrifuge assembly disposed in the centrifuge chamber, and in the retracted state, the loop holder body is arranged offset a second distance from the centrifuge assembly disposed in the centrifuge chamber. The second distance may be larger than the first distance. In at least one example embodiment, the loop holder body may include a connector lock that engages with the connector of a flexible loop so as to lock the flexible loop relative to the loop holder body and the loop connection space.

In at least one example embodiment a method for loading a centrifuge filler of an apheresis system is provided. The method may include providing an apheresis system that includes a housing having a front side and a rear side, a centrifuge chamber disposed in the housing, a centrifuge assembly disposed in the centrifuge chamber, and a moving loop holder disposed in the centrifuge chamber. The centrifuge assembly may have a split housing that includes a lower housing portion and an upper housing portion, where the upper housing portion hinges relative to the lower housing portion. The centrifuge housing may have a loading state and an operating state. The moving loop holder may include a loop holder body and a loop connection space disposed in the loop holder body. The loop connection space may be sized to receive a connector of a flexible loop. The moving loop holder may be moveable between an extended state inside the centrifuge chamber and a retracted state inside the centrifuge chamber, where in the extended state, the loop holder body may be arranged offset a first distance from the centrifuge assembly, and in the retracted state, the loop holder body is arranged offset a second distance from the centrifuge assembly. The second distance may be larger than the first distance. The upper housing portion may hinge along an arc when moving between the operating state and the loading state, where the split housing may be prevented from moving from the operating state to the loading state when the moving loop holder is in the extended state, and the split housing may be allowed to move from the operating state to the loading state when the moving loop holder is in the extended state. The method for loading a centrifuge filler may further include actuating a release latch so as to unlock the moving loop holder from a locked state to an unlocked state; moving the moving loop holder from the extended state to the retracted state; hinging, while the moving loop holder is in the retracted state, the upper housing portion relative to the lower housing portion such that the upper housing portion is at least partially disposed outside of the centrifuge chamber and the upper housing portion is in the loading state; coupling a blood component collection bladder and flexible loop of a blood component collection set with a filler disposed in the upper housing portion while the upper housing portion is in the loading state; hinging, while the moving loop holder is in the retracted state, the upper housing portion relative to the lower housing portion such that the upper housing portion is disposed inside of the centrifuge chamber and the upper housing portion is in the operating state; and moving the moving loop holder from the retracted state to the extended state causing the release latch to lock the moving loop holder in the locked state.

Example Bottle Tray with Magnetic Coupling and Load Cell Overload Protection

FIGS. 15A-15M show various views of a load cell assembly and components thereof according to at least one example embodiment. FIG. 15A is a perspective view of the load cell assembly according to at least one example embodiment. FIG. 15B is an exploded perspective view of the load cell assembly of FIG. 15A according to at least one example embodiment.

In at least the example embodiment shown, the load cell assembly 1500 is a bottle tray load cell assembly. The load cell assembly 1500 includes a fixed portion, a deflection portion (FIG. 15B), and a load cell 1506. In at least one example embodiment, the fixed portion includes a plate 1508 (also referred to as a "mount plate") and a bracket 1510 (also referred to as a "load cell support bracket"). In at least one example embodiment, the deflection portion includes a first component 1512 (also referred to as a "load interface plate"), a second component 1514 (also referred to as an "overload support bar"), and a cradle 1516 (also referred to as a "bottle cradle" or a "plasma collection cradle"). The load cell assembly 1500 may extend along a central or longitudinal axis 1517. In at least one example embodiment, the longitudinal axis 1517 passes through a center of the load cell 1506.

In at least one example embodiment, the cradle 1516 may be similar to the plasma collection cradle 232C of FIG. 2A. The plasma collection cradle 1516 may be attached to the overload support bar 1514. As described above, the plasma collection cradle 1516 may be configured to receive, orient, and/or hold a vessel, such as a plasma collection bottle (e.g., bottle 1598 of FIG. 15M or vessel 2716 if FIG. 26J), in an apheresis system, such as the apheresis system 200 shown in (FIG. 1A). In at least one example embodiment, the load cell 1506 is configured to deflect and sense a load and/or weight of a vessel. The load cell 1506 may be sensitive to forces within a predetermined (or alternatively, desired) range. For example, when forces applied to the load cell 1506 are below outside of predetermined range (e.g., over), the accuracy of the load measurements and/or integrity of the load cell 1506 may be compromised.

In at least one example embodiment, the cradle 1516 is coupled to the load cell 1506 via a magnetic coupling and interface. The magnetic coupling may be configured to mechanically separate the cradle 1516 from the load cell 1506, thereby reducing or preventing mechanical forces from continuing to be applied to the flexure beams and/or load cell 1506. In at least one example embodiment, as will be described in greater detail below, upon reaching a predetermined load amount, the cradle 1516 may break a magnetic interconnection force separating the cradle 1516, the plate 1508, and the second component 1514 from the apheresis system 200. Among other things, this magnetic interconnection may reduce or prevent damage to the load cell 1506, sensing components, support elements, flexure beams, and/or other mechanical elements disposed between cradle 1516 and the load cell 1506.

In at least one example embodiment, the first component 1512 includes a first magnet 1518 and the second component 1514 includes a second magnet 1520. The first magnet 1518 may be coupled to the first component 1512 by a first fastener 1522A. The second magnet 1520 may be coupled to the second component 1514 by a second fastener 1522B. As will be described in greater detail below, the load cell 1506 may be coupled to the bracket 1510 by one or more third fasteners 1522C. The first component 1512 may be coupled to the load cell 1506 by one or more fourth fasteners 1522D. The mount plate 1508 may be coupled to bracket 1510 by one or more fifth fasteners 1522E. The second component 1514 may be coupled to the cradle 1516 by one or more sixth fasteners 1522F. In at least one example embodiment, the fasteners 1522A, 1522B, 1522C, 1522D, 1522E, 1522F may be independently selected from flat head screws, socket head cap screws, hex head screws, bolts, and/or the like.

Figure 15A:
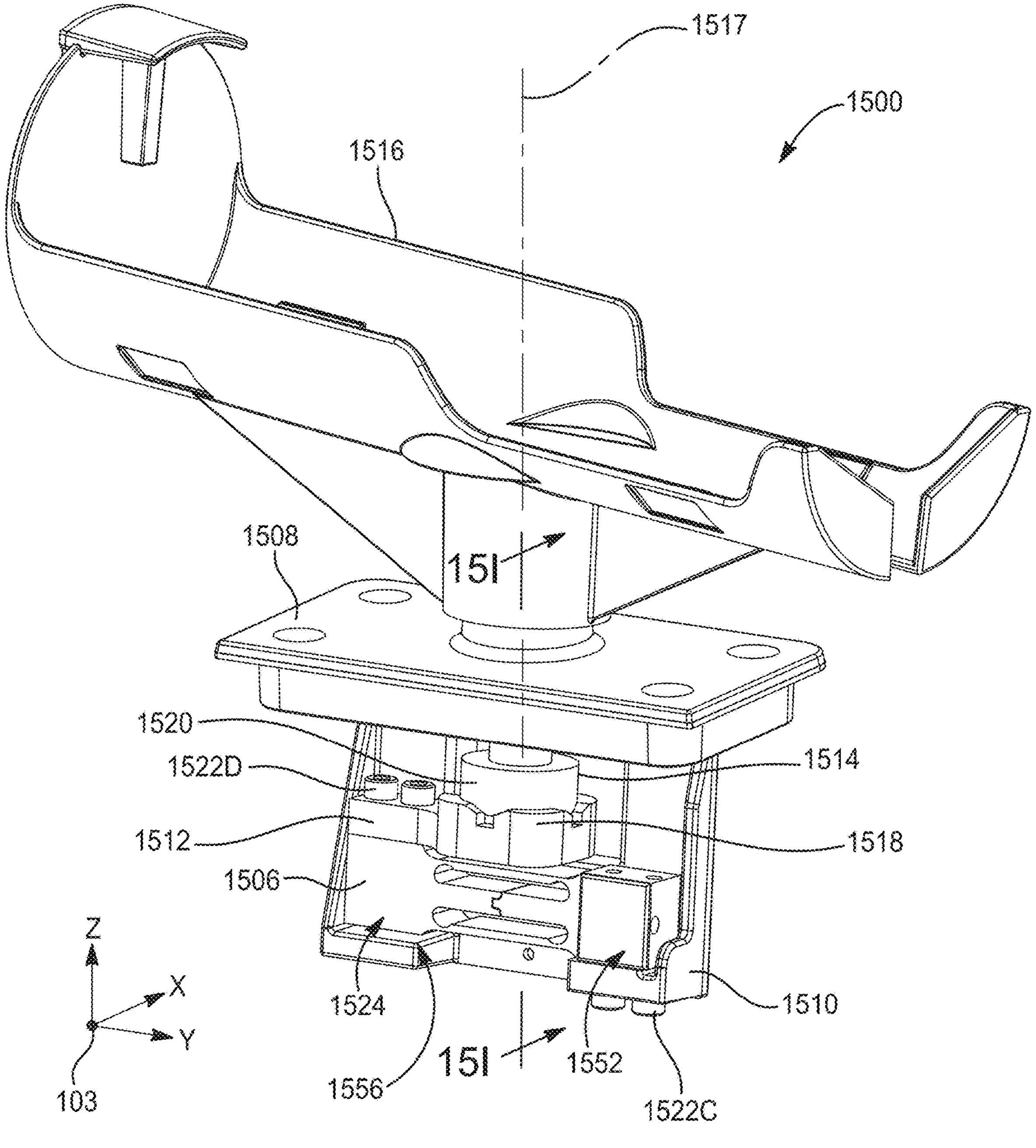
FIG. 15A is a perspective view of a load cell assembly in accordance with at least one example embodiment of the present disclosure.
Figure 15B:
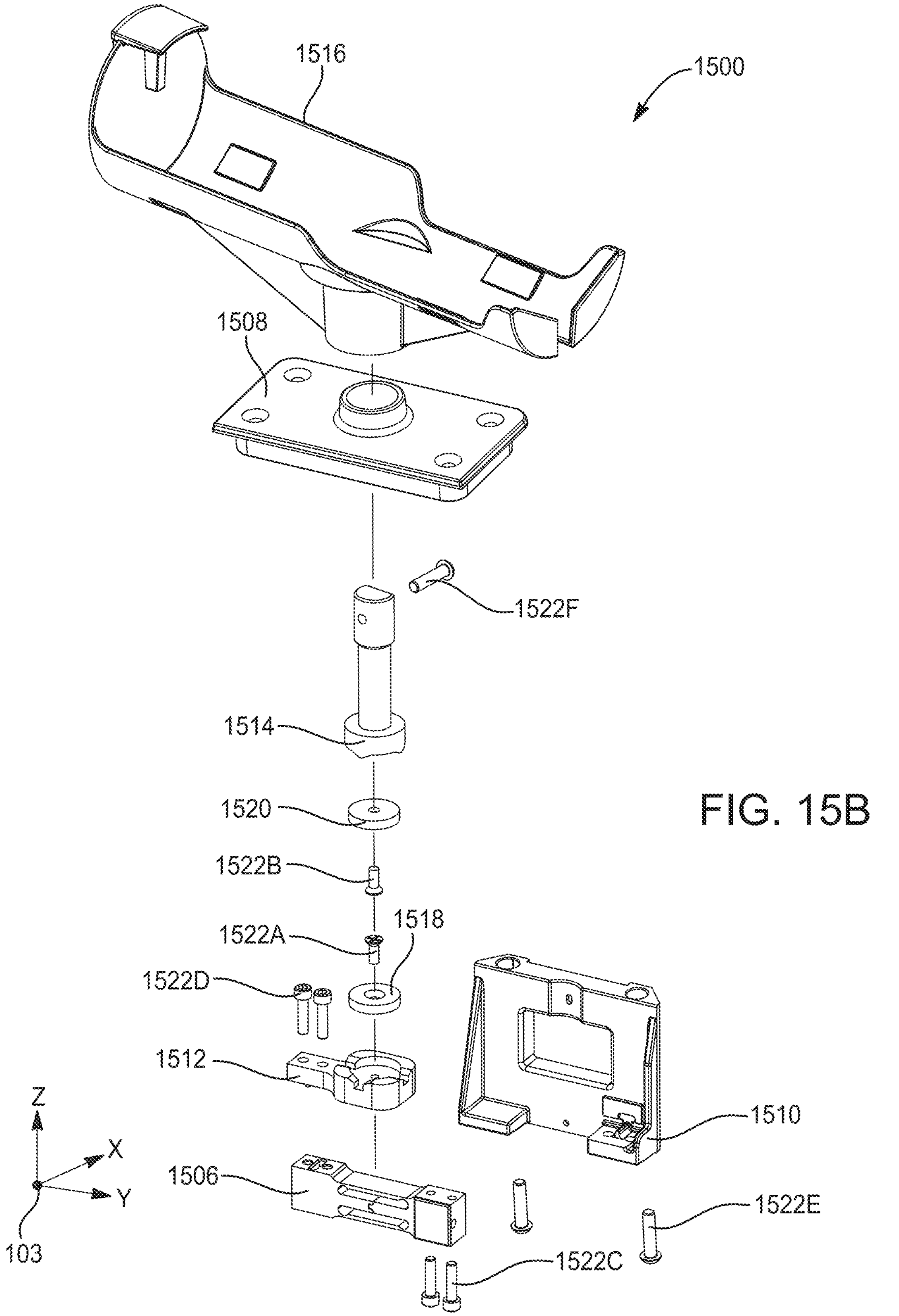
FIG. 15B is an exploded perspective view of the load cell assembly of FIG. 15A in accordance with at least one example embodiment of the present disclosure.
Figure 15C:
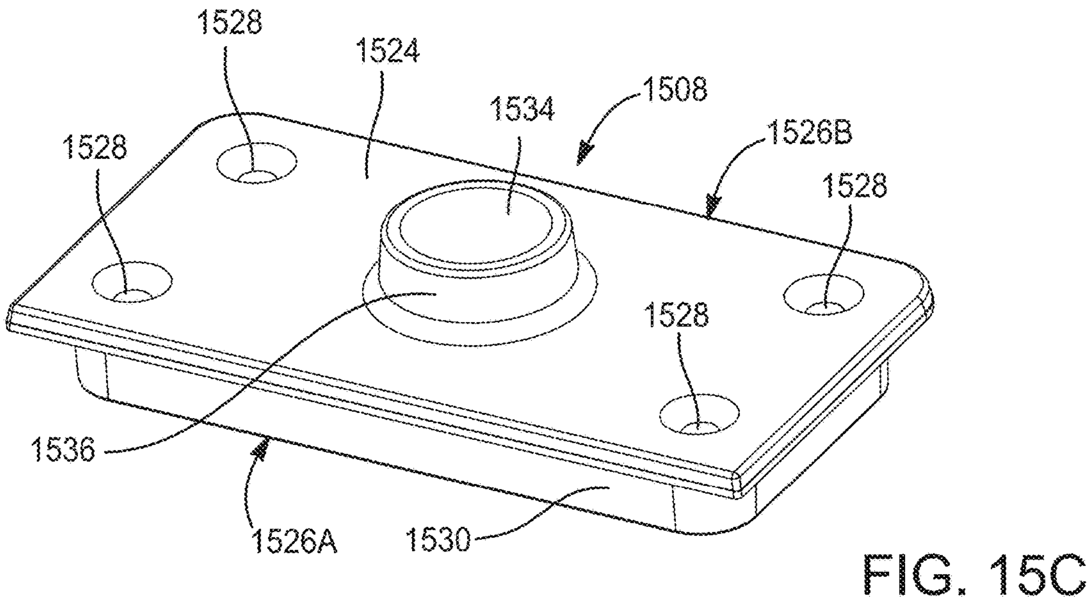
FIG. 15C is a top perspective view of a mount plate of the load cell assembly of FIG. 15A in accordance with at least one example embodiment of the present disclosure.
Figure 15D:
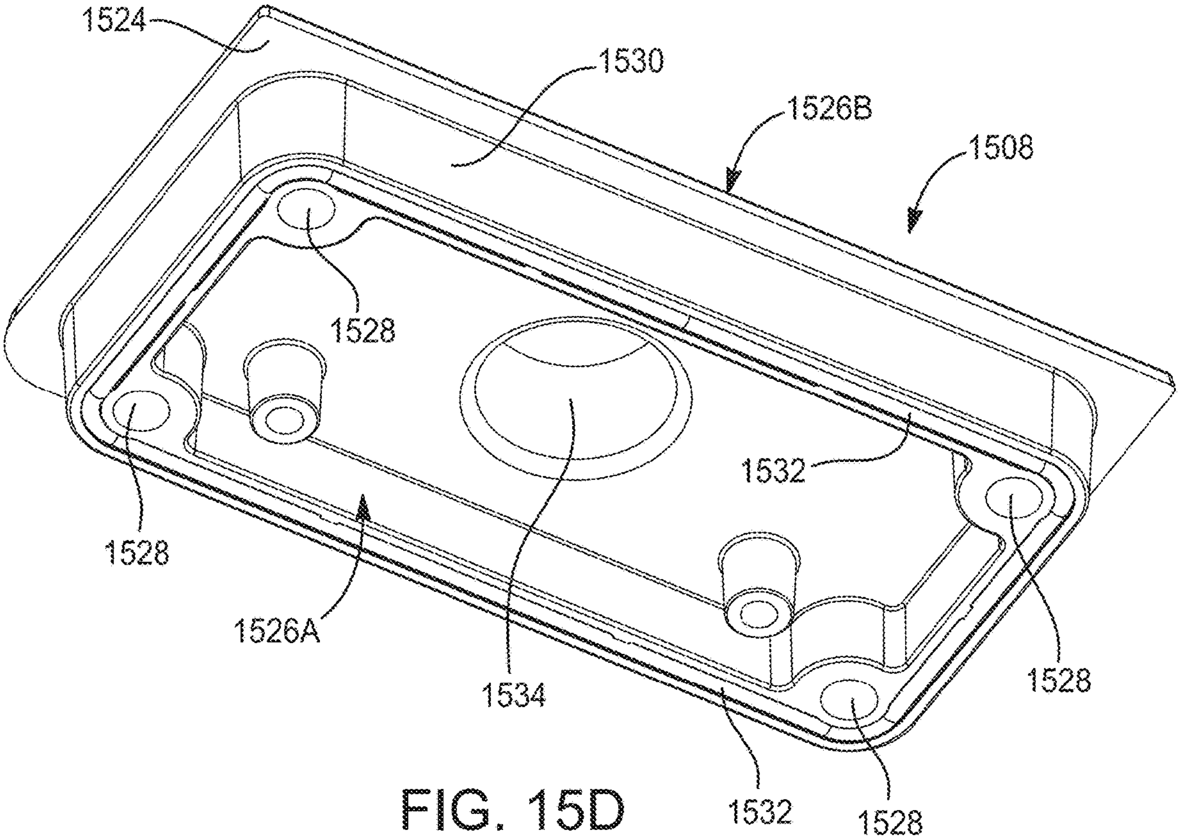
FIG. 15D is a bottom perspective view of the mount plate of FIG. 15C in accordance with at least one example embodiment of the present disclosure.

FIG. 15C is a top perspective view of a mount plate of the load cell assembly of FIG. 15A according to at least one example embodiment. FIG. 15D is a bottom perspective view of the mount plate of FIG. 15C according to at least one example embodiment.

In at least one example embodiment, as shown in FIGS. 15C-15D, the mount plate 1508 includes a substantially planar body 1524 having a first side 1526A and a second side 1526B. The planar body 1524 may define a substantially rectangular perimeter (e.g., a rectangle having rounded corners).

In at least one example embodiment, the planar body 1524 defines one or more first apertures 1528 (e.g., four apertures 1528, as shown). Fasteners (not shown) may extend through the first apertures 1528 to couple the load cell assembly 1500 (shown in FIGS. 15A-15B) to the apheresis system 200 (shown in FIG. 1A) via the mount plate 1508. In at least one example embodiment, the bottle tray load cell assembly 1500 may be completely removed from the apheresis system 200 via removal of the fasteners. Among other things, this feature allows quick replacement and/or serviceability of the bottle tray load cell assembly 1500 and/or any component of the bottle tray load cell assembly 1500, as will be described in greater detail below in the discussion accompanying FIG. 18A.

In at least one example embodiment, a first flange 1530 extends from the planar body 1524 on the first side 1526A. The first flange 1530 may define a rectangular shape. In at least one example embodiment, the mount plate 1508 includes a gasket 1532 (shown in FIG. 15D) on the first side 1526A. The gasket 1532 may be adjacent to the first flange 1530. When the load cell assembly 1500 (shown in FIGS. 15A-15B) is coupled to the apheresis system 200 (shown in FIG. 1A), the gasket 1532 is between the planar body 1524 of the plate 1508 and the housing 204 (shown in FIG. 2A). In at least one example embodiment, the gasket 1532 may be or include an O-ring, a flat seal gasket, or another compliant sealing member. Additionally or alternatively, the gasket 1532 may be or include an electromagnetic interference (EMI) shielding gasket (e.g., metal gasket, spring, metalized gasket, and/or the like).

In at least one example embodiment, the planar body 1524 defines a second aperture 1534. The second aperture 1534 may be a central aperture. In at least one example embodiment, a second flange 1536 may extend from the second side 1526B of the planar body 1524. The second flange 1536 may be a circular flange. The second flange 1536 may extend around the second aperture 1534. In at least one example embodiment, a portion of the second component 1514 (shown in FIGS. 15A-15B) extends through the second aperture 1534. The second component 1514 may be configured to translate along the longitudinal axis 1517 as the deflection portion (shown in FIGS. 15A-15B) of the load cell assembly 1500 deflects. In at least one example embodiment, an amount of the deflection may be very small, such as less than or equal to about 0.05 inches (e.g., less than or equal to about 0.01 inches, or less than or equal to about 0.005 inches).

Figure 15E:
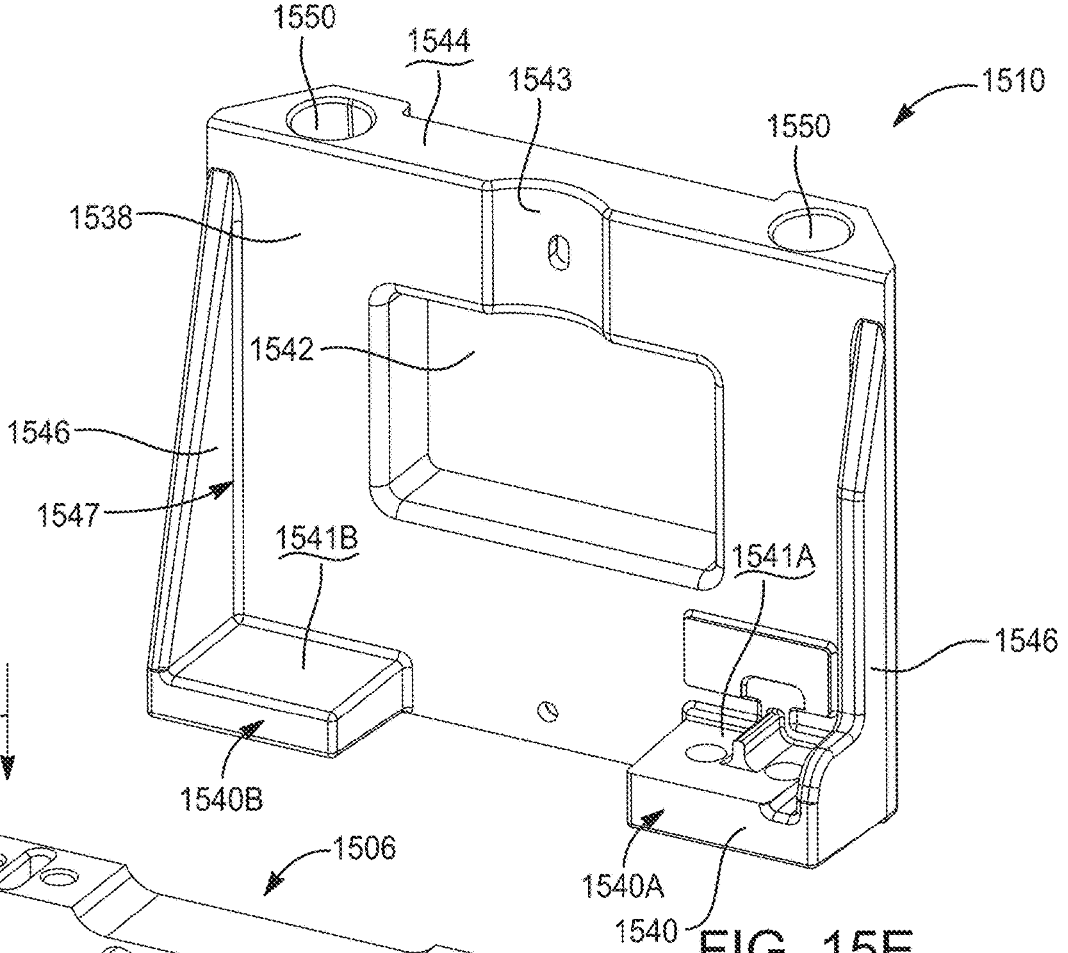
FIG. 15E is a perspective view of a bracket of the load cell assembly of FIG. 15A in accordance with at least one example embodiment of the present disclosure.

FIG. 15E is a perspective view of a bracket of the load cell assembly of FIG. 15A according to at least one example embodiment.

In at least one example embodiment, as shown in FIG. 15E, the bracket 1510 includes a wall 1538 and a third flange 1540. The third flange 1540 may include a first flange portion 1540A and a second flange portion 1540B. The first and second flange portions 1540A, 1540B may be spaced apart from one another. The first and second flange portions 1540A, 1540B may include respective upper surfaces 1541A, 1541B. The upper surfaces 1541A, 1541B may be coplanar.

In at least one example embodiment, the wall 1538 defines a receptacle 1542. The receptacle 1542 may define a substantially rectangular shape. The receptacle 1542 may receive at least a portion of the load interface plate 1512 and/or at least a portion of the overload support bar 1514, as shown in FIG. 15I.

The wall 1538 may further define a depression 1543. The depression 1543 may define a semi-cylindrical shape. The depression 1543 may extend between the receptacle 1542 and an upper surface 1544 of the wall 1538. The depression may receive at least a portion of the overload support bar 1514, as shown in FIG. 15I.

In at least one example embodiment, the bracket 1510 may further include gussets 1546 extending between the wall 1538 and the third flange 1540. In at least one example embodiment, the wall 1538, the third flange 1540, and the gussets 1546 may cooperate to define an interior bracket region 1547. As will be described in greater detail below, in at least one example embodiment, the load cell 1506, the first component 1512, and a portion of the second component 1514 may be in the interior bracket region 1547. Accordingly, when the mount plate 1508 is attached to the housing 204 of the apheresis system 200 (shown in FIG. 2A), the bracket 1510 may be inside a guarded portion of the apheresis system 200 (e.g., protecting the load cell 1506 and/or other components of the load cell assembly 1500 from damage, tampering, and/or an environment outside of the apheresis system 200, etc.).

In at least one example embodiment, the bracket 1510 is attached to the mount plate 1508. In the example embodiment shown, the bracket 1510 is attached to the first side 1526A of the mount plate 1508. The upper surface 1544 of the wall 1538 of the bracket 1510 may define one or more third apertures 1550. The fifth fasteners 1522E may extend through the third apertures 1550 and the plate 1508 to couple the bracket 1510 to the mount plate 1508. The second flange portion 1540B may define one or more fourth apertures 1551. In at least the example embodiment shown, the third fasteners 1522C may extend through the fourth apertures 1551 to couple the load cell 1506 (shown in FIGS. 15A-15B) to the bracket 1510, as will be described in greater detail below.

Figure 15F:
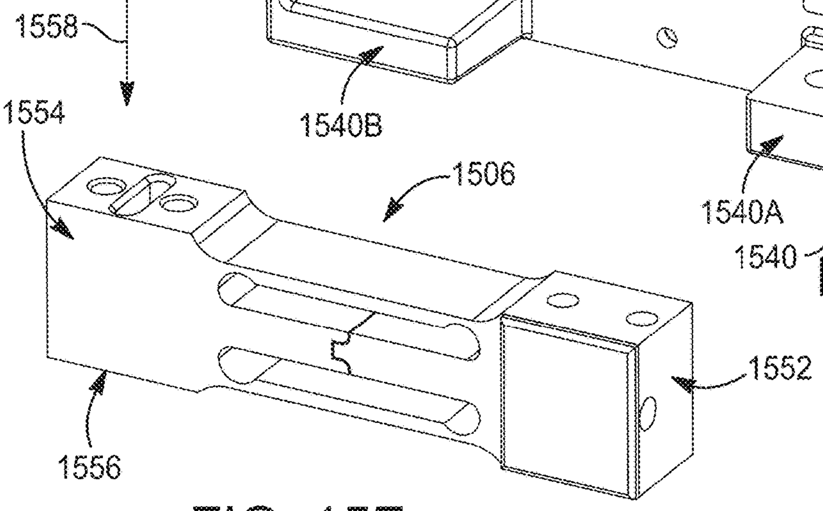
FIG. 15F is a perspective view of a load cell of the load cell assembly of FIG. 15A in accordance with at least one example embodiment of the present disclosure.

FIG. 15F is a perspective view of a load cell of the load cell assembly of FIG. 15A according to at least one example embodiment.

In at least one example embodiment, as shown in FIG. 15F, the load cell 1506 includes a fixed end 1552 (or fixed side) and a free end 1554 (or free side or load deflection side). As shown in FIG. 15A, the fixed end 1552 is fixed to the bracket 1510. Specifically, the fixed end 1552 of the load cell 1506 may be in contact with the second flange portion 1540B. In at least one example embodiment, the fixed end 1552 of the load cell 1506 may be in direct contact with the second flange portion 1540B. The load cell 1506 may be at least partially within the interior bracket region 1547 of the bracket 1510.

In at least one example embodiment, the free end 1554 of the load cell 1506 is spaced apart from at least a portion of the bracket 1510, such as the first flange portion 1540A, to define a deflection region 1556 (also shown in FIGS. 15A and 15I). The free end 1554 of the load cell 1506 load cell 1506 is configured to move within the deflection region 1556 in response to the application of a force or load in a first direction 1558. The first direction 1558 may be substantially parallel to the central axis 1517.

In at least one example embodiment, the load cell 1506 is a flexure-based load cell. As the free end 1554 moves or translates relative to the fixed end 1552, the load cell 1506 may determine a force, weight, or load associated with the measured deflection. While the load cell 1506 may be capable of receiving forces received perpendicular to a flexure member of the load cell 1506 (e.g., in the first direction 1558), the load cell 1506 may be sensitive to rotational, twisting, or parallel forces received. Examples of the load cell 1506 include, but are not limited to, a shear beam load cell, an S-beam load cell, a single point load cell, a dual shear beam load cell, a bending beam load cell, a canister load cell, a strain gauge, a flexure load cell, and/or combinations thereof.

Returning to FIGS. 15A-15B, in at least one example embodiment, the load cell assembly 1500 includes a magnetic coupling between the load interface plate 1512 and the overload support bar 1514. In at least the example embodiment shown, the load interface plate 1512 includes the first magnet 1518 and the overload support bar 1514 includes the second magnet 1520. The magnets 1518, 1520 may be arranged such that opposite poles are facing one another when the overload support bar 1514 is engaged with the load interface plate 1512, as shown in FIG. 15I. This arrangement causes a magnetic force between the magnets 1518, 1520 to maintain the overload support bar 1514 in an engaged state with the load interface plate 1512.

Figure 15G:
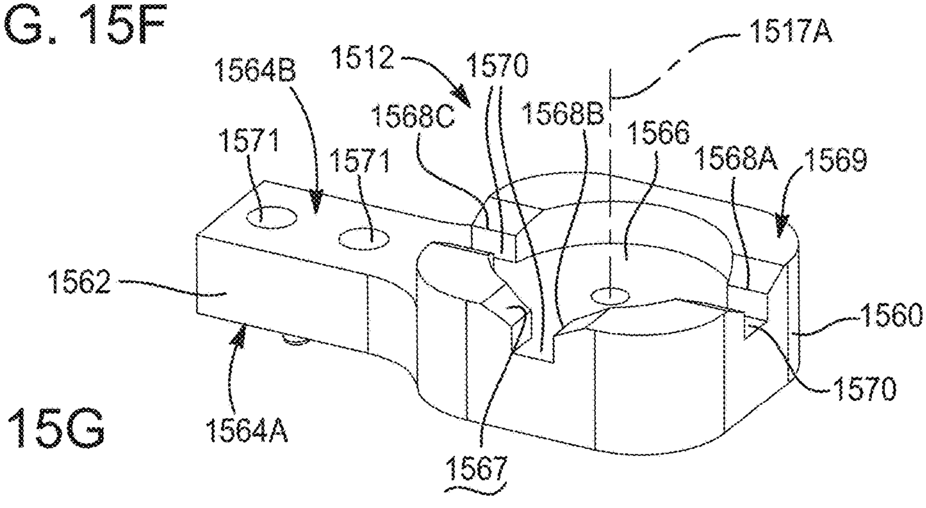
FIG. 15G is a perspective view of a load interface plate of the load cell assembly of FIG. 15A in accordance with at least one example embodiment of the present disclosure.

FIG. 15G is a perspective view of a load interface plate of the load support assembly of FIG. 15A according to at least one example embodiment.

In at least one example embodiment, as shown in FIG. 15G, the load interface plate 1512 includes an interface body or first cam body 1560 and an extension or mount 1562. The load interface plate 1512 may define a first or load cell side 1564A and a second or interface side 1564B. The first cam body 1560 may define a first recess or depression 1566. The load interface axis 1517A may be aligned with the central axis 1517 (shown in FIG. 15A) when the load cell assembly 1500 (shown in FIG. 15A) is assembled. The first magnet 1518 may be at least partially in the first recess 1566. A load interface axis 1517A may extend through a center of the first recess 1566. The first magnet 1518 (shown in FIG. 15B) may be glued, pinned, crimped, or otherwise fastened within first recess 1566. In at least the example embodiment shown, the first magnet 1518 may be attached to the overload support bar 1514 via the first fastener 1522A, such as flat head cap screw. In at least one example embodiment, a surface of the first magnet 1518 may be disposed flush with, or under, a first cam surface 1567 of the overload support bar 1514.

In at least one example embodiment, the first cam surface 1567 defines a plurality of valleys 1568. In at least the example embodiment shown, the plurality of valleys 1568 includes a first valley 1568A, a second valley 1568B, and a third valley 1568C. the valleys 1568 may be asymmetrically disposed about the load interface axis 1517A (e.g., having centers disposed about 90° apart from one another). In at least one example embodiment, each of the valleys 1568 may be configured as a dwell or recess having at least one sloped, chamfered, or tapered side.

In at least one example embodiment, the first cam surface 1677 may further define a first flat portion 1569. In the example embodiment shown, the first flat portion 1569 is between the first valley 1568A and the third valley 1568C. The first flat portion 1569 may extend uninterrupted between the first valley 1568A and the third valley 1568C. The valleys 1568A, 1568B, 1568C and the first flat portion 1569 may be circumferentially around the first recess 1566.

In at least one example embodiment, the second side 1564B of the first cam body 1560 may further define a plurality of notches 1570. Each of the plurality of notches 1570 may correspond to a respective one of the valleys 1568. The notches 1570 may be centered within each of the respective valleys 1568.

The extension 1562 may be adjacent to the first cam body 1560. In at least the example embodiment shown, the extension 1562 defines a substantially rectangular cross section. The extension 1562 may define one or more fourth apertures 1571. The fourth apertures 1571 may receive fourth fasteners 1522D to couple the load interface plate 1512 to the load cell 1506 (shown in FIG. 15B).

Figure 15H:
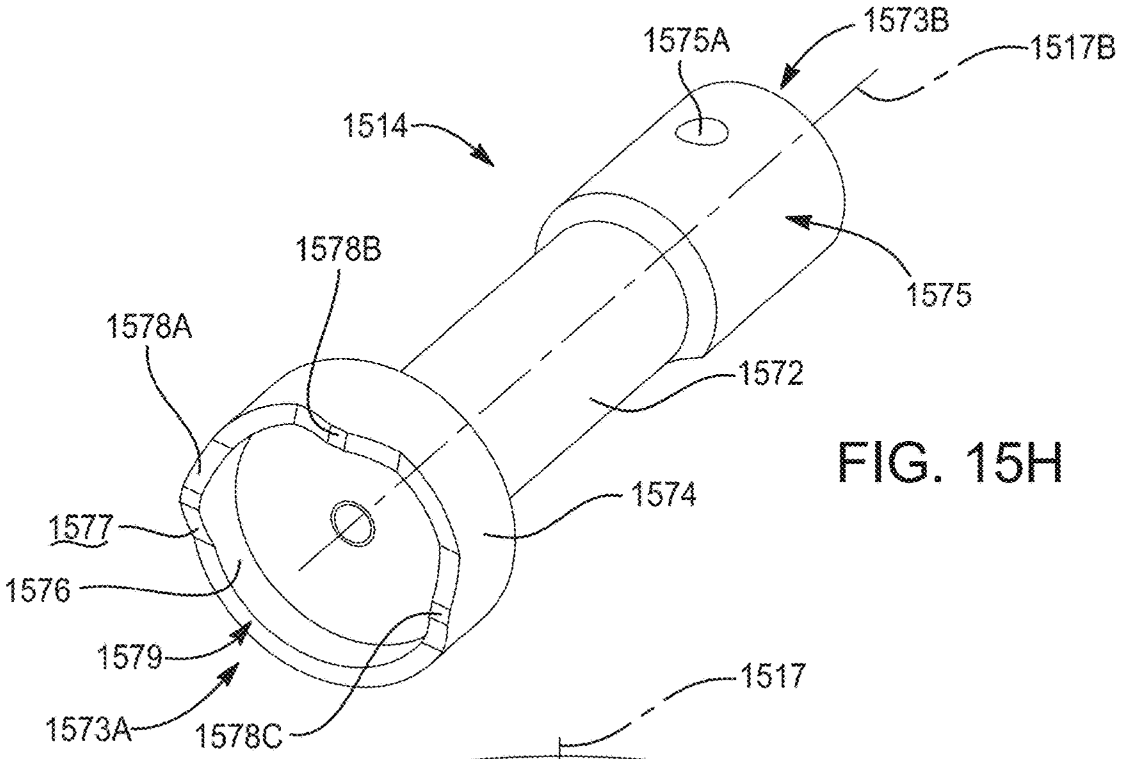
FIG. 15H is a perspective view of an overload support bar of the load cell assembly of FIG. 15A in accordance with at least one example embodiment of the present disclosure.
Figure 15I:
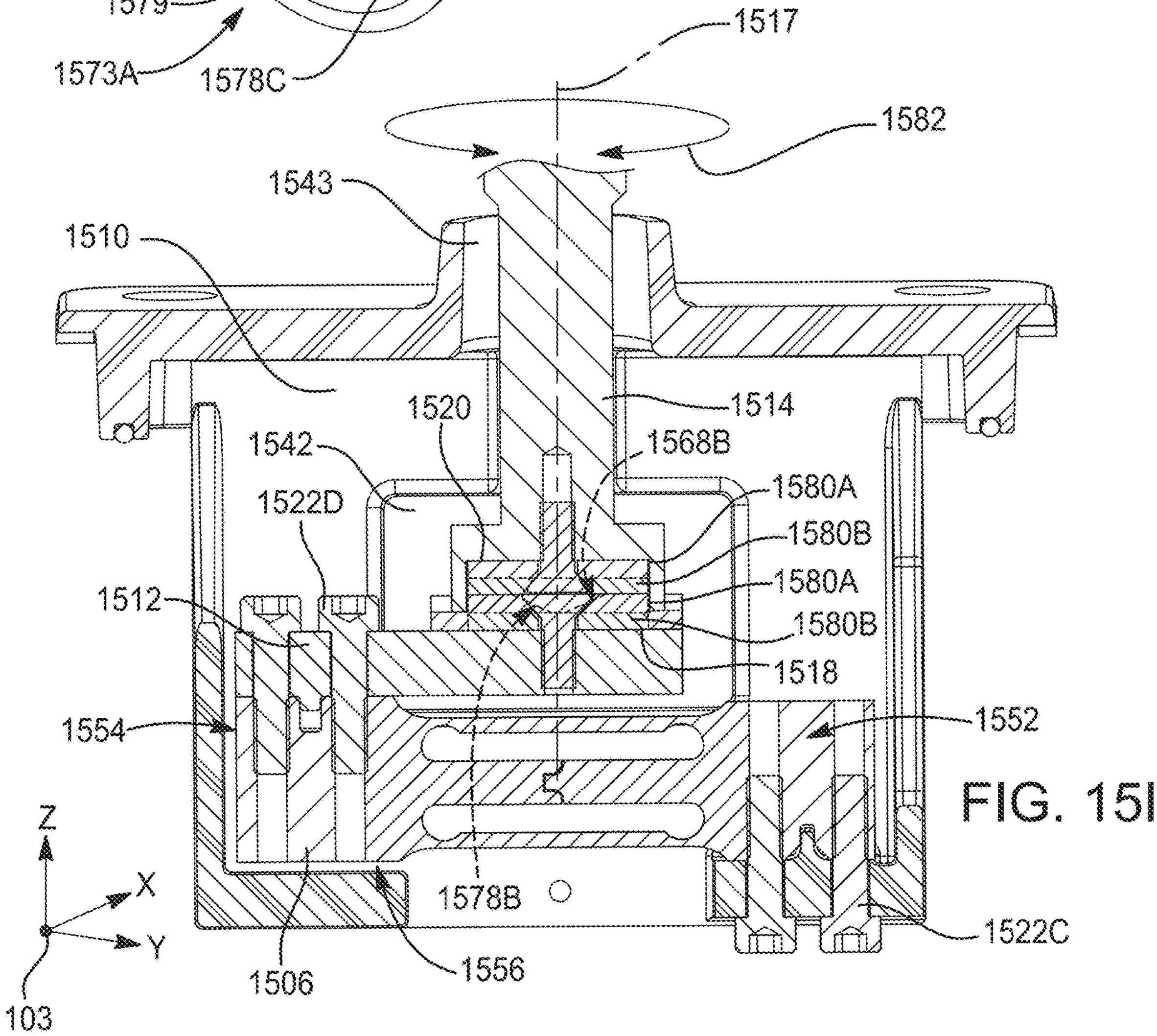
FIG. 15I is a partial sectional view of the load cell assembly of FIG. 15A in an engaged state in accordance with at least one example embodiment of the present disclosure.

FIG. 15H is a perspective view of an overload support bar of the load cell assembly of FIG. 15A according to at least one example embodiment.

Referring to FIG. 15H, in at least one example embodiment, the overload support bar 1514 includes a mandrel 1572 extending a length along a longitudinal or support bar axis 1517B (e.g., coinciding with axis 1517 of FIG. 15A) from a first end 1573A to a second end 1573B. In at least one example embodiment, the overload support bar 1514 includes a second cam body 1574 at the first end 1573A and a coupling portion 1775 at the first end 1573A.

In at least one example embodiment, the coupling portion 1575 has a larger diameter than that of the mandrel 1572. The coupling portion 1575 may define a receptacle, such as a fifth aperture 1575A. The fifth aperture 1575A may cooperate with the sixth fastener 1522F to couple the cradle 1516 (shown in FIG. 15A) the overload support bar 1514.

In at least one example embodiment, the second cam body 1574 is substantially cylindrical. The second cam body 1574 may define a second recess or depression 1576. The support bar axis 1517B may extend through a center of the second recess 1576. The support bar axis 1517B may be aligned with the central axis 1517 when the load cell assembly 1500 (shown in FIG. 15A) is assembled. The second magnet 1520 may be at least partially in the second recess 1576. The second magnet 1520 (shown in FIG. 15B) may be glued, pinned, crimped, or otherwise fastened within second recess 1576. In at least the example embodiment shown, the magnet second 1520 may be attached to the overload support bar 1514 via the second fastener 1522B, such as a flat head cap screw. In at least one example embodiment, a surface of the second magnet 1520 may be disposed flush with, or under, a second cam surface 1577 of the overload support bar 1514.

In at least one example embodiment, second cam surface 1577 defines a plurality of lobes 1578. In at least the example embodiment shown, the plurality of lobes 1578 includes a first lobe 1578A, a second lobe 1578B, and a third lobe 1578C. the lobes 1578 may be asymmetrically disposed about the support bar axis 1517B (e.g., having centers disposed about 90° apart from one another). In at least one example embodiment, each of the lobes 1578 may be configured as a protrusion having at least one sloped, or tapered, side extending from a tip of the protrusion.

In at least one example embodiment, the second cam surface 1577 of the second cam body 1574 may further define a second flat portion 1579. In the example embodiment shown, the second flat portion 1579 is between the first lobe 1578A and the third lobe 1578C. The second flat portion 1579 may extend uninterrupted between the first lobe 1578A and the third lobe 1578C. The lobes 1578 and the second flat portion 1579 may be circumferentially around the second recess 1576.

In at least one example embodiment, a benefit of the asymmetrical arrangement of lobes 1578 and valleys 1568 (shown in FIG. 15G) is that the overload support bar 1514 may engage with the load interface plate 1512 in only one orientation (e.g., preventing improper mounting of the plasma collection cradle 1516 to the apheresis system 200, etc.). In at least one example embodiment, among other things, this asymmetrical arrangement can ensure that plasma collection cradle 1516 is always mounted in substantially the same orientation with the apheresis system 200.

In at least one example embodiment, with reference to FIGS. 15G-15H, the arrangement of valleys 1568 (FIG. 15G) may provide at least one mating surface at each location of the valleys 1568 that is configured to contact a corresponding surface of the lobes 1578 (FIG. 15H). When the overload support bar 1514 is engaged with the load interface plate 1512 (e.g., in an engaged state), the first cam lobe 1578A may align with and be within first valley 1568A, the second lobe 1578B may align with and be within the second valley 1568B, and the third lobe 1578C may align with and be within the third valley 1578C. In at least one example embodiment, the first cam surface 1567 may be in continuous and uninterrupted contact with the second cam surface 1577.

In at least one example embodiment, when the overload support bar 1514 is caused to tilt, twist, or rotate relative to the load interface plate 1512 (e.g., via an external force applied to the plasma collection cradle 1516, shown in FIG. 15A, and/or a plasma collection bottle in the plasma collection cradle 1516, etc.), at least a portion of the second cam surface 1577 may be disengaged from (e.g., not directly contacting) the first cam surface 1567. In at least this example embodiment, as the overload support bar 1514 rotates about the axis 1517B, one or more of the plurality of lobes 1578 may be caused to contact the first flat portion 1569 of the load interface plate 1512.

Figure 15J:
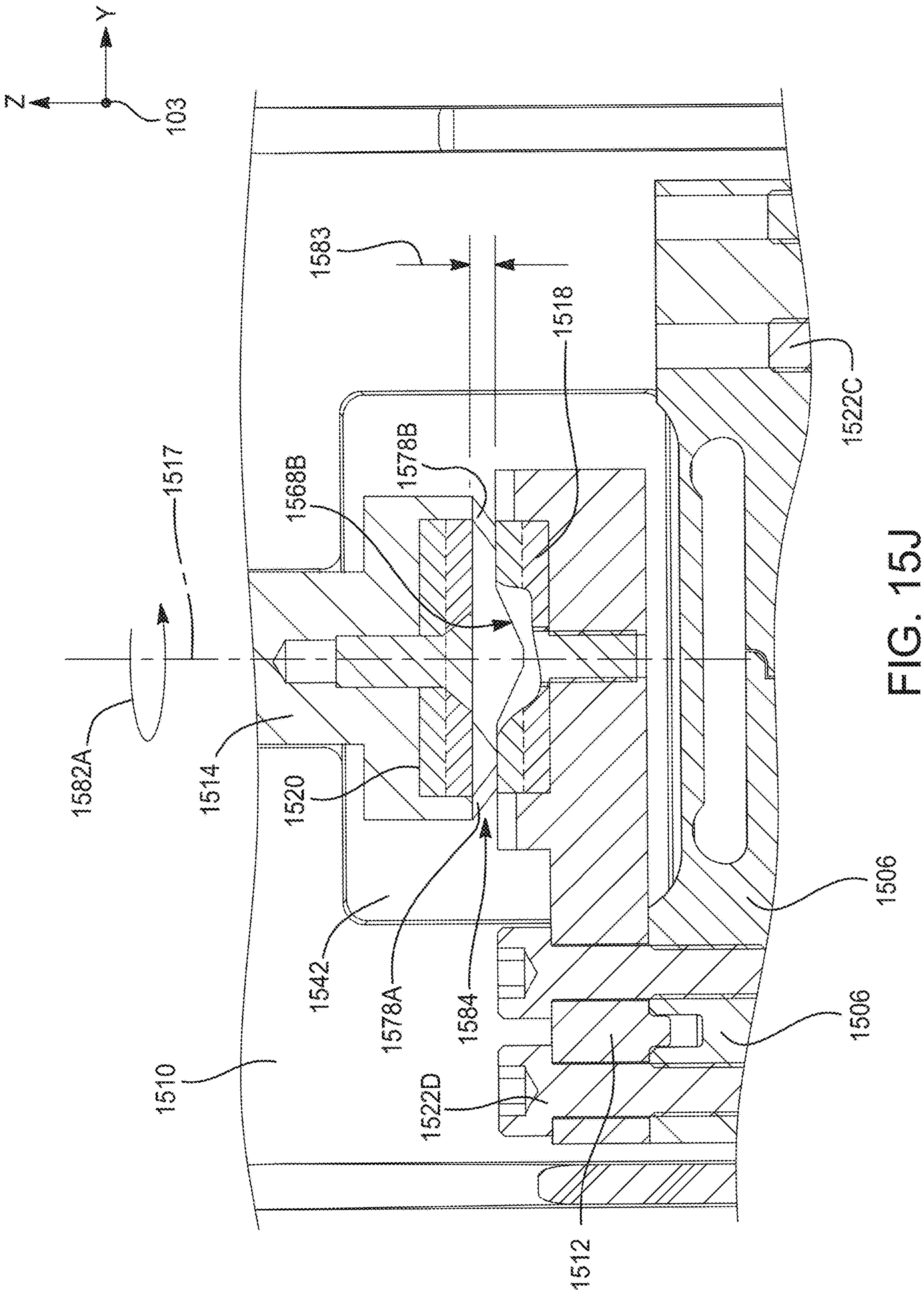
FIG. 15J is a partial sectional view of the load cell assembly of FIG. 15A in a disengaged state, with a portion of a first magnet cut away, in accordance with at least one example embodiment of the present disclosure.

FIG. 15I is a partial sectional view of the load cell assembly of FIG. 15A in an engaged state according to at least one example embodiment. FIG. 15J is a partial sectional view of the load cell assembly of FIG. 15A in a disengaged state, with a portion of a first magnet cut away, according to at least one example embodiment.

In at least one example embodiment, as shown FIGS. 15I-15J, each of the magnets 1518, 1520 has a first pole side 1580A (e.g., a north pole) and a second pole side 1580BB (e.g., a south pole). The first pole side 1580A has a first polarity and the second pole side 180B has a second polarity that is opposite the first polarity. The magnets 1518, 1520 are arranged respectively such that opposite poles (i.e., poles having opposite polarity) are facing one another. In the example embodiment shown, the first magnet 1518 is in the first recess 1566 of the load interface plate 1512 such that the first pole side 1580A of the first magnet 1518 is facing the overload support bar 1514. The second magnet 1520 is in the second recess 1576 of the overload support bar 1514 such that the second pole side 1580B of the second magnet 1520 is facing the load interface plate 1512. In at least one other example embodiment, a load cell assembly may include a single magnet disposed in a load interface plate or an overload support bar with a magnetically attractive metal (e.g., iron, steel, etc.) disposed in the other of the load interface plate or the overload support bar.

The bottle tray load cell assembly 1500 may be capable of providing overload protection for the load cell 1506 and/or other components by the overload support bar 1514 moving between the engaged state shown in FIG. 15I to the disengaged state shown in FIG. 15J when a predetermined movement and/or force is received by the overload support bar 1514. The movement and/or force may correspond to a rotation about the central axis 1517 in the rotation direction 1582, a moment about the axis 1517, a moment about the y-axis shown, a moment about the x-axis shown, and/or combinations thereof. Among other things, the ability to disengage the overload support bar 1514 from the load interface plate 1512 prevents nonlinear forces (e.g., forces that are not acting along the z-axis alone providing a weight vector, etc.) from damaging the load cell 1506 and/or the components of the bottle tray load cell assembly 1500.

In at least one example embodiment, as shown in FIG. 15J, a force is received in first rotation direction 1582A causing the overload support bar 1514 to rotate counterclockwise relative to the load interface plate 1512. This force may be caused by an accidental knocking and/or twisting, of the cradle 1516 causing the overload support bar 1514 to rotate about the axis 1517. As the overload support bar 1514 rotates, the lobes 1578 may travel along the sloped, or tapered, sides of the valleys 1568, raising the overload support bar 1514 relative to the load interface plate 1512, and causing the overload support bar 1514 to at least partially separate from the load interface plate 1512. In at least one example embodiment, in a fully disengaged state, the overload support bar 1514 is separated from the load interface plate 1512 by a separation offset distance 1583. In this position, the lobes 1578 may be in contact with the first flat portion 1569 of the load interface plate 1512 and removed or disengaged from the valleys 1568.

When the overload support bar 1514 separates from the load interface plate 1512, a separation space 1584 may be defined between the overload support bar 1514 and the load interface plate 1512. This separation space 1584 may cause enough of a gap between the first and second magnets 1518, 1520 such that continued rotational forces applied to the overload support bar 1514 do not exert a specific force (e.g., twisting, rotational, and/or moment, etc.) to the load interface plate 1512. In at least one example embodiment, the magnetic force between the magnets 1518, 1520 when in the disengaged state (e.g., due in part to the separation offset distance 1583) is less than the magnetic force between the magnets 1518, 1520 when in the engaged state (shown in FIG. 15I). Accordingly, the load cell 1506 is protected from any continued rotational or moment forces. To reset the bottle tray load cell assembly 1500, the overload support bar 1514 may be rotated until the lobes 1578 line up with the valleys 1568, the overload support bar 1514 moves toward the load interface plate 1512, and the separation offset distance 1583 is reduced and/or closed.

Figure 15K:
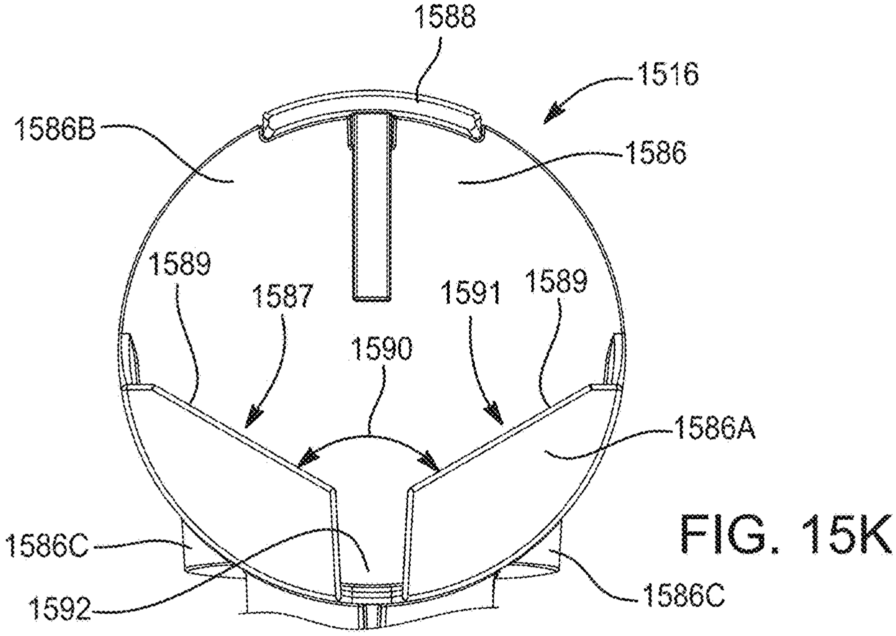
FIG. 15K is a side elevation view of a cradle of the load cell assembly of FIG. 15A in accordance with at least one example embodiment of the present disclosure.

FIG. 15K is a side elevation view of a cradle of the load cell assembly of FIG. 15A according to at least one example embodiment.

In at least one example embodiment, as shown in FIG. 15K, the cradle 1516 includes a wall 1586 at least partially defining a vessel region 1587. The wall 1586 may be partially cylindrical. A cap 1588 may be coupled to the wall 1586 to facilitate alignment and/or retention of a vessel within the vessel region 1587. In at least one example embodiment, the cap 1588 facilitates proper removal of the of a vessel (see, e.g., vessel 1598 of FIG. 15M) from the cradle 1516 by lifting a port end or top of a vessel prior to a bottom of the vessel, thereby reducing or preventing leaks of vessel contents from a vent port of the vessel.

The wall 1586 may extend between a first end 1586A and a second end 1586B. In at least one example embodiment, the second end 1586B of the wall 1586 includes a pair of alignment surfaces 1589. An alignment angle 1590 may be defined between the alignment surfaces 1589. In at least one example embodiment, the alignment angle 1590 is greater than or equal to about 90° (e.g., greater than or equal to about 100°, greater than or equal to about 110°, greater than or equal to about 120°, greater than or equal to about 130°, greater than or equal to about 140°, or greater than or equal to about 150°). The alignment angle 1590 may be less than or equal to about 160° (e.g., less than or equal to about 150°, less than or equal to about 140°, less than or equal to about 130°, less than or equal to about 120°, less than or equal to about 110°, or less than or equal to about 100°). The alignment surfaces 1589 may cooperate at least partially define an alignment region 1591. In at least one example embodiment, the wall 1586 further defines a slot 1592 between the alignment surfaces 1589. The alignment surfaces 1589 and/or the slot 1592 may, in at least one example embodiment, facilitate proper alignment of a vessel within the cradle 1516, as will be described in greater detail below.

In at least one example embodiment, the wall 1586 defines one or more receptacles 1586C. The receptacles 1586C may be configured to receive at least a portion of a calibration weight. In at least the example embodiment shown, the receptacles 1586C are sized and shaped to receive a bottom portion of a cylindrical calibration weight. When the cylindrical calibration weight is at least partially within the receptacles 1586C, a longitudinal axis of the cylindrical calibration weight is substantially parallel to the central axis 1517 (shown in FIG. 15A) of the load cell assembly 1500 (shown in FIG. 15A).

Figure 15L:
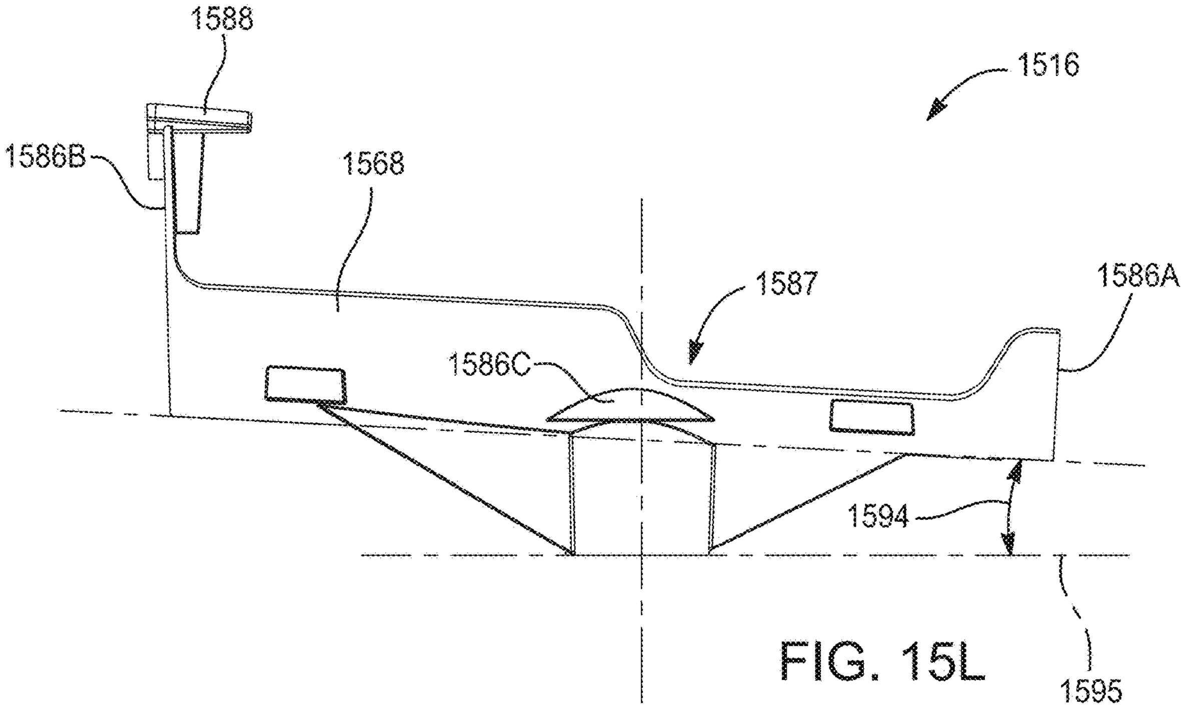
FIG. 15L is a front elevation view of the cradle of FIG. 15K in accordance with at least one example embodiment of the present disclosure.

FIG. 15L is a front elevation view of the cradle of FIG. 15K according to at least one example embodiment.

In at least one example embodiment, as shown in FIG. 15L, the cradle 1516 may be configured to retain a vessel in a desired orientation. The cradle 1516 may define a vessel angle 1594 between a bottom of the wall 1586 and a horizontal plane 1595 (i.e., a plane that is perpendicular to the direction of gravity). In at least one example embodiment, the angle may be greater than about 0° (e.g., greater than or equal to about 1°, greater than or equal to about 2°, greater than or equal to about 3°, greater than or equal to about 5°, or greater than or equal to about) 10°. The vessel angle 1594 may be less than or equal to about 45° (e.g., less than or equal to about 40°, less than or equal to about 35°, less than or equal to about 30°, less than or equal to about 25°, less than or equal to about 20°, less than or equal to about 15°, less than or equal to about 10°, less than or equal to about 8°, or less than or equal to about 5').

Figure 15M:
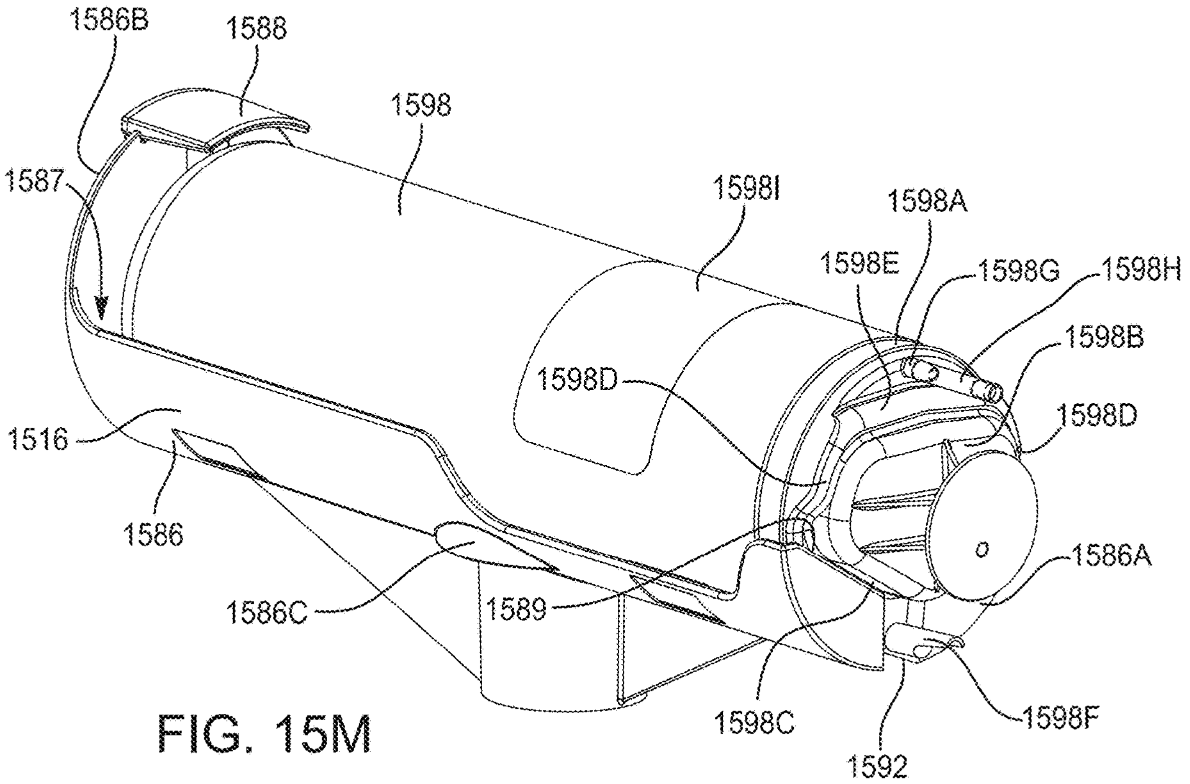
FIG. 15M is perspective view of a vessel in the cradle of FIG. 15K in accordance with at least one example embodiment of the present disclosure.

FIG. 15M is perspective view of a vessel in the cradle of FIG. 15K according to at least one example embodiment.

In at least one example embodiment, as shown in FIG. 15M, the cradle 1516 is configured to retain a vessel in a desired orientation. In at least the example embodiment shown, the vessel is a bottle 1598. The bottle 1598 may be similar to or the same as the bottle 1900 of FIG. 19A. The bottle 1598 may include a cap 1598A. The cap 1598A may include a protrusion 1598B including a pair of vessel alignment surfaces 1598C, a pair of side surfaces 1598D, and an opposing surface 1598E. The cap 1598A may further include a fluid port 1598F and a vent port 1598G. In at least one example embodiment, when the bottle 1598 is installed in the cradle 1516 for use, a vent cap 1598H may be removed from the vent port 1598G and a tube and connector may be connected to the fluid port 1598F (see, e.g., FIGS. 191, 19J).

In at least one example embodiment, when the bottle 1598 is properly oriented in the cradle 1516, the protrusion 1598B is at least partially within the alignment region 1591. The alignment surfaces 1589 of the cradle 1516 engage (e.g., are in direct contact with) the vessel alignment surfaces 1598C and the fluid port 1598F is at least partially within the slot 1592. Accordingly, the vent port 1598G is oriented at a higher location than the fluid port 1598F, at a location above a predetermined (or alternatively, desired) fluid level. In this orientation, filling capacity of the bottle 1598 may be increased or maximized compared to other orientations since placement of the vent port 1598G at the top allows greater fill volume without contents overflowing through the vent port 1598G. Moreover, this orientation may reduce or minimize residual volume such that fluid can be drawn back out of the bottle 1598 without drawing air. The vessel 1598 is oriented at the vessel angle 1594. The vessel angle 1594 may be selected to balance residual needs with high fill volume.

Figure 26A:
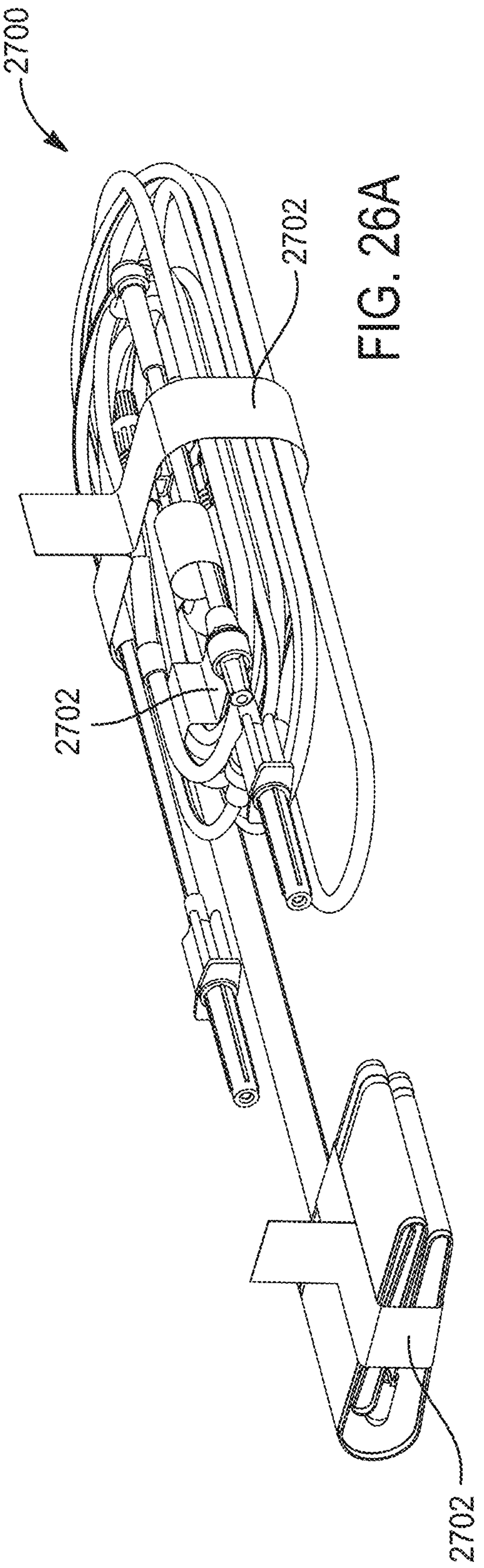
FIG. 26A is a perspective view of a separation set in a packaged state in accordance with at least one example embodiment of the present disclosure.
Figure 26B:
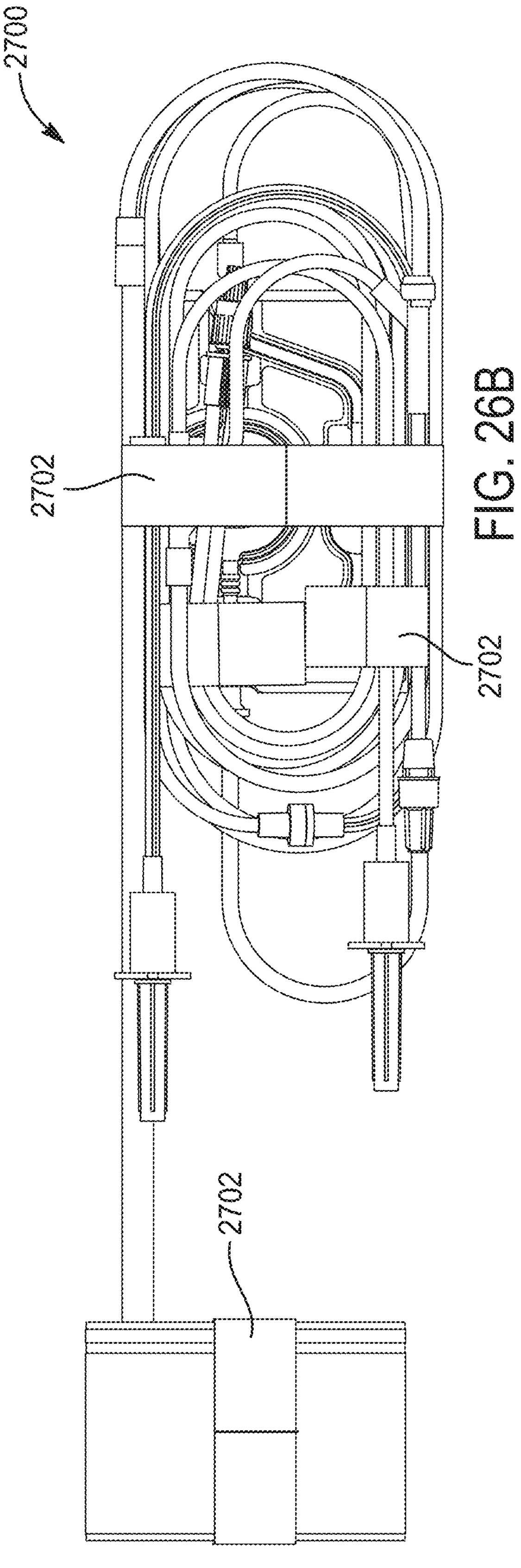
FIG. 26B is an elevation view of the separation set of FIG. 26A in the packaged configuration in accordance with at least one example embodiment of the present disclosure.
Figure 26C:
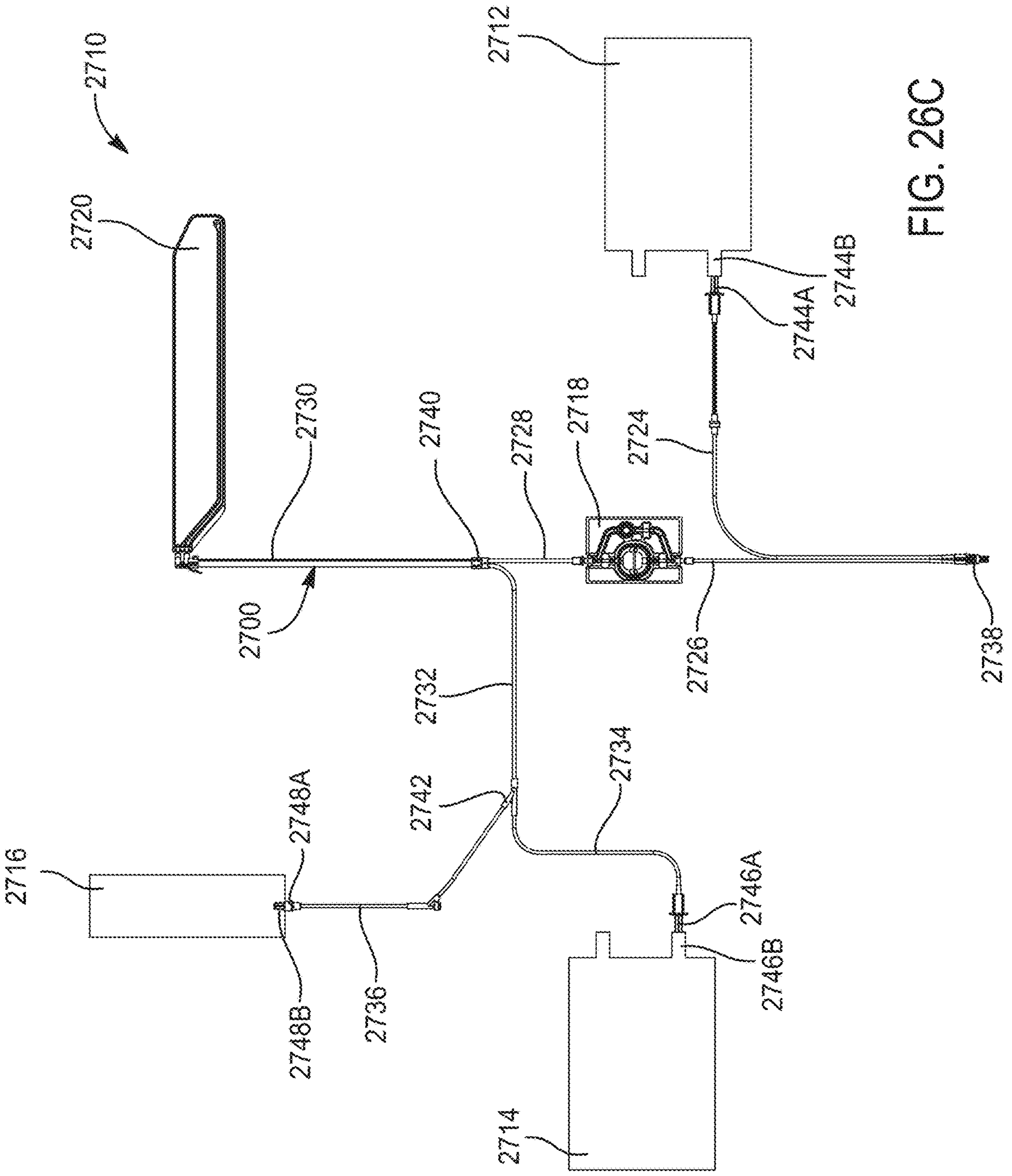
FIG. 26C is a schematic view of a separation assembly including the separation set of FIG. 26A in accordance with at least one example embodiment of the present disclosure.
Figure 26D:
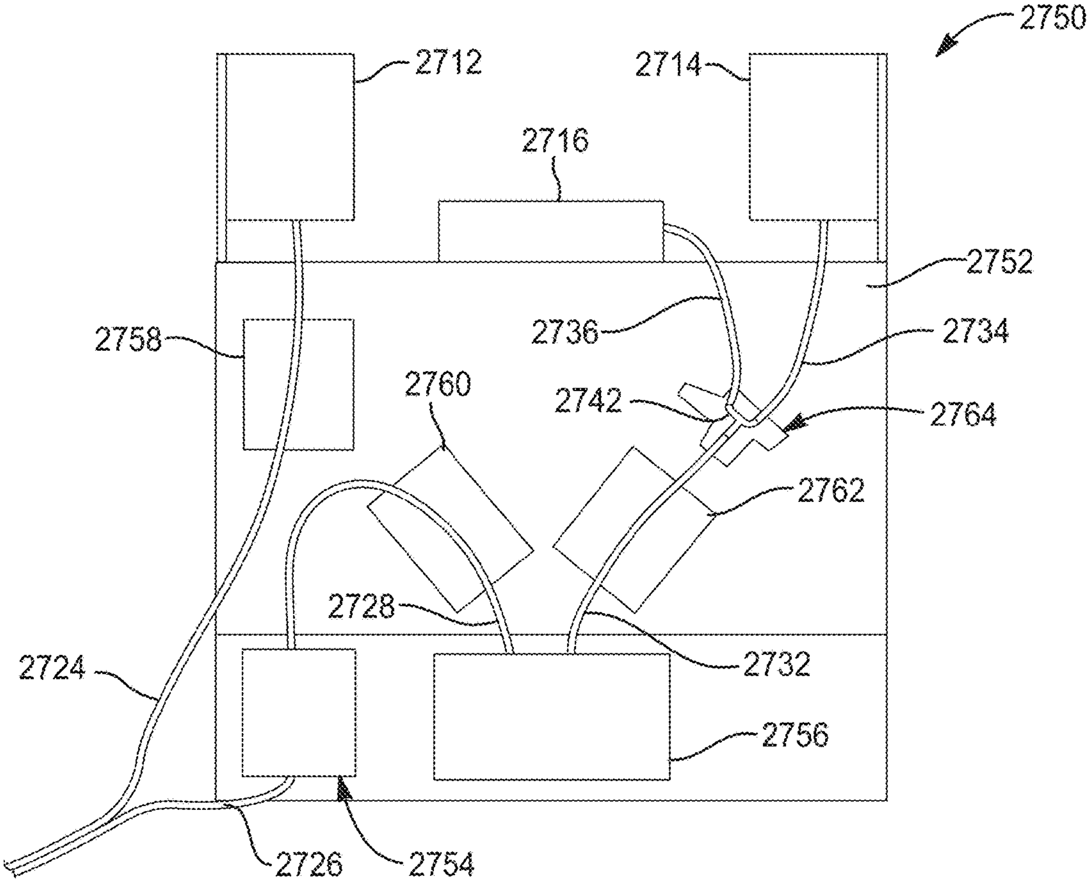
FIG. 26D is a schematic view of an apheresis system including a properly installed component collection assembly in accordance with at least one example embodiment of the present disclosure.
Figure 26E:
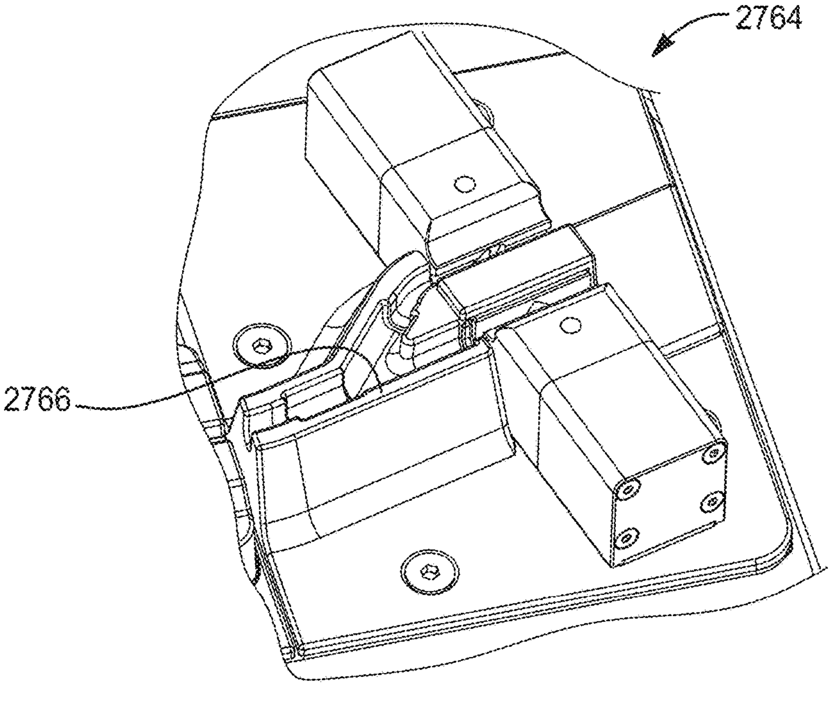
FIG. 26E is a partial perspective view of a valve housing of the apheresis system of FIG. 26D in accordance with at least one example embodiment of the present disclosure.
Figure 26F:
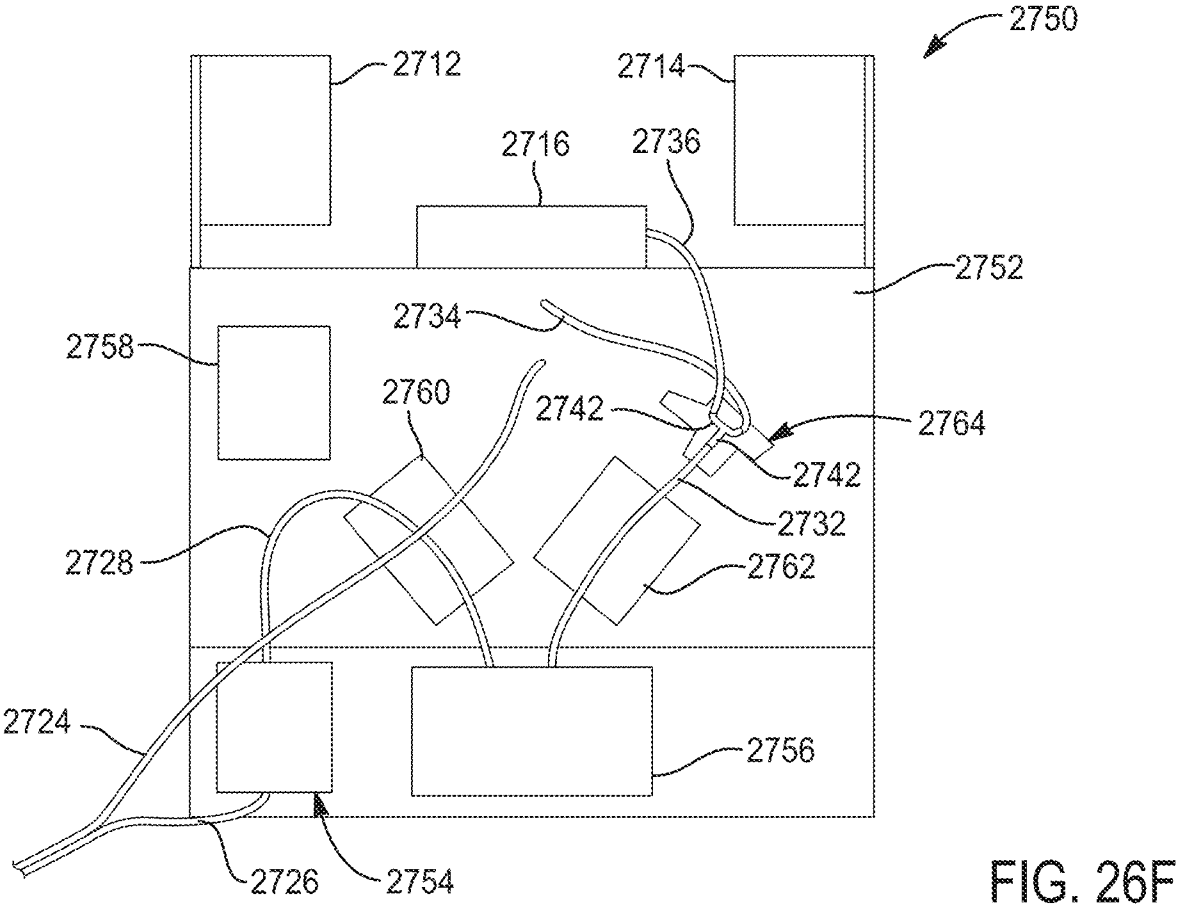
FIG. 26F is a schematic view of an apheresis system including an improperly installed component collection assembly in accordance with at least one example embodiment of the present disclosure.

In at least one example embodiment, as will be discussed in greater detail below in the discussion accompanying FIG. 26J, the bottle 1598 and/or cap 1598A may be sized and shaped to ensure proper placement of the cap 1598A of the bottle 1598 below a bottom of the bottle 1598 in the cradle 1516. That is, the cap 1598A may be oriented toward the first end wall 1586A and the bottom of the bottle 1598 may be oriented toward the second end wall 1586B.

In at least one example embodiment, the bottle 1598 and cradle 1516 include one or more features to facilitate visual identification of improper loading. A user may readily identify when the bottle 1598 is disposed at an angle other than the vessel angle 1594 (FIG. 15K), that is, when a longitudinal axis of the bottle 1598 is not parallel to the cradle 1516. Additionally or alternatively, a user may readily identify when the vessel alignment surfaces 1598C are not fully seated on the alignment surfaces 1589 of the cradle 1516. Additionally or alternatively, a user may identify when the ports 1598F, 1598G are not vertically aligned, with the fluid port 1598F within the slot 1592G. Additionally or alternatively, a user may identify when a label 15981 of the bottle 1598 is not visible, facing upward, and/or substantially centered within the cradle 1516.

In contrast, in at least one example embodiment, when the bottle 1598 is in an improper orientation within the cradle 1516, the opposing surface engages one or both of the alignment surfaces 1589, thereby preventing the protrusion 1598B from being in the alignment region 1591. In the improper orientation, fluid may be pushed from the bottle 1598 through the vent port 1598G, which may be below the fluid level in the improper orientation. When flow is reversed, air would be drawn from the bottle 1598 rather than the intended fluid.

Exemplary aspects are directed to a bottle tray load cell assembly, comprising: a support bracket; a load cell comprising a fixed side and a load deflection side offset from the fixed side, wherein the fixed side of the load cell is attached to the support bracket; an interface plate attached to the load deflection side of the load cell, the interface plate comprising: a body; a first magnet recess disposed in the body; and a plurality of cam lobe valleys at least partially around the first magnet recess, wherein the plurality of cam lobe valleys interrupt a first contact surface of the body; a support bar comprising: a mandrel extending a length along a longitudinal axis from a first end of the mandrel to a second end of the mandrel; a cam body disposed at the second end of the mandrel; a second magnet recess disposed in the cam body; and a plurality of cam lobes extending from the cam body, the plurality of cam lobes arranged at least partially around the second magnet recess; wherein the support bar is moveable between an engaged state with the interface plate and a disengaged state from the interface plate, wherein, in the engaged state, the plurality of cam lobes are disposed in contact the plurality of cam lobe valleys, and wherein, in the disengaged state, the plurality of cam lobes are disposed out of contact with the plurality of cam lobe valleys and are in contact with the first contact surface of the body.

Any one or more of the above aspects further comprising: a first magnet disposed in the first magnet recess, the first magnet comprising a first-magnet pole having a first polarity, the first-magnet pole facing away from the body of the interface plate; and a second magnet disposed in the second magnet recess, the second magnet comprising a second-magnet pole having a second polarity, the second-magnet pole facing away from the cam body of the support bar, wherein the first-magnet pole faces the second-magnet pole, and wherein the first polarity is opposite the second polarity. Any one or more of the above aspects include wherein the support bar is maintained in the engaged state with the interface plate by a magnetic force between the first magnet and the second magnet, and wherein a first movement of the support bar relative to the interface plate causes the support bar to separate a distance from the interface plate and move the support bar from the engaged state with the interface plate to the disengaged state from the interface plate. Any one or more of the above aspects include wherein the first movement comprises a rotational movement about the longitudinal axis, and wherein the rotational movement comprises a force greater than the magnetic force. Any one or more of the above aspects further comprising: a collection cradle fixedly attached to the first end of the mandrel. Any one or more of the above aspects include wherein the load deflection side moves independently of the support bracket. Any one or more of the above aspects include wherein the plurality of cam lobe valleys comprise at least three cam lobe valleys arranged asymmetrically around an axis running through a center of the first magnet recess, and wherein the plurality of cam lobes comprises at least three cam lobes. Any one or more of the above aspects include wherein the at least three cam lobe engage with the at least three cam lobe valleys in a single rotational orientation about the axis running through the center of the first magnet recess. Any one or more of the above aspects include wherein the support bar rotates about the longitudinal axis in the disengaged state without imparting rotational force to the load cell via the interface plate.

Exemplary aspects are directed to a method of disengaging a support member from a weigh scale assembly, comprising: providing a load cell assembly, comprising: a support bracket; a load cell comprising a fixed side and a load deflection side offset from the fixed side, wherein the fixed side of the load cell is attached to the support bracket; an interface plate attached to the load deflection side of the load cell, the interface plate comprising: a body; a first magnet recess disposed in the body; and a plurality of cam lobe valleys at least partially around the first magnet recess, wherein the plurality of cam lobe valleys interrupt a first contact surface of the body; a support bar comprising: a mandrel extending a length along a longitudinal axis from a first end of the mandrel to a second end of the mandrel; a cam body disposed at the second end of the mandrel; a second magnet recess disposed in the cam body; and a plurality of cam lobes extending from the cam body, the plurality of cam lobes arranged at least partially around the second magnet recess; wherein the support bar is moveable between an engaged state with the interface plate and a disengaged state from the interface plate, wherein, in the engaged state, the plurality of cam lobes are disposed in contact the plurality of cam lobe valleys, and wherein, in the disengaged state, the plurality of cam lobes are disposed out of contact with the plurality of cam lobe valleys and are in contact with the first contact surface of the body; positioning the support bar in the engaged state with the interface plate such that the plurality of cam lobes are in contact with the plurality of cam lobe valleys; receiving a movement force at the support bar causing the support bar to move from the engaged state to the disengaged state, wherein the movement force comprises a rotational force about the longitudinal axis; and moving, while in the disengaged state, the support bar independently of the interface plate and without imparting a specific rotational force to the interface plate and the load cell.

Example Communication Methods of the Apheresis System

In at least one example embodiment, the apheresis system 200, as described herein, may comprise one or more computer systems, such as the computer system 1627. The processor 1630 of the computer system 1627 may be configured to execute one or more of the processes and methods described herein. The processor 1630 may execute software. For example, the software may include firmware, applications, and/or operating systems which may manage execution of the apheresis system 200.

Software, including firmware, applications, operating systems, and other programmable features of the apheresis system 200, may be updated from time to time to ensure the apheresis system 200 is operating as needed.

The apheresis system 200 may include an application that, among other things, performs fleet management and allows customers to install software for bulk groups of devices. Software systems implemented by the apheresis system 200 may be configured to generate and/or compile device logs (D-logs) to send to a cloud storage location. D-logs may be used for predictive analytics or other purposes. Each apheresis system 200 may be in communication with a remote system server 1621 (e.g., over a communications network 1618, in the cloud, etc.), as illustrated in FIG. 16B. During startup, each apheresis system 200 may communicate information about the software, including a firmware version, error logs encountered, etc., to the server 1621 using a method such as illustrated in FIG. 16A.

The system server 1621 may be configured to determine whether the software and/or the firmware version of the apheresis system 200 needs updating (e.g., is out of date, etc.). In at least one example embodiment, the system server 1621 may force a software and/or a firmware update automatically or give a user an option to update the software and/or the firmware. In at least one example embodiment, an external device may be connected to the apheresis system 200 to update the software. For example, the external device may be a computer or laptop configured to be connected to the apheresis system 200 and to update the software of the apheresis system 200. In any event, if the software for an apheresis system 200 is not updated, the apheresis system 200 may be prevented from operating. This prevention may be based on a lock signal sent by the system server 1621 or by the apheresis system 200 not receiving an unlock signal from the system server 1621 that allows operation.

Figure 16A:
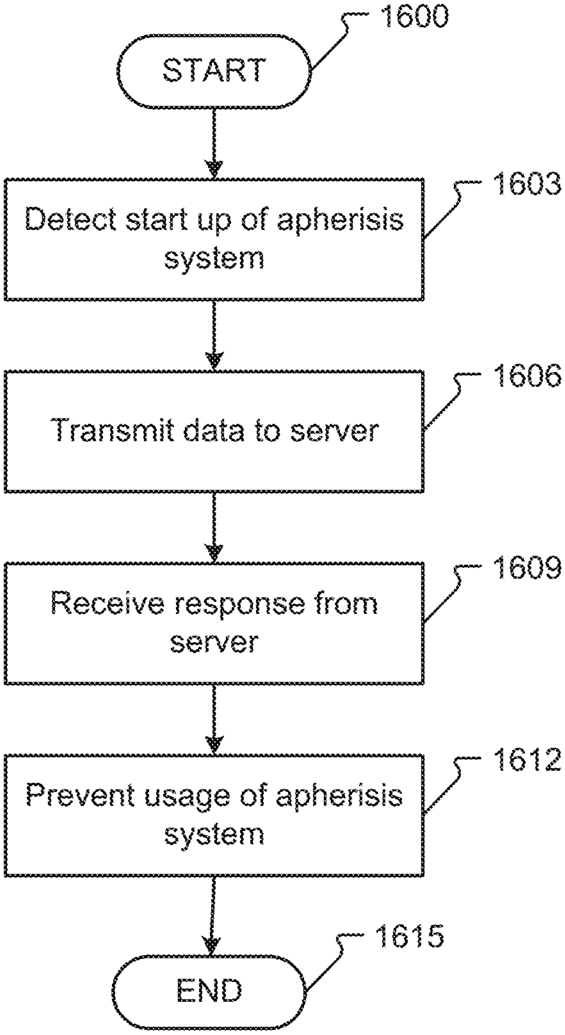
FIG. 16A is a flowchart of a method in accordance with at least one example embodiment of the present disclosure.

The method of FIG. 16A may begin at 1600 in which the apheresis system 200 may be in an off or unused state. At 1603, the apheresis system 200 may be powered and may run through a power-up process. A computer system 1627, such as illustrated in FIG. 16D, may be configured to detect a startup of the apheresis system 200 or may be configured to automatically perform a process such as described herein upon startup.

Figure 16B:
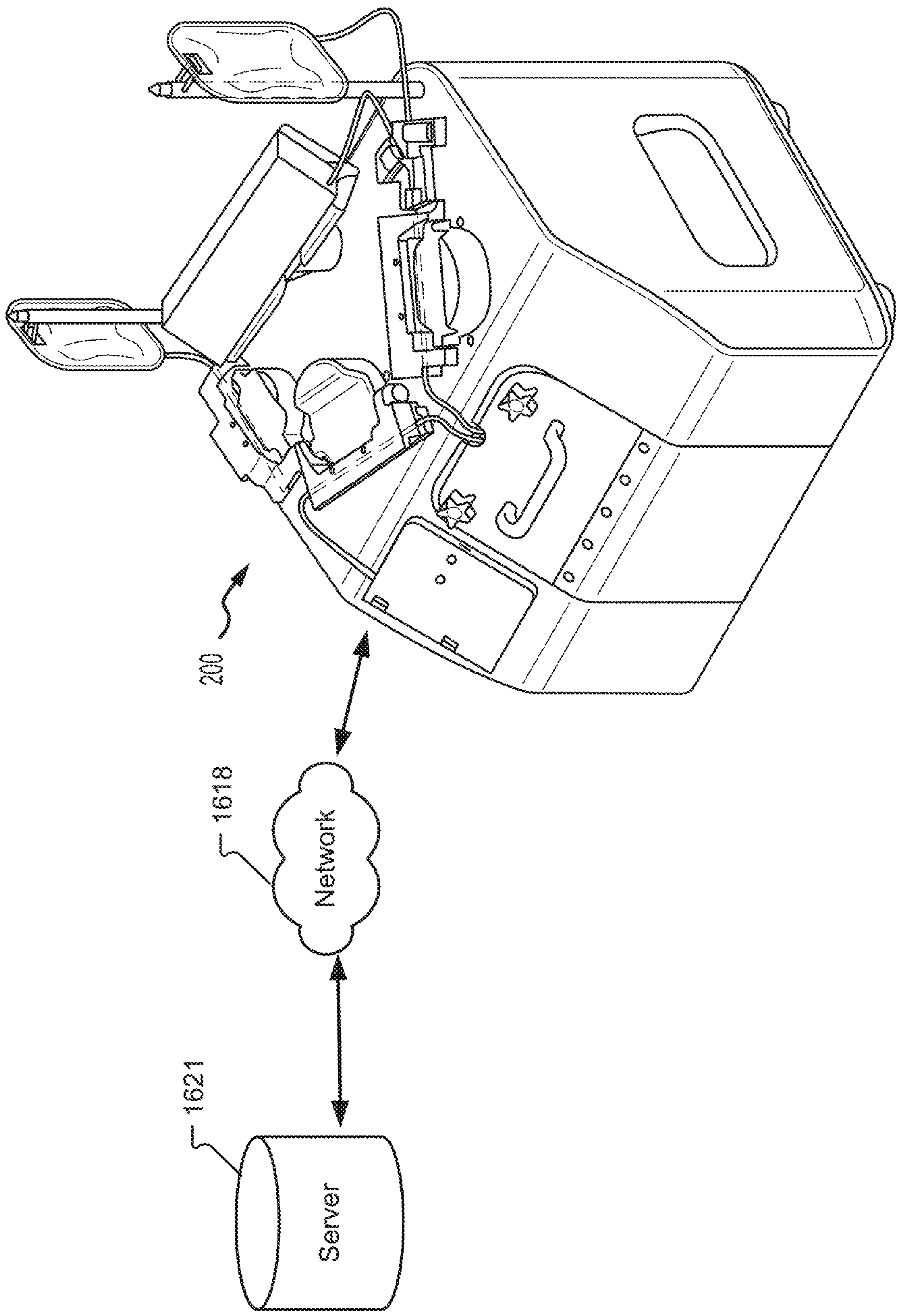
FIG. 16B shows an apheresis system connected to a network in accordance with at least one example embodiment of the present disclosure.

In response to detecting start up, the computer system 1627 may transmit data to a server 1621 via a connection to a network 1618, as illustrated in FIG. 16B. The data transmitted to the server 1621 may comprise one or more of a data log, a firmware version identifier, and an error log.

At 1609, the apheresis system 200 may receive a response from the server 1621 in response to the data transmitted to the server 1621. The server 1621 may be configured to determine, based on the data, whether the software of the apheresis system 200 is a current and/or up-to-date version. If the software is out-of-date or is not the current version, the server 1621 may send a lockout signal or other type of data packet instructing the apheresis system 200 to require a software update before being used. In at least one example embodiment, an apheresis system 200 may not be usable until a positive confirmation that the software is up to date is received from the server 1621 via the network connection 1618. In this way, the risks associated with using an outdated apheresis 200 system may be avoided. For example, at 1612, usage of the apheresis system 200 may be prevented based on the response received from the server.

In at least one example embodiment, if the server 1621 determines the software is out-of-date, the server may send, as part of its response, one or more files for updating the software. Additionally or alternatively, the software of the apheresis system 200 may be automatically updated. For example, the software update may be automatically initiated after receiving the one or more files for updating the software from the server. In at least one example embodiment, the apheresis system 200 may enable a user to manually update the system once the one or more files for updating the software are received. For example, the user may manually initiate the software update after receiving the one or more files. Once the software has been updated, the apheresis system 200 may be configured to unlock and allow usage of the system.

In at least one example embodiment, the method illustrated in FIG. 16A may further comprise, after preventing usage of the apheresis machine, determining whether an unlock requirement has been met. For example, the unlock requirement may include properly updating the software. In response to determining the unlock requirement has been met, the apheresis system 200 may enable usage.

Figure 16C:
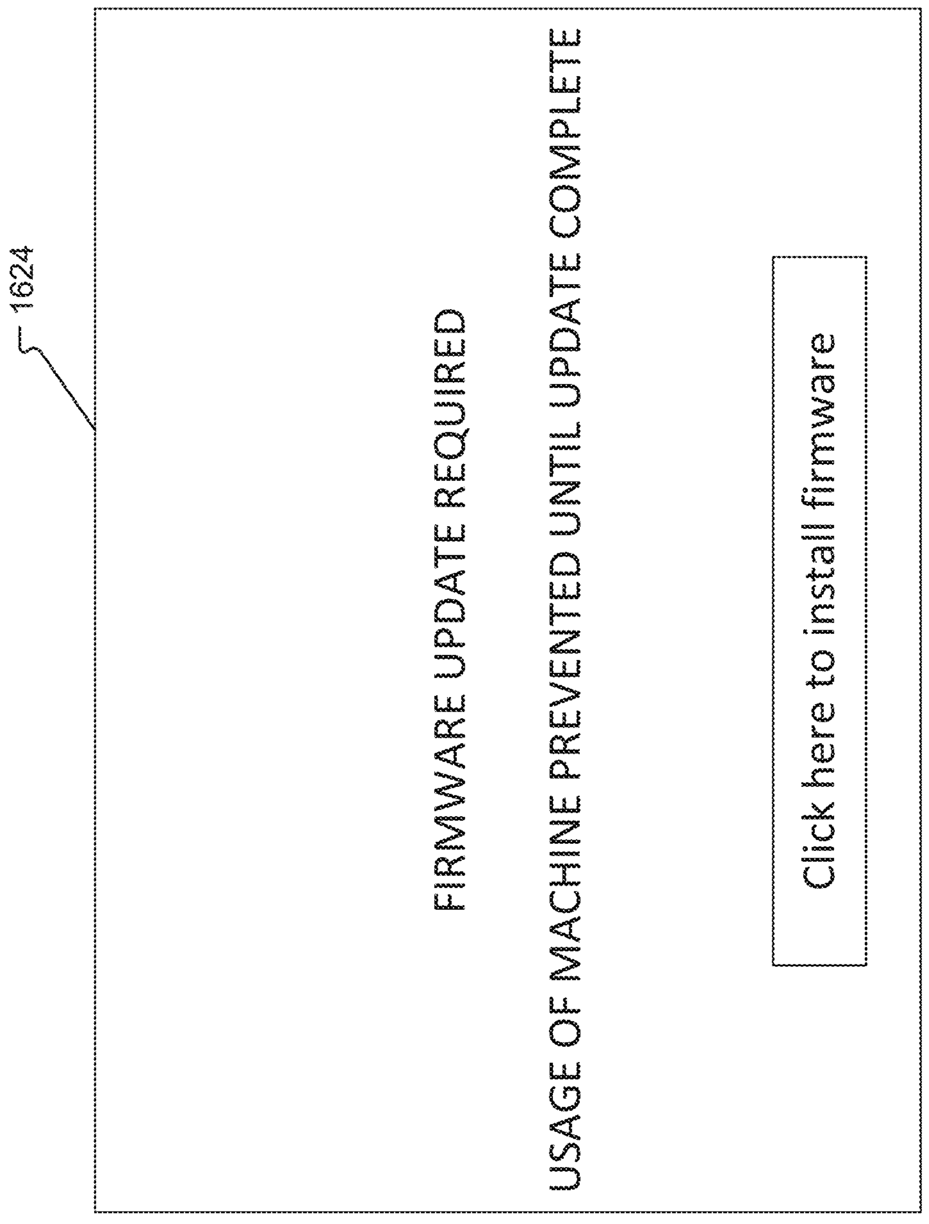
FIG. 16C shows a graphical user interface in accordance with at least one example embodiment of the present disclosure.
Figure 16D:
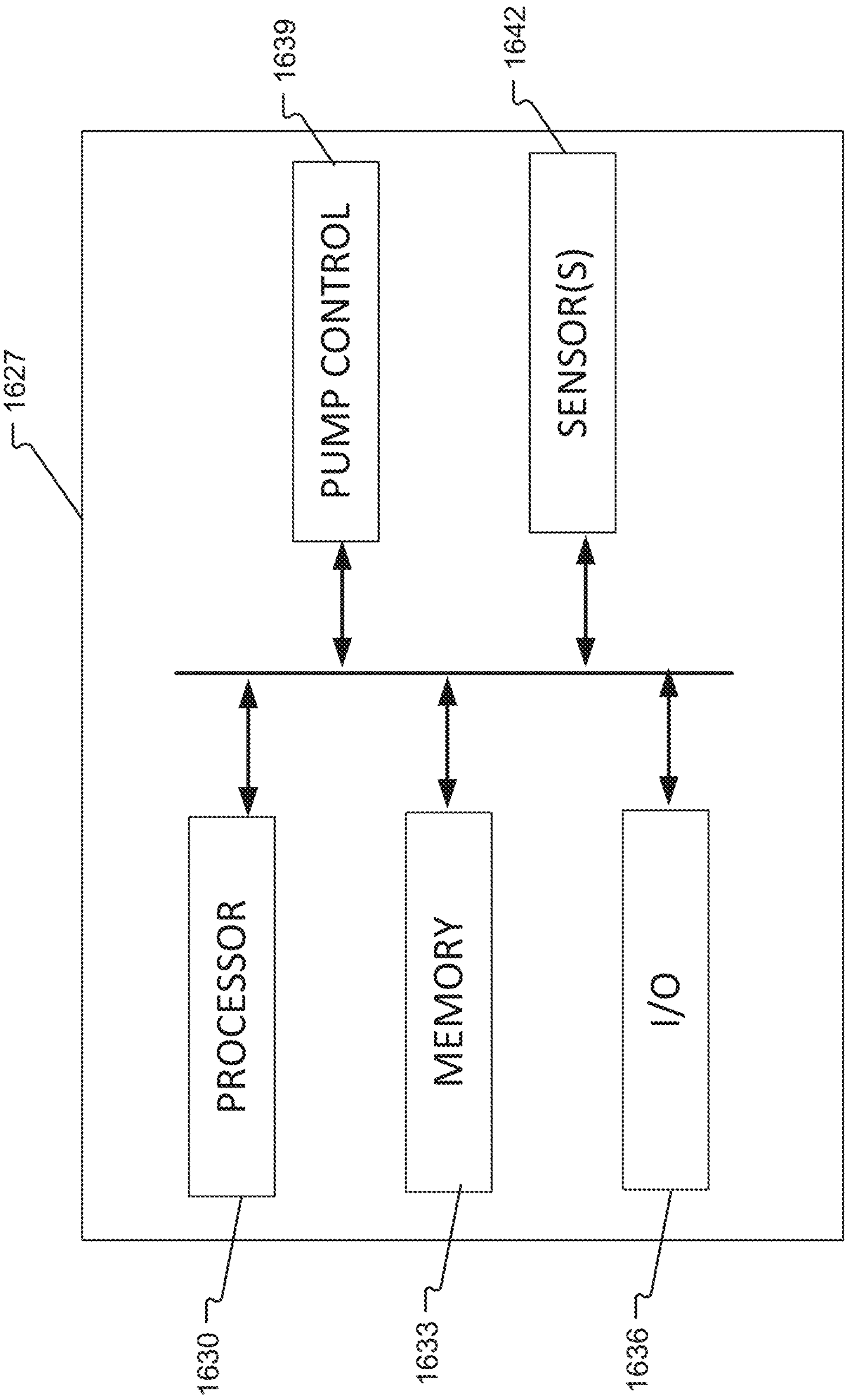
FIG. 16D is a block diagram of a computing system in accordance with at least one example embodiment of the present disclosure.

In at least one example embodiment, a message may be displayed on a graphical user interface 1624 of the apheresis system 200, as illustrated in FIG. 16C. The message may inform a user as to whether the apheresis system 200 is locked due to out-of-date software and may enable a user to manually install an update to the software as needed. In at least one example embodiment, the user may manually initiate installation of the update to the software using the graphical user interface (GUI) 1624. In other embodiments, the user may connect an external device including the update to the software to the apheresis system 200 to initiate and install the software update.

At least one example embodiment includes a method comprising: detecting a startup of an apheresis machine; in response to detecting start up, transmitting data to server; receiving, in response to data, a response from the server; and based on the response from the server, preventing usage of apheresis machine.

Aspects of the above embodiment include wherein the data transmitted to the server comprises one or more of a data log, a firmware version identifier, and an error log. Aspects of the above embodiment include wherein the response comprises a lockout signal. Aspects of the above embodiment include wherein the response comprises a firmware update. Aspects of the above embodiment include wherein the firmware update is installed automatically. Aspects of the above embodiment include wherein the apheresis machine ceases to prevent usage following installation of the firmware update. Aspects of the above embodiment include wherein the firmware update is installed manually by a user. Aspects of the above embodiment include, based on the response from the server, displaying a message on a graphical user interface. Aspects of the above embodiment include wherein the graphical user interface enables a user to begin a firmware installation. Aspects of the above embodiment include, after preventing usage of the apheresis machine, determining an unlock requirement has been met; and, in response to determining the unlock requirement has been met, enabling use of the apheresis machine. Aspects of the above embodiment include wherein the unlock requirement is associated with an updated firmware.

Example Methods and Processes Providing Donation Process Feedback

The apheresis system 200 may include one or more interface elements (e.g., display devices, LEDs, alarms, etc.) that provide indications to a user and/or the donor 102 regarding information about the donation process. In one example, these interfaces may indicate to the donor 102 that the donor 102 should squeeze (e.g., when pressure or flow falls below a predetermined threshold, etc.). Additionally or alternatively, the interface elements may indicate to the donor 102 how far in the donation process they are. In any event, this feedback may be provided in audible and/or visual output by the apheresis system 200 (e.g., via one or more speakers, display devices, LEDs, etc.). In at least one example embodiment, LEDs may be arranged on the side of the apheresis system 200 that provides this feedback to the donor 102.

Figure 17A:
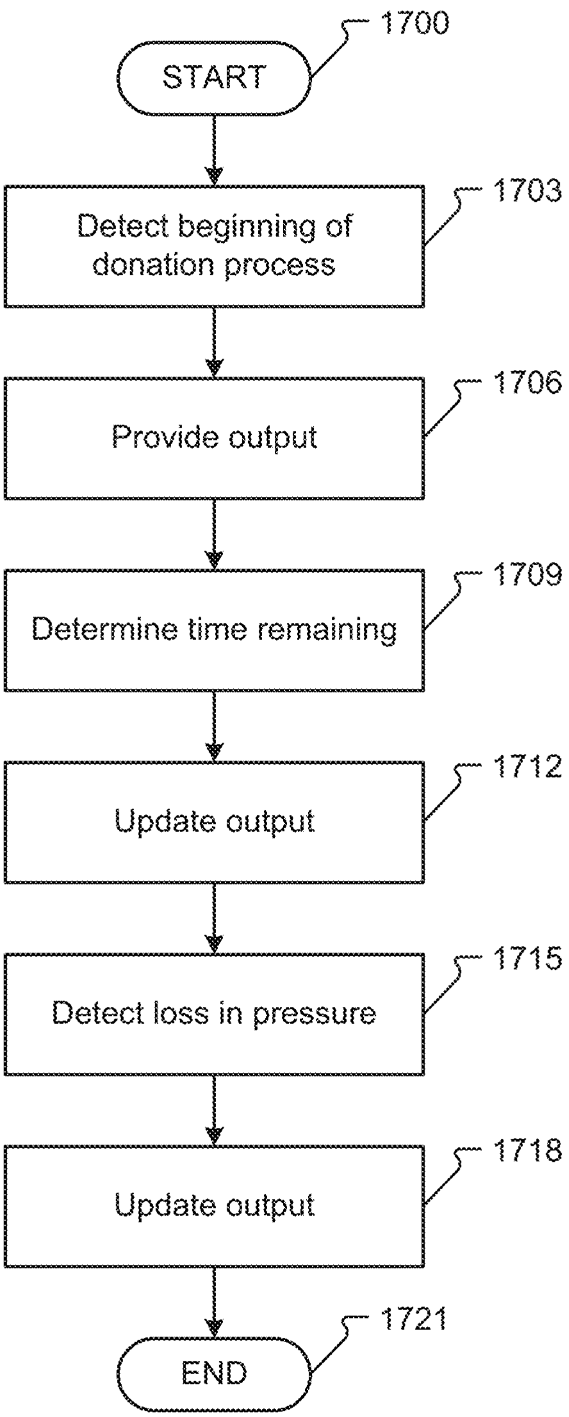
FIG. 17A is a flowchart of a method in accordance with at least one example embodiment of the present disclosure.

The method illustrated by the flowchart of FIG. 17A may begin at 1700. At the beginning of the method, an apheresis system, such as the apheresis system 200, may be powered on and connected to a donor, such as the donor 102.

At 1703, a computer system of the apheresis system 200 may detect a beginning of a donation process. In at least one example embodiment, no detection per se may be required, but instead the method illustrated in FIG. 17A may be performed automatically as part of the donation process. For example, detecting the beginning of a donation process may comprise initiating the donation process. In at least one example embodiment, detecting the beginning of the donation process may comprise detecting a flow of fluid, for example, by using one or more sensors, such as the fluid sensor 316.

Figure 17B:
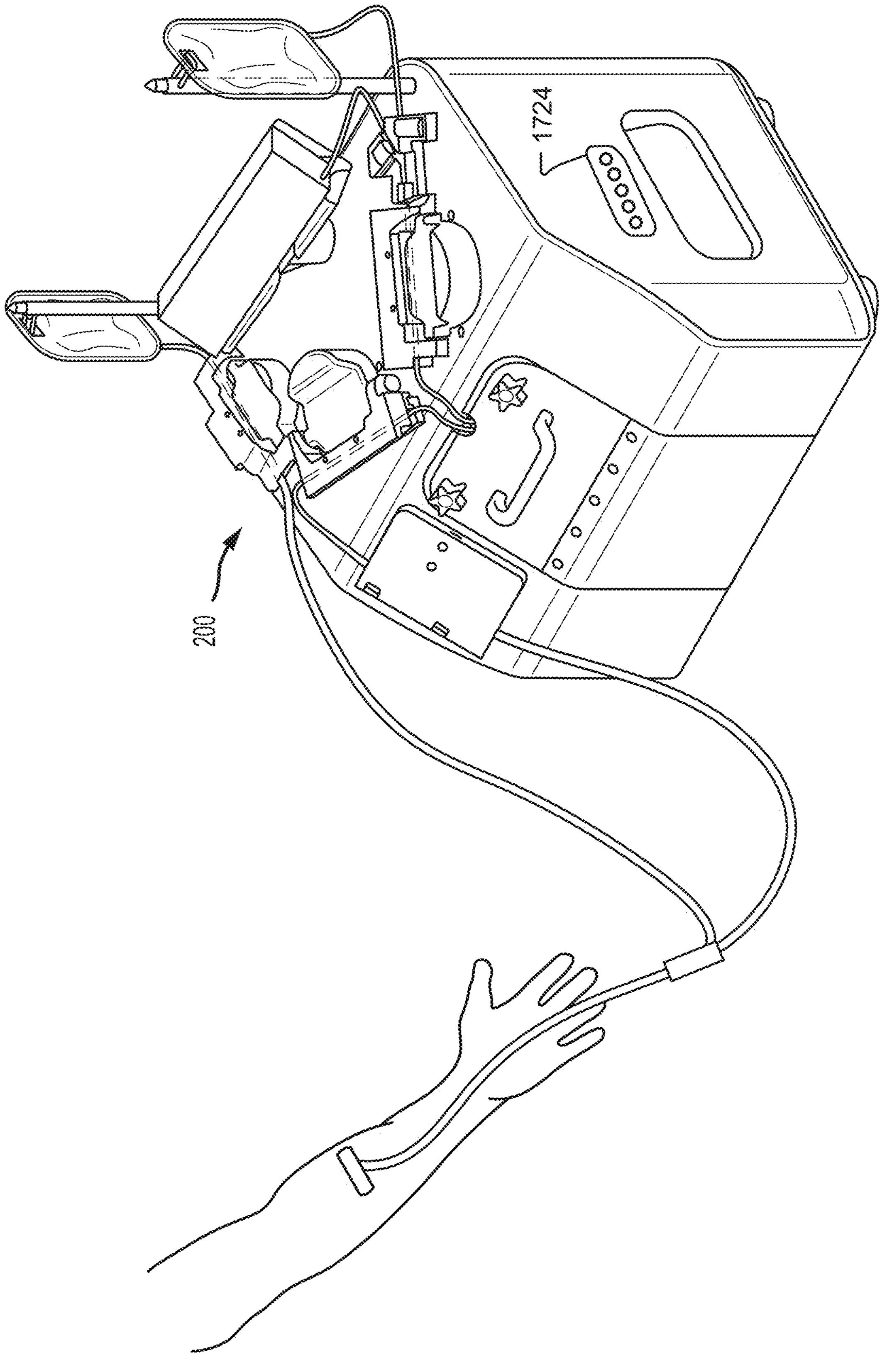
FIG. 17B shows an apheresis system in accordance with at least one example embodiment of the present disclosure.

At 1706, once the donation process begins, the apheresis system may provide an output which is noticeable by the donor 102. For example, the output may be a light, sound, GUI display, etc. The output may be provided in view of the donor 102. In at least one example embodiment, a side of the apheresis system 200 may include an output 1724, as illustrated in FIG. 17B. For example, the output 1724 may comprise a series of lights, such as light emitting diodes (LEDs). While displayed as being on a particular side of the apheresis system 200, it should be appreciated that the output 1724 may be on any side of the apheresis system 200 and may be within a range of the donor 102 such that the output may be one or more of viewed and heard by the donor 102.

In at least one example embodiment, the output 1724 may be a display device. For example, the output 1724 may illuminate or glow in such a way as to visualize to a donor, or other user of the apheresis system, information such as how much time is remaining in the donation process, whether the donor should squeeze her hand to improve a flow of blood into the apheresis system, or other information. The output 1724 may be configured to illuminate or glow in a pulsing manner, in which a rate of the pulses of light may be synchronized with a rate at which the donor should squeeze her hand to reach an optimal rate of flow.

At 1709, the method may comprise determining a percentage of the donation process completed and/or remaining. For example, this may include determining an amount of time remaining for the donation process. Determining an amount of time remaining may comprise first determinizing an amount of plasma expected to be donated by the donor 102. Determining the amount of plasma expected to be donated by the donor may comprise receiving donor information as part of an initiation process. For example, the donor information may be received from a donor's ID card via a reader or scanner, such as the reader 1221 described above.

Determining an amount of time remaining may comprise dividing the amount of plasma expected to be donated by a donor by an expected flow rate. For example, if the apheresis system 200 determines there is an expected one liter of plasma yet to be donated, and that plasma is expected to be donated at a rate of one liter per minute, the apheresis system 200 may determine there is one minute remaining for the donation process.

At 1712, the method may comprise, in response to detecting the amount of time remaining for the donation process, updating the output.

Figure 17C:
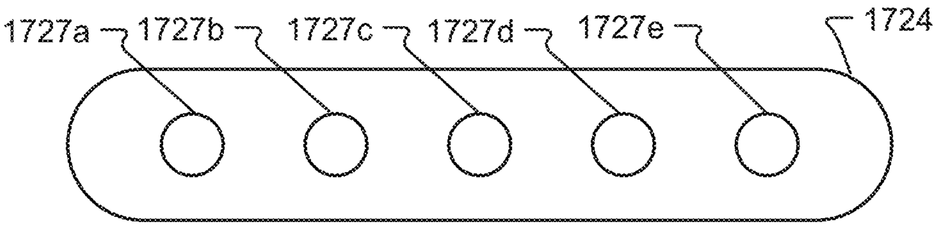
FIGS. 17C-17E show output devices in accordance with at least one example embodiment of the present disclosure.
Figure 17D:
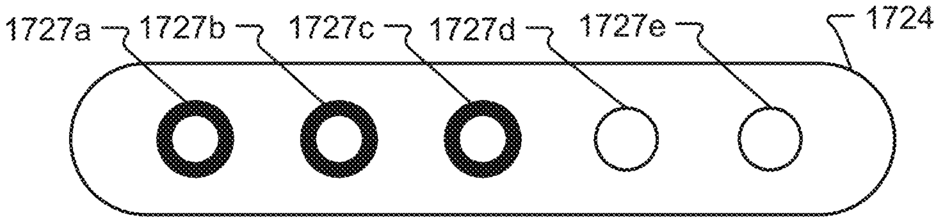
Figure 17E:
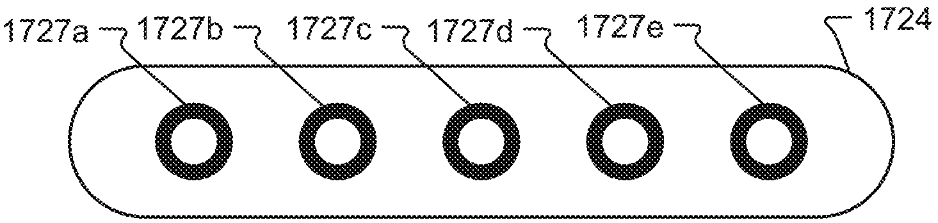

In at least one example embodiment, updating the output, such as the output 1724, may comprise adjusting a number of lights or a percentage of a display illuminated. For example, as illustrated in FIGS. 17C-17E, the output 1724 may comprise five lights, 1727*a-e*. Each of the five lights 1727*a-e* may be independently illuminated based on an amount of time remaining. Further, as discussed above, the lights 1727*a*—e may be capable of being pulsed, that is, a brightness of each light may be independently adjusted so that a pulsing effect may be achieved.

As illustrated in FIG. 17C, each light of the output 1724 may be turned off or otherwise not illuminated to illustrate to a donor that the donation process has just begun. As illustrated in FIG. 17D, a subset of the lights 1727*a-e* may be illuminated based on an amount of time remaining as compared to a total time for the donation process. For example, if the donation process is sixty percent complete, sixty percent of the lights may be illuminated. As illustrated in FIG. 17E, every light of the output 1724 may be illuminated to illustrate to a donor that the donation process is or is near complete. In at least one example embodiment, a color of the lights 1727*a*—e of the output 1724 may change upon completion of the donation process.

At 1715, the method may comprise detecting a loss in pressure. Detecting a loss in pressure may comprise detecting that a pressure of a fluid in the apheresis machine 200 drops below a predetermined threshold. A loss in pressure may be attributed to poor circulation in the donor 102, a collapsed vein, an insufficiently powered pump, or other reasons. In some cases, the donor 102 may be required to squeeze her hand to increase the rate of flow into the apheresis system 200. By squeezing her hand at a particular rate, the donor 102 may be enabled to control the rate of flow into the apheresis system 200.

At 1718, in response to detecting the loss in pressure, the method may comprise updating the output 1724. For example, in response to detecting a loss in pressure, the apheresis system 200 may update the output 1724 such that the output 1724 instructs the donor 102 to squeeze. Updating the output 1724 to instruct the donor to squeeze may comprise flashing. For example, one or more of the lights 1727*a-e* may be turned on and off. In at least one example embodiment, a brightness of one or more of the lights 1727*a-e* may be pulsed at a particular rate. The rate at which the lights are pulsed or flashed may be based on a particular flow rate which needs to be achieved in order to complete the donation process.

At 1721, the method may end when the donation is complete. In at least one example embodiment, ending the method may comprise detecting the ending of the donation process. Ending the method may comprise turning off the output 1724. For example, after detecting and ending of the donation process, the apheresis system 200 may perform an output routine, indicating to the donor 102 that the donation process is complete. Such an output routine may comprise one or more of flashing the lights of the output 1724 in a particular order, changing a color of the lights of the output 1724, generating a noise, or making some other noticeable output, which may indicate to the donor 102 that the donation process is complete. After the output routine, the apparatus or system may cease making any noise, and may turn off any lights.

In at least one example embodiment, during a donation process, the apheresis system 200 may be configured to detect alarm events and, in response, alert a user as to the alarm. For example, during a plasma donation process, a processor of a computer system or microcontroller within the apheresis system 200 may be configured to detect a factor such as temperature, pressure, flow rate, color, weight, input data from a scanner, or other factors. If any of the factors are incorrect, too high, too low, etc., the processor may generate a graphical output which may alert a user as to the alarm event and/or instruct the user as to how to resolve the alarm event.

Detecting an alarm event associated with an apheresis system may comprise monitoring factors such as temperature, pressure, flow rate, color of fluid, weight of plasma received, data received from a scanner, motor control, centrifuge speed, software failure modes, and/or other factors relating to the donation process.

Detecting the alarm event may comprise receiving data from one or more sensors such as temperature sensors, pressure sensors, flow rate sensors, color sensors, valve sensors, weight sensors, a scanner, or other device.

The sensors may be placed throughout the apheresis system 200 and may be configured to monitor a number of aspects of the donation process, such as weight of the plasma donation bottle, flow rates and flow pressures of tubing, speed of the centrifuge, and/or other elements.

The alarm event may be detected when one of the factors crosses a threshold or reaches a particular value. The threshold may be an upper threshold or a lower threshold or may be a particular amount or a range. In the case of the alarm being related to a color of fluid, for example, the threshold may be a particular color or range of colors.

The threshold may also be related to a time or time range. For example, an alarm event may be detected when data received from a scanner, such as donor identification data, is out-of-date or expired. In at least one example embodiment, the alarm event may be detected when data received from the scanner indicates one or more of an expired instrument or device, an invalid instrument or device, and an incompatible instrument or device.

In at least one example embodiment, an alarm event may be based on data from multiple sensors. For example, an alarm event may occur when both pressure and temperature cross particular thresholds.

After detecting the alarm, the processor may generate or retrieve a graphical presentation output based on the alarm event detected.

Generating a graphical presentation output may comprise providing text describing the alarm event, providing one or more images describing the alarm event, and/or providing other content aimed towards instructing a user as to how to resolve the alarm.

Retrieving a graphical presentation output may comprise pulling from memory one or more of text describing the alarm event, one or more images describing the alarm event, and/or other content aimed towards instructing a user as to how to resolve the alarm.

The instructions comprise at least one instruction to move the apheresis system 200 from an alarm state to an operating state. An instruction to move the apheresis system 200 from an alarm state to an operating state may comprise visual aids and/or text informing a user as to what steps may be performed which may resolve the issue underlying the alarm event. For example, the instructions may comprise information instructing a user to perform one or more of connect a tube, close a latch, and remove a kink from a tube. In at least one example embodiment, the instructions may include instructing the user to end the donation process and disconnect a donor from the apheresis system 200.

After generating and/or retrieving the graphical presentation output based on the alarm event detected, the processor may render the graphical presentation output to a graphical user interface of the apheresis system.

In at least one example embodiment, the processor may additionally, or alternatively to rending the graphical presentation output to a GUI, such as the GUI 1230 shown in FIG. 12B; illuminate one or more light emitting diodes (LEDs); and/or output an audible sound upon detection of the alarm event. The LEDs may be switchable between a plurality of colors, such as orange, yellow, red, and cyan. The color of the LEDs may be selected by the processor to correspond to a type of the alarm event detected. In at least one example embodiment, the LEDs may include one or more lights 2339, as will be discussed below with respect to FIG. 22C.

In at least one example embodiment, each color may be associated with a different type and/or level of alarm. For example, a type of alarm may indicate the alarm is associated with a one or more of temperature, pressure, flow rate, color, and weight.

A level of alarm may indicate, for example, a severity or priority of the alarm. In at least one example embodiment, different thresholds may be used to determine whether a particular factor is at a mild or severe level. For example, if a normal pressure is 10 PSI, a mild level alarm may be set for pressures under 5 PSI and a severe level alarm may be set for pressures of zero PSI. In at least one example embodiment, a high severity alarm may be red. In at least one example embodiment, a medium priority alarm may be yellow or orange. In at least one example embodiment, a low priority alarm may be green or blue. In at least one example embodiment, the light may be off or not illuminated if no alarm event is presently detected.

In at least one example embodiment, the level of severity or priority of the alarm may be indicated by blinking or flashing of the light. The rate at which the light blinks may also indicate the severity of the alarm. For example, a light blinking at a faster rate or tempo may be of higher severity and priority and a light blinking at a slower rate or tempo may be of lower priority.

In at least one example embodiment, an audible alert or sound may indicate the level of severity or priority of the alarm event. For example, various sounds, sound patterns, and sound frequencies may indicate a level of priority. For example, higher frequency sounds may indicate higher priority alarm events and lower frequency sounds may indicate lower priority alarm events In at least one example embodiment, the rate at which a sound is made may indicate the level of severity of the alarm event. For example, a sound that occurs, such as a beep, more frequently within a period of time may indicate a higher priority alarm event.

The color of the alarm may be set based on both the type of alarm as well as the severity. For example, an alarm relating to temperature may be a blue light and the brightness or shade of color may be adjusted based on alarm severity.

In at least one example embodiment, the graphical presentation output may comprise a timestamp indicating a time the alarm event occurred.

In at least one example embodiment, the graphical presentation may comprise a description of the alarm and a list of actions to resolve the alarm.

In at least one example embodiment, the graphical presentation output may comprise an illustration associated with the alarm event. For example, a photo or illustration may be displayed so that a user may be instructed how to resolve the alarm state.

In at least one example embodiment, the graphical presentation comprises GUI elements enabling a user to one or more of reset, continue, and end the donation process.

In at least one example embodiment, after rendering the graphical presentation output, the method may comprise performing a system check. In at least one example embodiment, the system check may be performed continuously through the donation process. Performing a system check may comprise polling data associated with the alarm event to determine whether the factor causing the alarm event has returned to a normal level. If the factor causing the alarm event has returned to the normal level, the alarm may then be resolved and ended. In at least one example embodiment, the alarm event may require the donation process to be ended and the donor disconnected from the apheresis system 200. In such embodiments, the system check may determine that the alarm event may not be resolved or recoverable and may trigger an alarm and/or provide instructions to end the donation process and disconnect the donor 102.

For example, if a temperature dropping below a predetermined threshold caused the alarm event, performing the system check may comprise determining whether the temperature is at or above the predetermined threshold.

At least one example embodiment includes a method comprising: detecting a beginning of a donation process; in response to detecting the beginning of the donation process, providing an output; determining an amount of time remaining for the donation process; in response to detecting the amount of time remaining for the donation process, updating the output; detecting a loss in pressure; in response to detecting the loss in pressure, updating the output; detecting an ending of the donation process; and in response to detecting the ending of the donation process, updating the output.

Aspects of the above embodiment include wherein the donation process is a plasma donation using an apheresis machine. Aspects of the above embodiment include wherein detecting the beginning of the donation process comprises detecting a flow of fluid. Aspects of the above embodiment include wherein the output is one or more of a light and a sound. Aspects of the above embodiment include wherein the output is provided on a side of an apheresis machine. Aspects of the above embodiment include wherein the output is within a range of a donor. Aspects of the above embodiment include wherein the output may be one or more of viewed and heard by the donor. Aspects of the above embodiment include wherein the output is a display device. Aspects of the above embodiment include wherein the display device displays a series of lights. Aspects of the above embodiment include wherein the series of lights updates to illustrate to a donor an amount of time remaining in the donation process. Aspects of the above embodiment include wherein the series of lights pulses to instruct the donor to squeeze. Aspects of the above embodiment include wherein the pulsing of the lights is of a tempo associated with a rate at which the donor should squeeze to maintain pressure. Aspects of the above embodiment include wherein detecting a loss in pressure comprises detecting pressure of a fluid in the apheresis machine drops below a predetermined threshold. Aspects of the above embodiment include, in response to detecting the loss in pressure, updating the output comprises instructing a donor to squeeze. Aspects of the above embodiment include, in response to detecting the ending of the donation process, updating the output comprises ceasing an audible noise or turning off a light.

At least one example embodiment of the present disclosure includes a method comprising: detecting an alarm event associated with an apheresis system, retrieving a graphical presentation output based on the alarm event detected, and rendering the graphical presentation output to a graphical user interface of the apheresis system.

Aspects of the above method include wherein the method is performed by an apheresis system being used to perform a plasma donation process. Aspects of the above method include wherein the alarm event is related to one or more of the following factors: temperature; pressure; flow rate; color of fluid; excessive amount of plasma received; and data received from a scanner. Aspects of the above method include wherein the alarm event is associated with out-of-date data received from the scanner. Aspects of the above method include wherein the alarm event is detected when one of the factors crosses a threshold. Aspects of the above method include wherein detecting the alarm event comprises receiving data from one or more sensors. Aspects of the above method include wherein retrieving the graphical presentation output comprises generating the graphical presentation output. Aspects of the above method include wherein the graphical presentation output comprises instructions describing the alarm event. Aspects of the above method include wherein the instructions comprise at least one instruction to move the apheresis system from an alarm state to an operating state. Aspects of the above method include wherein the instructions comprise instructing a user to one or more of connect a tube, close a latch, and remove a kink from a tube. Aspects of the above method include illuminating a light emitting diode (LED) upon detection of the alarm event. Aspects of the above method include wherein a color of the light emitting diode is selected by the processor to correspond to a type of the alarm event detected; wherein the color is selected from orange, yellow, red, and cyan; and wherein the type of the alarm is associated with one or more of: temperature, pressure, flow rate, color, and weight. Aspects of the above method include, after rendering the graphical presentation output, performing a system check. Aspects of the above method include wherein performing the system check comprises polling data associated with the alarm event. Aspects of the above method include wherein the graphical presentation output comprises a timestamp indicating a time the alarm event occurred. Aspects of the above method include wherein the graphical presentation output comprises an illustration associated with the alarm event. Aspects of the above method include wherein the illustration instructs the user to resolve the alarm state. Aspects of the above method include wherein the graphical presentation comprises a description of the alarm and a list of actions to resolve the alarm. Aspects of the above method include wherein the graphical presentation comprises GUI elements enabling a user to one or more of reset, continue, and end the donation process.

Example Modular Serviceability Sled and Interconnections

In at least one example embodiment, an apheresis system (e.g., the apheresis system 200 or the apheresis system 1800) includes one or more subsystems (e.g., electrical power subassembly, pneumatic control subassembly, communications subassembly, pumps 208, 212, 216, bottle tray load cell assembly 1500, etc.) that are attached to a sled, or mechanical frame, that is capable of being separated completely from the apheresis system for service, maintenance, and/or replacement. The modular serviceability sleds may include one or more mechanical and/or electrical interconnections that can be selectively decoupled from a respective one or more mechanical and/or electrical interconnection of the apheresis system. Once decoupled, an entire subsystem on a particular modular serviceability sled may be removed from the apheresis system, for example, independently of other subsystems and modular serviceability sleds.

In at least one example embodiment, the modular serviceability sled may be separated into discrete and/or combination subsystem sleds. For instance, one modular serviceability sled may include a plurality of pneumatic systems (e.g., two or more manifolds, valves, etc.) for the apheresis system, another modular serviceability sled may include a plurality of electrical systems (e.g., two or more processors, controllers, memory devices, power supplies, wiring harnesses, connectors, etc.), and/or other modular serviceability sleds may comprise electrical and/or mechanical subsystems that are grouped together based on predicted and/or historical serviceability requirements.

In at least one example embodiment, one or more of the pumps 208, 212, 216 (shown in FIG. 2A) may be quickly replaceable via removing a limited number of fasteners (e.g., screws, bolts, nuts, etc.) associated with a respective modular serviceability sled. After the fastener(s) are removed, the entire respective modular serviceability sled and associated system (e.g., pump 208, 212, 216) may be removed from the apheresis system without requiring teardown of the apheresis system and/or the removal of other panels, frames, etc.

Among other things, these modular serviceability sleds may allow components to be quickly separated from the apheresis system and serviced separately from the apheresis system. In at least one example embodiment, once a modular serviceability sled has been removed from the apheresis system, a different (e.g., new, refurbished, etc.) modular serviceability sled may be replaced in the apheresis system and the apheresis system may continue to operate (e.g., while the removed modular serviceability sled is being serviced, returned to manufacturing, or repaired/reworked). This approach may allow for the single-minute exchange of subsystems providing, among other things, enhanced operability and reduced down time for an apheresis system when compared to the maintenance required for other apheresis systems, which could take hours or longer to service.

Figure 18A:
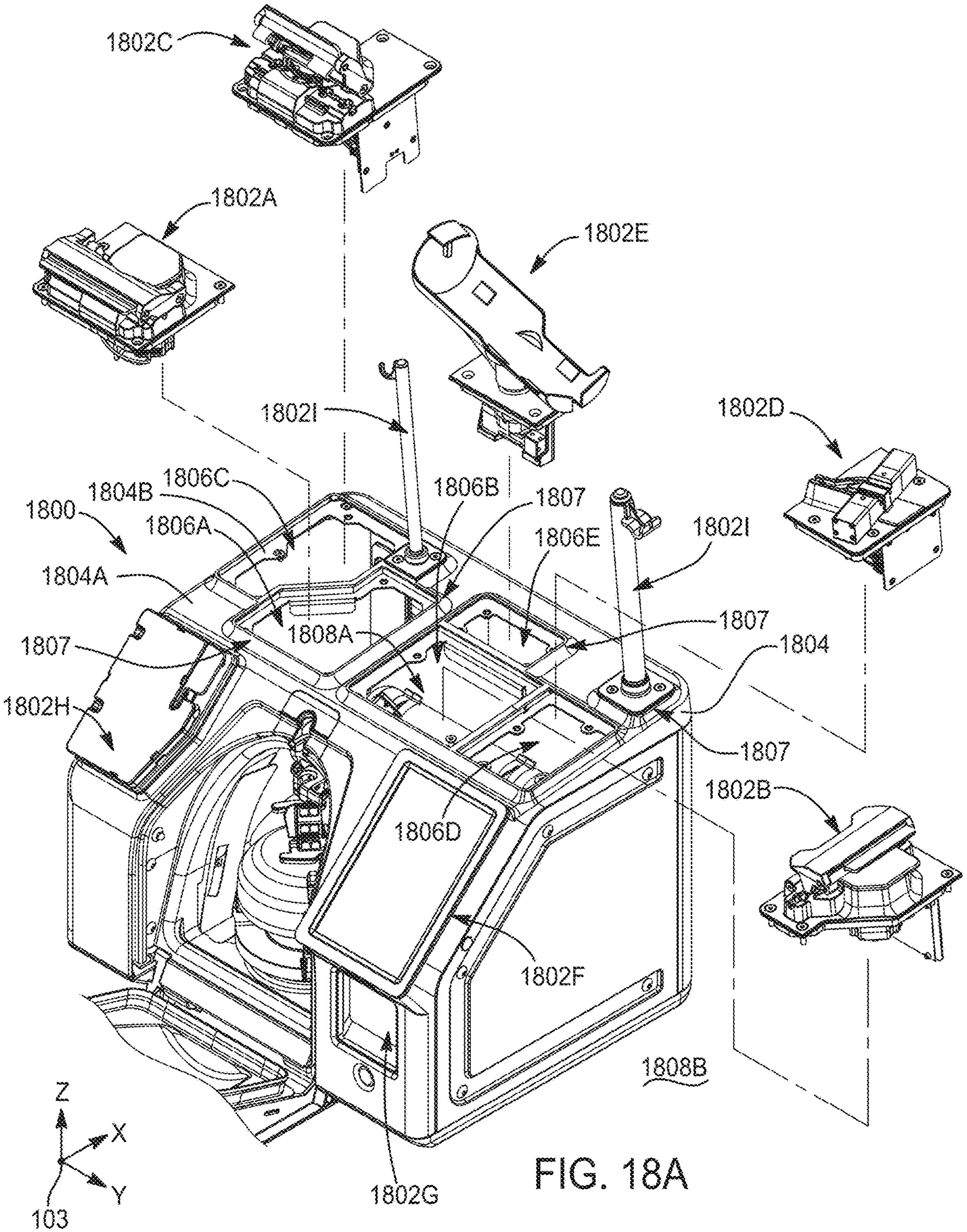
FIG. 18A is a partially exploded perspective view of an apheresis system including modular serviceability sleds in accordance with at least one example embodiment of the present disclosure.

FIG. 18A is a partially exploded perspective view of an apheresis system including modular serviceability sleds according to at least one example embodiment.

In at least one example embodiment, as shown in FIG. 18A, an apheresis system 1800 includes one or more modular serviceability sleds 1802. The apheresis system 1800 may be similar to the apheresis system 200 of FIG. 1A. In at least the example embodiment shown, the sleds 1802 include a first sled 1802A, a second sled 1802B, a third sled 1802C, a fourth sled 1802D, a fifth sled 1802E, a sixth sled 1802F, a seventh sled 1802G, an eighth sled 1802H, and ninth sleds 1802I (collectively referred to as the "sleds 1802"). The apheresis system 1800 may further include a base assembly 1804. The base assembly 1804 may define a plurality of receiving spaces 1806. The receiving spaces 1806 may be defined in any surfaces (or multiple surfaces) of the base assembly 1804, including a top surface, side surfaces, and/or back surfaces, etc. Each of the sleds 1802 may be at least partially within one of the receiving spaces 1806. Each of the sleds 1802 may include a modular frame that is configured to be selectively engaged with the apheresis system, as will be described in greater detail below.

In at least one example embodiment, the base assembly 1804 includes a housing 1804A and a frame 1804B. The housing 1804A may comprise plastic and the frame 1804B may comprise metal. In at least one other example embodiment, a base assembly may include an integral housing and frame. In at least one example embodiment, the housing 1804A may include sloped or countered regions 1807 at peripheries of some or all of the receiving spaces 1806. The sloped or contoured regions 1807 may be configured to direct fluid away from the sled 1802 (e.g., a gasket 1818 of the sled 1802) to reduce or prevent pooling of liquid near the gasket 1818 and/or facilitate ease of cleaning of the housing 1804A.

In at least one example embodiment, the first modular serviceability sled 1802A includes a draw pump. The draw pump may be similar to or the same as the draw pump 208 of FIG. 2A. The draw pump may be configured to have an electrical power connection, an electrical communication connection, and a pneumatic connection with the base assembly 1804. The first modular serviceability sled 1802A may have an environmental or fluid gasket and a shielding component configured to engage the base assembly 1804.

In at least one example embodiment, the second modular serviceability sled 1802B includes a return pump. The return pump may be similar to or the same as the return pump 212 of FIG. 2A. The return pump may be configured to have an electrical power connection, an electrical communication connection, and a pneumatic connection with the base assembly 1804. The second modular serviceability sled 1802B may have an environmental or fluid gasket and a shielding component configured to engage the base assembly 1804.

In at least one example embodiment, the third modular serviceability sled 1802C includes an AC pump. The AC pump may be similar to or the same as the AC pump 216 of FIG. 2A. The AC pump may be configured to have an electrical power connection and an electrical communications connection with the base assembly 1804. The third modular serviceability sled 1802C may have an environmental or fluid gasket and a shielding component configured to engage the base assembly 1804.

In at least one example embodiment, the fourth sled 1802D includes a fluid valve control system. The fluid valve control system may be similar to or the same as the fluid valve control system 228 of FIG. 2A. The fluid valve control system may be configured to have an electrical power connection, an electrical communication connection, and a pneumatic connection with the base assembly 1804. The fourth modular serviceability sled 1802D may have an environmental or fluid gasket and a shielding component configured to engage the base assembly 1804.

In at least one example embodiment, the fifth sled 1802E includes a bottle tray load cell assembly. The bottle tray load cell assembly may be similar to or the same as the load cell assembly 1500 of FIGS. 15A-15M. The bottle tray load cell assembly may be configured to have an electrical power connection and a signal connection with the base assembly 1804. The fifth modular serviceability sled 1802E may have an environmental or fluid gasket and a shielding component configured to engage the base assembly 1804.

In at least one example embodiment, the sixth sled 1802F includes a user interface device or screen. The user interface device may be configured to have an electrical power connection and a signal connection with the base assembly 1804. The sixth modular serviceability sled 1802F may have an environmental or fluid gasket and a shielding component configured to engage the base assembly 1804.

In at least one example embodiment, the seventh sled 1802G includes a barcode scanner configured to have an electrical power connection and a signal connection with the base assembly 1804. The seventh modular serviceability sled 1802A may have an environmental or fluid gasket and a shielding component configured to engage the base assembly 1804.

In at least one example embodiment, the eighth sled 1802H includes a soft cassette assembly. The soft cassette assembly may be similar to or the same as the soft cassette assembly 300 of FIG. 3A. The soft cassette assembly may be configured to have an electrical power connection, an electrical communication connection, and a pneumatic connection with the base assembly 1804. The eighth modular serviceability sled 1802H may have an environmental or fluid gasket and a shielding component configured to engage the base assembly 1804.

In at least one example embodiment, the ninth sleds 1802I include hanger assemblies (e.g., for AC and/or saline bags). The hanger assemblies may be similar to or the same as the soft the first and second hanger assemblies 2200, 2202 of FIG. 21A. One or both of the hanger assemblies (e.g., a hanger assembly for the saline bag) may be configured to have electrical power connections with the base assembly 1804. The ninth modular serviceability sleds 1802I may have environmental or fluid gaskets and shielding components configured to engage the base assembly 1804.

Figure 18B:
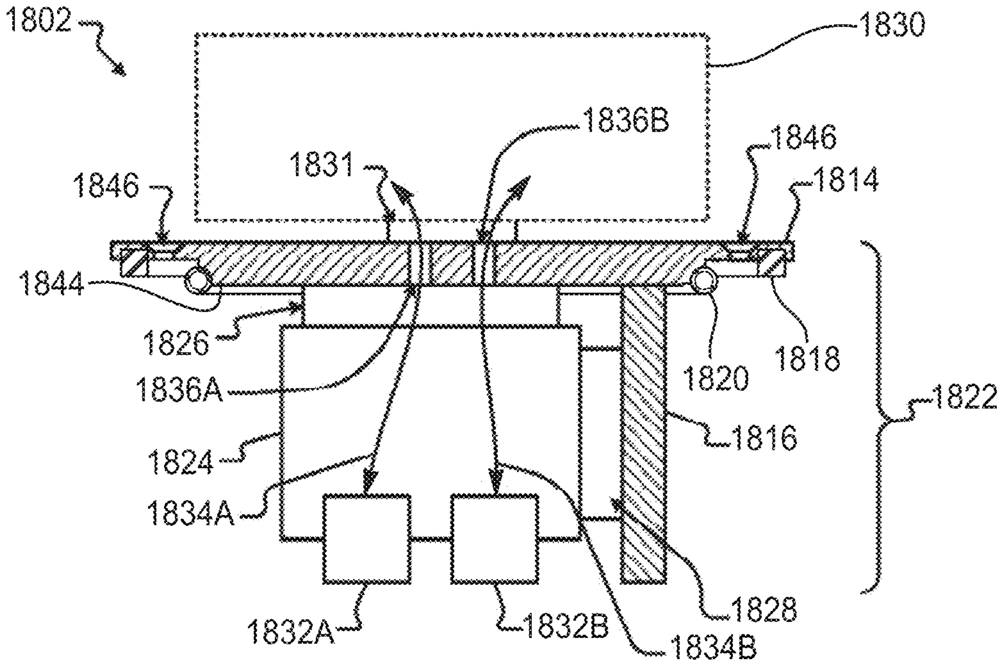
FIG. 18B is a schematic elevation section view of a modular serviceability sled in a disengaged state from a base of the apheresis system in accordance with at least one example embodiment of the present disclosure.
Figure 18C:
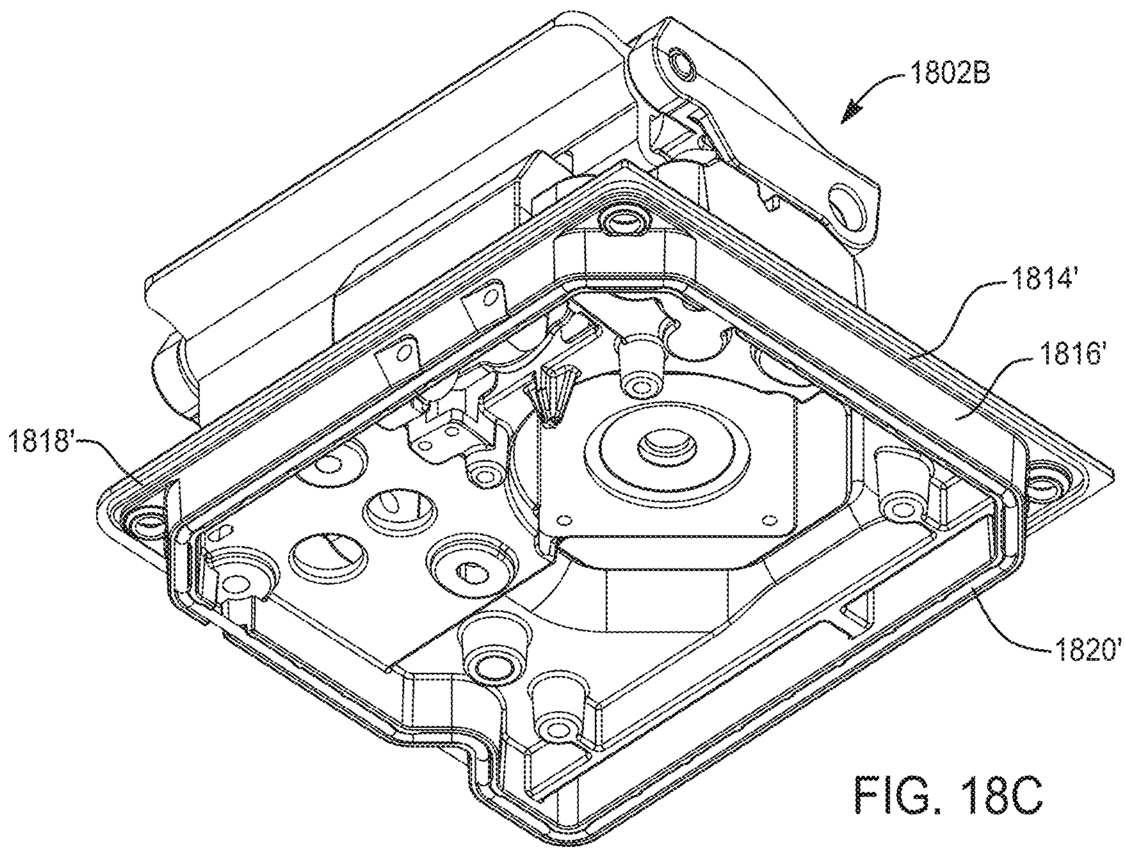
FIG. 18C is a bottom perspective view of a return pump assembly of the apheresis system of FIG. 18A in accordance with at least one example embodiment of the present disclosure.
Figure 18D:
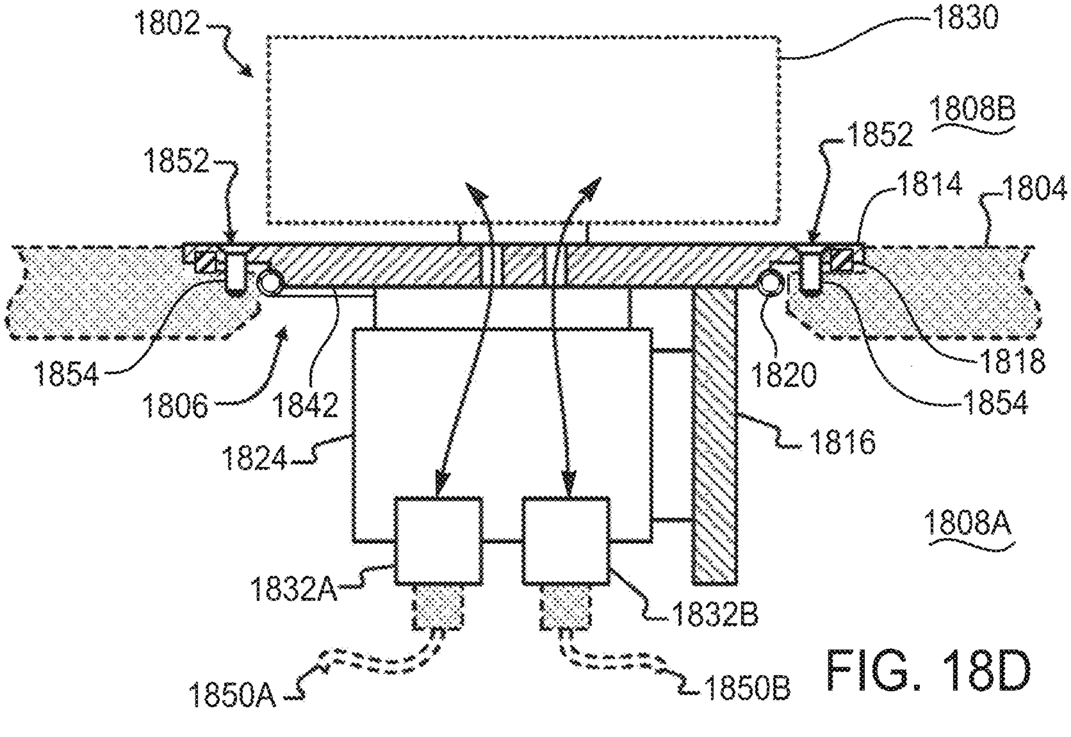
FIG. 18D is a schematic elevation section view of the modular serviceability sled of FIG. 18C in an engaged state with the base of apheresis system in accordance with at least one example embodiment of the present disclosure.

In at least one example embodiment, when the modular serviceability sleds 1802 are in respective receiving spaces 1806 of the apheresis system 1800 and coupled to the base assembly 1804, an interior region 1808A of the apheresis system 1800 is electrically shielded from an exterior region 1808B of the apheresis system 1800 via at least one metal component (e.g., base plate, shielding gasket) between the interior region 1808A and the exterior region 1808, as shown and described below in the discussion accompanying FIG. 18D.

FIG. 18B is a schematic sectional view of a modular serviceability sled of the apheresis system of FIG. 18A in a disengaged state according to at least one example embodiment.

In at least one example embodiment, the sled 1802 (e.g., any of the sleds 1802A, 1802B, 1802C, 1802D, 1802E, 1802F, 1802G, 1802H, 1802I) includes a base plate 1814, an internal support structure 1816, a gasket 1818 (e.g., an environmental or fluid gasket), and a shielding component 1820. In the example embodiment shown, the gasket 1818 and the shielding component 1820 are distinct components; however, in other example embodiments, a single component may be configured to replace the gasket 1818 and shielding component 1820. In at least one example embodiment, the internal support structure 1816 is an internal support panel. One or more of the base plate 1814, the internal support structure 1816, the gasket 1818, and the shielding component 1820 may cooperate to define a modular frame 1822.

In at least one example embodiment, the modular serviceability sled 1802 includes at least one internal system subassembly 1824 attached to the modular frame (e.g., one or more of the base plate 1814 and the internal support structure 1816). The internal system subassembly 1824 may be attached to the base plate 1814 and/or the internal support structure 1816 via a first bracket 1826 and/or a second bracket 1828. The brackets 1826, 1828 may be independently selected from a standoff, a washer, captured nut, a sheet metal adapter, a spacer block, other mechanical elements, or any combination thereof.

In at least one example embodiment, the internal system subassembly 1824 is a discrete station, portion, or assembly of the apheresis system 1800. In at least one example embodiment, the apheresis system 1800 includes a plurality of internal system subassemblies 1824. Each of the internal system subassemblies 1824 may be configured to operate independently of other internal system subassemblies 1824 (e.g., on other sleds 1802).

In at least one example embodiment, each of the sleds 1802 includes a memory storage device (e.g., similar to or the same as memory 1008 and/or memory 1108) that forms a part of the internal system subassembly 1824 and/or external system subassembly 1830. The memory storage device may store, embed, or otherwise include a code that uniquely identifies the sled 1802 and distinguishes it from the other sleds 1802. When the modular serviceability sled 1802 is communicatively coupled with the apheresis system 1800 (e.g., via at least one of the interconnections 1832) the apheresis system 1800 (e.g., the controller 1004, 1104, etc.) may be configured to read the code of the memory storage device to identify the sled 1802.

In at least one example embodiment, the internal system subassembly 1824 includes one or more sled interconnections 1832 (e.g., two or more, three or more, or four or more). In at least the example embodiment shown, the internal system subassembly 1824 includes a first sled interconnection 1832A and a second sled interconnection 1832B. The interconnections 1832 may be independently selected from a pneumatic connection, a hydraulic connection, an electrical power connection, an electrical communications connection (CAN), and a signal connection. In at least one example embodiment, the first sled interconnection 1832A is a pneumatic connection and a second sled interconnection 1832B is an electrical connection (e.g., power and/or communications).

In at least one example embodiment, a respective communication path 1834 may connect the internal system subassembly 1820 to each of the sled interconnections 1832. The base plate 1814 may include or define one or more junctions 1836 through which the communications paths 1834 extend. The junctions 1836 may be independently selected from sealed and/or hermetic pass-throughs, an electrical vias, and/or passages or holes. In at least the example embodiment shown, the first communication path 1834A connects the external system subassembly 1830 to the first sled interconnection 1832A via a first junction or passage 1836A and the second communication path 1834B connects the external system subassembly 1830 to the second sled interconnection via a second junction or 1836B. In at least one other example embodiment, more than one communication path extends through a common or shared junction in a base plate.

In at least one example embodiment, the sled 1802 further includes the gasket 1818. The gasket 1818 may be on an underside 1842 of the base plate 1814. The gasket 1818 may be configured to engage the base assembly 1804, such as the housing 1804A of the base assembly 1804 (shown in FIG. 18A) to form a fluid and/or environmental seal between the interior and exterior regions 1808A, 1808B (shown in FIG. 18A) of the base assembly 1804. In at least the example embodiment shown, the gasket 1818 is a flat gasket; however, a gasket may have any desired cross-sectional shape, such as rectangular, square, round, etc., and may be solid or hollow. In at least one example embodiment, the gasket 1818 includes an O-ring, an O-ring chord, a chord seal, a die-cut gasket, a foam gasket, a form-in-place gasket (e.g., a robotically-applied resin that cures to form a gasket, a foam-in-place gasket) or any combination thereof.

In at least one example embodiment, the sled 1802 further includes the shielding component 1820. In at least the example embodiment shown, the shielding component 1820 is a conductive gasket (e.g., a hollow chord gasket having metal shavings therein); however, a shielding component may have any desired form and include a metal, including gaskets having other cross-sectional shapes or a metal component (e.g., a metal spring, canted coil spring, metallized fabric, metal contact spring, or any combination thereof). The shielding component 1820 may be on the underside 1842 of the base plate 1812 (e.g., in direct contact with the underside 1842 of the base plate 1814). The shielding component may be configured to engage (e.g., directly contact) the base assembly 1804, such as the frame 1804B of the base assembly 1804 (shown in FIG. 18A) when the sled 1802 is attached to the apheresis system 1800. The shielding component 1820 may be configured to shield electromagnetic interference (EMI) and/or radio frequency interference (RFI). In at least the example embodiment shown, the shielding component 1820 is a shielding gasket that is concentrically inside of the gasket 1818.

In at least one example embodiment, the sled 1802 defines one or more receptacles 1846. In at least the example embodiment shown, the receptacles 1846 are countersunk holes; however, in at least one other example embodiment, the receptacles 1846 are through-holes, counterbored holes, countersunk holes, and/or any combination thereof. In at least one example embodiment, the receptacles 1846 may be sized and/or shaped to receive a respective fastener (see, e.g., fasteners 1852 shown in FIG. 18C) when the sled 1802 is in an engaged state with the base assembly 1804 (shown in FIG. 18D).

FIG. 18C is a bottom perspective view of the second sled 1802 in accordance with at least one example embodiment.

In at least one example embodiment, as shown in FIG. 18C, the second sled 1802B is provided. The second sled 1802 includes a base plate 1814' and an internal support structure 1816'. The sled 1802B further includes an environmental gasket 1818' a shielding component 1820'. The other sleds 1802A, 1802C, 1802D, 1802E, 1802F, 1802G, 1802H, 1802I may include similar features.

FIG. 18D is a schematic sectional view of the modular serviceability sled of FIG. 18B in an engaged state according to at least one example embodiment.

In at least one example embodiment, as shown in FIG. 18D, the sled 1802 may be operatively engaged with a base assembly 1804'. The base assembly 1804' may be a simplified version of the base assembly 1804 of FIG. 18A such that a housing and frame of the base assembly 1840' are shown as integral. However, the sled 1802 may alternatively be coupled to the base assembly 1804 of FIG. 18A, which includes the distinct housing 1804A and frame 1808B.

In the engaged state, each of the sled interconnections 1832 is operatively engaged with a respective machine interconnection 1850. In at least one example embodiment, the sled interconnections 1832 may be independently selected from a plug and a socket and the machine interconnections 1850 may be the other of the plug and the socket. Additionally or alternatively, sled interconnections may include push-to-connect fittings where tubing is directly inserted into a fitting and/or barb fittings (e.g., for pneumatics). In at least the example embodiment shown, the first sled interconnection 1832A is operatively connected to a first machine interconnection 1850A and the second sled interconnection 1832B is operatively connected to a second machine interconnection 1850B.

In at least one example embodiment, the sled 1802 is mechanically coupled to the base assembly 1804 by one or more fasteners 1852. Each of the fasteners 1852 may extend through a respective one of the receptacles 1846 in the base plate 1814 and engage the base assembly 1804 (e.g., the frame 1804B, with the housing 1804A disposed therebetween). In at least one the example embodiment shown, the fasteners 1852 include flat head cap screw that are threadedly engaged with threaded holes 1854 defined by the base assembly 1804 (e.g., press-in inserts in the frame 1804B). In at least one other example embodiment, the sled 1802 may be coupled to the base assembly 1804 by other fasteners that do not necessarily use threaded receptacles, such as quarter turns with custom receptacles.

In at least one example embodiment, the sled 1802 is configured to be completely removed from the apheresis system 1800 by removing the fasteners 1852. In at least one example embodiment, each of the sleds 1802 is configured to be coupled to the base assembly 1804 by a limited quantity of fasteners 1852 to facilitate quick removal, replacement, and/or attachment. In at least one example embodiment, the quantity of fasteners 1852 is less than or equal to 5 (e.g., less than or equal to 4, less than or equal to 3, or less than or equal to 2).

In at least one example embodiment, in the engaged state, the gasket 1818 engages (e.g., is compressed) between the base plate 1814 and the base assembly 1804 (e.g., the housing 1804A of the base assembly 1804). Accordingly, the gasket 1818 is configured to reduce or prevent transfer of fluid and/or particles between the external and internal regions 1808B, 1808A of the base assembly 1804. In at least one example embodiment, the gasket 1818 forms a fluid and/or environmental seal between the external and internal regions 1808B, 1808A of the base assembly 1804.

In at least one example embodiment, in the engaged state, the shielding component 1820 contacts the base plate 1804 and the base assembly 1804 (e.g., the frame 1804B of the base assembly 1804). In at least one example embodiment, the shielding component 1820 directly contacts the base plate 1814 and/or the base assembly 1804. In the engaged state, the shielding component 1820 forms an EMI or RFI shield between the external and internal regions 1808B, 1804A.

Figure 18E:
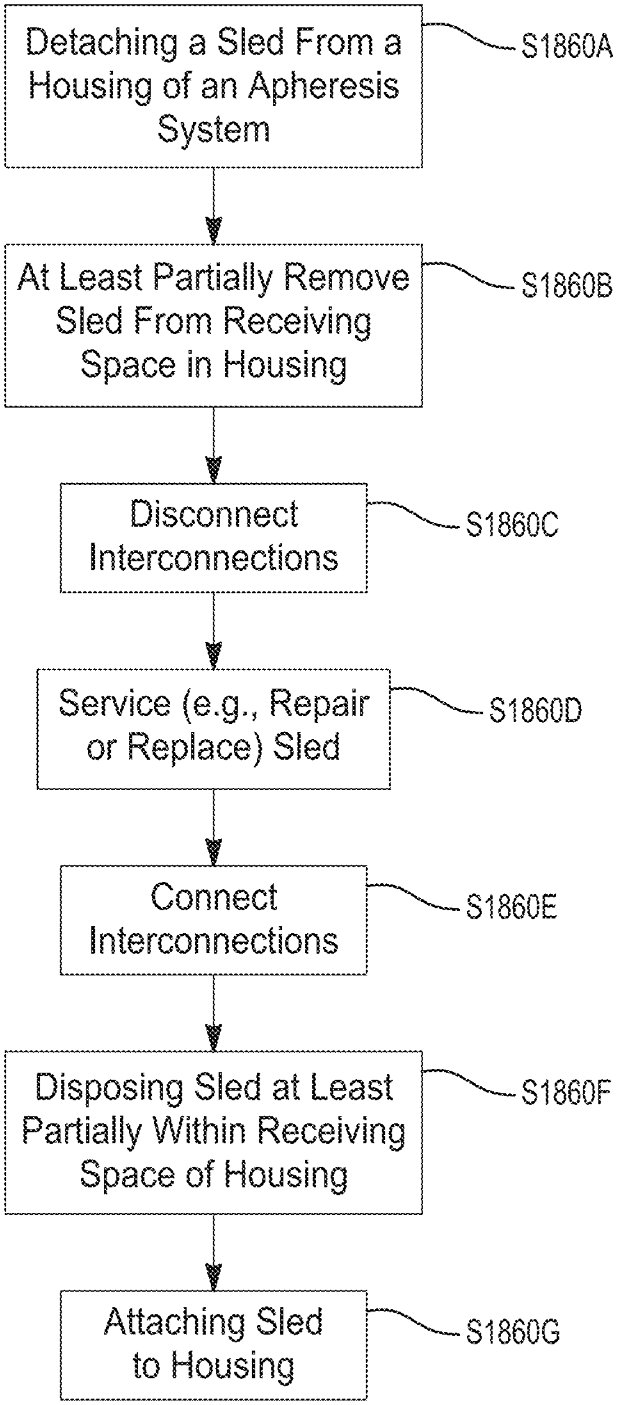
FIG. 18E is a flowchart illustrating a method of servicing an apheresis system in accordance with at least one example embodiment of the present disclosure.

FIG. 18E is a flowchart illustrating a method of servicing an apheresis system according to at least one example embodiment.

In at least one example embodiment, as shown in FIG. 18E, the method generally includes detaching a sled from a base assembly of the apheresis system at S1860A; at least partially removing the sled from a receiving space in the housing at S1860B; disconnecting sled interconnection(s) from machine interconnection(s) at S1860C; servicing the sled at S1860D; connecting the sled interconnections with the machine interconnections at S1860E; disposing the sled at least partially within the receiving space of the housing at S1860F; and attaching the sled to the housing at S1860G. Each of these steps is described in greater detail below. The method is described in the context of the apheresis system 1800 of FIGS. 18A-18D; however, it should be appreciated that the method is also applicable to other apheresis systems having modular serviceability sleds.

In at least one example embodiment, at S1860A, the method includes detaching a sled from a base assembly of the apheresis system. In at least the example embodiment shown, the sled 1802 may be detached from the base assembly 1804 by removing the fasteners 1852 from the threaded holes 1854 in the base assembly 1804 (e.g., the frame 1804B) and the receptacles 1846 in the sled 1802.

In at least one example embodiment, at S1860B, the method includes at least partially removing the sled from a receiving space in the base assembly. In at least the example embodiment shown, removing the sled 1802 from the receiving space 1806 includes moving the sled 1802 away from the base assembly 1804. When receiving space is in a top of the housing 1802, the sled 1802 may be lifted from the base assembly 1804. Travel of the sled 1802 away from the base assembly 1804 may be limited by shortest combined length of a pair of sled and machine interconnections 1832, 1850.

In at least one example embodiment, at S1860C, the method includes disconnecting sled interconnection(s) from machine interconnection(s). In at least the example embodiment shown, disconnecting may include separating plug and socket pairs of the interconnections 1832, 1850.

In at least one example embodiment, at S1860D, the method includes servicing the sled at S1860D. Servicing the sled may include maintaining, repairing, or replacing the sled 1802.

In at least one example embodiment, at S1860E, the method includes connecting the sled interconnections with the machine interconnections. In at least one example embodiment connecting the sled interconnections 1832 with the machine interconnections 1850 may include operatively engaging a plug of one of the connections with a socket of the other interconnection. Prior to operatively connecting, the sled 1802 may be moved toward the base assembly 1804 such that the sled interconnection 1832 can reach the respective machine interconnection 1850. This may include disposing the sled 1802 at least partially within the receiving space 1806.

In at least one example embodiment, at S1860F, the method includes disposing the sled at least partially within the receiving space of the housing. In at least one example embodiment, after operatively connecting the sled and machine interconnections 1832, 1850, the sled 1802 may be fully seated within the receiving space 1806.

In at least one example embodiment, at S1860G, the method includes attaching the sled to the base assembly. In at least the example embodiment shown, attaching the sled 1802 to the base assembly 1804 may include replacing the fasteners 1852 through the receptacles 1846 and into the threaded holes 1854. In at least one example embodiment, as the fasteners 1852 are tightened, the base plate 1814 is clamped against the base assembly 1804 and the gasket 1818 may compress therebetween. This clamping and compression of the gasket 1818 may provide an environmental and/or fluid seal between exterior and interior regions 1808B, 1808A, at least around the modular serviceability sled 1802. In at least one example embodiment, the shielding component 1820 simultaneously contacts both the base assembly 1804 and the modular frame 1822 to provide an EMI shield and/or an RFI shield.

In at least one example embodiment, the design of the modular serviceability sled 1802 facilitates a quick exchange of subassemblies within the apheresis system 1800, such as for maintenance, replacement, and/or repair of a defective, inoperable, or worn subassemblies, or a subassembly that is due for maintenance. In at least one example embodiment, a sled is configured to be serviced in a time period of less than about 15 minutes (e.g., less than or equal to about 10 minutes, less than or equal to about 5 minutes, less than or equal to about 4 minutes, less than or equal to about 3 minutes, less than or equal to about 2 minutes, or less than or equal to about 1 minutes).

Exemplary aspects are directed to a modular serviceability sled, comprising: a frame comprising a mount plate having a first surface facing an interior side of the frame and having a second surface facing an exterior side of the frame; a subassembly attached to the mount plate at the interior side of the frame; an interconnection operatively connected to the subassembly, the interconnection comprising at least one of a socket and plug that engages with a mating interconnection of a machine; a gasket attached to the mount plate adjacent a periphery of the mount plate, wherein the gasket comprises a compliant elastic material; and a shielding gasket attached to the mount plate within a periphery of the gasket on the interior side of the frame, the shielding gasket corresponding to at least one of an electromagnetic interference (EMI) shielding gasket, radio frequency interference (RFI) shielding gasket; wherein the modular serviceability sled, in an engaged state, is disposed at least partially within a receiving space of the machine and is attached to the machine via a fastener clamping the mount plate and the machine together, wherein the modular serviceability sled, in a disengaged state, is disposed outside of the receiving space of the machine, and wherein, in the engaged state, the subassembly is shielded from an environment outside of the machine via the mount plate and the shielding gasket.

Any one or more of the above aspects wherein the subassembly comprises at least one electrical component, pneumatic component, and mechanical component. Any one or more of the above aspects wherein the electrical component corresponds to a microcontroller, sensor, relay, printed circuit board, and transformer, wherein the pneumatic component corresponds to a fluid reservoir, compressor, solenoid valve, air valve, plenum, and manifold, and wherein the mechanical component corresponds to a linear actuator, load cell, strain gauge, pneumatic cylinder, bladder, balloon, air cylinder, and a motor. Any one or more of the above aspects further comprising: a second subassembly attached to the mount plate at the exterior side of the frame, wherein the second subassembly is disposed in the environment outside of the machine, and wherein at least one communication path is disposed between the subassembly and the subassembly through a portion of the mount plate. Any one or more of the above aspects wherein the shielding gasket corresponds to a metal spring. Any one or more of the above aspects wherein the gasket corresponds to an O-ring.

Exemplary aspects are directed to an apheresis system, comprising: a housing having a plurality of sides and a receiving space disposed in at least one side of the plurality of sides, the receiving space in communication with an interior space of the apheresis system; a machine interconnection disposed in the receiving space; a first modular serviceability sled, comprising: a frame comprising a mount plate having a first surface facing an interior side of the frame and having a second surface facing an exterior side of the frame; a subassembly attached to the mount plate at the interior side of the frame; an interconnection operatively connected to the subassembly, the interconnection comprising at least one of a socket and plug that selectively engages with the machine interconnection; a gasket attached to the mount plate adjacent a periphery of the mount plate, wherein the gasket comprises a compliant elastic material; and a shielding gasket attached to the mount plate within a periphery of the gasket on the interior side of the frame, the shielding gasket corresponding to at least one of an electromagnetic interference (EMI) shielding gasket, radio frequency interference (RFI) shielding gasket; wherein the first modular serviceability sled, in an engaged state with the apheresis system, is disposed at least partially within the receiving space and is attached to the housing via a fastener clamping the mount plate and the housing together, wherein the first modular serviceability sled, in a disengaged state, is disposed outside of the receiving space, and wherein, in the engaged state, the subassembly is shielded from an environment outside of the apheresis system via the mount plate and the shielding gasket.

Any one or more of the above aspects wherein, in the engaged state the subassembly of the first modular serviceability sled is electrically connected with the apheresis system via connection of the interconnection of the first modular serviceability sled with the machine interconnection, and wherein at least one of power and communication signals are provided via the connection. Any one or more of the above aspects wherein the first modular serviceability sled comprises a memory storage device and a code embedded in the memory storage device, the code uniquely identifying the first modular serviceability sled from other modular serviceability sleds. Any one or more of the above aspects wherein upon connecting the first modular serviceability sled with the apheresis system, the apheresis system reads the code embedded in the memory storage device and identifies the first modular serviceability sled. Any one or more of the above aspects wherein the receiving space comprises a plurality of receiving spaces, wherein the first modular serviceability sled is engaged with a first receiving space of the plurality of receiving spaces, and wherein the apheresis system further comprises: a second modular serviceability sled engaged with a second receiving space of the plurality of receiving spaces, wherein the second modular serviceability sled comprises: a frame comprising a mount plate having a first surface facing an interior side of the frame and having a second surface facing an exterior side of the frame; a subassembly attached to the mount plate at the interior side of the frame; an interconnection operatively connected to the subassembly, the interconnection comprising at least one of a socket and plug that selectively engages with the machine interconnection; a gasket attached to the mount plate adjacent a periphery of the mount plate, wherein the gasket comprises a compliant elastic material; and a shielding gasket attached to the mount plate within a periphery of the gasket on the interior side of the frame, the shielding gasket corresponding to at least one of an electromagnetic interference (EMI) shielding gasket, radio frequency interference (RFI) shielding gasket; wherein the first modular serviceability sled, in an engaged state with the apheresis system, is disposed at least partially within the receiving space and is attached to the housing via a fastener clamping the mount plate and the housing together, wherein the first modular serviceability sled, in a disengaged state, is disposed outside of the receiving space, and wherein, in the engaged state, the subassembly is shielded from an environment outside of the apheresis system via the mount plate and the shielding gasket.

Example Collection Bottle

FIGS. 19A-19J illustrate a collection bottle 1900 that can be used for various operations of the apheresis system 200. For example, the collection bottle 1900 may aid collection, storage, and transportation of plasma. In at least one example embodiment, the collection bottle 1900 may correspond to the plasma collection bottle 122, as described above.

The collection bottle 1900 may include a body (also referred to as a canister) 1904 and a cap (also referred to as a lid) 1908. As best illustrated, for example, in FIG. 19C, the body 1904 may have a first body end (also referred to as a top end or open end) 1928 and an opposing second body end (also referred to as a bottom end or closed end) 1930. An elongated portion 1924 may be disposed between the first body end 1928 and the second body end 1930 and an interior cavity or space 1932 may be defined therewithin. In at least one example embodiment, the body 1904 may include a sealing edge or surface (also referred to as a ring edge or surface) 1926 formed at the first body end 1928. For example, the sealing edge 1926 may be disposed along a periphery of the body 1924 at the first body end 1928. The sealing edge 1926 may include one or more recesses, counterbores, grooves, or any combination thereof. In at least one example embodiment, as illustrated, the body 1904 may be cylindrical (notwithstanding draft angles, base features, manufacturing tolerances, etc.) centered about a length of a longitudinal axis 1922 extending from the first body end 1928 to the second body end 1930. Although the collection bottle 1900 is illustrated as generally cylindrical, it should be appreciated that the collection bottle 1900 may have a variety of configurations and shapes. In at least one example embodiment, the body 1904 may be formed using a blow molding process, a thermoforming process, a vacuum forming process, an injection molding process, three-dimensional printing, or any combination thereof. In at least one example embodiment, the body 1904 may be transparent or translucent.

The lid 1908 may be coupled to the first body end 1928. In at least one example embodiment, the lid 1908 may be sealed to the body 1904. For example, at least a portion of a perimeter of the lid 1908 may be welded (e.g., laser welded) to a perimeter of first body end 1928. As best illustrated, for example, in FIG. 19D, the lid 1908 may include a lid body 1934 defining an outer lid perimeter 1909 and having a first lid side (also referred to as a top lid side or an outer lid side) 1933 and an opposing second lid side (also referred to as a bottom lid side or an inner lid side) 1935. In at least one example embodiment, the lid 1908 may include a lid rim 1940 extending from the lid body 1934 towards the second side 1935. The lid rim 1940 may be configured to be received within the interior space 1932. For example, the lid rim 1940 may be configured such that an interference fit exists between the lid 1908 and the sealing edge 1926 of the body 1924. The interference fit may ensure proper contact between the lid 1908 and the body 1904 or sealing or welding. In at least one example embodiment, the lid rim 1940 may include a chamfered, tapered, or radiused lead-in edge that can help to guide the lid 1908 when aligned with the body 1904 during assembly and/or manufacturing of the collection bottle 1900. In at least one example embodiment, the lid rim 1940 may include an undercut region that can serve as a flash trap for melt during welding and/or to eliminate stress concentration at the base of the lid rim 1940.

Figure 19A:
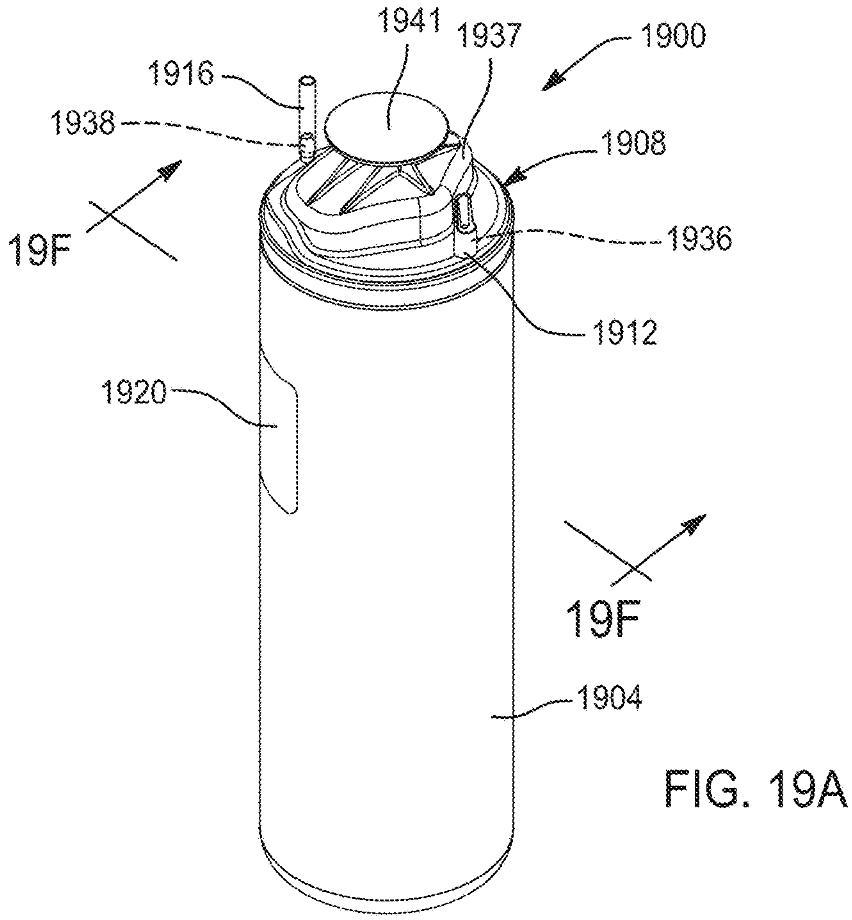
FIG. 19A is a perspective view of a collection bottle in accordance with at least one example embodiment of the present disclosure.
Figure 19B:
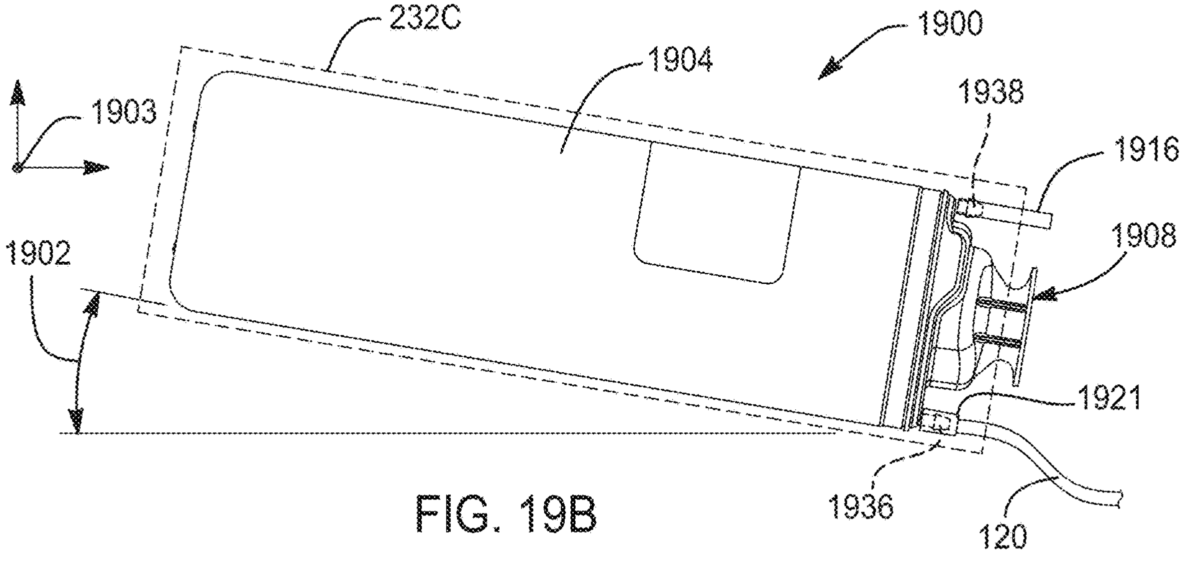
FIG. 19B is an elevated view of the collection bottle of FIG. 19A oriented in a plasma collection cradle of the apheresis system in accordance with at least one example embodiment of the present disclosure.
Figure 19C:
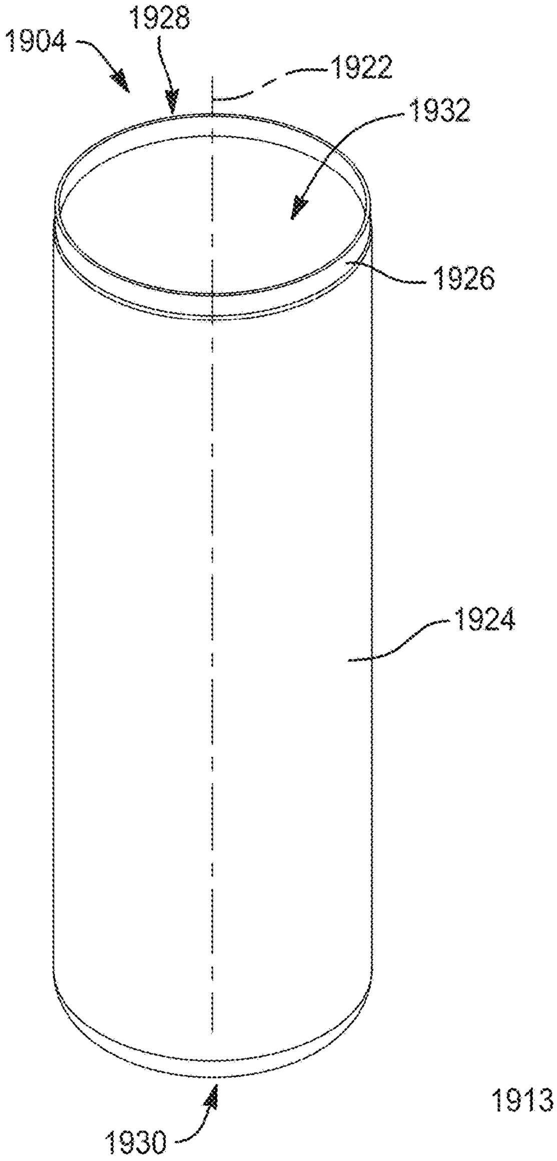
FIG. 19C is a perspective view of the canister of the collection bottle of FIG. 19A.
Figure 19D:
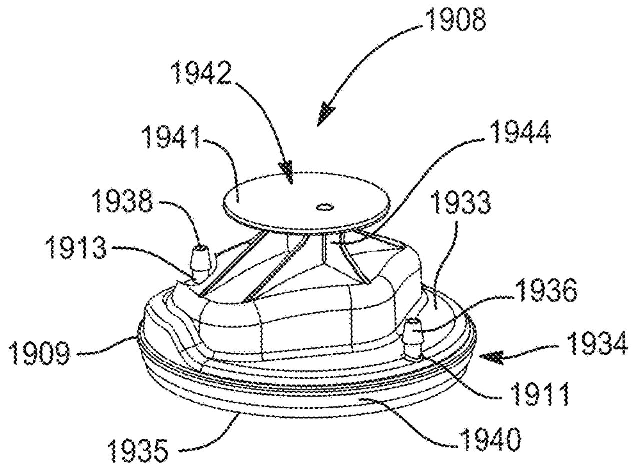
FIG. 19D is a top-down perspective view of the lid of the collection bottle of FIG. 19A.
Figure 19E:
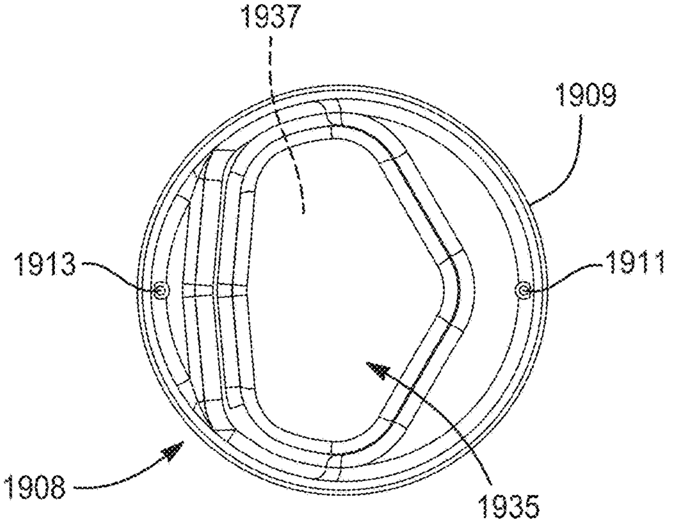
FIG. 19E is a bottom-up view of the lid of the collection bottle of FIG. 19A.
Figure 19F:
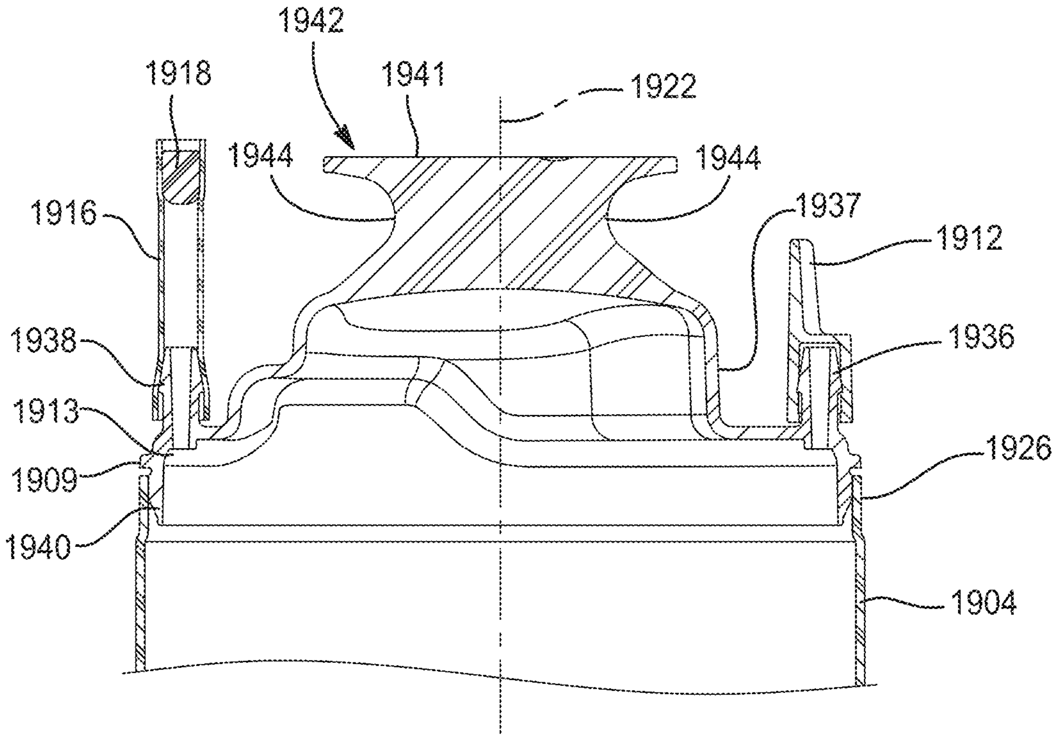
FIG. 19F is a partial, cross-sectional view of the collection bottle of FIG. 19A prior to collection (i.e., prior to use) in accordance with at least one example embodiment of the present disclosure.

In at least one example embodiment, as illustrated, for example, in FIG. 19F, the lid 1908 may be sealed to the body 1904 along a seal region that extends along the periphery of the body 1904 and also the periphery 1909 of the lid 1908. For example, preparing the collection bottle 1900 may include inserting the lid rim 1940 within the interior space 1932 of the body 1904 and moving the lid 1908 in a direction towards the closed bottom end 1930 of the body 1904 until at least a portion of the rim 1940 aligns with the sealing edge 1926 of the body 1904. In at least one example embodiment, the lid 1908 may be moved in the direction toward the closed bottom end 1930 until a flange of the lid 1908 contacts the open edge of the canister 1904. In at least one example embodiment, full contact of the rim 1940 and the sealing edge 1926 is not necessary. For example, the lid 1908 and the body 1904 may be positioned using automation and a gap between the rim 1940 and the sealing edge 1926 may be acceptable so as to accommodate variations in trimmed surfaces.

Once the lid 1908 is positioned such that the rim 1940 is adjacent or near the sealing edge 1926, the lid 1908 may be welded to the body 1904 and/or the body 1904 to the lid 1908. In at least one example embodiment, laser energy may be directed through the sealing edge 1926 toward the lid rim 1940. In at least one example embodiment, the body 1904 may be rotated about the longitudinal axis 1922 relative to a laser as the laser emits laser light and energy until the laser light welds the lid 1908 and the body 1904 together along a seal region. Since the body 1904 may include a translucent and/or transparent and/or transmitter material (for example, in at least one example embodiment, the body 1904 may be translucent and/or transparent) and the lid 1908 may include an absorber material (for example, in at least one example embodiment, the lid 1908 may be opaque), energy from the laser (or other welder) may pass through the body 1904 to the rim 1940 inside the interior space 1932 causing a temperature of the lid rim 1940 to increase and fuse with the body 1904 along the sealing edge 1926. In at least one example embodiment, the body 1904 and/or lid 1908 may be sterilized prior to and/or after the lid 1908 is attached to the body 1904.

In at least one example embodiment, the lid 1908 may include a shield handle 1942 coupled to the first lid side 1933. The shield handle 1942 may include a disk-shaped portion 1941 and a grip recess 1944 disposed between the disk-shaped portion 1941 and the first lid side 1933. In at least one example embodiment, the shield handle 1942 may extend from a central point of the first lid side 1933. Although illustrated as a disk, it should be recognized that the disk-shaped portion 1941 may take a variety of configurations. In at least one example embodiment, the lid 1908 may be formed using a blow molding process, a thermoforming process, a vacuum forming process, an injection molding process, three-dimensional printing, or any combination thereof.

Figure 19G:
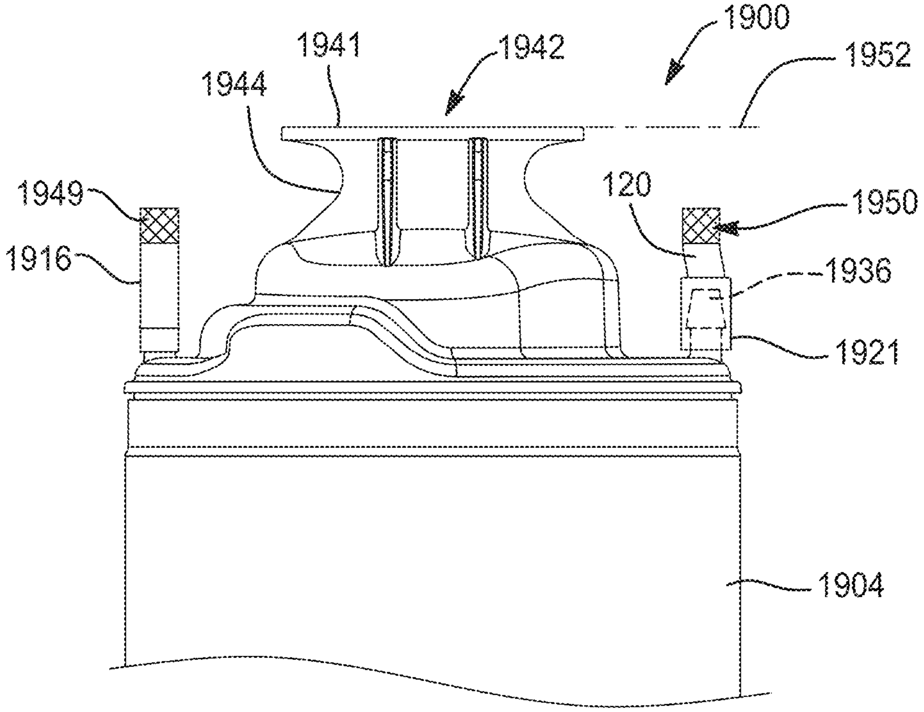
FIG. 19G is a partial view of the collection bottle of FIG. 19A after collection (i.e. after use) in accordance with at least one example embodiment of the present disclosure.
Figure 19H:
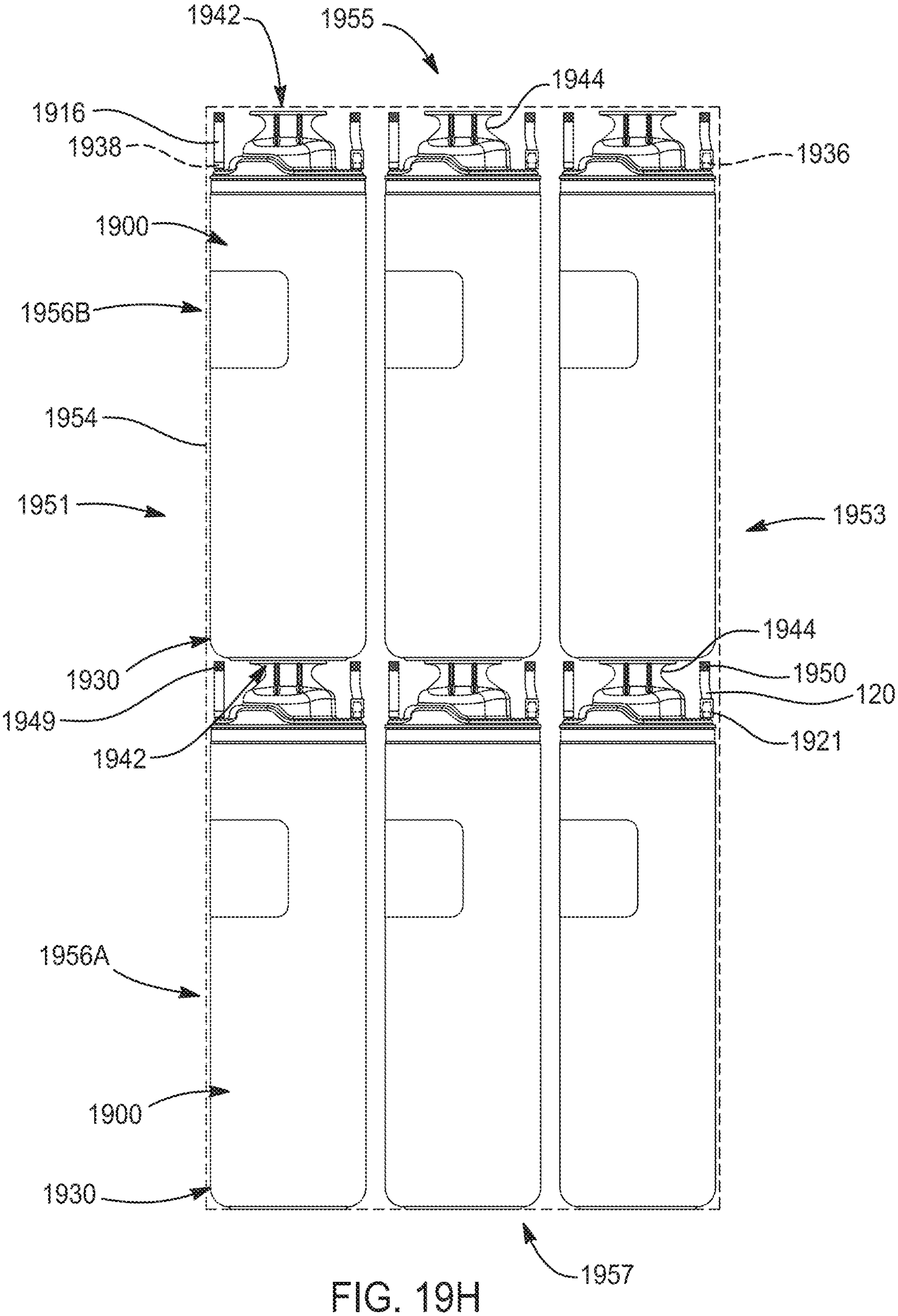
FIG. 19H is an elevation view of a collection bottle transport package including multiple rows of filled collection bottles (i.e., after collection) in accordance with at least one example embodiment of the present disclosure.
Figure 19I:
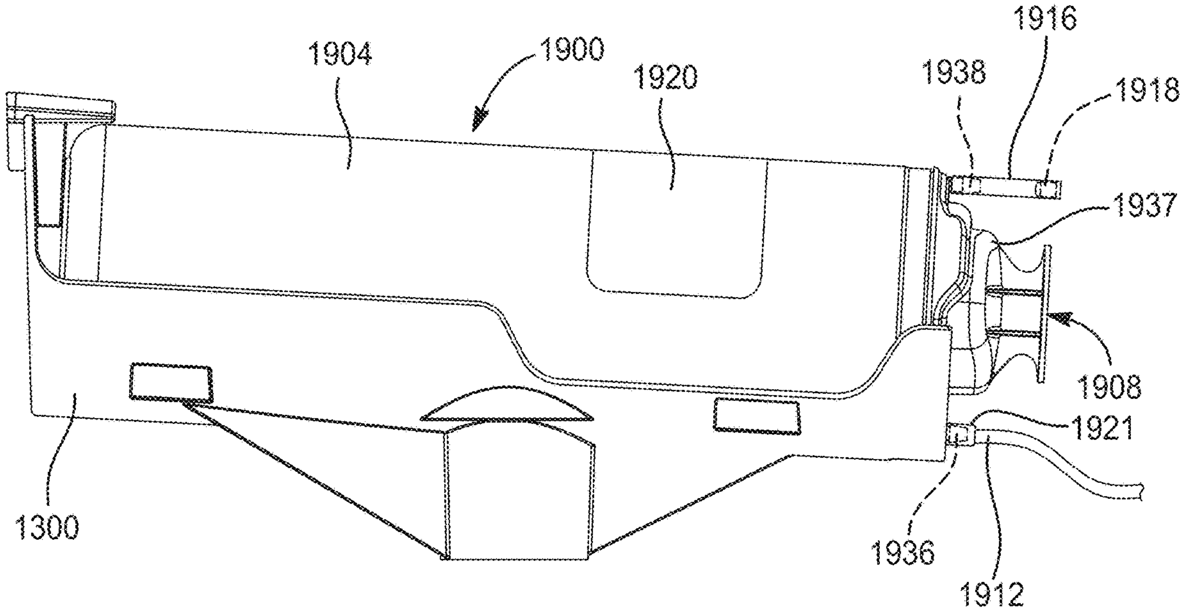
FIG. 19I is side view of the collection bottle of FIG. 19A disposed in a collection cradle in accordance with at least one example embodiment of the present disclosure.

In at least one example embodiment, the collection bottle 1900 includes a fluid port 1936 and a vent port 1938. The fluid port 1936 may be configured to receive fluid (e.g., plasma), including fluid entering and/or drawn back from the collection bottle 1900, while the vent port 1938 may be configured to help to control pressure within the collection bottle 1900, for example, by allowing air to move into and out of the collection bottle 1900. The fluid port 1936 may be positioned at a first point of the collection bottle 1900, and the vent port 1938 may be positioned at a second point of the collection bottle 1900 distinct from the first point. In at least one example embodiment, the second point may be as far as possible away from the first point. For example, the ports 1936, 1938 may be diametrically opposed on an outer periphery of the collection bottle 1900. In at least one example embodiment, the ports 1936, 1938 may be formed in the lid 1908. For example, the fluid port 1936 may be disposed at a first point 1911 of the lid 1908 adjacent to the perimeter 1909 and the vent port 1938 may be disposed at a second point 1913 adjacent to the perimeter 1909 distinct from the first point 1911. The first and second points 1911, 1913 may be diametrically opposed. In one example embodiment, prior to use, for example as illustrated in FIGS. 19A and 19F, a fluid port cap 1912 may be coupled to the fluid port 1936 to help maintain the sterility of the collection bottle 1900 during transport, shipping, and/or storage (i.e., before use). In at least one example embodiment, as illustrated in FIGS. 19B, 19G, and 19H, the tubing 120 of the apheresis system 200 may be coupled to the fluid port 1936. In at least one example embodiment the tubing 120 may include one or more connectors 1921. For example, as best illustrated, for example, in FIG. 19B, the connector 1921 may fit over the fluid port 1936. In at least one example embodiment, a vent tube 1916 may be coupled to the vent port 1938. The vent tube 1916 may provide a means to connect a filter (e.g., a microbial filter 1918) to the vent port 1938 that may be configured to seal the vent path, for example, when the collection bottle 1900 is filled.

In at least one example embodiment, the lid 1908 may be configured to protect the collection bottle 1900 during transportation, shipping, and/or handling. For example, the disk-shaped portion 1941 of the shield handle 1942 may help to protect the fluid port 1936 and/or the vent port 1938 and/or any tubing or the like (e.g., fluid port cap 1912, vent tube 1916, cut tubing section 120, etc.) attached thereto, which is often brittle. In at least one example embodiment, the disk-shaped portion 1941 of the shielded handle 1942 may define a shield plane 1952 and the fluid port 1936 and/or the outlet port 1938 and/or any tubing or the like attached thereto may be disposed beneath the shield plane 1952 (i.e., between the first lid side 1933 and an exterior-facing surface of the disk-shaped portion 1941). The shield plane 1952 may define a first or guard distance, while the fluid port 1936 and/or the outlet port 1938 and/or any tubing or the like attached thereto define a second or tubing distance that is less than the first distance.

In at least one embodiment, the disk-shaped portion 1941 provides a raised support structure that is configured to receive force or weight without transferring the force or weight to the fluid port 1936 and/or the outlet port 1938 and/or any tubing or the like attached thereto. For example, the disk-shaped portion 1941 a platform such that other collection bottles may be stacked (e.g., vertically along the longitudinal axis, etc.) during shipping and/or storage, for example, as shown in FIG. 19H. Although not illustrated, it should be recognized that in at least one example embodiment, a major dimension of the disk-shaped portion 1941 may be selected such that the disk-shaped portion 1941 extends to cover at least a portion of the fluid port 1936 and/or the outlet port 1938 and/or any tubing or the like attached thereto.

A collection bottle transport package (also referred to as a transport container) 1954 is illustrated in FIG. 19H. The transport container 1954 may be configured to carry and/or store one or more rows 1956A, 1956B of collection bottles 1900, for example, after collection (i.e., after use). For example, as illustrated, the transport container 1954 may include a first row 1956A of collection bottles 1900 and a second row 1956B of collection bottles 1900. The collection bottles 1900 in the first row 1956A may be arranged side-by-side in one or more columns. Although not illustrated, it should be appreciated that a divider may be disposed between the one or more columns of the first row 1956A. In at least one example embodiment, the divider may be a loose divider. In at least one example embodiment, the divider may include cardboard and/or paperboard. The collection bottles 1900 in the second row 1956B may also be arranged side-by-side in one or more columns. Although not illustrated, it should be appreciated that a divider may be disposed between the one or more columns of the second row 1956B. In at least one example embodiment, the divider may be a loose divider. In at least one example embodiment, the divider may include cardboard and/or paperboard. In at least one example embodiment, dividers separating the one or more columns of the first row 1956A may extend to divide the one or more columns of the second row 1956B.

The second row 1956B may be stacked on top of the first row of bottles 1956A. For example, the closed end 1930 of each collection bottle 1900 in the second row 1956B may be in contact with the shield handle 1942 of a respective collective bottle 1900 in the first row of bottles 1856A. In this stacked configuration, the fluid port 1936 and/or the outlet port 1938 and/or any tubing or the like attached thereto of each collection bottle 1900 in the first row of bottles 1956A is protected from contact with, and damage from, the second row of bottles 1956B, for example, via the shield handle 1942. For example, the fluid port 1936 and/or the outlet port 1938 and/or any tubing or the like attached thereto may be physically separated from the adjacent row of bottles, for example, via the shield handle 1942. Although two rows 1956A, 1956B are illustrated, it should be recognized that the transport container 1954 may be configured to include fewer or more rows, including, for example, five rows of collection bottles 1900.

A width of the transport container 1954 may be a length extending from a first or left side 1951 to a second or right side 1953. A height of the transport container 1954 may be a length extending from a third or top side 1955 to a fourth or bottom side 1957. A depth of the transport container 1954 may be defined as the length extending into and/or out of the page. Although the transport container 1954 is illustrated as defining an outer package, it should be recognized that in at least one example embodiment, the transport container 1954 may include a first container that encases the first row 1956A and a second container that encases the second row 1956B, where the first container and the second container define the transport container 1954. In at least one example embodiment, the transport container 1954, including the first container and/or the second container, may include a corrugated box. The collection bottles 1900 may be easily placed in and/or removed from the transport container 1954, including the first container and/or the second container, by grasping (by a user or robot) the shield handle 1942, and more specifically, the grip recess 1944.

In at least one example embodiment, the collection bottle 1900 may include a label 1920. In at least one example embodiment, the label 1920 may include a radio frequency identification (RFID) tag, a barcode (e.g., 2D, 3D, etc.), quick response (QR) code, visible code that is printed to the label, or any combination thereof configured to convey information. The information may include identification information, manufacturing information, and the like. In at least one example embodiment, the label 1920 may be read by the scanner 1221 of the apheresis system 200 during setup and/or use of the apheresis system 200.

The collection bottle 1900 can be used for various operations of the apheresis system 200. For example, in at least one example embodiment, as illustrated for example in FIGS. 191 and 19J, the collection bottle 1900 may be disposed in the plasma collection cradle 232C of the apheresis system 200. In at least one example embodiment, the plasma collection cradle 232C may be a holder like the holder 1300 illustrated in FIG. 13A. In at least one example embodiment, as best illustrated FIG. 19B, the collection bottle 1900 may be disposed on its side with a downward or declining angle 1902 when positioned in the plasma collection cradle 232C, such that the fluid port 1936 and/or the tubing 120 is at a lowermost position and the vent port 1938 and/or vent tube 1916 is at an uppermost position during use. The decline angle 1902 may be greater than or equal to about one degree to less than or equal to about thirty degrees, optionally greater than or equal to about two degrees to less than or equal to about five degrees. As a result of the declining angle 1902, as plasma (and/or other fluid) enters the collection bottle 1900, for example, via the fluid port 1936 and/or tubing 120, gases within the collection bottle 1900 may escape via the vent port 1938 and/or the vent tube 1916. Additionally, or alternatively, as the plasma (and/or other fluid) in the collection bottle 1900 is moved from the collection bottle 1900 through the tubing 120 and into the blood component collection set 500 (e.g., during final phases of the plasma collection process), air may be drawn into the collection bottle 1900, for example, via the vent port 1938 and/or vent tube 1916. In at least one example embodiment, the exchange of gases through the vent port 1938 and/or vent tube 1916 may be filtered by a filter 1918 (e.g., a microbial filter) disposed in the vent tube 1916. As can be appreciated, this arrangement including the filter 1918 may help to ensure that the pressure in the collection bottle 1900 is balanced with the environment outside of the collection bottle 1900, such that vacuum or pressure build up in the collection bottle 1900 does not affect collection efforts negatively and/or that no additional equipment is necessary to maintain pressures in the collection bottle 1900.

Figure 19J:
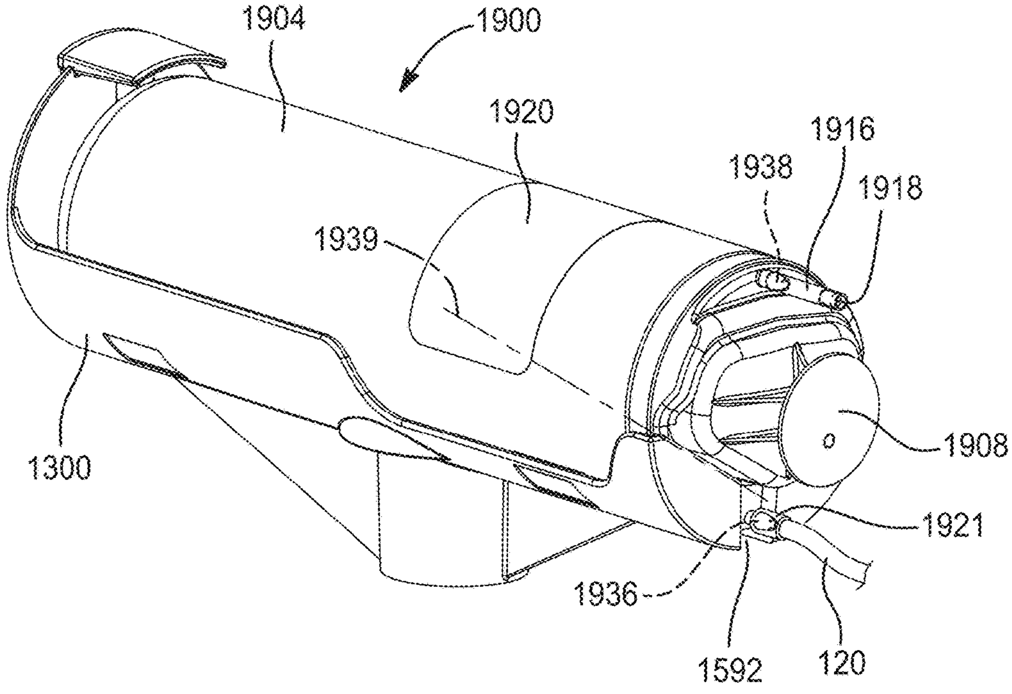
FIG. 19J is a perspective view of the collection bottle of FIG. 19A disposed in the collection cradle.

In at least one example embodiment, the collection bottle 1900 may include one or more tapered and/or keyed and/or angled surfaces configured to ensure the collection bottle 1900 is properly aligned with the apheresis system 200 and/or the plasma collection cradle 232C, 1300. For example, a base 1937 may be coupled to the first lid side 1933 and the shield handle 1942 may be coupled to a side of the base 1937 away from the first lid side 1933. The base 1937 may include, as illustrated in FIG. 19J, one or more angled portions configured to align with a corresponding angled portion of the cradle 1300, such as represented by line 1939. In at least one example embodiment, the sides of the base 1937 nearer to the fluid port 1936 may form a general shape (for example, a v-shape) that can be aligned with a corresponding shape of the cradle 1300 (e.g., alignment surface 1589 as discussed in FIGS. 15K-15L). For example, the general shape of the base 1937 may have an angle that corresponds with alignment angle 1590 of the cradle 1300. In at least one example embodiment, as illustrated, and discussed above in the context of FIGS. 15K-15L, the corresponding shape of the cradle 1300 may include a slot 1592 configured to receive the fluid port 1936. These features together work to ensure proper alignment of the collection bottle 1900 within the cradle 1300.

FIG. 19G is an illustration of the collection bottle 1900 after collection (i.e., after use). For example, the collection bottle 1900 shown in FIG. 19G may include plasma collected by operation of the apheresis system 200. In at least one example embodiment, once the collection bottle 1900 is filled with plasma (and/or other fluid), the tubing 120 may be sealed adjacent to the fluid port 1936. For example, the tubing 120 may include a sealed end 1950. In at least one example embodiment, the sealed end 1950 of the tubing 120 may be sealed using a crimping process, a heat-sealing process, a radio frequency (RF) sealing process, or any combination thereof. In at least one example embodiment, once the collection bottle 1900 is filled with plasma (and/or other fluid), the vent tube 1916 may be sealed adjacent to the vent port 1938 (i.e., between the filter 1918 and the vent port 1938). For example, the tubing 1916 may include a sealed end 1949. In at least one example embodiment, the sealed end 1949 of the tubing 1916 may be sealed using a crimping process, a heat-sealing process, a radio frequency (RF) sealing process, or any combination thereof.

In at least one example embodiment, the present disclosure provides a collection bottle. The collection bottle may include a canister and a lid. The canister may include an elongate body having a closed end and an open end disposed opposite to the closed end, where an interior space of the canister is defined extending from the open end to a point adjacent the closed end. The lid may include a body, a shield handle and a rim. The body may define an outer perimeter of the lid. The body may include a first side and a second side disposed opposite the first side. The shield handle may be attached to the first side of the body. The shield handle may be offset a distance from the body. The rim may be disposed around the outer perimeter of the lid. The rim may be disposed within the open end of the canister, and the lid may be sealed to the canister along the outer perimeter of the lid. In at least one example embodiment, the shield handle may include a disk-shaped portion having a handle outer perimeter that is disposed within an area of the outer perimeter of the lid. In at least one example embodiment, the shield handle may include a recessed area disposed between the disk-shaped portion and the body of the lid. In at least one example embodiment, the lid may further include a fluid port disposed on the first side of the body at a first point adjacent to the outer perimeter of the lid. The fluid port may include an inlet lumen that defines a first flow path extending from an exterior of the collection bottle to the interior space of the canister. In at least one example embodiment, the lid may further include a vent port disposed on the first side of the body at a second point adjacent to the outer perimeter of the lid, where the first point and the second point may be arranged diametrically opposed to one another. The vent port may include a vent lumen that defines a second flow path extending from the interior space of the canister to an exterior of the collection bottle. In at least one example embodiment, the lid may further include a vent tube attached to the vent port. The vent tube may include a filter disposed in the vent tube. The filter may be disposed in the second flow path. In at least one example embodiment, the lid may be sealed to the canister along the outer perimeter of the lid via a laser welded seam between the rim and a ring edge of the canister. In at least one example embodiment, the canister may be at least one of transparent and translucent and/or the lid may be opaque. In at least one example embodiment, after filling or after use, the lid may further include a sealed tubing section attached to the fluid port. For example, the shield handle may be arranged having a shield plane disposed a guard distance measured from the outer lid perimeter of the lid, and the sealed tubing section may include a sealed end that is disposed a tubing distance measured from the body of the lid. The guard distance may be greater than the tubing distance.

In at least one example embodiment, the present disclosure provides a collection bottle transport package. The collection transport package may include a container having a width and a height. The container includes an interior and an exterior, where the interior includes a base extending planarly along the width of the container. A first row of collection bottles may be arranged side-by-side in the interior of the container, and a second row of collection bottles may be arranged side-by-side in the interior of the container, where each collection bottle of the first row of collection bottles and the second row of collection bottles includes a canister and a lid. The canister includes an elongate body having a closed end and an open end disposed opposite the closed end, where an interior space of the canister is defined extending from the open end to a point adjacent the closed end. The lid includes a body and a shield handle attached to the body. The body may define an outer perimeter of the lid and may include a first side and a second side disposed opposite the first side. The shield handle may be attached to the first side of the body. The shield handle may be offset a distance from the body. The shield handle may include a disk-shaped portion that includes a handle outer perimeter that is disposed within an area of the outer perimeter of the lid. The lid may further include a rim disposed around the outer perimeter of the lid and a fluid port disposed on the first side of the body at a first point adjacent to the outer perimeter of the lid. The fluid port may include an inlet lumen defining a first flow path extending from an exterior of the collection bottle to the interior space of the canister. The lid may also include a sealed tubing section that may be attached to the fluid port, where the shield handle is arranged having a shield plane disposed a guard distance measured from the body of the lid. The sealed tubing section may include a sealed end that is disposed a tubing distance measured from the body of the lid, and the guard distance may be greater than the tubing distance. The lid may further include a vent port that may be disposed on the first side of the body at a second point adjacent to the outer perimeter of the lid, where the first point and the second point may be arranged diametrically opposed to one another. The vent port may include a vent lumen defining a second flow path extending from the interior space of the canister an exterior of the collection bottle. The lid may further include a vent tube attached to the vent port, where the vent tube includes a filter disposed in the vent tube, and the filter is disposed in the second flow path. The rim of the lid may be disposed in the open end of the canister, and the lid may be sealed to the canister along the outer perimeter of the lid. The closed end of each collection bottle of the first row of collection bottles may be in contact with the base of the container. The closed end of each collection bottle of the second row of collection bottles may be in contact with a respective shield handle of each collection bottle of the first row of collection bottles. The sealed tubing section of each collection bottle of the first row of collection bottles may be separate and apart from the second row of collection bottles in the container such that the sealed tubing section of each collection bottle of the first row of collection bottles may be protected by the shield handle of each collection bottle of the first row of collection bottles.

Methods for Providing Automatic Fluid Flow Adjustments

Figure 20:
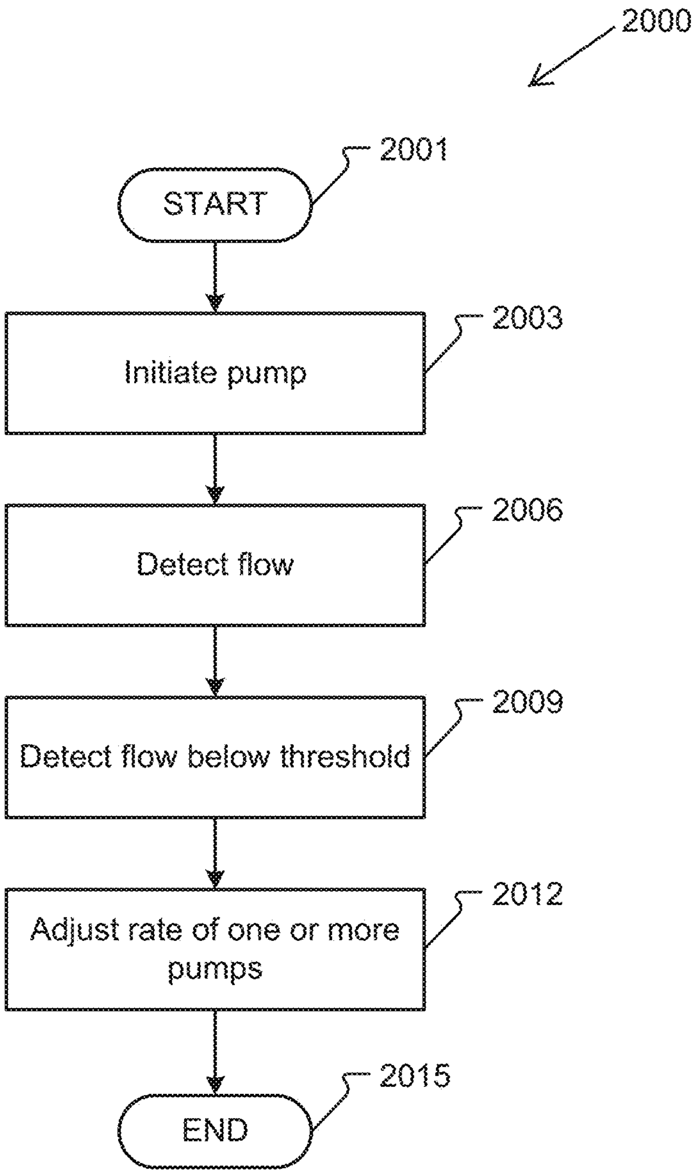
FIG. 20 is a flowchart of a method in accordance with at least one example embodiment of the present disclosure.

FIG. 20 shows an example embodiment of a method 2000. In at least one example embodiment, an apheresis system 200 as described herein may be configured to perform a process such as the method 2000 of automatically adjusting, in real time, flow rates for time optimization of operations by the apheresis system 200. These adjustments may be based on pressure, which may result in fewer alarms being activated during the use of the apheresis system 200 as compared to conventional systems. Such a process, as described herein, allows the apheresis system 200 to operate faster and selectively slow down to adjust and to avoid alarms.

At step 2001, the method 2000 may begin with a donor being connected to an apheresis system 200 as described herein.

At step 2003, a pump, such as one or more of the draw pump 208, the return pump 212, or the AC pump 216, may be initiated. The initiation of one or more of the pumps may prompt the beginning of a flow of fluid into and through the apheresis system 200.

The one or more pumps may be initiated by a microcontroller within the apheresis system 200. In at least one example embodiment, initiating one or more of the pumps may comprise applying power to the one or more pumps to begin the flow.

At step 2006, one or more sensors (e.g., sensors 284, 312, 316, 804, 808, 812, 816, and/or 912-924, etc.) in the apheresis system 200 may detect and/or monitor the flow of the fluid into and/or through the apheresis system 200. In at least one example embodiment, in addition to, or alternatively, a state of the tubing 358 may be monitored. For example, a sensor (e.g., sensors 284, 312, 316, 804, 808, 812, 816, and/or 912-924, etc.) may be used to determine whether the tubing 358 is largely round or whether the tubing 358 is collapsed or at all compressed.

The state of the tubing may correspond to an empty or a partially filled fluid state. Additionally or alternatively, the state of the tubing may comprise a type of a fluid (e.g., air, blood, blood components, plasma, red blood cells, platelets, etc.) contained within the tubing and/or other sections of the blood component collection set 500. For example, a tube may collapse due to an incorrectly connected tube or due to a collapsed vein in a donor. A collapsed tube may change shape due to pressure caused by one or more of the pumps drawing fluid into the tubing. In at least one example embodiment, the sensors (e.g., sensors 284, 312, 316, 804, 808, 812, 816, and/or 912-924, etc.) may be employed to determine the type of the fluid contained within a section of the tubing of the blood component collection set 500 based on a measured pressure, density, compressibility, resistance, and/or combinations thereof at one or more points along the section of the tubing 358.

At step 2009, the method 2000 may comprise detecting that the flow of fluid is below a predetermined threshold. In at least one example embodiment, the flow of fluid below a predetermined threshold may be detected automatically.

Detecting the flow of fluid is below a predetermined threshold may comprise measuring a rate of flow through the tubing, identifying a color of fluid within the tubing, determining a shape of the tubing, detecting a temperature of the fluid, or measuring or determining another factor relating to the tubing and/or the flow of fluid. The predetermined threshold may relate to any one or more of the rate of flow of fluid through the tubing, color of fluid in the tubing, shape of the tubing, or another factor. In at least one example embodiment, the apheresis system 200 may be configured to detect one or more of a red, a blue, or a green color of fluid within the tubing.

At step 2012, the method 2000 may comprise, in response to detecting the flow of fluid is below the predetermined threshold, adjusting a rate of one or more other fluids by adjusting a rate of pumping of the one or more pumps. For example, in response to detecting a flow of fluid is below a predetermined threshold rate, a computer system of the apheresis system 200 may adjust a rate of one or more of the pumps of the apheresis system 200. More specifically, if the detected flow of fluid has a pressure that is below a predetermined threshold pressure, the rate of pumping of the one or more pumps may be slowed down and if the flow of fluid has a pressure that is above a predetermined threshold pressure, the rate of pumping of the one or more pumps may be sped up. If the flow of fluid recovers such that it is equal to the predetermined threshold rate, the apheresis system 200 may adjust the one or more pumps back to their original state. Adjusting the rate of the one or more of the pumps of the apheresis system 200 may comprise altering an amount of power applied to the one or more pumps. In at least one example embodiment, adjusting the rate of the one or more pumps of the apheresis system 200 may include turning off the one or more pumps of the apheresis system 200. For example, the one or more pumps may be turned off if the detected flow of fluid is too low. Similarly, the one or more pumps may be stopped if the apheresis system 200 detects a color within the tubing. If the one or more pumps are turned off, the one or more pumps may not restart automatically. An operator may be required to acknowledge an alarm condition that caused the one or more pumps to stop and to manually restart the apheresis system 200.

By way of example, a first donor 102 may provide blood having a certain platelet content that is greater than the platelet content of another donor 102. Continuing this example, at a first-time during processing by the apheresis system 200, the first donor 102 may provide blood components that are denser than that of another donor 102 at the same time during processing. In this instance, the apheresis system 200 may determine the density, or packing, of the tubing at the first time and adjust the pump pressure from a first pressure to a higher second pressure. While the first pressure may be sufficient to pump the blood components through the blood component collection set 500 for another donor 102 in a given time period, the first pressure may be too low to pump the denser blood components of the first donor 102 within the given time period (e.g., requiring more time for the first donor 102 to be processed). At least one advantage of the automatic adjustment, described herein, is that the first donor 102 may be processed more efficiently and in accordance with the characteristics of the first donor 102.

Adjusting a rate of one or more pumps in response to detecting a flow below a threshold may enable the apheresis system 200 to efficiently pump denser blood components. Since this adjustment is automatic and based on a detected and determined state of the tubing, the operations may be adjusted in real time and without human input. This real-time automatic adjustment produces a fast, efficient, processing of donors 102, which can result in a more enjoyable donation experience.

Once the state of the tubing is determined, the apheresis system 200 may determine whether to adjust a pump pressure (e.g., increase or decrease from a predetermined pressure, etc.), cease an operation of the apheresis system 200, advance to a next step in an operation of the apheresis system 200, send a warning message and/or alarm (e.g., causing the warning message to be rendered to a display device associated with the apheresis system 200, etc.). In at least one example embodiment, this adjustment may allow processing of blood components to be optimized for any number of different donors 102.

At step 2015, the method 2000 may end when the donation process is complete. It should be appreciated that the method 2000 may continue throughout the entire donation process. Rates of flow may be monitored continuously or at intervals and adjustments may be made continuously or at intervals as needed.

At least one example embodiment may include a method comprising: initiating one or more pumps of an apheresis machine; detecting a flow of fluid through the apheresis machine; detecting the flow of the fluid is below a predetermined threshold; and in response to detecting the flow of the fluid is below the predetermined threshold, adjusting a rate of one or more pumps of the apheresis machine.

In at least one example embodiment, detecting the flow of the fluid is below the predetermined threshold comprises detecting a collapsed vein. In at least one example embodiment, detecting the flow of the fluid if below the predetermined threshold comprises using a sensor to detect a color of the fluid. In at least one example embodiment, the sensor detects one or more of red, blue, or green. In at least one example embodiment, detecting the flow of the fluid is below the predetermined threshold comprises using a sensor to detect a flow rate of the fluid. In at least one example embodiment, detecting the flow of the fluid is below the predetermined threshold comprises using a sensor to detect a pressure of the flow of the fluid. In at least one example embodiment, detecting the flow of fluid is below the predetermined threshold comprises using a sensor to detect a temperature of the fluid. In at least one example embodiment, adjusting the rate of the one or more pumps of the apheresis machine comprises sending a control signal to the one or more pumps. In at least one example embodiment, adjusting the rate of the one or more pumps of the apheresis machine comprises altering a power applied to the one or more pumps. In at least one example embodiment, adjusting the rate of the one or more pumps of the apheresis machine comprises turning off the one or more pumps.

Example Apheresis System Safety Features

An apheresis system according to at least one example embodiment may include one or more safety features. Safety features may facilitate proper placement of AC and saline bag hooks, provide override access to an interior of a housing, route air to facilitate cooling, and/or reduce or prevent rotation of an unlocked centrifuge.

Figure 21A:
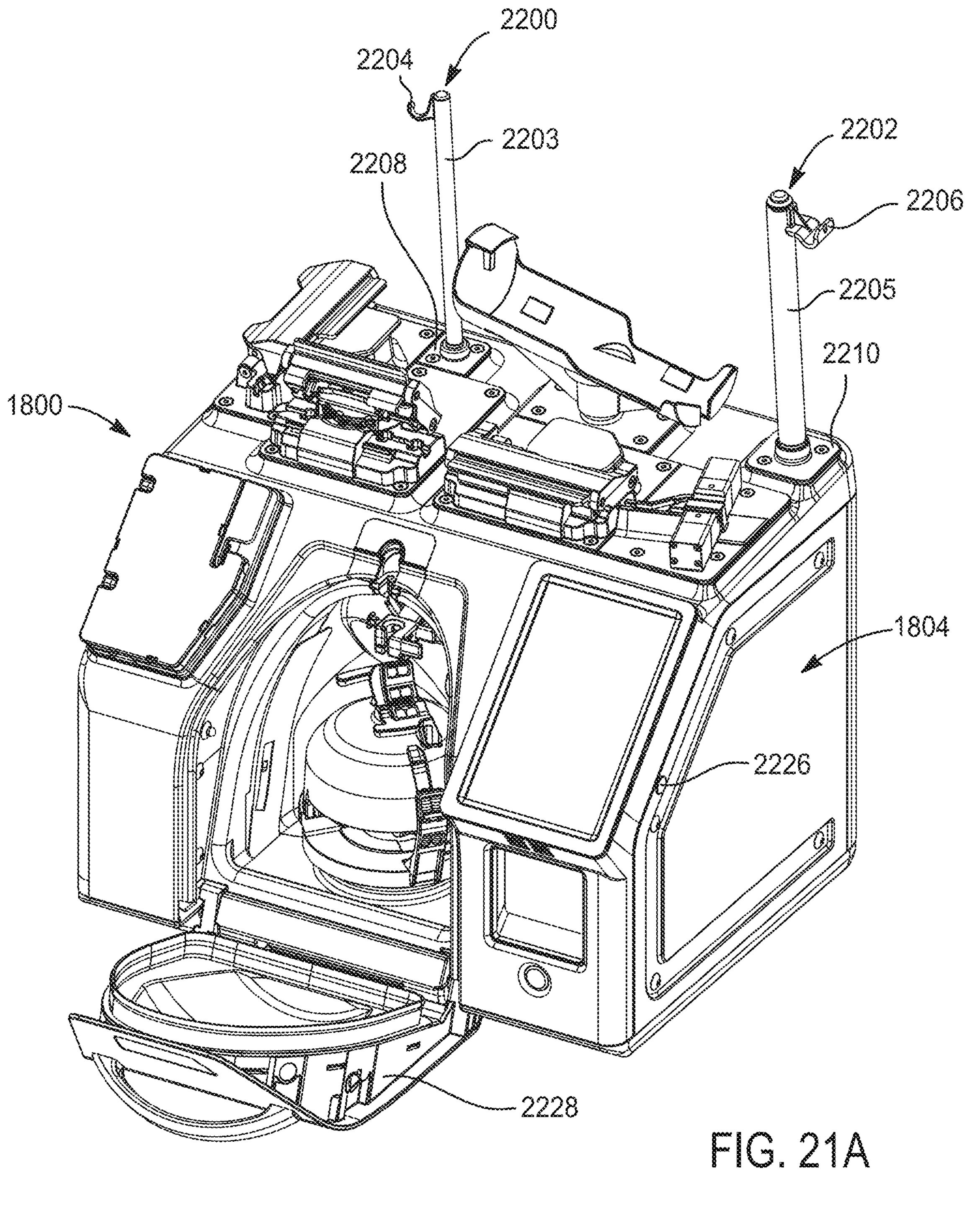
FIG. 21A is a partial perspective view of the apheresis system of FIG. 18A in accordance with at least one example embodiment of the present disclosure.

FIG. 21A is a partial perspective view of the apheresis system of FIG. 18A according to at least one example embodiment.

In at least one example embodiment, as shown in FIG. 21A, the apheresis system 1800 includes a first hanger assembly 2200 and a second hanger assembly 2202. The first hanger assembly 2200 includes a first post 2203 and a first hook 2204 on the first post 2203. The second hanger assembly 2202 includes a second post 2205 and a second hook 2206 on the second post 2205.

Figure 26G:
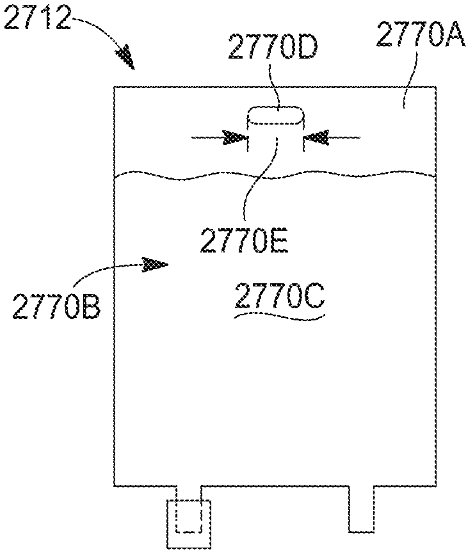
FIG. 26G is a schematic view of an AC bag of the separation assembly of FIG. 26C in accordance with at least one example embodiment of the present disclosure.

The first hanger assembly 2200 is configured to hold a first media bag, such as an AC bag (see, e.g., AC bag 114 of FIG. 1 or AC bag 2712 of FIG. 26G). The second hanger assembly 2202 is configured to hold a second media bag, such as a saline bag (see, e.g., saline bag 118 of FIG. 1 or saline bag 2714 of FIG. 26H). The first hanger assembly 2200 may be attached to the base assembly 1804 via a first base 2208. The second hanger assembly 2202 may be attached to the base assembly 1804 via a second base 2210. An apheresis system according to at least one example embodiment may include more post and hooks, such as to hold additional media bags.

In at least one example embodiment, as will be discussed in great detail below, the first and second bases 2208, 2210 may each be differently and/or uniquely keyed for receiving one of the first and second posts 2203, 2205, but not the other of the first and second posts 2203, 2205. The keyed bases 2208, 2210 may facilitate proper placement of the posts 2203, 2205 in the respective bases 2208, 2210. In at least one example embodiment, the first post 2203 cannot be inserted into the second base 2210 and the second post 2205 cannot be inserted into the first base 2208. Additionally or alternatively, the posts 2203, 2205 and corresponding bases 2208, 2210 may include colors and/or other indicia to facilitate proper placement in the base assembly 1804.

In at least one example embodiment, the first and second hooks 2204, 2206 have different shapes, sizes, and/or colors to facilitate proper placement of media bags. In at least one example embodiment, the first hook 2204 is configured to receive and/or hang a first media bag, but not a second media bag and the second hook 2206 is configured to receive and/or hang the second media bag, but not the first media bag. Such a configuration may reduce or prevent inadvertent exposure of a donor to AC.

Figure 21B:
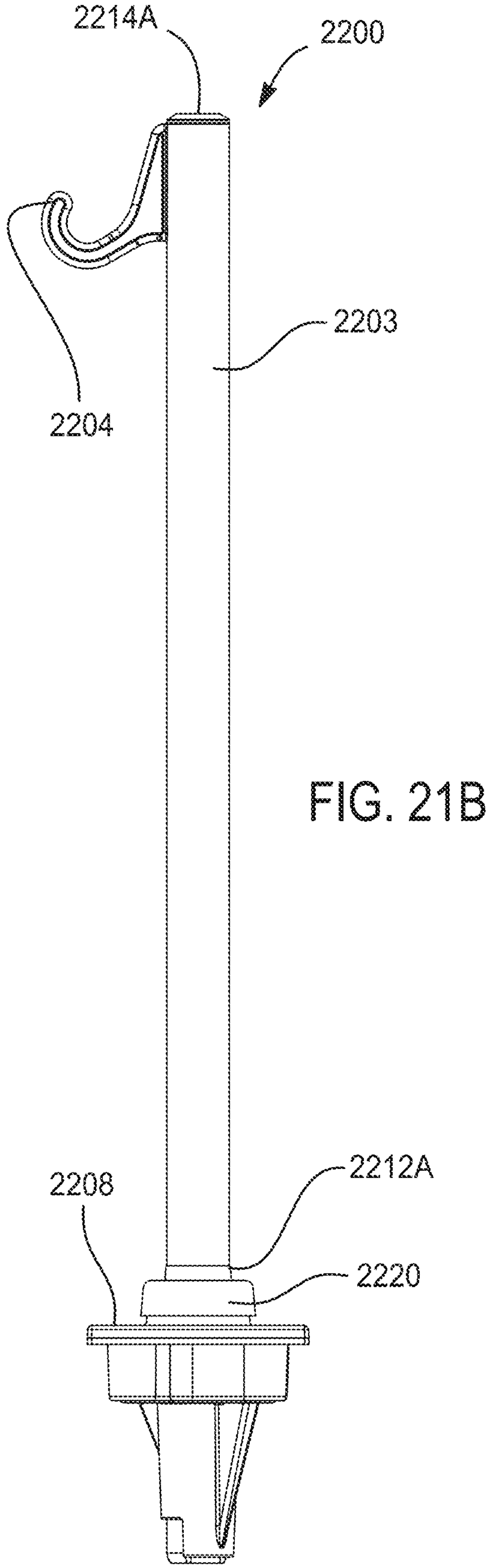
FIG. 21B is an elevation view of a first hanger assembly of the apheresis system of FIG. 21A in accordance with at least one example embodiment of the present disclosure.
Figure 21C:
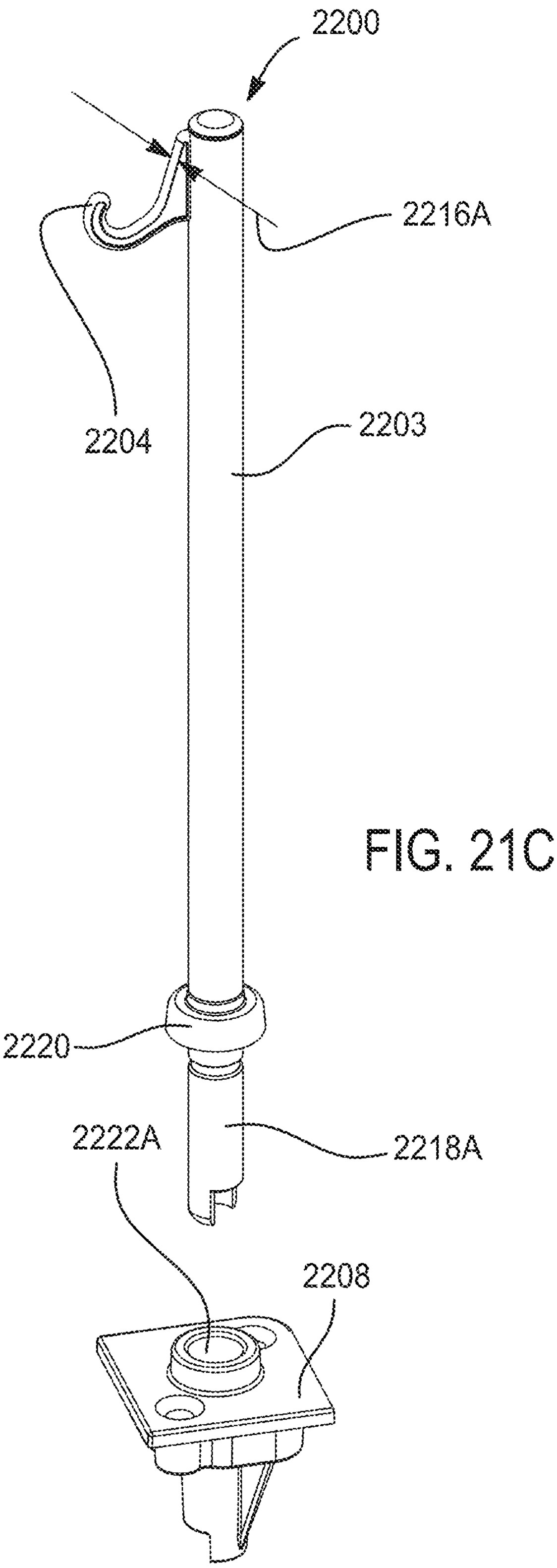
FIG. 21C is an exploded perspective view of the first hanger assembly of FIG. 21B in accordance with at least one example embodiment of the present disclosure.

FIG. 21B is an elevation view of a first hanger assembly of the apheresis system of FIG. 21A according to at least one example embodiment. FIG. 21C is an exploded perspective view of the first hanger assembly of FIG. 21B according to at least one example embodiment.

In at least one example embodiment, as shown in FIGS. 21B-21C, the first post 2203 extends between a first proximal end 2212A and a first distal end 2214A. The first hook 2204 may be at the first distal end 2214A. The first hook 2204 may define a first transverse dimension or width 2216A.

In at least one example embodiment, a first projection 2218A extends from the first proximal end 2212A of the first post 2203. A flange 2220 may be between the first proximal end 2212A and the first projection 2218A. The first base 2208 may define a first receptacle 2222A. The first receptacle 2222A may be configured to receive at least a portion of the first projection 2218A to couple the first post 2203 to the first base 2208. In at least one example embodiment, the first base 2208 is uniquely and/or specifically keyed to receive the first projection 2218A.

Figure 21D:
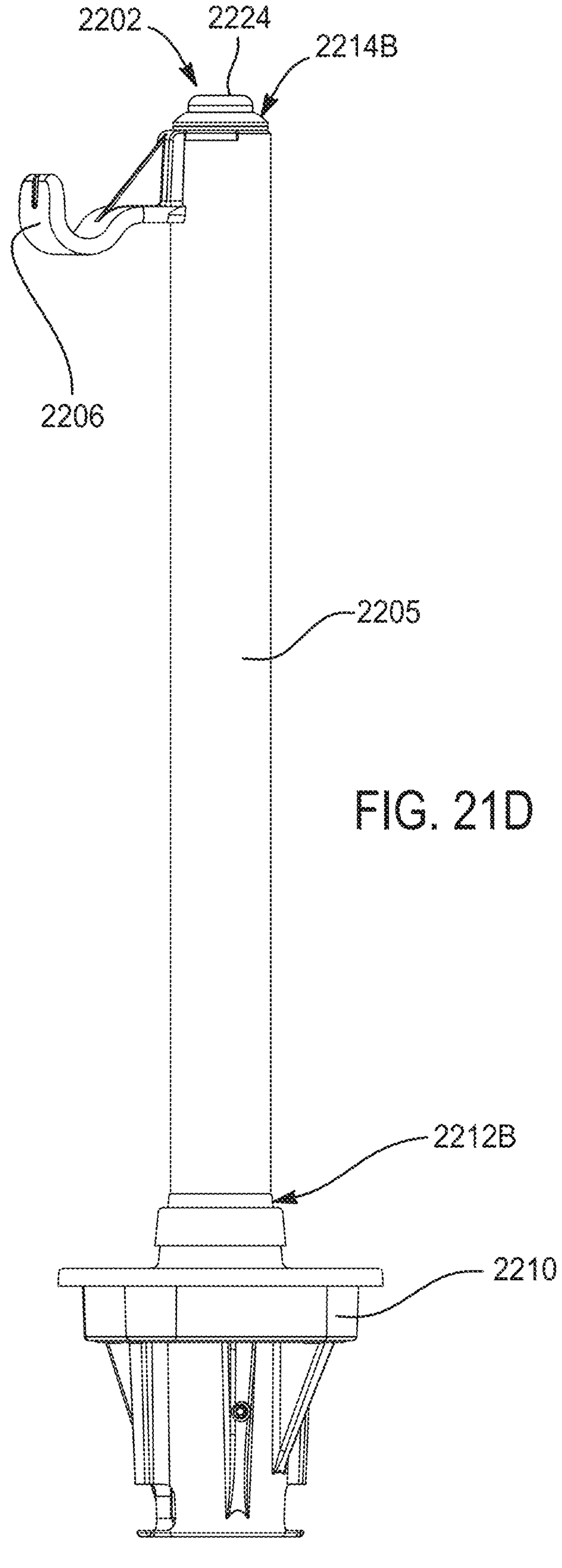
FIG. 21D is an elevation view of a second hanger assembly of the apheresis system of FIG. 21A in accordance with at least one example embodiment of the present disclosure.
Figure 21E:
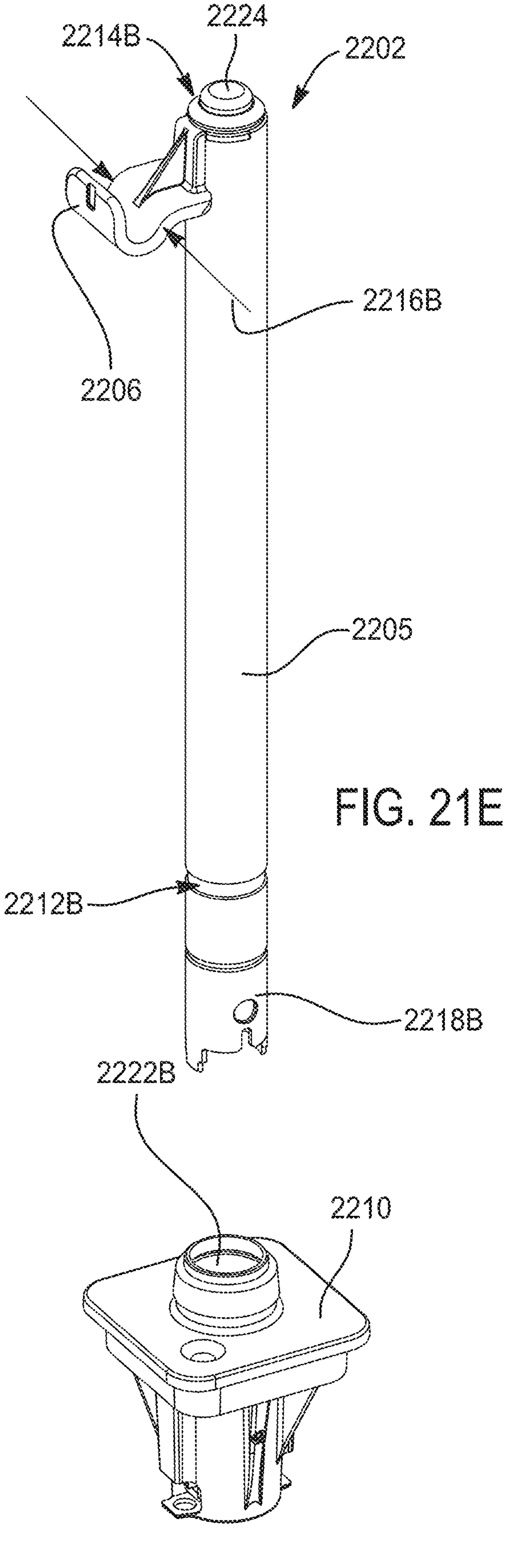
FIG. 21E is an exploded perspective view of the second hanger assembly of FIG. 21D in accordance with at least one example embodiment of the present disclosure.

FIG. 21D is an elevation view of a second hanger assembly of the apheresis system of FIG. 21A according to at least one example embodiment. FIG. 21E is an exploded perspective view of the second hanger assembly of FIG. 21D according to at least one example embodiment.

In at least one example embodiment, as shown in FIGS. 21D-21E, the second post 2205 extends between a second proximal end 2212B and a second distal end 2214B. The second hook 2206 may be at the second distal end 2214B. The second hook 2206 may define a second transverse dimension or width 2216B. The second transverse dimension 2216B may be different than the first transverse dimension 2216A (shown in FIG. 21C). In at least one example embodiment, the second transverse dimension 2216B is greater than the first transverse dimension 2216A.

In at least one example embodiment, a second projection 2218B extends from the second proximal end 2212B of the second post 2205. The second base 2210 may define a second receptacle 2222B. The second receptacle 2222B may be configured to receive at least a portion of the second projection 2218B to couple the second post 2205 to the second base 2210. In at least one example embodiment, the second base 2210 is uniquely and/or specifically keyed to receive the second projection 2218B.

In at least one example embodiment, the first and second posts 2203, 2205 have electrical ground connections. The electrical ground connections may include a metal canted spring that electrically connects the respective post 2203, 2205 to a metal frame of the base assembly 1804. The electrical ground connection may reduce or prevent EMI limits, so as to meet IEC 60601-1.

In at least one example embodiment, the first post 2203 and/or the second post 2205 may be configured to form a further electrical connection to the apheresis system 1800 (shown in FIG. 21A) when inserted into the respective receptacle 2208, 2210. In at least one example embodiment, the further electrical connection is formed by a multiple conductor electrical connector (not shown) that is configured to mate with a connector within the base assembly 1804. In at least one example embodiment, when an electrical connection is present, the first post 2203 and/or the second post 2205 may include an indicator such as a visual indicator. The indicator may, for example, display various colors which may indicate corresponding statuses of the apheresis system 1800. In at least one example embodiment, an indicator may display green when the apheresis system 1800 is in use and the indicator may display red when the apheresis system 1800 is not in use (e.g., due to an end of an apheresis process, an emergency stop, or otherwise). In at least the example embodiment shown, the second post 2205 includes a further electrical connector and an indicator lamp 2224.

Returning to FIG. 21A, in at least one example embodiment, the apheresis system 1800 may include an override 2226. The override 2226 may be a cord and/or a button that can be depressed by a finger or push rod, or any other type of override. An access panel or door 2228 of the apheresis system 1800 may be locked in the event of a power loss, thereby blocking access to a centrifuge assembly (see, e.g., centrifuge assembly 400 of FIG. 4A or centrifuge assembly 2200 of FIG. 21G) in the base assembly 1804. The override 2226 may be engaged (e.g., pressed, pulled, etc.) to override the lock and permit opening of the access panel 2228. The override 2226 may be connected to a pneumatic actuator that controls the access panel 2228. The override 2226 may be configured to cause the pneumatic actuator to unlock the access panel 2228, thereby enabling access to the centrifuge assembly. In at least the example embodiment shown, the override 2226 is on a side of the base assembly 1804. However, an override may be disposed anywhere on the aphesis system that would be accessible in the event of power loss.

Figure 21F:
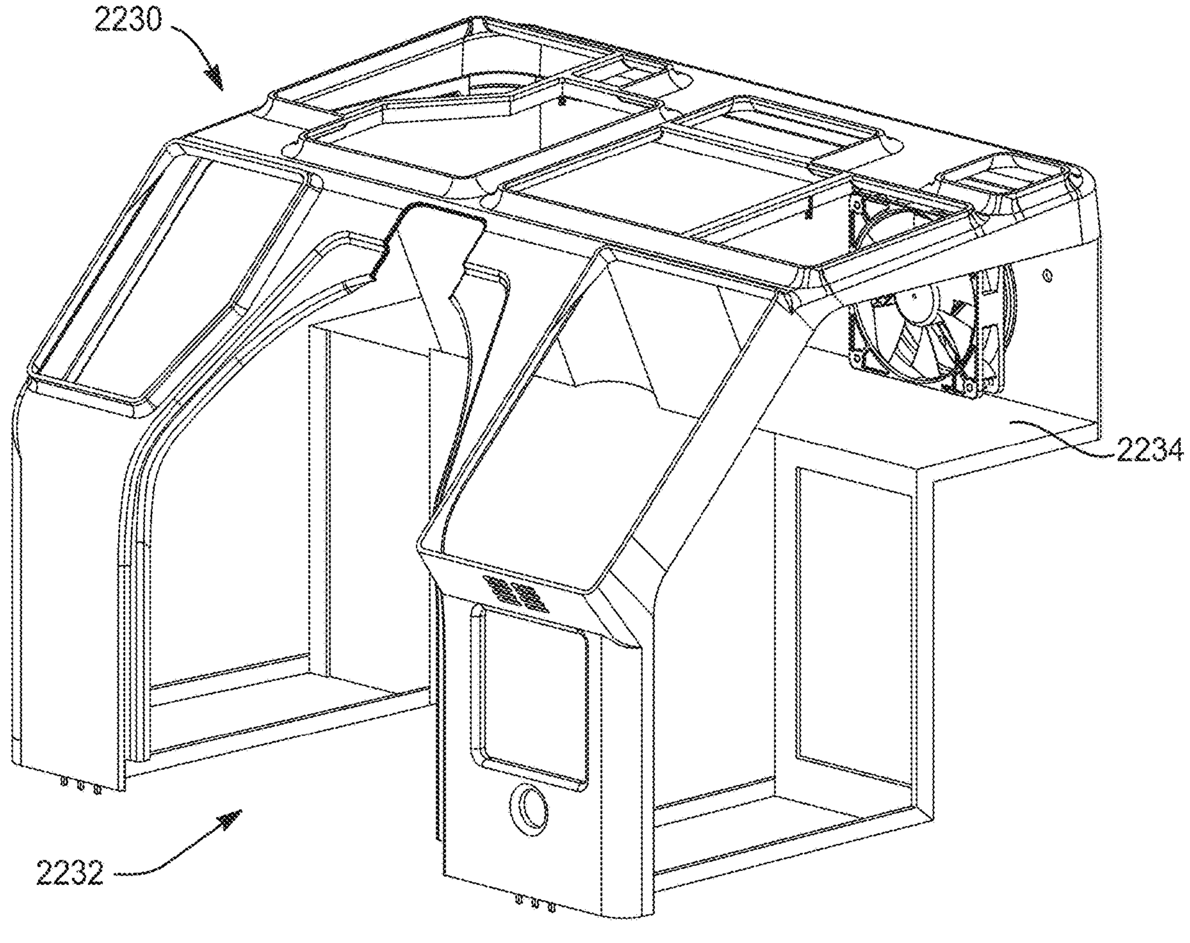
FIG. 21F is a perspective view of an air assembly of the apheresis system of FIG. 21A in accordance with at least one example embodiment of the present disclosure.

FIG. 21F is a perspective view of an air assembly of the apheresis system of FIG. 21A according to at least one example embodiment.

In at least one example embodiment, as shown in FIG. 21F, the apheresis system 1800 may include an air assembly 2230. The air assembly 2230 may be in an internal region of the base assembly 1804 (shown in FIG. 21A). The air assembly 2230 may at least partially define a centrifuge region or chamber 2232 in which the centrifuge is housed. In at least one example embodiment, the air assembly 2230 may be configured to maintain a predetermined (or alternatively, desired) temperature or a temperature range in the centrifuge chamber 2232. As the centrifuge assembly operates, the temperature in the chamber 2232 may rise above a predetermined threshold. In response, the air assembly 2220 may circulate air in the chamber 2232, and/or vent air from the chamber 2232 to an area outside of the apheresis system 1800.

In at least one example embodiment, the air assembly 2230 includes one or more blowers or fans 2234 configured to circulate air inside the chamber 2232. The blower or fan 2234 may induce an air path that is a convoluted air path to reduce or prevent fluid (e.g., blood, etc.) from reaching the air assembly 2230 and/or leaving the apheresis system 1800 in the event of a failure or leak from the centrifuge assembly 2240. In at least one example embodiment, the blower 2234 is configured to draw air out of the chamber 2232.

Figure 21G:
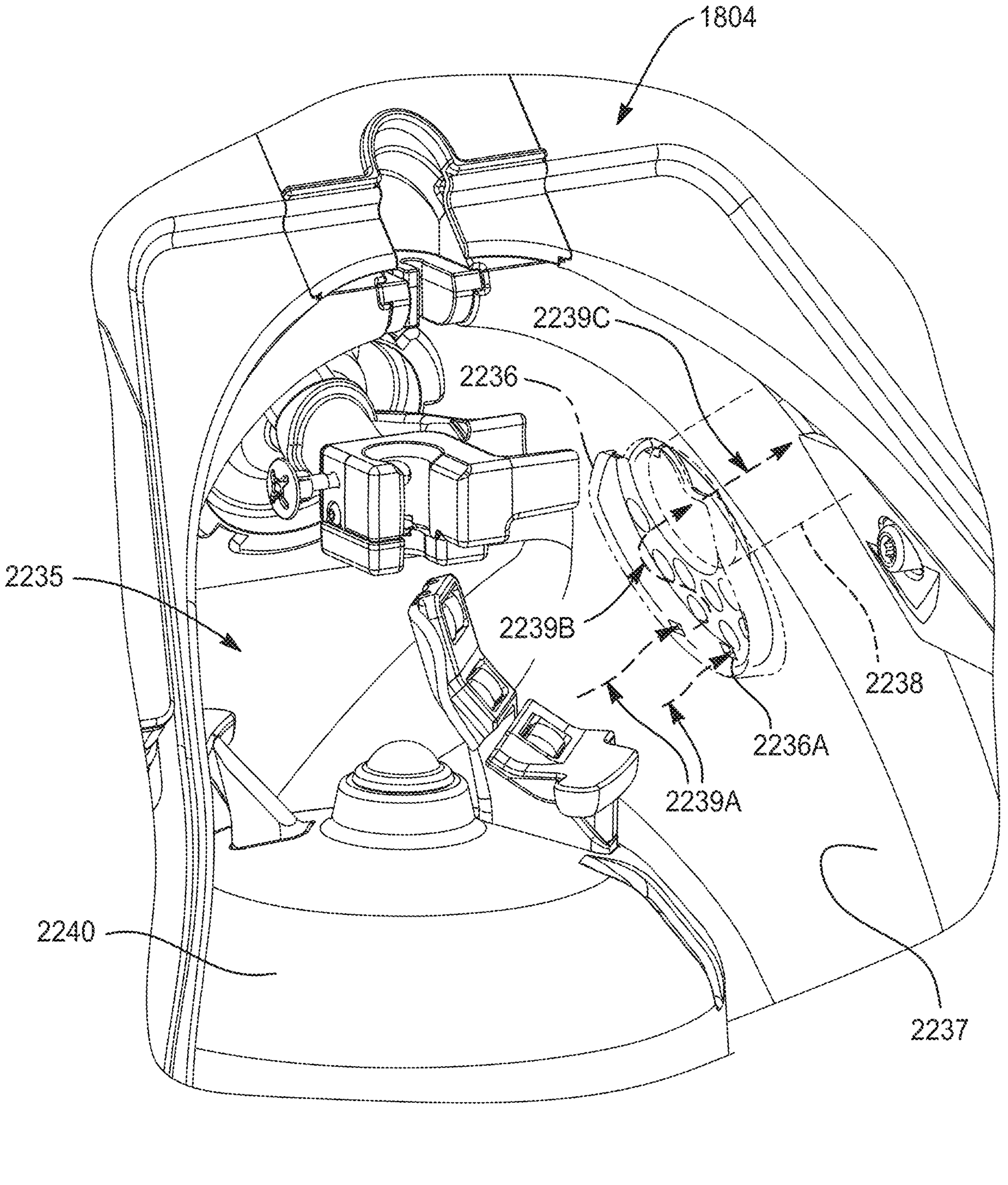
FIG. 21G is a partial perspective view of a centrifuge housing of the apheresis system of FIG. 21A in accordance with at least one example embodiment.

FIG. 21G is a partial perspective view of a centrifuge chamber of the apheresis system of FIG. 21A according to at least one example embodiment.

In at least one example embodiment, as shown in FIG. 21G, the base assembly 1804 may at least partially define a centrifuge chamber 2235. A snorkel cap 2236 may be coupled to a wall 2237 of the centrifuge chamber 2235. A snorkel 2238 may fluidly connect the centrifuge chamber 2235 to an exterior of the base assembly 1804.

In at least one example embodiment, an airflow path for air exiting the centrifuge chamber 2235 may include a first portion 2239A, a second portion 2239B, and/or a third portion 2239C. The first portion 2239A passes through the snorkel cap 2236 via one or more apertures 2236A. Air may travel generally horizontally in the first path 2239A. A shape of the snorkel cap 2236 may force air in the second portion 2239B to travel inwardly and/or upward. To exit into the snorkel 2238 in the third portion 2239C, the air may make about a 90° turn from the second portion 2239B. Accordingly, the airflow path including the first, second, and third portions 2239A, 2239B, 2239C may define multiple bends or curves that facilitate trapping of liquid (e.g., blood) while permitting passage of air. The airflow path may therefore reduce or prevent the transfer of liquid into the chamber 2232. A centrifuge assembly 2240 may be in the centrifuge chamber 2235.

Figure 21H:
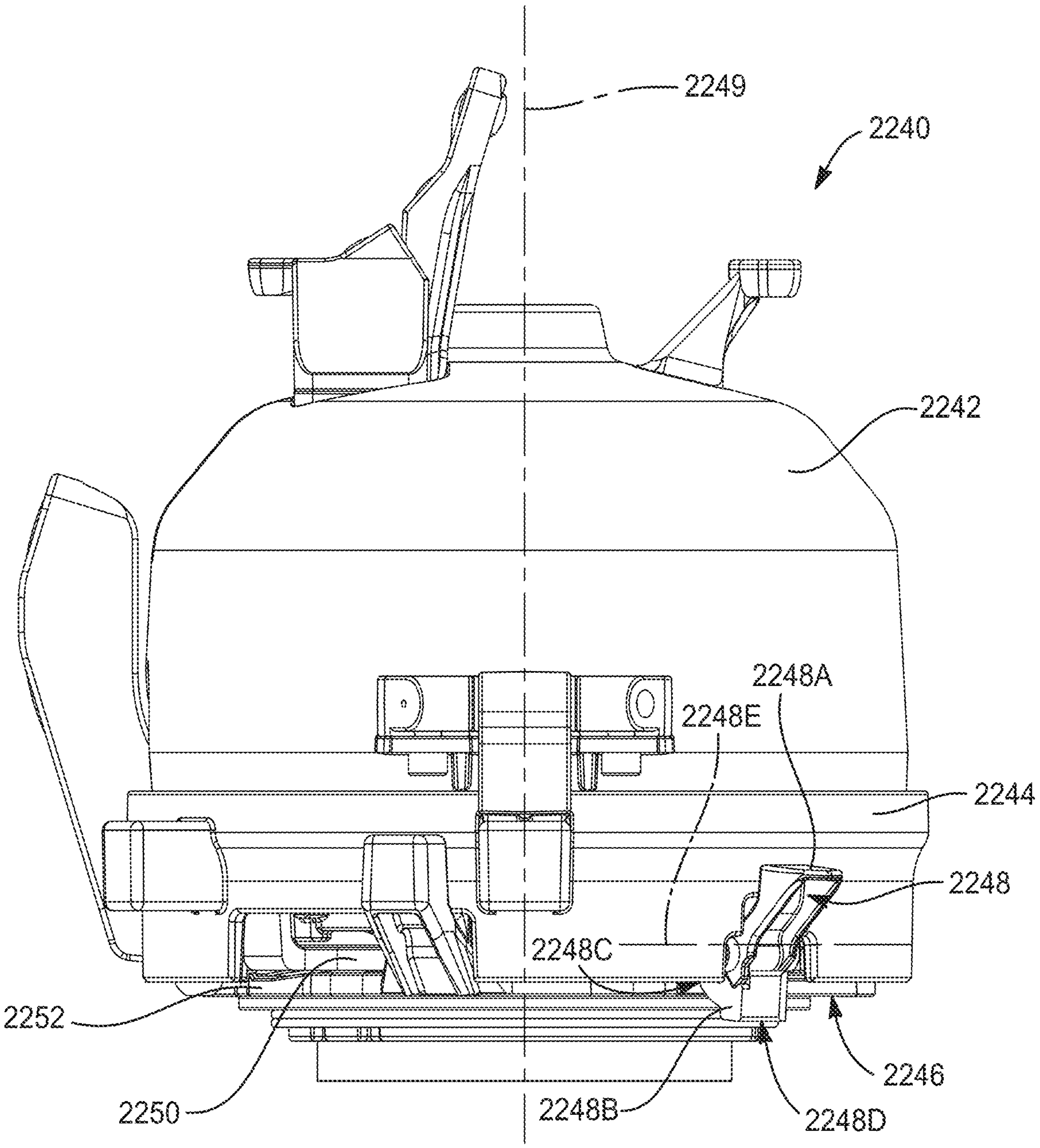
FIG. 21H is a perspective view of a centrifuge assembly of the apheresis system of FIG. 21A in a cover lock state in accordance with at least one example embodiment of the present disclosure.

FIG. 21H is a perspective view of a centrifuge assembly in a cover lock state according to at least one example embodiment.

In at least one example embodiment, as shown in FIG. 21H, the centrifuge assembly 2240 includes a cover or bell 2242 and a base 2244. The centrifuge assembly 2240 further includes a lock assembly 2246 rotatably coupled the base 2244. The centrifuge assembly 2240 may further include a latch assembly 2248 pivotally coupled to the base 2242. The centrifuge assembly 2240 may be configured to move between a cover lock state in which the cover 2242 is fixed with respect to the base 2244 and a cover unlock state in which the cover 2242 is movable with respect to the base 2244. The lock assembly 2246 may be configured to move between a latch state, as shown, and an unlatch state, as shown in FIG. 21O, below.

The centrifuge assembly 2240 may define a centrifuge axis 2249. In at least one example embodiment, lock assembly 2246 includes a first or cover engagement plate 2252 and a second or latch engagement plate 2252. The cover engagement plate 2250 may be coupled to the latch engagement plate 2252 and configured to rotate about the centrifuge axis 2249 together with the latch engagement plate 2252.

In at least one example embodiment, the latch assembly 2248 includes a lever 2248A and an engagement component 2248B. The engagement component 2248B includes an engagement portion 2248CB, and a counterweight portion 2248D. The latch assembly 2248 may be configured to pivot about a latch axis 2248E. In at least one example embodiment, in the latch assembly may be configured to automatically move from the unlatch state to the latch state during operation of the centrifuge assembly 2240. In at least the example embodiment shown, the counterweight portion 2248D is configured to be acted upon by centrifugal force to move the lock assembly 2246 from the unlatch state to the latch state (i.e., pivot the lever 2248A and the engagement portion 2248B about the latch axis 2248E).

Figure 21I:
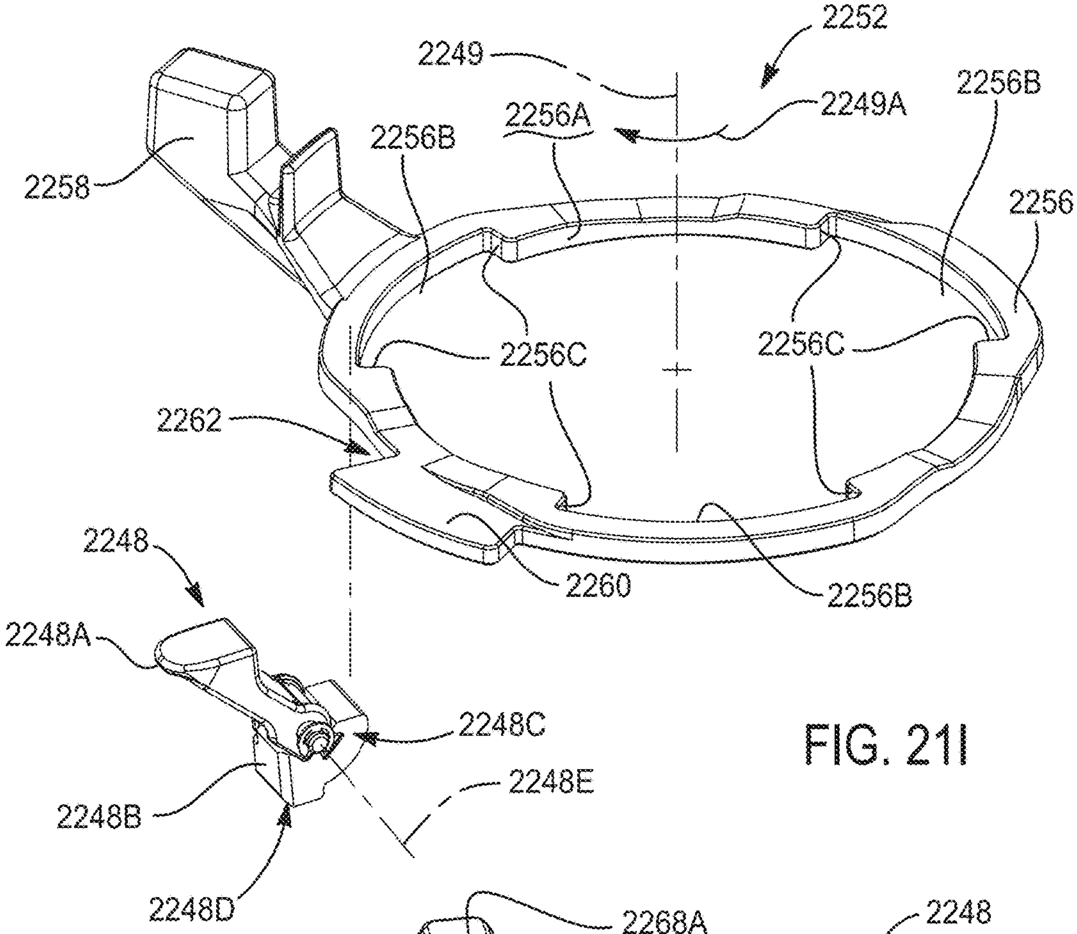
FIG. 21I is partial exploded perspective view of a latch engagement plate and a latch assembly of the centrifuge of FIG. 21H in accordance with at least one example embodiment of the present disclosure.

FIG. 21I is partial exploded perspective view of a latch engagement plate and a latch assembly according to at least one example embodiment.

In at least one example embodiment, as shown in FIG. 21I, the latch engagement plate 2252 includes a first annular body 2256, a handle 2258, and a tab 2260. The handle 2258 may be accessible from an exterior of the centrifuge assembly 2240 (shown in FIG. 21H) such that a user may engage the handle 2258 to rotate the latch engagement plate 2252 about the centrifuge axis 2249. The tab 2260 may cooperate with the first annular body 2256 to at least partially define a receptacle 2262.

In the latched state, the engagement portion 2248C of the latch assembly 2248 is at least partially in the receptacle 2262 to prevent rotation of the latch engagement plate 2252 in a first rotational direction 2249A about the centrifuge axis 2249. In the latch state, as will be described in greater detail below, the engagement component 2248B of the latch assembly 2248 is outside of the receptacle 2262 to permit rotation of the latch engagement plate 2252 in the first rotational direction 2249A.

In at least one example embodiment, the first annular body 2256 of the latch engagement plate 2252 includes an interior surface 2256A. The interior surface 2256A may define a plurality of cutouts 2256B. Each of the cutouts 2256B may include a pair of engagement walls 2256C. As will be described in greater detail below, the engagement walls 2256C may be configured to engage a portion of the cover engagement plate 2250 (shown in FIGS. 21A and 21H) to rotate the cover engagement plate 2250 together with the latch engagement plate 2252.

Figure 21J:
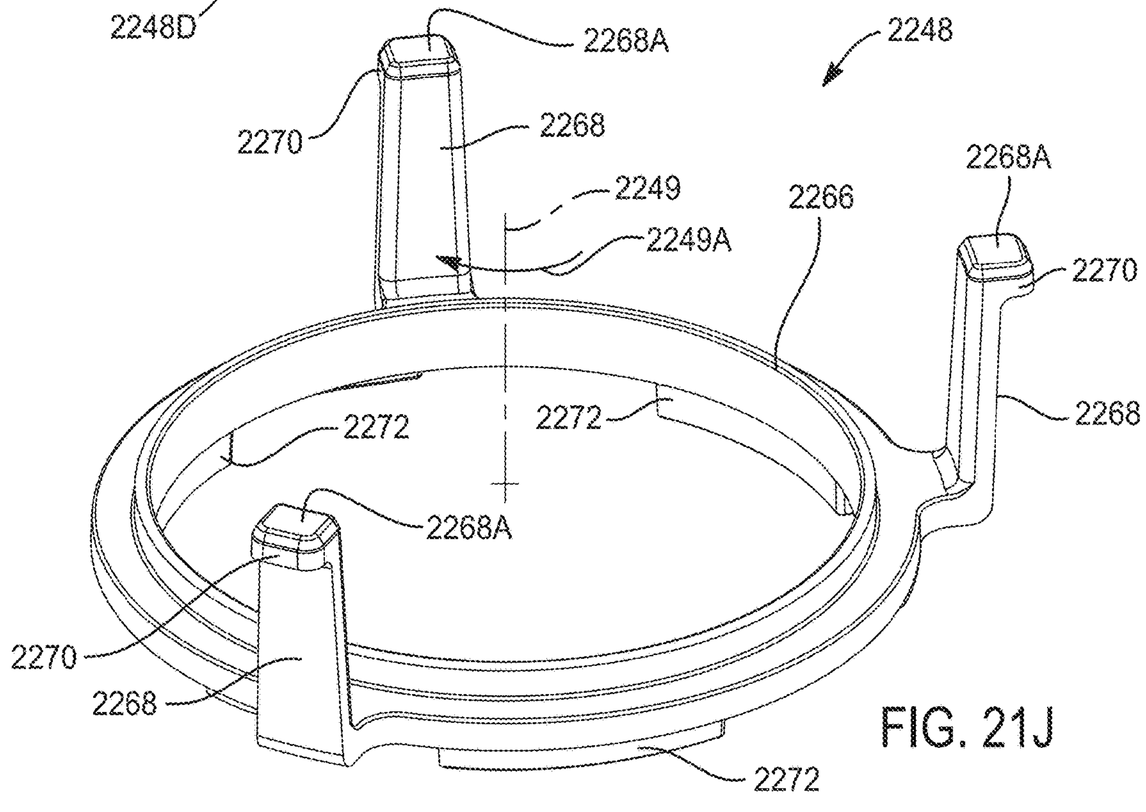
FIG. 21J is a perspective view of a cover engagement plate of the centrifuge assembly of FIG. 21H in accordance with at least one example embodiment of the present disclosure.

FIG. 21J is a perspective view of a cover engagement plate 2250 of the centrifuge assembly of FIG. 21H according to at least one example embodiment.

In at least one example embodiment, as shown in FIG. 21J, the cover engagement plate 225 includes a second annular body 2266, a plurality of arms 2268, and a respective plurality of lock tabs 2270. Each of the arms 2268 may extend axially (i.e., substantially parallel to the centrifuge axis 2249) from the second annular body 2266. Each of the arms 2268 may include a respective one of the plurality of lock tabs 2270. In the example embodiment shown, each of the lock tabs 2270 extends radially outwardly from a distal end 2268A of a respective one of the arms 2268. The lock tabs 2270 are configured to engage the cover 2242 (shown in FIG. 21K) to retain the cover 2242 in the cover lock state, as will be described in greater detail below.

In at least one example embodiment, the cover engagement plate 2250 further includes a plurality of protrusions 2272. The protrusions 2272 may extend axially from the first annular body 2256. The protrusions 2272 may be configured to engage the latch engagement plate 2252 (shown in FIG. 21I) to facilitate rotation of the cover engagement plate 2250 together with the latch engagement plate 2252. In at least the example embodiment shown, each of the protrusions 2272 is configured to engage the engagement walls 2256C (shown in FIG. 21I) of the latch engagement plate 2252.

Figure 21K:
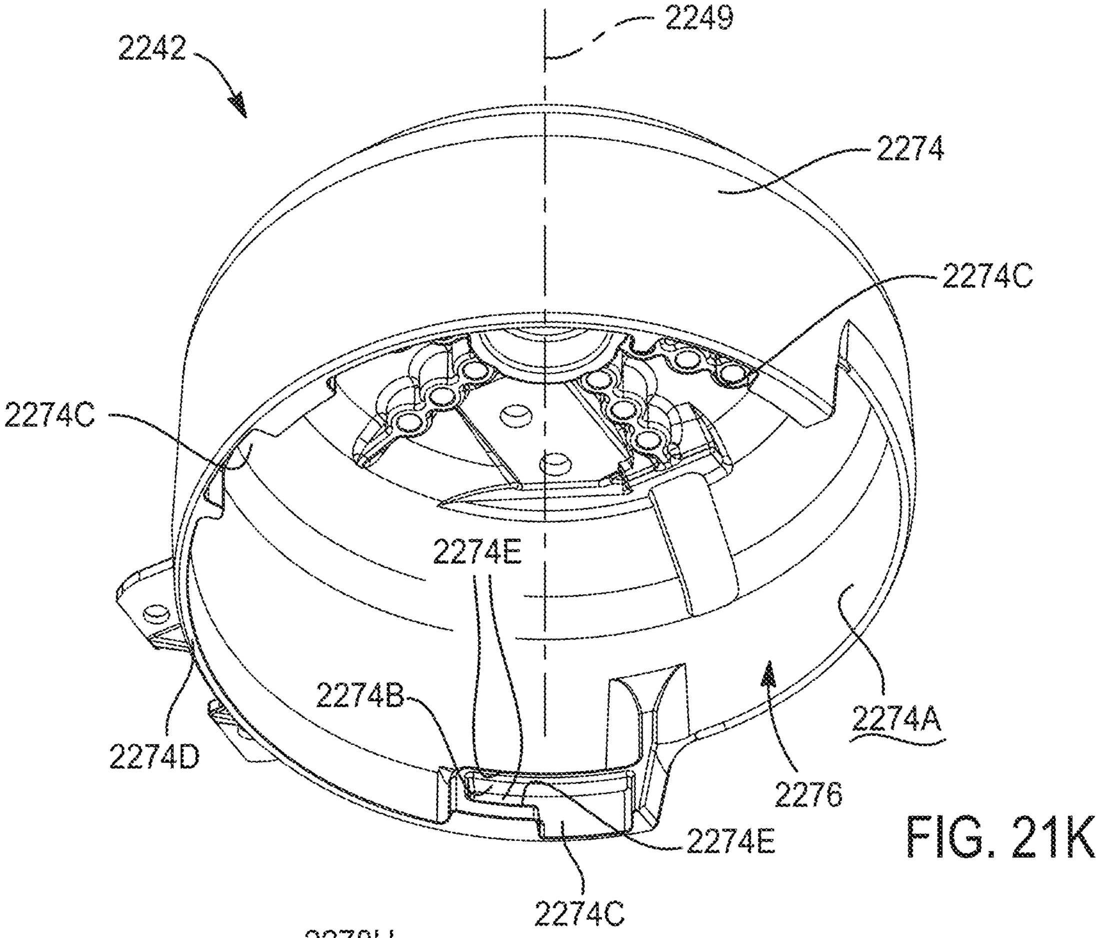
FIG. 21K is a perspective view of a cover of the centrifuge assembly of FIG. 21H in accordance with at least one example embodiment of the present disclosure.

FIG. 21K is a perspective view of a cover of the centrifuge assembly of FIG. 21H according to at least one example embodiment.

In at least one example embodiment, as shown in FIG. 21K, the cover 2242 includes a body 2274. The body 2274 may at least partially define an interior region 2276. In at least the example embodiment shown, the body 2274 is dome shaped.

The body 2274 includes an interior surface 2274A. In at least one example embodiment, the interior surface 2274A defines a plurality of slots 2274B and a respective plurality of openings 2274C. Each of the slots 2274B may extend in a circumferential direction (e.g., about the centrifuge axis 2249). Each of the openings 2274C may extend in an axial direction (i.e., substantially parallel to the centrifuge axis 2249). Each of the openings 2274C may extend between a respective one of the slots 2274B and an end 2274D of the body 2274. In at least the example embodiment shown, the cover 2242 may include three slots 2274B and three openings 2274C.

In at least one example embodiment, when the centrifuge 2240 (shown in FIG. 21H) is in a cover lock state, the lock tabs 2270 of the cover engagement plate 2250 (shown in FIG. 21J) may be at least partially in the slots 2274B, respectively. The lock tabs 2270 may engage slot walls 2274E to reduce or prevent motion of the cover 2242 along the centrifuge axis 2249. In at least one example embodiment, when the centrifuge 2240 is in a cover unlock state, the lock tabs 2270 may be aligned with the openings 2274C so that the cover 2242 can be moved with respect to the base 2244 (shown in FIGS. 21G and 21J) along the centrifuge axis 2249. The lock tabs 2270 may move through the openings 2274C as the cover 2242 is lifted from the base 2244.

Figure 21L:
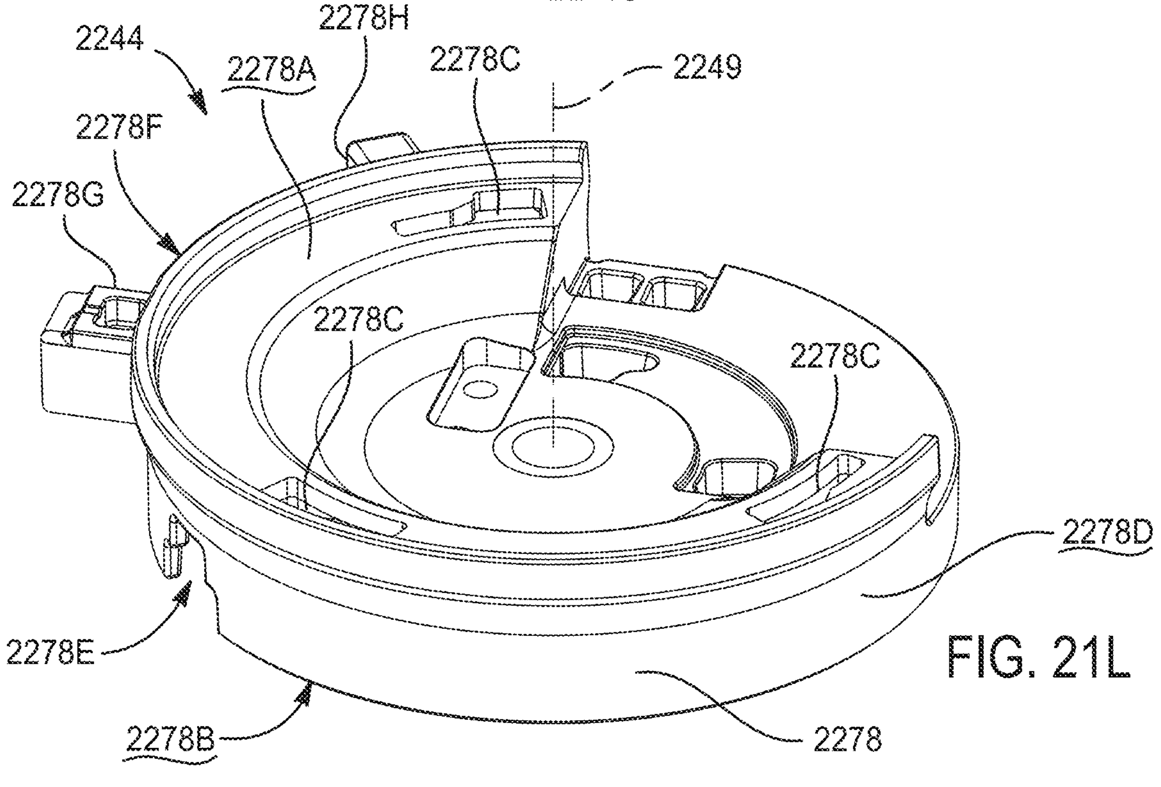
FIG. 21L is a perspective view of a base of the centrifuge assembly of FIG. 21H in accordance with at least one example embodiment of the present disclosure.

FIG. 21L is a perspective view of a base of the centrifuge assembly of FIG. 21H according to at least one example embodiment.

In at least one example embodiment, as shown in FIG. 21L, the base 2244 includes a cylindrical body 2278 extending between a first or top surface 2278A and a second or bottom surface 2278B. The top surface 2278A may be configured to engage the end 2274D of the cover 2242. The cylindrical body 2278 may define a plurality of apertures 2278C extending between the top and bottom surfaces 2278A. 2278B. Each of the arms of the cover engagement plate (shown in FIG. 21J) may extend through a respective one of the apertures 2278C.

In at least one example embodiment, the cylindrical body 2278 of the base 2244 includes an outer annular surface 2278D. The outer annular surface 2278D may define a latch region 2278E. The latch assembly 2248 (shown in FIG. 21H) may be at least partially in the latch region 2278E.

In at least one example embodiment, the base 2244 defines a handle region 2278F. The handle 2258 of the latch engagement plate 2252 may be configured to move within the handle region 2278F. The handle 2258 (shown in FIG. 21I) may be at a first end 2278G of the handle region 2278F in the cover lock state and a second end 2278H of the handle region 2278F in the cover lock state.

Figure 21M:
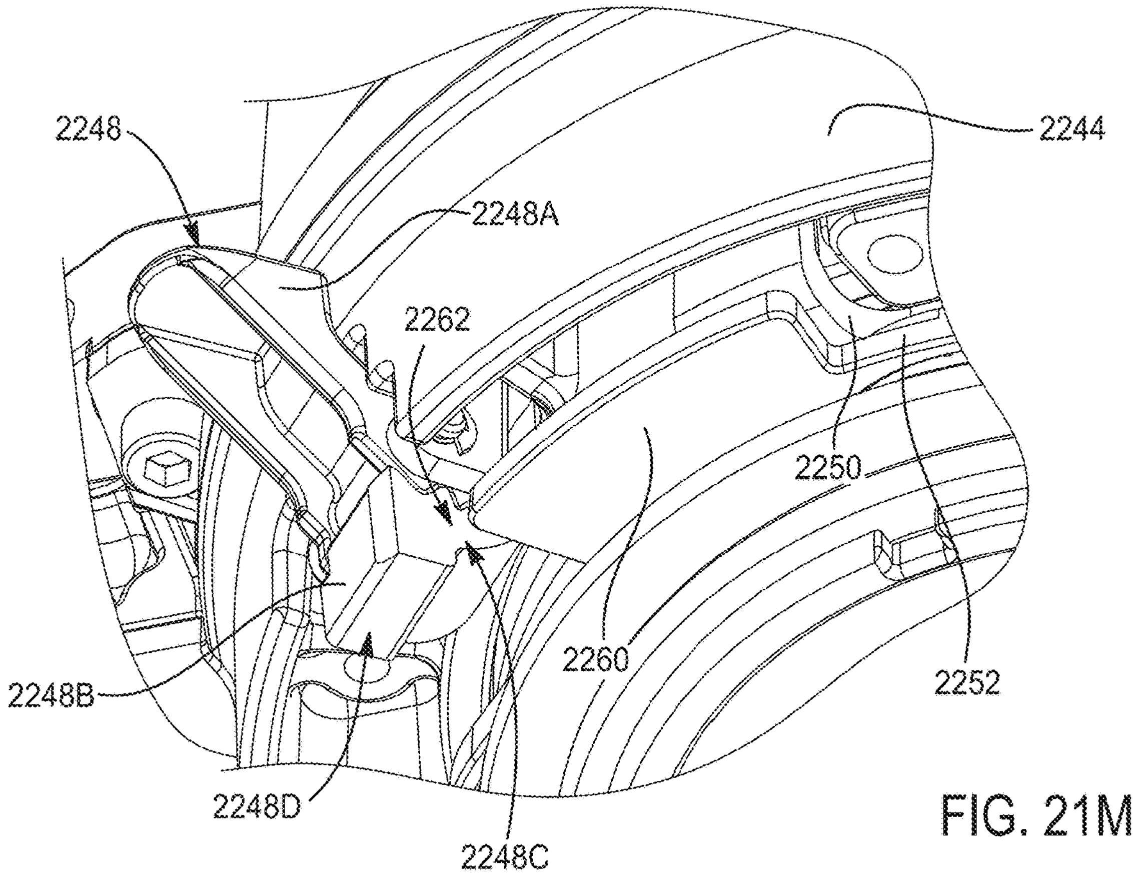
FIG. 21M is partial bottom perspective view of the centrifuge assembly of FIG. 21H in the latched state in accordance with at least one example embodiment of the present disclosure.

FIG. 21M is partial bottom perspective view of the centrifuge assembly of FIG. 21H in the latched state according to at least one example embodiment.

In at least one example embodiment, as shown in FIGS. 21L and 21A, in the latched state, the engagement component 2248B of the latch assembly 2248 is at least partially in the recess of the latch engagement plate 2252. The tab 2260 of the latch engagement plate 2252 is configured to engage the engagement component 2248B to reduce or prevent motion of the latch engagement plate 2252 in the first rotational direction 2249A. Movement of the cover engagement plate 2250, which is coupled to the latch engagement plate 2252, in the first rotational direction 2249A is also reduced or prevented. Accordingly, the lock tabs 2270 (shown in FIG. 21J) of the cover engagement plate 2250 may be prevented from moving within the slots 2274B (shown in FIG. 21K) to axially align with the openings 2274C (shown in FIG. 21I). Thus, in the latched state, the cover 2242 cannot be removed from the base 2244.

In at least one example embodiment, the latch assembly may be moved from the latched state to the unlatched state by pivoting the lever about the latch axis. The engagement component 2248B may pivot together with the lever 2248A such that it is removed from the receptacle 2262.

Figure 21N:
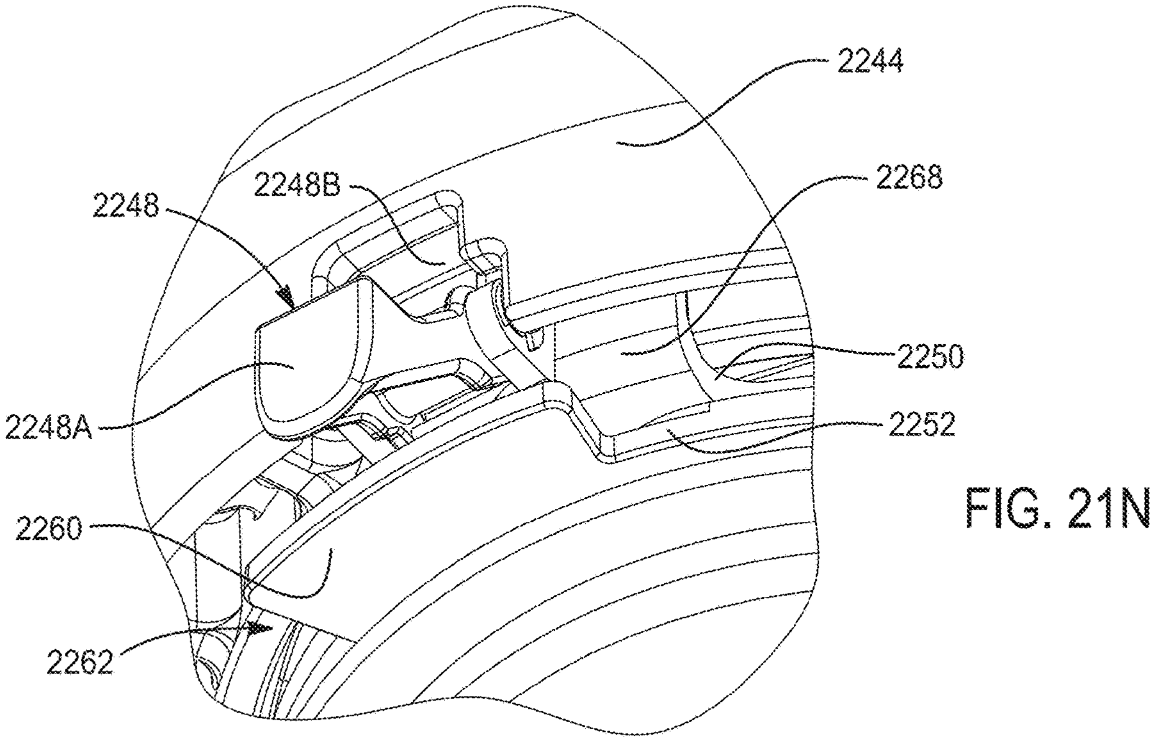
FIG. 21N is partial bottom perspective view of the centrifuge assembly of FIG. 21M in the unlatched state in accordance with at least one example embodiment of the present disclosure.
Figure 21O:
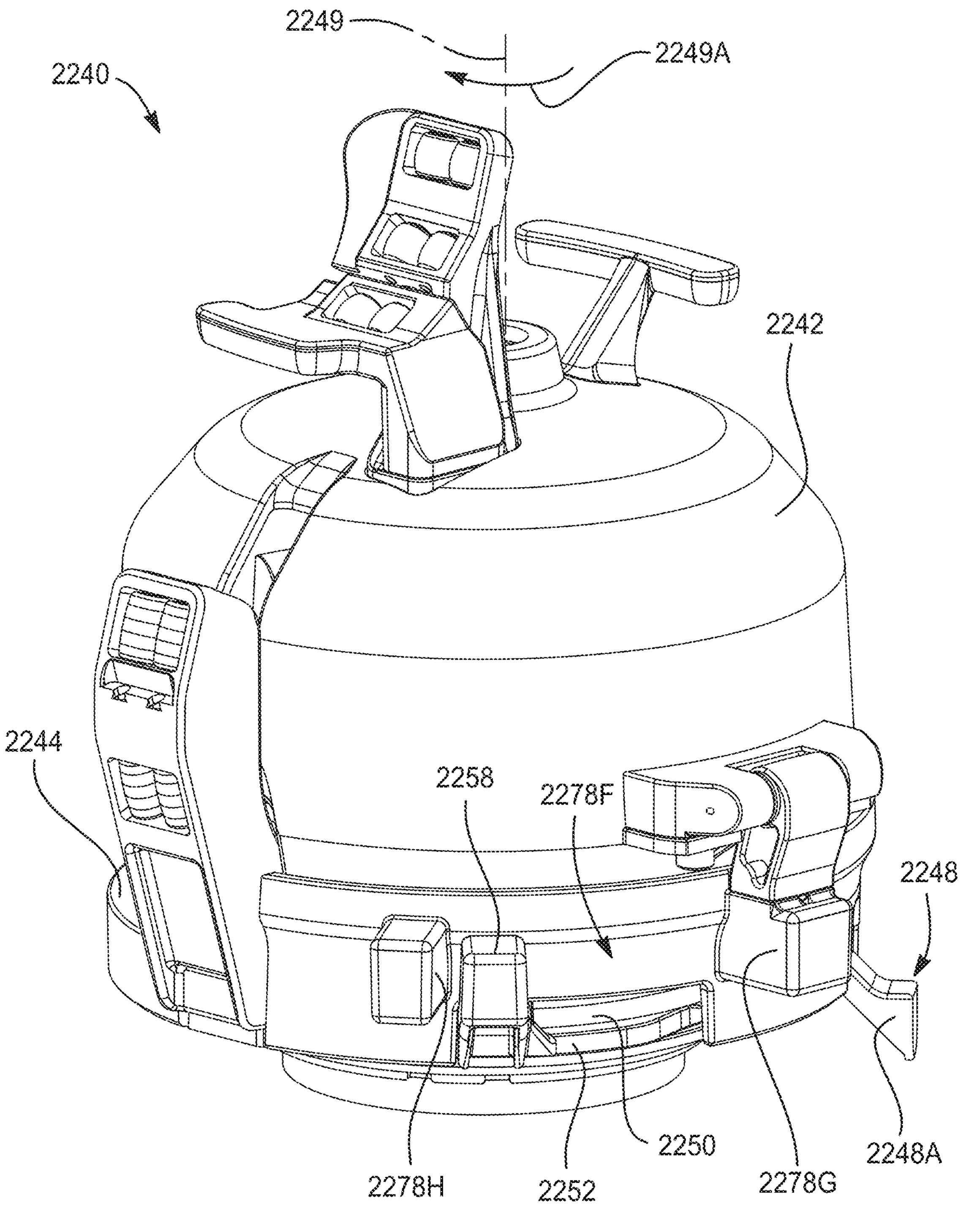
FIG. 21O is a perspective view of the compressor assembly of FIG. 21H in a cover unlock state in accordance with at least one example embodiment of the present disclosure.

FIG. 21N is partial bottom perspective view of the centrifuge assembly of FIG. 21M in the unlatched state according to at least one example embodiment.

In at least one example embodiment, as shown in FIG. 21N, when the latch assembly 2248 is in the unlatch state, the engagement component 2248B is not in the receptacle 2262 of the latch engagement plate 2252. Accordingly, the latch engagement plate 2252 is free to rotate in the first rotational direction 2249A without interference from the engagement component 2248B, as shown. The engagement component 2248B may be spaced apart from the latch engagement plate 2252 along the centrifuge axis 2249 to define a clearance gap (not shown). In at least one example embodiment, the latch engagement plate 2252 may be rotated in the first rotational direction 2249A (e.g., by operator engagement with the handle 2258, shown in FIG. 21I) until the lock tabs 2270 (shown in FIG. 21J) of the cover engagement plate 2250 are aligned with the openings 2272 (shown in FIG. 21K) of the cover 2242 (shown in FIG. 21K).

FIG. 21O is a perspective view of the compressor assembly of FIG. 21H in a cover unlock state according to at least one example embodiment.

In at least one example embodiment, the centrifuge assembly 2240 may be moved from the cover lock state (shown in FIGS. 21A & 21L) to a cover unlock state, as shown in FIG. 21O. To move the centrifuge assembly 2240 from the cover lock state to the cover unlock state, the lock assembly 2246 may be moved from the latch state to the unlatched state by pivoting the lever 2248A of the latch assembly 2248 about the latch axis 2248E. When the lock assembly 2246 is in the unlatched state, the lock assembly 2246 may be rotated in a first rotational direction 2249A about the centrifuge axis 2249, such as by operator engagement with the handle 2258 of the latch engagement plate 2252. The operator may move the handle 2258 from the first end 2278G of the handle region 2278F to the second end 2278H of the handle region 2278F to place the centrifuge assembly 2200 in the cover unlock state. In the cover unlock state, the cover 2242 can be separated from the base 2244, as described above.

In at least one example embodiment, the latch assembly 2248 may correspond to an over center latch. The apheresis system 1800 may control an initiation, startup, and/or rotation of the centrifuge assembly 2240 by applying a momentary motor output and monitoring hall effect sensors associated with the centrifuge motor. Detection by the hall effect sensors a change in voltage beyond a predetermined range may indicate that the motor is mot turning and a jam may be present. In response, the apheresis system 1800 may prevent operation of the apheresis system 1800 and determine that the centrifuge 2240 is not locked. Further, the latch assembly 2248 (e.g., the lever 2248A) may abut against a chamber of the apheresis system 1800. An alarm may be presented to the GUI describing the alarm. This arrangement may reduce or prevent the inclusion of additional sensors to the centrifuge.

Embodiments include a system for separating a component from a multi-component fluid comprising: a housing comprising an access door and a top cover, the access door providing access to a chamber; a centrifuge housed in the chamber and configured to receive the multi-component fluid, the centrifuge configured to rotate to separate the component the multi-component fluid; a first fluid bag and a second fluid bag; and a first hook configured to support the first fluid bag and a second hook configured to support the second fluid bag, wherein the first hook is shaped to receive the first fluid bag and the second hook is shaped to receive the second fluid bag.

Aspects of the system further comprise a first post and a second post, the first hook disposed at an end of the first post and the second hook disposed at an end of the second post. Aspects of the system include the top cover comprising a first recess configured to receive the first post and a second recess configured to receive the second post. Aspects of the system include the first recess being keyed to receive the first post and the second recess being keyed to receive the second post. Aspects of the system include at least one of the first post and the second post comprising an indicator configured to provide a visual display. Aspects of the system include the visual display comprising one or more colors. Aspects of the system further comprise an override configured to unlock the access cover when power is lost to the system. Aspects of the system further comprise an air assembly configured to maintain a temperature range in the chamber. Aspects of the system include the air assembly comprising a fan configured to provide a circulation to the chamber and a temperature sensor configured to sense a temperature in the chamber. Aspects of the system include the centrifuge comprising a lock configured to prevent the centrifuge from rotating when the lock is in an unlocked position, wherein the lock protrudes from the centrifuge and contacts the chamber, thereby preventing rotation when in the unlocked position.

Example Operational Controls Based on Detected Environmental State

During use of the apheresis system 200, if a vein collapses, or flow otherwise drops below a predetermined threshold, the apheresis system 200 may be configured to issue an alarm and/or lower the flow rate automatically. In at least one example embodiment, the vein is stabilized. In at least one example embodiment, the user may check that a needle is properly inserted into a donor. The apheresis system 200 may, in at least one example embodiment, automatically attempt to restart the process and increase the flow rate. In at least one example embodiment, the apheresis system 200 may also automatically increase a speed of the centrifuge. For example, while the centrifuge continues to spin, the speed of the centrifuge may be lowered (e.g., from 5,000 rpm to 1,950 rpm) to maintain blood in the bladder of the apheresis system 200 at a controlled, predetermined temperature, while the alarm is being addressed. The speed of the centrifuge may be configured to maintain the temperature of the blood at about 42° Celsius or below to prevent damage to the blood. The alarm may be provided to the GUI of the device and may include instructions on how to address and/or resolve the alarm.

Figure 22B:
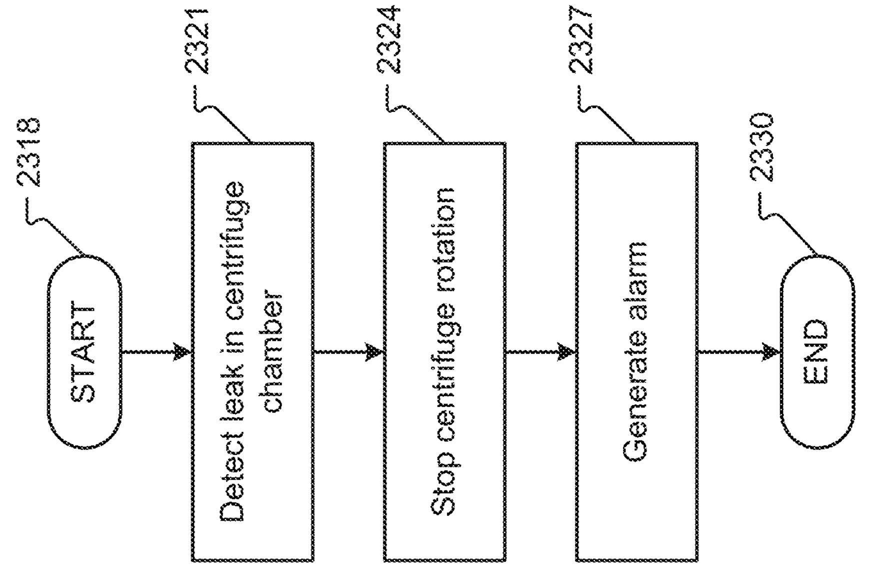
FIG. 22B is a flowchart of a method in accordance with at least one example embodiment of the present disclosure.
Figure 22A:
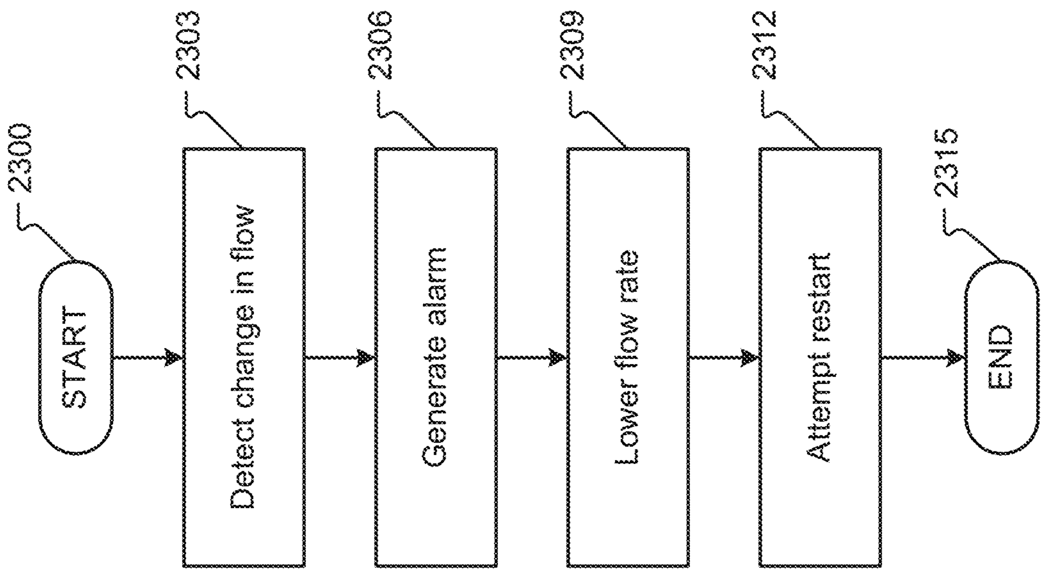
FIG. 22A is a flowchart of a method in accordance with at least one example embodiment of the present disclosure.

The process of issuing alarms and/or lowering flow rates to stabilize veins may be performed as part of a method such as illustrated in FIG. 22A. At 2300, the method of FIG. 22A may begin at which point a donor, such as the donor 102, may be connected to an apheresis system, such as the apheresis system 200, which may be performing a donation process.

The apheresis system 200 may determine the state of tubing (e.g., in the blood component collection set 500, etc.) engaged with one or more receiving features (e.g., recesses, channels, raceways, etc.) of the apheresis system 200. Based on the determined state of the tubing, the apheresis system 200 may automatically adjust one or more settings to optimize operations of the apheresis system 200.

At 2303, the apheresis system 200 may detect a change in flow of a fluid and/or a change in composition of the fluid in one or more tubes connected to the apheresis system 200. Detecting a change in flow and/or a change in composition of a fluid may comprise analyzing, such as through the use of a sensor, flow rate, flow pressure, temperature, color of fluid, shape of tubing, and/or other factors relating to the flow of fluid throughout the apheresis system 200 and tubes connected to the apheresis system 200. In at least one example embodiment, a change in composition of the fluid may be detected by a change in pressure in the one or more tubes connected to the apheresis system 200.

In at least one example embodiment, one or more pressure sensors may be used to detect a pressure of fluid and/or air through one or more tubes. For example, if a vein of a donor collapses, a pressure within a tube may rise or fall. Upper and lower thresholds may be set to detect such an occasion. In at least one example embodiment, a pressure increase may indicate that the centrifuge is full or almost full, and thus flow should be reversed such that blood is returned to the donor.

In at least one example embodiment, one or more color sensors may be used to identify a color of fluid through one or more tubes. Monitoring of situations, conditions, and/or other factors that may affect the end product. Conventional systems only monitor a color gram. Among other things, the apheresis system 200 may monitor fluids to ensure saline does not enter the plasma collection bottle 122. In at least one example embodiment, the apheresis system 200 may utilize one or more of a fluid sensor and a color sensor against red, blue, and/or green reflection and/or transmission. Once red blood cells are detected, the apheresis system 200 can cease an operation and proceed to push the red blood cells back to the donor 102.

In at least one example embodiment, the apheresis system 200 may include at least one temperature sensor. In at least one example embodiment, a temperature sensor may be used to detect a temperature of fluids within the apheresis system 200. For example, the apheresis system 200 may be enabled to detect if a fluid, such as blood, falls above or below a particular temperature. In at least one example embodiment, a temperature sensor may be used to assess a circuit card component and/or detect a temperature of ambient air.

At 2306, in response to detecting a change in flow of a fluid, the apheresis system 200 may generate and/or issue one or more alarms. For example, if a monitored aspect of a flow falls below or rises above a predetermined threshold, an alarm may be triggered.

A threshold may be, for example, a range of colors detectable by a color sensor, a range of flow rates detectable by a flow rate sensor, a shape of tubing detectable by a sensor, a range of pressure detectable by a pressure sensor, a range of temperatures detectable by a temperature sensor, etc.

An alarm may comprise one or more of sounds, lights, and a GUI display and may be configured to alert a user to an occurrence of an event or condition, such as a threshold being crossed. A GUI display, such as the GUI 1230 shown in FIG. 12B, may, for example, explain the issue or condition, provide information regarding the issue or condition, and/or provide instructions to the user.

Generating an alarm may comprise, for example, generating a GUI to be displayed on a display device, determining one or more lights on the apheresis system 200 to illuminate, and/or determining one or more audio files or sounds to play through speakers, etc.

Figure 22C:
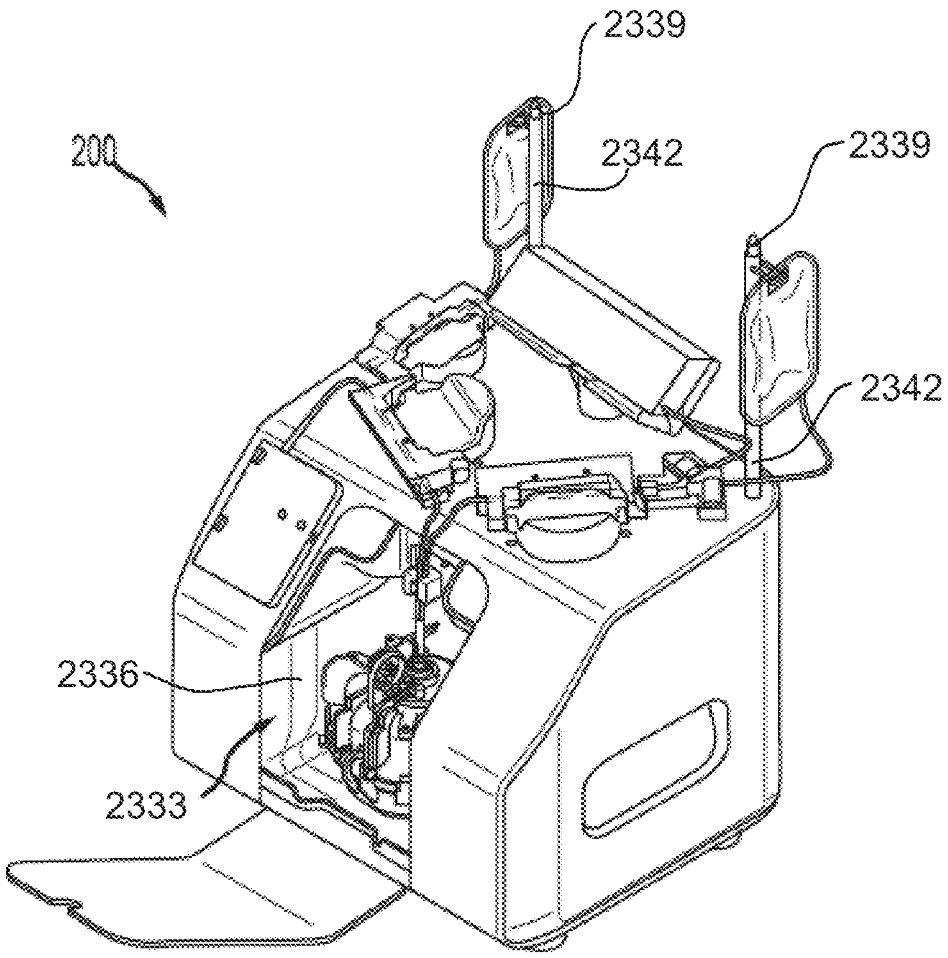
FIG. 22C shows a centrifugal chamber in accordance with at least one example embodiment of the present disclosure.

Issuing an alarm may comprise displaying a GUI on a display device, illuminating one or more lights on the apheresis system 200, and/or playing one or more audio files or sounds through speakers, etc. In at least one example embodiment, the apheresis system 200 may include one or more lights 2339 positioned at the end of one or more supports 2342, as shown in FIG. 22C. Generating and/or issuing an alarm may include illuminating one or more of the lights 2339. Each of the lights 2339 may switch between a plurality of colors depending on the type of the alarm and/or a severity of the alarm, as discussed above.

At 2309, in response to detecting a change in a flow of a fluid, the apheresis system 200 may lower a flow rate through one or more tubes on the apheresis system 200 such as by adjusting an amount of power applied to one or more pumps in the apheresis system 200 and/or by adjusting a speed of the centrifuge. Lowering a flow rate may enable the apheresis system 200 to stabilize a vein of a donor. Lowering the speed of the centrifuge may comprise lowering the speed from, for example, 5,000 rpm to 2,500 rpm. In at least one example embodiment, the speed of the centrifuge may be lowered to about 1,950 rpm. Lowering the speed of the centrifuge may enable the apheresis system 200 to keep a temperature of blood in the centrifuge at a particular level.

At 2312, after detecting the change in the flow of the fluid and lowering the flow rate, the apheresis system 200 may be configured to attempt to restart the donation process back to a standard level, for example, by increasing the flow rate back to a relatively normal rate.

At 2315, the method may end. It should be appreciated that the method described in relation to FIG. 22A may be repeated as necessary. For example, after restarting the donation process, the apheresis system 200 may return to step 2303 and continue monitoring flows to detect any changes.

In at least one example embodiment, a flexible circuit 2336 may be disposed inside the centrifuge chamber 2333 of the apheresis system 200, as illustrated in FIG. 22C. The flexible circuit 2336 may extend along one or more walls inside the centrifuge chamber 2333. In at least one example embodiment, the flexible circuit 2336 may include traces exposed on a surface facing an interior of the centrifuge chamber 2333. In the event of a fluid leak (e.g., a blood leak, etc.) inside the chamber 2333, the fluid may contact the exposed traces resulting in an electrical detection of the fluid. This detection may be a difference in resistance, voltage change, and/or the like. In at least one example embodiment, the traces may comprise a separation distance between about 0.50 mm and about 0.52 mm. In at least one example embodiment, the separation distance of the traces may be about 0.51 mm. In response to detecting the leak, the apheresis system 200 may cease operations and stop the centrifuge assembly 400 from spinning. In at least one example embodiment, a greater separation distance of the traces requires a larger amount of fluid to detect the leak and a smaller separation distance of the traces requires a smaller amount of fluid to detect a leak. In at least one example embodiment, the flexible circuit 2336 may comprise reduced susceptibility to changes in humidity. For example, the flexible circuit 2336 may be more resistant to humidity when the traces are farther apart. In at least one example embodiment, the flexible circuit 2336 may operate at humidity levels up to about 80%. For example, as illustrated in FIG. 22B, a method of using a flexible circuit, such as the flexible circuit 2336, to detect, and respond to, a leak inside a centrifuge chamber may be executed by an apheresis system. In other example embodiments, the flexible circuit 2336 may be of a type not susceptible to changes in humidity.

At 2318, the method illustrated by FIG. 22B may begin. At the beginning of the method, a centrifuge chamber 2333 of an apheresis system 200 may contain a spinning centrifuge which may include a liquid. A flexible circuit 2336 may be installed on an interior wall of the centrifuge chamber. The flexible circuit 2336 may be electrically connected to one or more microcontrollers and/or computer systems in communication with or of the apheresis system.

At 2321, a processor of the one or more microcontrollers may detect, based on a signal received from the flexible circuit 2336, a leak in a centrifuge chamber, such as the centrifuge chamber 2333.

Detecting a leak may comprise detecting a change in one or more of a resistance, a voltage, a current, or another electrical aspect of the flexible circuit 2336. For example, the processor may monitor a resistance of the flexible circuit 2336. The processor may be configured to detect the resistance of the flexible circuit 2336 exceeding an upper threshold or falling below a lower threshold. In response, the processor may determine a leak has occurred.

Similarly, the processor may monitor a voltage and/or a current of the flexible circuit. The processor may be configured to detect the voltage and/or current of the flexible circuit exceeding an upper threshold or falling below a lower threshold. In response, the processor may determine a leak has occurred.

At 2324, in response to the detection of the leak, the processor may stop the rotation of the centrifuge. Stopping the rotation of the centrifuge may comprise sending a stop signal to a controller in communication with a motor controlling the speed of the centrifuge or may comprise ceasing an application of power to a motor, such as by flipping a switch. In at least one example embodiment, the processor may determine that a leak has occurred when the centrifuge is not rotating. For example, a standing leak of fluid in a bottom portion of the centrifuge chamber 2333. In such embodiments, the method may proceed from detecting a leak in the centrifuge chamber at 2321 directly to generating an alarm at 2327, discussed below.

At 2327, in at least one example embodiment, an alarm may be generated. For example, lights, sounds, and/or a GUI element on a display device of the apheresis system 200 may be altered to inform a user of the apheresis system 200 that the leak has occurred. In this way, a user may be enabled to quickly determine a reason as to why the centrifuge stopped. A display device, such as the GUI 1230, may instruct the user with instructions as to how best to remedy the situation. At 2330, the method may end.

Example embodiments include a method comprising: detecting a change in flow of a fluid; issuing an alarm; lowering a flow rate; and attempting to restart process and increase the flow rate.

Aspects of the above embodiment include wherein the change in flow is a change in pressure. Aspects of the above embodiment include wherein the change in flow is associated with a collapsed vein. Aspects of the above embodiment include wherein detecting the change in flow of a fluid comprises detecting a flow rate falls below a threshold. Aspects of the above embodiment include wherein the change in flow is associated with a color. Aspects of the above embodiment include wherein detecting the change in flow comprises using a color sensor to detect a red, blue, and/or green reflection and/or transmission to detect red blood cells. Aspects of the above embodiment include wherein issuing the alarm comprises using one or more of sound, lights, and a GUI. Aspects of the above embodiment include wherein the GUI explains an issue and/or provides instructions to stabilize the vein. Aspects of the above embodiment include lowering the flow rate comprising lowering a speed of a centrifuge from 5,000 rpm to 2,500 rpm to keep temperature of blood at a particular level.

Example embodiments include a method comprising: detecting, with a flexible circuit, a leak in a centrifuge chamber; and in response to the detecting of the leak, stopping rotation of a centrifuge.

Aspects of the above embodiment include wherein detecting the leak comprises detecting liquid contacting exposed traces in the flexible circuit. Aspects of the above embodiment include wherein the liquid affects one or more of a resistance, a voltage, and a current. Aspects of the above embodiment include wherein the flexible circuit is not susceptible to changes in humidity.

Flexure-Based Tubing State Sensor

FIGS. 23A-23D show various views of a flexure-based tubing state sensor 2400 and a flexure block 2404 in accordance with examples of the present disclosure. The apheresis system 200 monitors pressure of fluid coming into and out of the centrifuge assembly 400. In some examples, this pressure may be monitored directly from the surface of one or more sections of the tubing of the blood component collection set 500. The pressure sensors (e.g., CPS 808, 816, etc.) may measure the pressure using a lever arm that is in contact with the tubing of the blood component collection set 500 inserted into the apheresis system 200. As the pressure changes, the lever arm may move transmitting pressure from the tubing to a pressure sensor. The present disclosure describes a flexure-based tubing state sensor 2400 that is capable of repeatably providing pressure measurements without excessive tolerance stack-up between the tubing face and the pressure sensor and utilizing fewer components than those associated with other designs. Benefits of the flexure-based tubing state sensor 2400 may include, but are in no way limited to, reduced tolerance stack-up compared to conventional arrangements (e.g., walls that touch, or contact, the tubing are in the same flexure block part, which reduces tolerance stack-up, etc.), the spring force of flexures in the flexure block of the flexure-based tubing state sensor 2400 can be closely controlled (e.g., the flexures can be molded or machined with high repeatability between parts, etc.), the flexure block of the flexure-based tubing state sensor 2400 can be removed from the apheresis system 200 and replaced with a new (e.g., different) flexure block without the need for re-calibration of the system (e.g., there is no variations in friction around a pivot pin, etc., since the flexure pivot is part of the flexure block), etc. An additional benefit of the flexure-based tubing state sensor 2400 may be versatility because it may be configured to measure pressure of any soft-walled tubing filled with any liquid, ga, or vapor such that the pressure of the Referring to FIG. 23A, an elevation section view of the flexure-based tubing state sensor 2400 is shown in accordance with examples of the present disclosure. The flexure-based tubing state sensor 2400 may be mounted to a mount block 2402 (e.g., a portion of the soft cassette assembly 300, a portion of at least one of the pumps 208, 212, 216, a portion of the housing 204, and/or some other portion of the apheresis system 200, etc.). In some examples, the flexure-based tubing state sensor 2400 may be used as the CPS 808, 816 described above. The flexure-based tubing state sensor 2400 may comprise a flexure block 2404 and a pressure sensor 2408 interconnected with a controller (e.g., controller 1004, 1104, etc.) via the electrical connector 2412. A tubing receiving space 2406 may be disposed on a first side of the mount block 2402 and may extend through a top portion of the mount block 2402. In some example embodiments, the flexure block 2404 may extend through one or more openings in the mount block 2402 to form the tubing receiving space 2406 in the mount block 2402. The tubing receiving space 2406 may be separated from the pressure sensor 2408 via at least one seal 2410. In some example embodiments, the seal 2410 may provide a fluid seal or fluid barrier between the tubing receiving space 2406 and the pressure sensor 2408. The seal 2410 may correspond to a flexible diaphragm seal, a gasket, an O-ring, and/or some other sealing member.

Figure 23A:
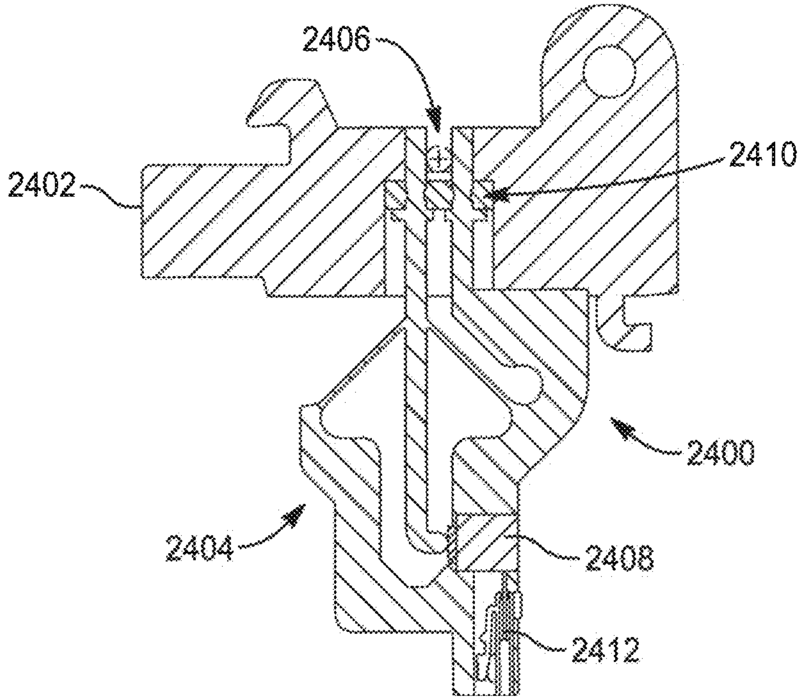
FIG. 23A is an elevation section view of a flexure-based tubing state sensor in accordance with at least one example embodiment of the present disclosure.
Figure 23B:
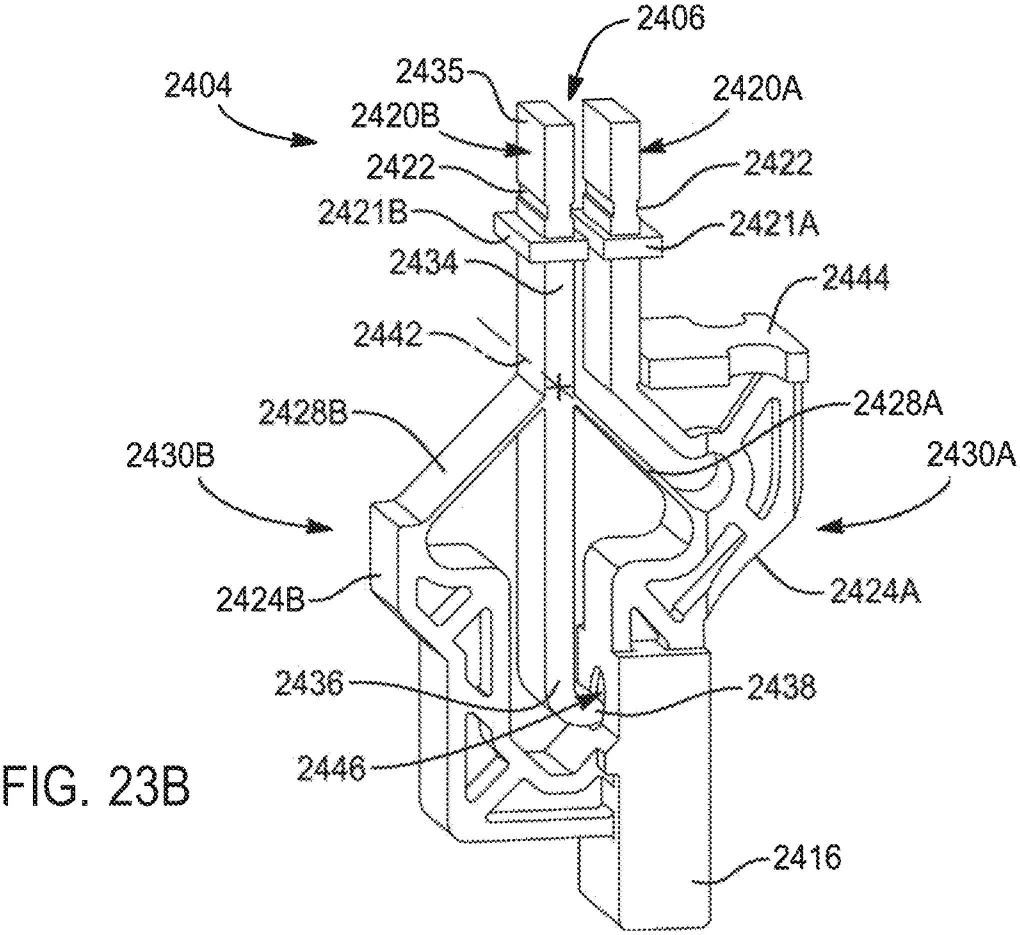
FIG. 23B is a perspective view of the flexure block of the flexure-based tubing state sensor of FIG. 23A.

FIG. 23B shows a perspective view of the flexure block 2404 of the flexure-based tubing state sensor 2400 in accordance with examples of the present disclosure. The flexure block 2404 may include a flexure block body 2416 including a first flexure support arm 2424A extending in a first direction from a first side 2430A of the flexure block body 2416. In some examples, the first side 2430A may be a fixed element of the flexure-based tubing state sensor 2400 and/or the flexure block 2404. The flexure block body 2416 may include a second flexure support arm 2424B extending in second direction from a second side 2430B of the flexure block body 2416. The second side 2430B may also be a fixed element of the flexure-based tubing state sensor 2400 and/or the flexure block 2404.

In some example embodiments, the flexure block 2404 may include a lever arm 2434 disposed between the first side 2430A and the second side 2430B and, more specifically, between the first flexure support arm 2424A and the second flexure support arm 2424B. The lever arm 2434 may include a tubing contact section 2435 and a sensor contact section 2436 with a contact finger 2438 such that the lever arm 2434 extends from the tubing receiving space 2406 to a sensor aperture 2446 of the flexure block body 2416. The tubing receiving space 2406 may be arranged between a tubing contact area of a fixed wall 2420A and the tubing contact section of a moving wall 2420B. The fixed wall 2420A may have a first seal contact 2421A and the lever arm 2434 may have a second seal contact 2421B. In some example embodiments, the moving wall 2420B may be a portion of the lever arm 2434 disposed above the second seal contact 2421B. In some example embodiments, the seal 2410 may be disposed proximate to the first seal contact 2421A and the second seal contact 2421B. For example, the seal 2410 may be coupled with the first seal contact 2421A and the second seal contact 2421B. In some example embodiments, one or more of the fixed wall 2420A and the moving wall 2420B may optionally include a notch 2422 that may be configured to receive the seal 2410 to create the fluid seal between the tubing receiving space 2406 and the pressure sensor 2408. In some example embodiments, the first seal contact 2421A and the second seal contact 2421B may not be included in the flexure block 2404 if the notch 2422 is included in the fixed wall 2420A and the moveable wall 2420B. In some example embodiments, the seal 2410 may optionally include a thin membrane or diaphragm portion surrounding the moving wall 2420B. The thin membrane or diaphragm portion of the seal 2410 may allow movement of the lever arm 2434 upon a force being applied to the lever arm 2434 from a pressure change in a tube within the tubing receiving space 2406.

The lever arm 2434 may be a moveable element of the flexure-based tubing state sensor 2400 and/or the flexure block 2404 and may be pivotable about a pivot axis 2442. Among other things, the lever arm 2434 pivots around two flexures, a first flexure 2428A and a second flexure 2428B. The first flexure 2428A and the second flexure 2428B may allow the lever arm 2434 to pivot, while minimizing vertical, lateral, and horizontal movement of the lever arm 2434. The first flexure 2428A and the second flexure 2428B may maintain the lever arm 2434 in a desired plane and may prevent movement of the lever arm 2434 in a perpendicular plane. In some embodiments, the first flexure 2428A and the second flexure 2428B may be about 13 millimeters (mm) thick. In other embodiments, the first flexure 2428A and the second flexure 2428B may be thicker, such as about 25 mm thick, to further prevent movement of the lever arm 2434 in a non-desirable plane. In some embodiments, the first flexure 2428A and/or the second flexure may be formed from a photochemically etched metal. In some embodiments, forming the first flexure 2428A and/or the second flexure 2428B from a photochemically etched metal may produce a tight-tolerance flexure and the manufacturing process may be repeatable.

In some example embodiments, the first flexure 2428A may extend from the first flexure support arm 2424A and join with the lever arm 2434 on a first side of the lever arm 2434. The second flexure 2428B extends from the second flexure support arm 2424B and joins with the lever arm 2434 on a second side of the lever arm 2434. In some examples, the virtual intersection of the first flexure 2428A and the second flexure 2428B may define the location of the pivot axis 2442. In some embodiments, the pivot axis 2442 may be adjusted to a different location relative to the flexure block 2404 such that movement of the lever arm 2434 is amplified which may amplify the measured pressure measurements. In some example embodiments, the features that surround the first flexure 2428A and the second flexure 2428B may be stiffer than the first flexure 2428A and the second flexure 2428B to minimize all movement outside of the first flexure 2428A and the second flexure 2428B.

When the apheresis system 200 is operational, pressure may change in a section of tubing positioned in the tubing receiving space 2406 between the fixed wall 2420A and the moving wall 2420B, the changes in pressure may cause the section of tubing to expand or contract. Expansion of the section of tubing may cause a tubing gap distance between the fixed wall 2420A and the moving wall 2420B to expand and pivot the lever arm 2434 such that the contact finger 2438 moves closer to the sensor aperture 2446 of the flexure block body 2416. The pressure sensor 2408 may be disposed adjacent to the sensor aperture 2446 such that movement of the contact finger 2438 may apply a pressure to a pressure detection region of the pressure sensor 2408. Accordingly, the pressure sensor 2408 may determine a pressure inside the tubing based on the translated movement to the pressure sensor 2408 via the pivoting of the lever arm 2434 of the flexure block 2404. In some example embodiments, a tip of the finger 2438 may be curved or rounded such that force from the finger is applied normal to a surface of the pressure sensor 2408.

In some examples, the flexure block 2404 may be mounted to the mount block 2402 via the mount flange 2444. The mount flange 2444 may correspond to at least one mount surface and may include holes, slots, recesses, and/or apertures that are configured to receive a fastener (e.g., screw, bolt, pin, etc.) to couple the flexure block 2404 to the mount block 2402.

The flexure block 2404 may be integrally formed (e.g., machined, molded, wire electrical discharge machined, extruded, 3D printed, selective laser sintered, and/or otherwise formed) from a material. The material may include plastic, stainless steel, titanium, aluminum, brass, or may be a different material or a composite such that the flexure block 2404 includes more than one material. For example, the first flexure 2428A and the second flexure 2428B may be formed from a first material and the remainder of the flexure block 2404 may be formed from a second material. In some example embodiments, the first material may be more flexible than the second material to facilitate movement of the first flexure 2428A and the second flexure 2428B upon a pressure change in a tube received by the tubing receiving space 2406 while maintaining the remainder of the flexure block 2404 in a rigid or unmoving position or state.

Figure 23C:
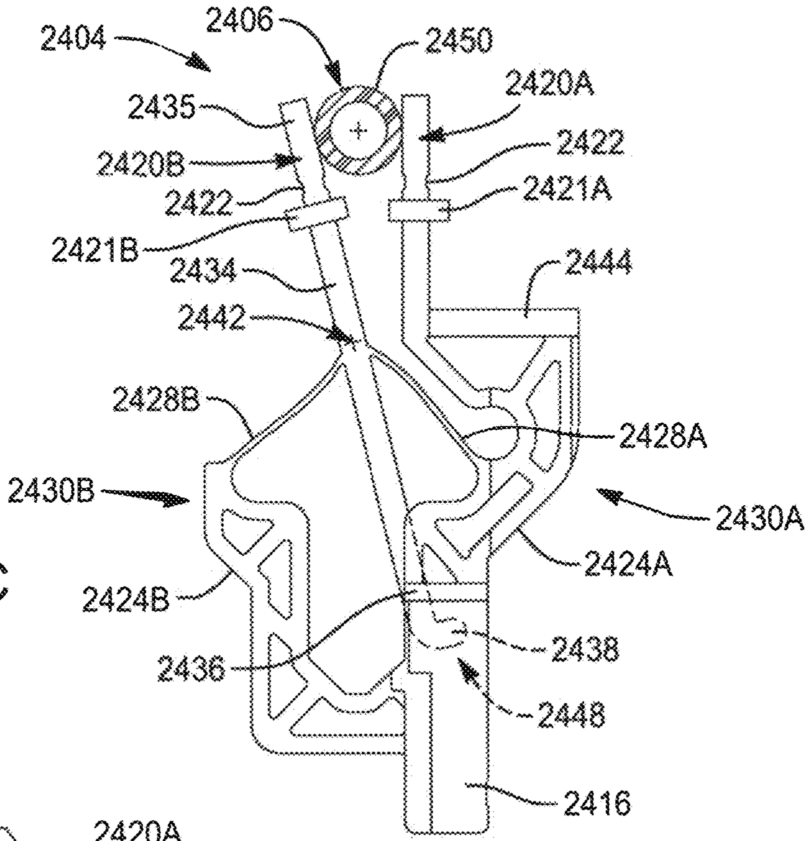
FIG. 23C is a schematic diagram of an exaggerated displacement of the flexure block when a pressure is applied to a tubing section engaged with the flexure block of FIG. 23B.

FIG. 23C shows a schematic diagram of an exaggerated displacement of the first flexure 2428A and the second flexure 2428B of the flexure block 2404 when a pressure is applied to a tubing section 2450 disposed in the tubing receiving space 2406 of the flexure-based tubing state sensor 2400. For example, when the tubing section 2450 is subjected to a pressure of 40 pounds per square inch (psi), the tubing section 2450 expands in size and increases the gap distance between the fixed wall 2420A and the moving wall 2420B at the tubing receiving space 2406. This increase in gap distance causes the lever arm 2434 to pivot about the pivot axis 2442 and move the contact finger 2438 closer to the first side 2430A of the flexure block body 2416. The amount of the displacement is exaggerated to better show the bending motion of the first flexure 2428A and the second flexure 2428B. For instance, as the lever arm 2434 of the flexure block 2404 moves from the unpivoted state shown in FIGS. 23A and 23B, to the pivoted state shown in FIG. 23C, the first flexure 2428A may bend in a direction away from the center of the flexure block 2404 and the second flexure 2428B may bend in a direction toward the center of the flexure block 2404. In some example embodiments, in the pivoted state the first flexure 2428A may be bent or curved as compared to the unpivoted state and the second flexure may be stretched or curved as compared to the unpivoted state. As the pressure decreases in the tubing section 2450, the lever arm 2434, the first flexure 2428A, and the second flexure 2428B may return to the position shown in FIGS. 23A and 23B.

Figure 23D:
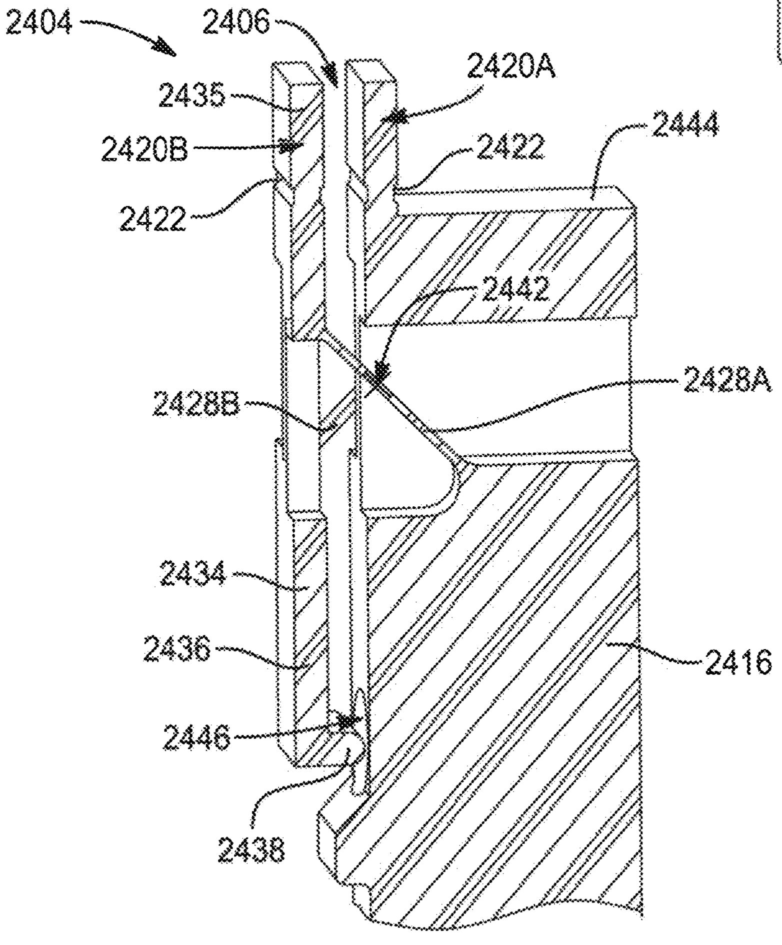
FIG. 23D is a perspective view of another example of the flexure block of the flexure-based tubing state sensor in accordance with at least one example embodiment of the present disclosure.

FIG. 23D shows a perspective view of another example embodiment of the flexure block 2404 of the flexure-based tubing state sensor 2400. The flexure block 2404 shown in FIG. 23D includes the first flexure 2428A and the second flexure 2428B that both interconnect with a lever arm 2434. The pivot axis 2442 may be disposed between the lever arm 2434 and the body 2416 such that the first flexure 2428A contacts the lever arm 2435 between the tubing contact section 2435 and a position on the lever arm 2435 even with the pivot axis and the second flexure 2428B contacts the lever arm 2434 between the sensor contact section 2436 and a position on the lever arm 2434 even with the pivot axis. Additionally, the pivot axis 2442 of the flexure block 2404 of FIG. 23D, however, is positioned at a point where the first flexure 2428A and the second flexure 2428B overlap but are not in contact with one another. In particular, the first flexure 2428A and the second flexure 2428B shown in FIG. 23D are offset from one another in a depth direction and join with the lever arm 2434 at different points along the length of the lever arm 2434. It should be appreciated that the description of the components associated with the flexure block 2404 illustrated in FIGS. 23A-23C may apply to the components associated with the flexure block 2404 illustrated in FIG. 23D.

Exemplary aspects are directed to a flexure-based tubing state sensor, comprising: a flexure block, including a body having a sensor aperture; a lever arm configured to pivot about a pivot axis, the lever arm including a tubing contact section and a sensor contact section; a first flexure extending from the body, the first flexure configured to couple with the lever arm; a second flexure extending from the body, the second flexure configured to couple with the lever arm; and a fixed wall section coupled to the body, the fixed wall section disposed offset a tubing gap distance from the tubing contact section; wherein the lever arm is pivotable about the pivot axis between an unpivoted state and a pivoted state, wherein the sensor contact section of the lever arm is arranged a first distance from the sensor aperture in the unpivoted state and a second distance from the sensor aperture in the pivoted state the first distance being greater than the second distance; and a pressure sensor comprising a pressure region disposed adjacent the sensor aperture and in contact with the sensor contact section of the lever arm, wherein the pressure sensor detects pressure at the tubing contact section via rotation of the lever arm and the sensor contact section acting on the pressure region.

Any one or more of the above aspects further comprising: a section of tubing disposed in between the fixed wall section of the flexure block and the tubing contact section of the lever arm, wherein a pressure inside the section of tubing causes the section of tubing to change in size, an increase in size of the section of tubing is measured by the pressure sensor as an increased pressure inside the section of tubing and a decrease in size of the section of tubing is measured by the pressure sensor as a decreased pressure in the section of tubing.

At least one example embodiment is directed to a flexure block, comprising: a body having a sensor; a lever arm configured to pivot about a pivot axis, the lever arm including a tubing contact section and a sensor contact section; a first flexure extending from the body, the first flexure configured to couple with the lever arm; a second flexure extending from the body, the second flexure configured to couple with the lever arm; and a fixed wall section coupled to the body, the fixed wall section disposed offset a tubing gap distance from the tubing contact section of the lever arm; wherein the lever arm is pivotable about the pivot axis between an unpivoted state and a pivoted state, wherein the sensor contact section of the lever arm is arranged a first distance from the sensor aperture in the unpivoted state and a second distance from the sensor aperture in the pivoted state the first distance being greater than the second distance.

In some example embodiments, an increase to the tubing gap distance pivots the lever arm about the pivot axis and proportionally moves the sensor contact section closer to the sensor aperture. In some example embodiments, the flexure block further comprises a first flexure support arm and a second flexure support arm, the first flexure support arm configured to couple with the body and be positioned on a first side of the lever arm, the second flexure support arm configured to couple with the body and be positioned on a second side of the lever arm. In some example embodiments, the first flexure is configured to couple between the first flexure support arm and the lever arm and the second flexure is configured to couple between the second flexure support arm and the lever arm. In some example embodiments, the body, the first flexure support arm, the second flexure support arm, the lever arm, the first flexure, the second flexure, and the fixed wall section are integrally formed from a material. In some example embodiments, the material is at least one of plastic, aluminum, brass, titanium, or stainless steel. In some example embodiments, the body, the first flexure support arm, the second flexure support arm, the lever arm, and the fixed wall section are formed from a first material and the first flexure and the second flexure are formed from a second material, wherein the first material is different from the second material. In some example embodiments, the first material is more rigid than the second material. A In some example embodiments, the flexure block further comprises a seal configured to provide a fluid barrier between the sensor aperture and the tubing contact section of the lever arm. In some example embodiments, at least one of the lever arm or the fixed wall section includes a notch configured to receive the seal. In some example embodiments, at least one of the first flexure or the second flexure is etched with a geometric pattern. In some example embodiments, moving the lever arm from the unpivoted state to the pivoted state causes the first flexure to move away from a center of the flexure block and causes the second flexure to move toward the center of the flexure block. In some example embodiments, the pivot axis is defined by a virtual intersection point of the first flexure and the second flexure. In some example embodiments, the pivot axis is disposed along a length of the lever arm between the tubing contact section and the sensor contact section. In some example embodiments, the sensor contact section comprises a finger protrusion extending in a direction perpendicular to an axis running along a length of the lever arm. In some example embodiments, the first flexure joins the lever arm at a first point adjacent the pivot axis, wherein the second flexure joins the lever arm at a second point adjacent the pivot axis, and wherein a distance between the first point and the second point define a width of the lever arm. In some example embodiments, the pivot axis is disposed between the lever arm and the body. In some example embodiments, the first flexure joins the lever arm at a first point between the pivot axis and the tubing contact section and the second flexure joins the lever arm at a second point between the pivot axis and the sensor contact section.

Example Blood Component Collection Bladder

FIGS. 24A-24J illustrate a blood component collection in accordance with at least one example embodiment of the present disclosure. In at least one example embodiment, the bladder 536 may be folded and packaged to create creases that aid in retaining the blood component collection bladder 536 inside the collection insert channel 466 of the filler 460 of the centrifuge assembly 400. For instance, the blood component collection bladder 536 of the blood component collection set 500 may be folded and fastened (e.g., via tape, wrap, etc.) in a folded state during packaging. When in the folded state, each fold of the folded blood component collection bladder 536 may form a crease in the blood component collection bladder 536. Each crease may remain in the blood component collection bladder 536 when unfolded or unfurled. When the blood component collection bladder 536 is unfolded and then inserted into the filler 460, the creases engage with the insert channel of the filler 460 retaining the blood component collection bladder 536 in place. In some examples, the filler 460 may comprise a number of tabs disposed around the collection insert channel 466. The tabs may aid in retaining the blood component collection bladder 536 inside the collection insert channel 466 of the filler 460. In at least one example embodiment, the locations of the tabs may be selected based on a location of a crease in the blood component collection bladder 536 and/or a location of a curve disposed between creases in the blood component collection bladder 536.

Figure 24A:
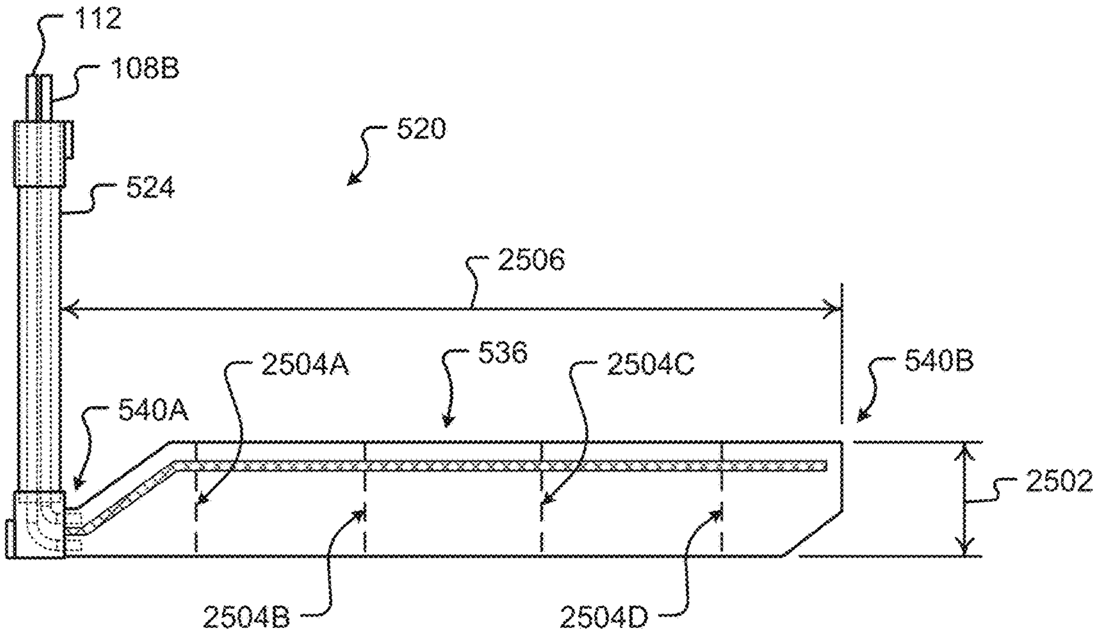
FIG. 24A is an elevation view of the blood component collection loop of FIG. 5A in accordance with examples of the present disclosure.

FIG. 24A shows an elevation view of the blood component collection loop of FIG. 5B in accordance with examples of the present disclosure.

In at least one example embodiment, as shown in FIG. 24A, the blood component collection loop 520 may correspond to the blood component collection loop 520 shown in FIG. 5B. For instance, the blood component collection loop 520 may include a flexible loop 524 and a blood component collection bladder 536. The blood component collection bladder 536 may be connected to the flexible loop 524 at a bladder loop end 540A and extend a length 2506 from the bladder loop end 540A to the bladder free end 540B. In at least one example embodiment, the blood component collection bladder 536 may correspond to a laminate sheet (e.g., a multi-layered sheet, etc.) having an overall height 2502 spanning across the length 2506.

The blood component collection bladder 536 may be folded along the length 2506 to form a folded bladder 2500A. A portion of the folded bladder 2500A may be wrapped with tape (e.g., a seal tape wrap 2516, etc.), an elastic band (e.g., a rubber band, a silicone band, etc.), shrink wrap, etc., and/or combinations thereof. In at least one example embodiment, the folded bladder 2500A may be packaged and shipped in a sealed bag.

Figure 24B:
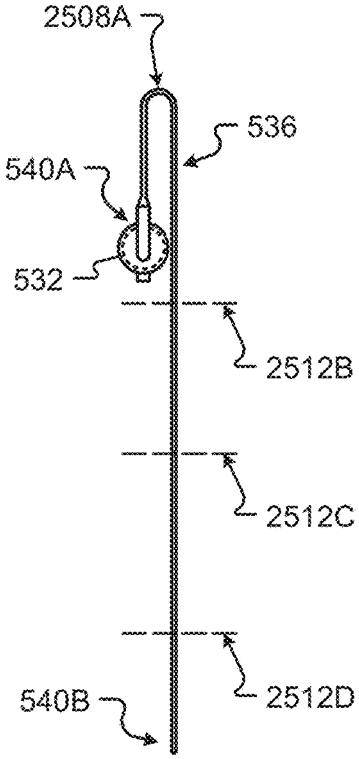
FIG. 24B is an elevation view of the blood component collection loop of FIG. 24A in a first folded state in accordance with at least one example embodiment.
Figure 24C:
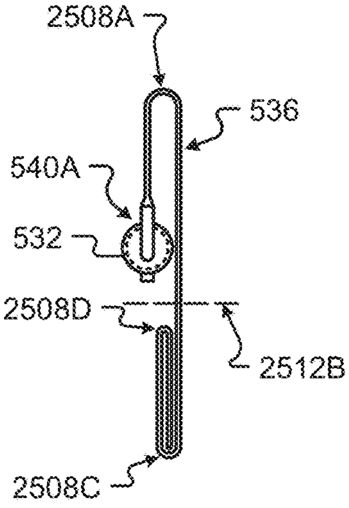
FIG. 24C is an elevation view of the blood component collection loop of FIG. 24A in a second folded state in accordance with at least one example embodiment.
Figure 24D:
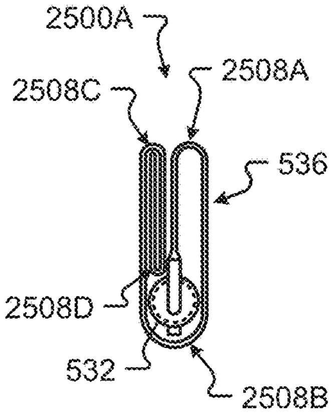
FIG. 24D is an elevation view of the blood component collection loop of FIG. 24A in a third folded state in accordance with at least one example embodiment.

As shown in FIG. 24A, the blood component collection bladder 536 may be folded along one or more fold lines 2504A-2504D. Although shown as "mountain" fold lines 2504A-2504D, the fold lines 2504A-2504D may correspond to "valley" fold lines. In one example, the fold lines 2504A-2504D may comprise a combination of mountain and valley fold lines. The fold lines 2504A-2504D may be arranged at different distances from the bladder loop end 540A and/or the bladder free end 540B. For instance, a first fold line 2504A is shown disposed a first distance from the bladder loop end 540A, a second fold line 2504B is shown disposed a second distance from the bladder loop end 540A greater than the first distance, a third fold line 2504C is shown disposed a third distance from the bladder loop end 540A greater than the second distance, and a fourth fold line 2504D is shown disposed a fourth distance from the bladder loop end 540A greater than the third distance. Although shown having four separate fold lines 2504A-2504D, the blood component collection bladder 536 may be folded along more or fewer than the fold lines 2504A-2504D shown in FIG. 24A. FIGS. 24B-24D show a bottom plan view of the blood component collection loop 520 as the blood component collection bladder 536 is folded along the fold lines 2504A-2504D.

FIG. 24B shows the blood component collection loop of FIG. 24A in a first folded state in accordance with at least one example embodiment.

In at least one example embodiment, as shown in FIG. 24B, the blood component collection bladder 536 is folded about the first fold line 2504A forming a first fold 2508A in the blood component collection bladder 536. The remaining fold lines 2504B-2504D, are indicated by the fold line location centerlines 2512B-2512D running from the bladder loop end 540A to the bladder free end 540B of the blood component collection bladder 536. The second fold location centerline 2512B corresponds to the location of the second fold line 2504B, the third fold location centerline 2512C corresponds to the location of the third fold line 2504C, and the fourth fold location centerline 2512D corresponds to the location of the fourth fold line 2504D. As illustrated in FIG. 24B, the first fold 2508A is made on a first side of the filler loop connector 532.

FIG. 24C shows the blood component collection loop of FIG. 24A in a second folded state in accordance with at least one example embodiment.

In at least one example embodiment, as shown in FIG. 24C, the fourth fold 2508D is formed adjacent the bladder free end 540B (e.g., at the fourth fold line 2504D), and the third fold 2508C is formed (e.g., at the third fold line 2504C) such that a portion of the blood component collection bladder 536 overlaps with itself and the bladder free end 540B is protected, or covered, at least partially by the third fold 2508C.

FIG. 24D shows the blood component collection loop of FIG. 24A in a third folded state in accordance with at least one example embodiment.

In at least one example embodiment, as shown in FIG. 24D, the blood component collection bladder 536 is folded at the second fold line 2504B forming the second fold 2508B. The second fold 2508B is disposed on a second side of the filler loop connector 532 and the third fold 2508C and the fourth fold 2508D are brought to the first side of the filler loop connector 532. In this folded bladder 2500A arrangement, the first fold 2508A, the third fold 2508C, and the fourth fold 2508D are disposed on the first side of the filler loop connector 532. Additionally or alternatively, the third fold 2508C is disposed adjacent to the first fold 2508A, and the fourth fold 2508D is disposed adjacent to the filler loop connector 532.

Figure 24E:
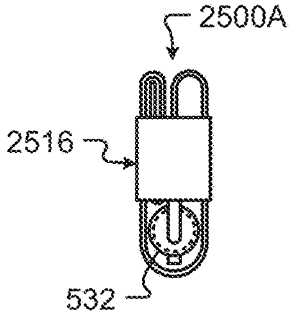
FIG. 24E is a bottom plan view of the blood component collection loop with a folded and packaged bladder in accordance with at least one example embodiment of the present disclosure.

FIG. 24E is a bottom plan view of the blood component collection loop with a folded and packaged bladder in accordance with at least one example embodiment of the present disclosure;

In at least one example embodiment, the folded bladder 2500A may be held together with a seal tape wrap 2516. The seal tape wrap 2516 may correspond to a cold seal tape and/or the like. The seal tape wrap 2516 may be fastened around the folded bladder 2500A such that the folded sections of the blood component collection bladder 536 are held close to, or in contact with, one another. In some examples, the seal tape wrap 2516 may be wrapped around the folded bladder 2500A on the first side of the filler loop connector 532. The seal tape wrap 2516 is removed from the folded bladder 2500A before the folded bladder 2500A can be unfolded, or unfurled.

Figure 24F:
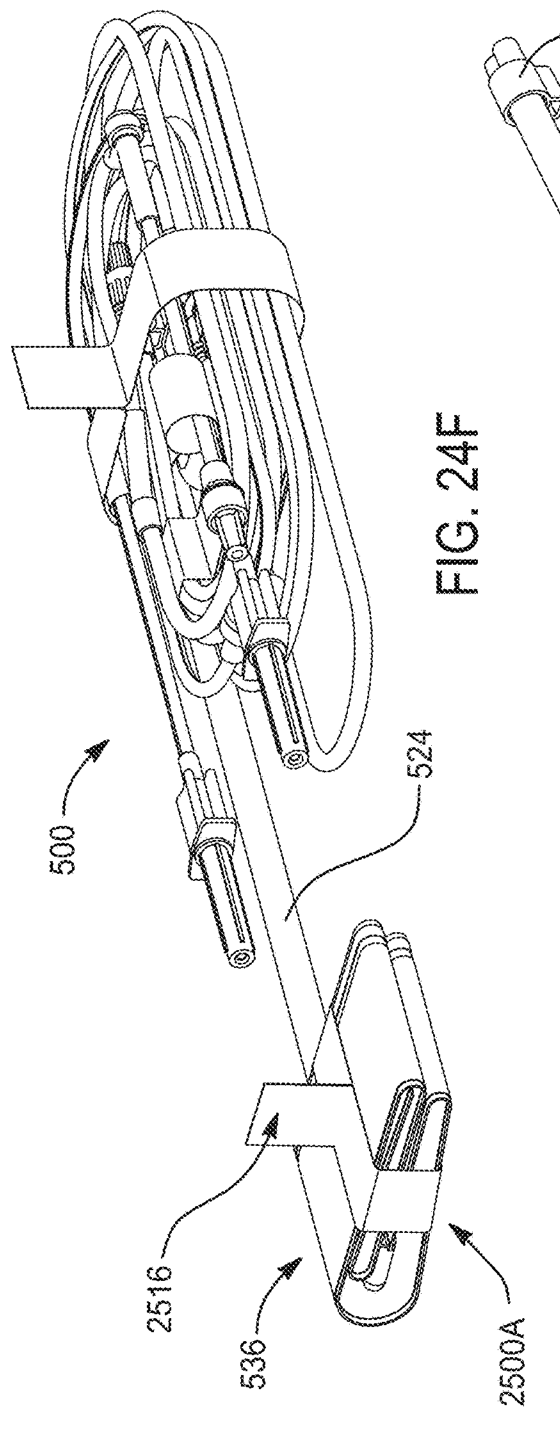
FIG. 24F is a perspective view of the blood component collection set of FIG. 5A in accordance with at least one example embodiment.

FIG. 24F is a perspective view of the blood component collection set of FIG. 5A in accordance with at least one example embodiment.

In at least one example embodiment, as shown in FIG. 24F, the blood component collection set 500 includes the blood component collection loop 520 and the folded bladder 2500A in a packaging arrangement. In this packaging arrangement, the blood component collection set 500 may be sealed inside a plastic bag for transport and/or storage. As shown, the folded bladder 2500A is wrapped with the seal tape wrap 2516, holding the folded bladder 2500A in a folded state.

Figure 24G:
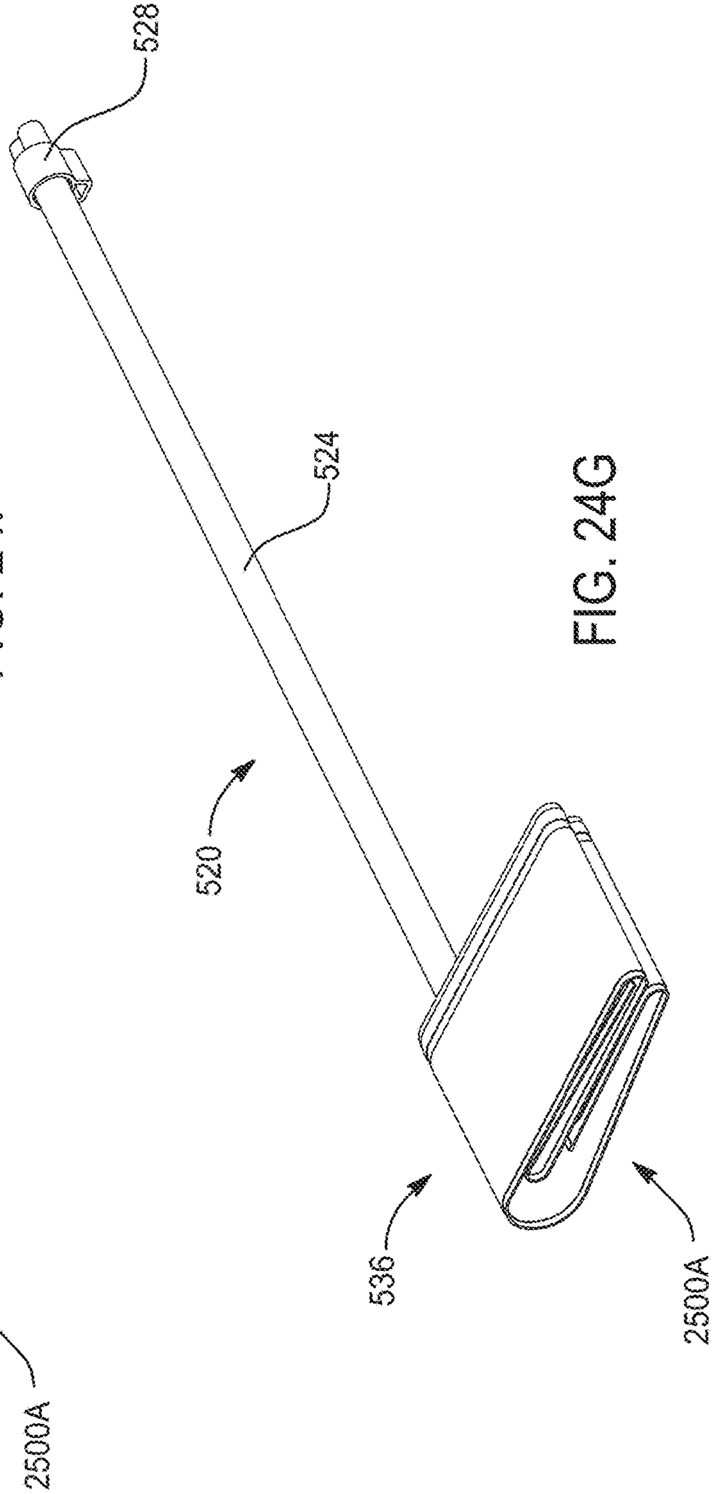
FIG. 24G is a perspective view of the blood component collection loop of FIG. 24F without seal tape wrap in accordance with at least one example embodiment.

FIG. 24G is a perspective view of the blood component collection loop of FIG. 24F without seal tape wrap in accordance with at least one example embodiment.

In at least one example embodiment, as shown in FIG. 24G, the blood component collection loop 520 is shown without the seal tape wrap 2516. For the sake of clarity in disclosure, the blood component collection loop 520 is shown without the other components of the blood component collection set 500. In some examples, the folded bladder 2500A may remain in the folded state even when the seal tape wrap 2516 has been removed. Stated another way, the folds in the folded bladder 2500A may form creases in the blood component collection bladder 536 that, among other things, give a set shape to the blood component collection bladder 536. These creases may remain set in the blood component collection bladder 536 even when the folded bladder 2500A is unfolded, or unfurled.

Figure 24H:
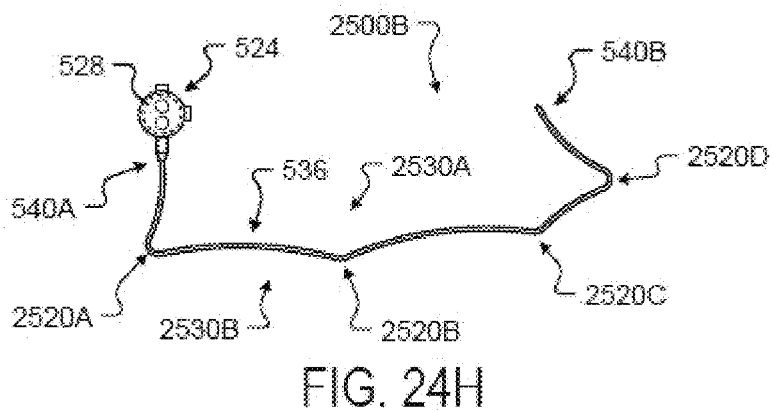
FIG. 24H is a top plan view of the blood component collection loop of FIG. 24A in accordance with at least one example embodiment.

FIG. 24H is a top plan view of the blood component collection loop of FIG. 24A in accordance with at least one example embodiment.

In at least one example embodiment, as shown in FIG. 24H, the blood component collection loop 520 as the blood component collection bladder 536 of the folded bladder 2500A is unfolded from the folded state (shown in FIG. 24G) to an unfolded state. In the unfolded state, the blood component collection bladder 536 corresponds to a creased bladder 2500B. For example, the blood component collection bladder 536 includes a number of creases 2520A-2520D that remain set in the material of the blood component collection bladder 536 along the length 2506. Each of the creases 2520A-2520D may be formed at a corresponding location of each of the folds 2508A-2508D. Stated another way, the folds 2508A-2508D of the folded bladder 2500A form the creases 2520A-2520D in the creased bladder 2500B.

In at least one example embodiment, the creased bladder 2500B includes a first crease 2520A disposed a first distance from the bladder loop end 540A, a second crease 2520B disposed a second distance from the bladder loop end 540A, a third crease 2520C disposed a third distance from the bladder loop end 540A, and a fourth crease 2520D disposed a fourth distance from the bladder loop end 540A. As the creased bladder 2500B is unfurled the creases 2520A-2520D may cause the laminate sheet of the blood component collection bladder 536 to bend in one or more regions. For instance, a first bend in the blood component collection bladder 536 may be disposed between the bladder loop end 540A and the first crease 2520A. The first bend is shown bending toward a first side 2530A of the blood component collection bladder 536. In at least the example embodiment shown, the first bend may form a concave shape on the second side 2530B of the blood component collection bladder 536 and a convex shape on the first side 2530A of the blood component collection bladder 536. A similar bend may be disposed between the first crease 2520A and the second crease 2520B. This second bend may form a convex shape on the first side 2530A of the blood component collection bladder 536 and a concave shape on the second side 2530B of the blood component collection bladder 536. Other similar bends may be disposed between the second crease 2520B and the third crease 2520C, the third crease 2520C and the fourth crease 2520D, and the fourth crease 2520D and the bladder free end 540B of the blood component collection bladder 536. In at least the example embodiment shown, each of these bends may form a convex shape on the first side 2530A of the blood component collection bladder 536 and a concave shape on the second side 2530B of the blood component collection bladder 536.

Figure 24J:
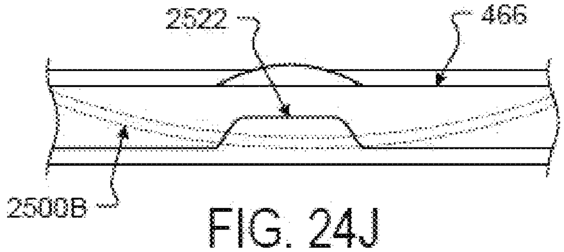
FIG. 24J is a detail schematic plan view of a section of a collection insert channel of the centrifuge assembly of FIG. 24I in accordance with at least one example embodiment.
Figure 24I:
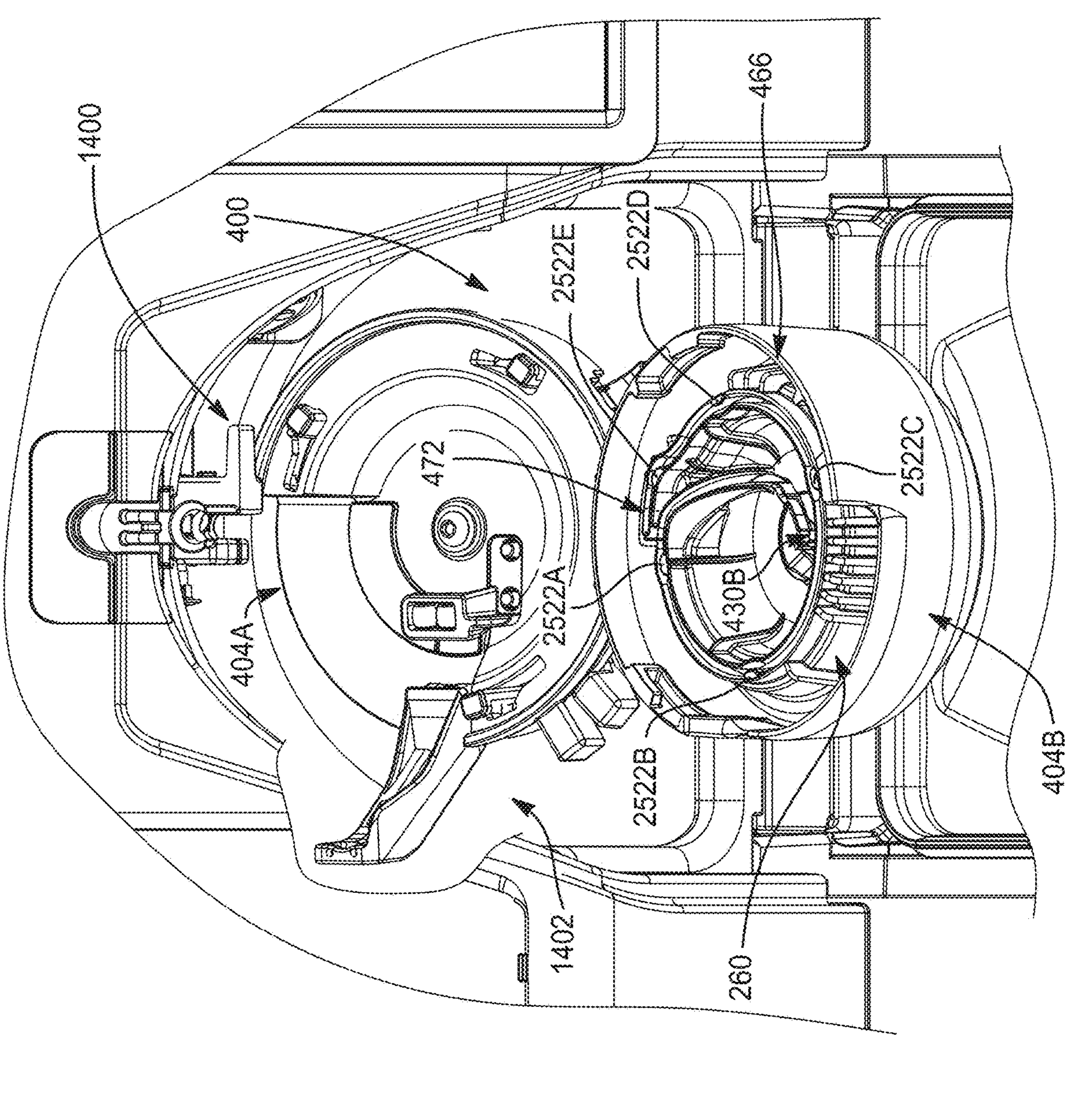
FIG. 24I is a perspective view of a filler of the centrifuge assembly of FIG. 4B in accordance with at least one example embodiment of the present disclosure.

FIG. 24I is a perspective view of a filler of the centrifuge assembly of FIG. 4B in accordance with at least one example embodiment of the present disclosure.

In at least one example embodiment, as shown in FIG. 24I, the filler 460 of the centrifuge assembly 400 is shown in a loading state. In at least one example embodiment, the filler 460 may comprise a number of retaining tabs 2522A-2522E disposed along a length of the spiral shape of the collection insert channel 466. In particular, the plurality of retaining tabs 2522A-2522E may be disposed, or arranged, along the spiral path at different locations. Each tab of the plurality of retaining tabs 2522A-2522E may cover a portion of the collection insert channel 466. The retaining tabs 2522A-2522E may be arranged to coincide with the bends and/or creases 2520A-2520D in the creased bladder 2500B. In one example, the first retaining tab 2522A may be positioned along the substantially spiral path of the collection insert channel 466 to coincide with the first bend or the first crease 2520A of the creased bladder 2500B. The second retaining tab 2522B may be positioned along the substantially spiral path of the collection insert channel 466 to coincide with the second bend or the second crease 2520B of the creased bladder 2500B. The third retaining tab 2522C may be positioned along the substantially spiral path of the collection insert channel 466 to coincide with the third bend or the third crease 2520C of the creased bladder 2500B. The fourth retaining tab 2522D may be positioned along the substantially spiral path of the collection insert channel 466 to coincide with the fourth bend or the fourth crease 2520D of the creased bladder 2500B. The fifth retaining tab 2522E may be positioned along the substantially spiral path of the collection insert channel 466 to coincide with the fifth bend or the fourth crease 2520D of the creased bladder 2500B.

FIG. 24J is a detailed schematic plan view of a section of a collection insert channel of the centrifuge assembly of FIG. 24I in accordance with at least one example embodiment.

In at least one example embodiment, as shown in FIG. 24J, the collection insert channel 466 includes a retaining tab 2522 covering a portion of the collection insert channel 466. A portion of the creased bladder 2500B (shown in dashed lines) is shown being retained in the retaining tab 2522 under the retaining tab 2522. In addition to the frictional contact between the creases 2520A-2520D and the walls of the collection insert channel 466, the creased bladder 2500B may be retained in the collection insert channel 466 via a retaining surface of the retaining tab 2522 that blocks a path running from the inside of the collection insert channel 466 to an outside of the collection insert channel 466.

Exemplary aspects are directed to a blood component collection bladder, comprising: a laminate sheet extending a length from a first end of the laminate sheet to a second end of the laminate sheet; and a first fold disposed in the laminate sheet a first distance from the first end of the laminate sheet; wherein the first fold forms a first crease in the laminate sheet extending from a first side of a height of the laminate sheet to a second side of the height of the laminate sheet, and wherein the first crease remains in the laminate sheet when the laminate sheet is in a folded state and when the laminate sheet is in an unfolded state.

Any one or more of the above aspects further comprising: a second fold disposed in the laminate sheet a second distance from the first end of the laminate sheet, wherein the second distance is greater than the first distance, wherein the second fold forms a second crease in the laminate sheet extending from the first side of the height of the laminate sheet to the second side of the height of the laminate sheet, and wherein the second crease remains in the laminate sheet when the laminate sheet is in the folded state and when the laminate sheet is in the unfolded state. Any one or more of the above aspects further comprising: a third fold disposed in the laminate sheet a third distance from the first end of the laminate sheet, wherein the third distance is greater than the second distance, wherein the third fold forms a third crease in the laminate sheet extending from the first side of the height of the laminate sheet to the second side of the height of the laminate sheet; and a fourth fold disposed in the laminate sheet a fourth distance from the first end of the laminate sheet, wherein the fourth distance is greater than the third distance, wherein the fourth fold forms a fourth crease in the laminate sheet extending from the first side of the height of the laminate sheet to the second side of the height of the laminate sheet; wherein the third crease and the fourth crease remain in the laminate sheet when the laminate sheet is in the folded state and when the laminate sheet is in the unfolded state. Any one or more of the above aspects wherein the laminate sheet comprises a connector disposed at the first end, and wherein the laminate sheet is sealed at the second end. Any one or more of the above aspects wherein, in the folded state, the first fold is disposed on a first side of the connector, the second fold is disposed on a second side of the connector, the third fold is disposed on the first side of the connector, and the fourth fold is disposed on the first side of the connector. Any one or more of the above aspects wherein, in the folded state, the first fold is disposed adjacent to the third fold and the fourth fold is disposed adjacent the connector. Any one or more of the above aspects wherein, in the folded state, the laminate sheet is maintained in the folded state by a section of material wrapped around the laminate sheet on the first side of the connector. Any one or more of the above aspects wherein, in the unfolded state, the blood component collection bladder, when inserted in a collection insert channel of a centrifuge filler is maintained in the collection insert channel by the first crease, the second crease, the third crease, and the fourth crease contacting a wall of the collection insert channel.

Exemplary aspects are directed to a method of loading a centrifuge filler, comprising: providing a blood component collection bladder, comprising: a laminate sheet extending a length from a first end of the laminate sheet to a second end of the laminate sheet; and a plurality of folds disposed in the laminate sheet, each fold of the plurality of folds arranged at a respective point along the length of the laminate sheet, wherein the respective point is arranged at a respective distance from the first end of the laminate sheet, and wherein the respective distance is different for each fold of the plurality of folds; wherein the plurality of folds form a plurality of creases in the laminate sheet, each crease of the plurality of creases extending from a first side of a height of the laminate sheet to a second side of the height of the laminate sheet at the respective point of each fold of the plurality of folds, and wherein the plurality of creases remain in the laminate sheet when the laminate sheet is in a folded state and when the laminate sheet is in an unfolded state; inserting the blood component collection bladder in the unfolded state into a collection insert channel of a centrifuge filler such that each crease of the plurality of creases contacts at least one wall of the collection insert channel; and inverting the centrifuge filler while the blood component collection bladder is maintained inside the collection insert channel via frictional contact between the laminate sheet and the collection insert channel.

Exemplary aspects are directed to a centrifuge assembly, comprising: a centrifuge housing having an internal cavity, wherein the centrifuge housing rotates about a rotation axis of the centrifuge assembly; and a fluid separating body disposed at least partially within the internal cavity of the centrifuge housing and configured to rotate relative to the centrifuge housing about the rotation axis, wherein the fluid separating body includes a fluid collection insert channel disposed in the fluid separating body following a substantially spiral path running from a first point adjacent to the rotation axis spirally outward to a second point disposed adjacent to a periphery of the fluid separating body; wherein the fluid collection insert channel comprises a plurality of tabs arranged along the substantially spiral path at different locations, wherein each tab of the plurality of tabs covers a portion of the a fluid collection insert channel, wherein each location of the different locations is associated with a corresponding location of a bend or crease formed in a blood component collection bladder, and wherein each tab of the plurality of tabs provides a retaining surface that blocks a path from inside the fluid collection insert channel to an outside of the fluid collection insert channel.

Second Example of Soft Cassettes with Integrated Features

Figure 25A:
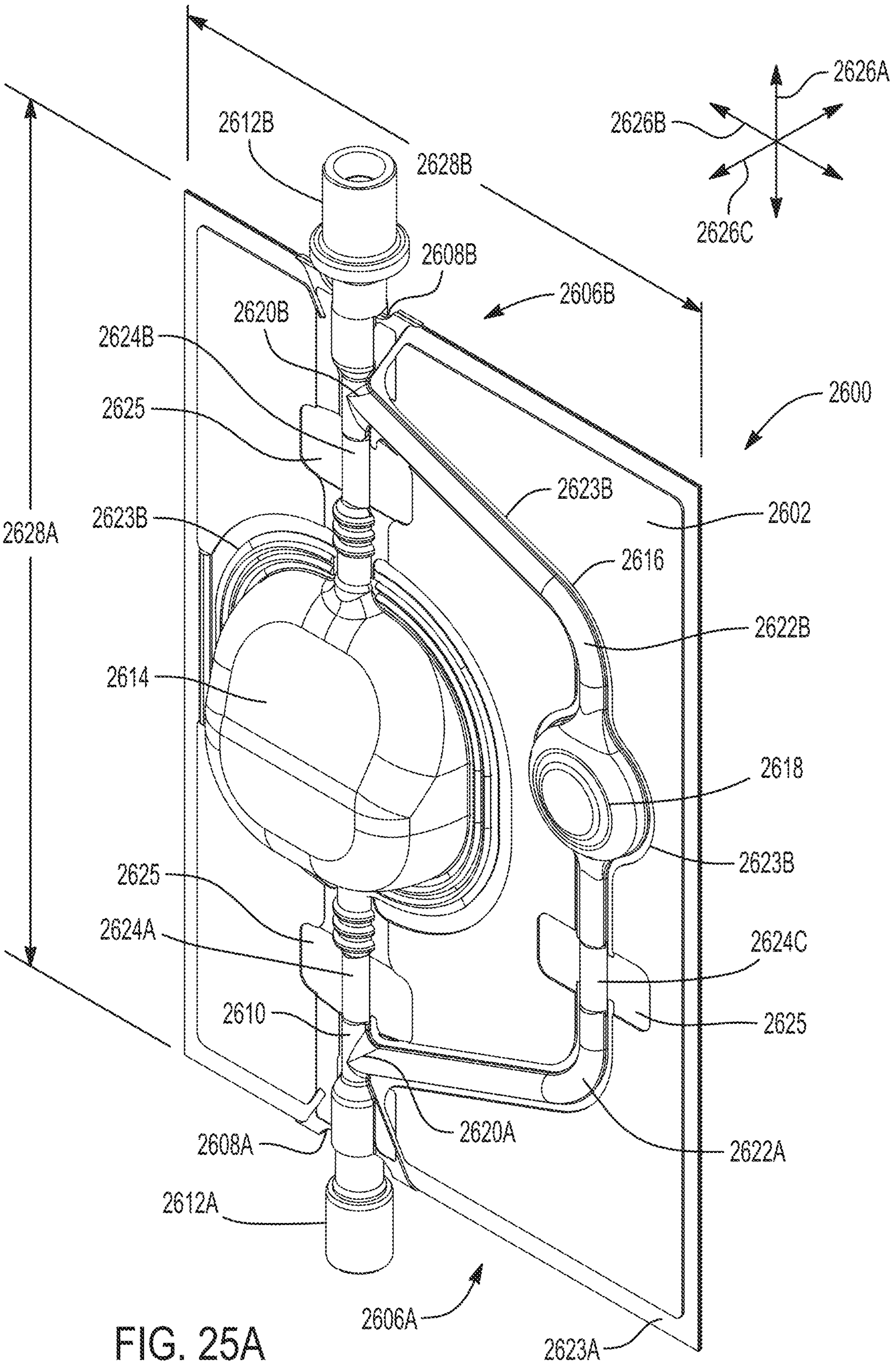
FIG. 25A is a perspective view of another soft cassette in accordance with at least one example embodiment of the present disclosure.

FIG. 25A is a perspective view of a soft cassette according to at least one example embodiment.

In at least one example embodiment, as shown in FIG. 25A, a soft cassette 2600 may include one or more features that are similar to or the same as those of the soft cassette 314 of FIGS. 3A-3D (e.g., having the same or similar portions, chambers, flow paths, and/or valve regions). Moreover, the soft cassette 2600 may be used in a soft cassette assembly (see, e.g., soft cassette assembly 300 of FIG. 3A or soft cassette assembly 2650 of FIGS. 25D-25E).

In at least one example embodiment, the soft cassette 2600 includes a body 2602. The body may be formed from the same materials as described in the discussion of the soft cassette 314, above. In at least one example embodiment, the body 2602 defines a first port aperture 2608A, a second port aperture 2608B, and a first or direct flow lumen 2610 between and fluidly connecting the first and second port apertures 2608A, 2608B. In at least the example embodiment shown, the soft cassette 2600 further includes a first port 2612A at least partially in the first port aperture 2608A and a second port 2612B at least partially in the second port aperture 2608B. In at least one other example embodiment, a soft cassette is free of distinct ports, and tubing of a collection set is directly fluidly connected to port apertures without distinct ports therebetween.

In at least one example embodiment, a flow path associated with the direct flow lumen 2610 may be referred to herein as a "return path." In at least one example embodiment, a first chamber 2614 (referred to in other example embodiments as a "drip chamber") is disposed along the direct flow lumen 2610 between the first and second port apertures 2608A, 2608B. The first chamber 2614 is fluidly connected to the direct flow lumen 2610 such that fluid passing through the direct flow lumen 2610 also passes through the first chamber 2614.

In at least one example embodiment, the first chamber 2614 is configured to trap air and/or filter blood components passing therethrough. The shape of the first chamber 2614 may facilitate trapping air so that it cannot continue through the direct flow lumen 2610 and be passed to a donor. The first chamber 2614 may include a filter (see, e.g., filter 2668) therein, as will be described in greater detail below.

In at least one example embodiment, the soft cassette 2600 includes a second or bypass flow lumen 2616. A second or pressure sensing chamber 2618 may be disposed along the bypass flow lumen 2616. The pressure sensing chamber 2618 is fluidly connected to the bypass flow lumen 2616 such that fluid passing through the bypass flow lumen 2616 also passes through the pressure sensing chamber 2618.

In at least one example embodiment, a flow path associated with the bypass flow lumen 2616 may be referred to herein as a "draw path." In at least one example embodiment, the bypass flow lumen 2616 extends between a first junction 2620A with the direct flow lumen 2610 and a second junction 2620B with the direct flow lumen 2610. The bypass flow lumen 2616 may include a first bypass branch 2622A extending between the first junction 2620A and the pressure sensing chamber 2618 and a second bypass branch 2622B extending between the second junction 2620B and the pressure sensing chamber 2618.

In at least one example embodiment, the body 2602 includes a perimeter weld or bond 2623A. The perimeter weld 2623A may extend continuously and uninterrupted around a periphery of the body 2602. In at least one example embodiment, the body 2602 includes one or more feature welds or bonds 2623B at least partially surrounding other features, such as the lumens 2610, 2616 and the chambers 2614, 2618.

In at least one example embodiment, the soft cassette 2600 includes a plurality of compliant regions or valve paths 2624A, 2624B, 2624C (collectively referred to herein as the "compliant regions 2624"). The compliant regions 2624 may be configured to be engaged by respective valves of a soft cassette assembly (see, e.g., valves 320A, 320B, 320C of FIG. 3A) to selectively control fluid flow at a respective location in the return path or the draw path. In at least the example embodiment shown, the soft cassette 2600 includes three compliant regions 2624. A first compliant region 2624A is between the first junction 2620A and the first chamber 2614. A second compliant region 2624B is between the second junction 2620B and the first chamber 2614. A third compliant region 2624C is between the first junction 2620A and the pressure sensing chamber 2618.

As described above, the soft cassette assembly may include one or more valves for selectively controlling the flow of blood to and/or from the donor 102 (shown in FIG. 1A). In at least one example embodiment, A soft cassette assembly may include valve pads or valve regions 2625 disposed at or adjacent to one more discrete flow path points. The valve pads 2625 may be disposed to be adjacent to and/or surround compliant regions 2624A, 2624B, 2624C of the soft cassette 2600. In at least one example embodiment, the valve pads 2625 may provide pinch valve areas at points along the lumens 2610, 2616 of the soft cassette 2600. Forming the valve pads 2625 requires a carefully defined geometry (e.g., especially in cross-section), as will be described in greater detail below in the discussing accompanying FIGS. 25I-25K. In at least one example embodiment, a cross-section of the valve pads 2625 may include a semicircular shape on one side of the soft cassette 2600 and a mating opposing (e.g., mirrored) semicircular shape on the other side of the soft cassette 2600. When joined, the semicircular shapes form a circular cross-sectional shape.

The soft cassette 2600 may define an orthogonal coordinate system including a first or vertical axis 2626A, a second or horizontal axis 2626B, and a third or depth axis 2626C. The body 2602 may define a first dimension or height 2628A parallel to the vertical axis 2626A. The body 2602 may define a second dimension or width 2628B parallel to the horizontal axis 2626B.

Figure 25C:
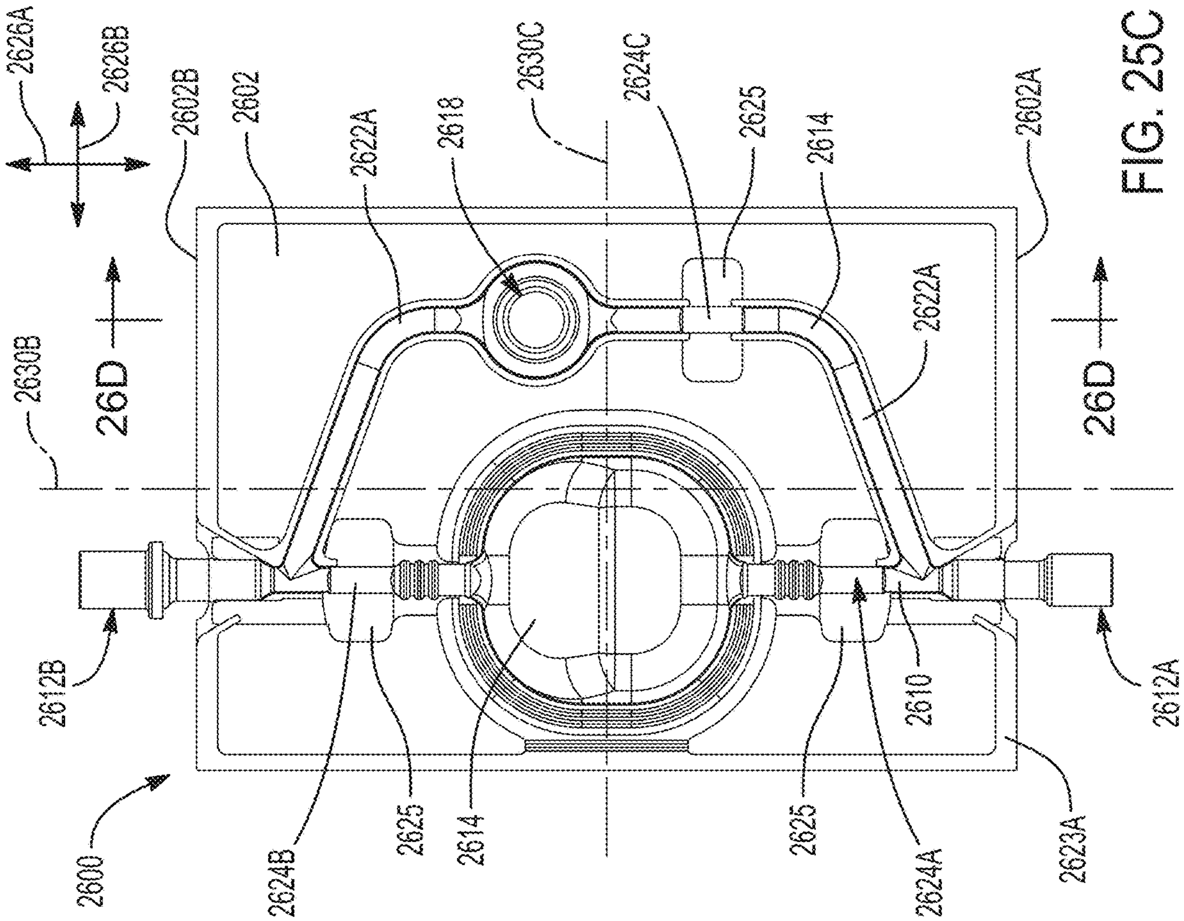
FIG. 25C is a front elevation view of the soft cassette of FIG. 25A in accordance with at least one example embodiment of the present disclosure.
Figure 25B:
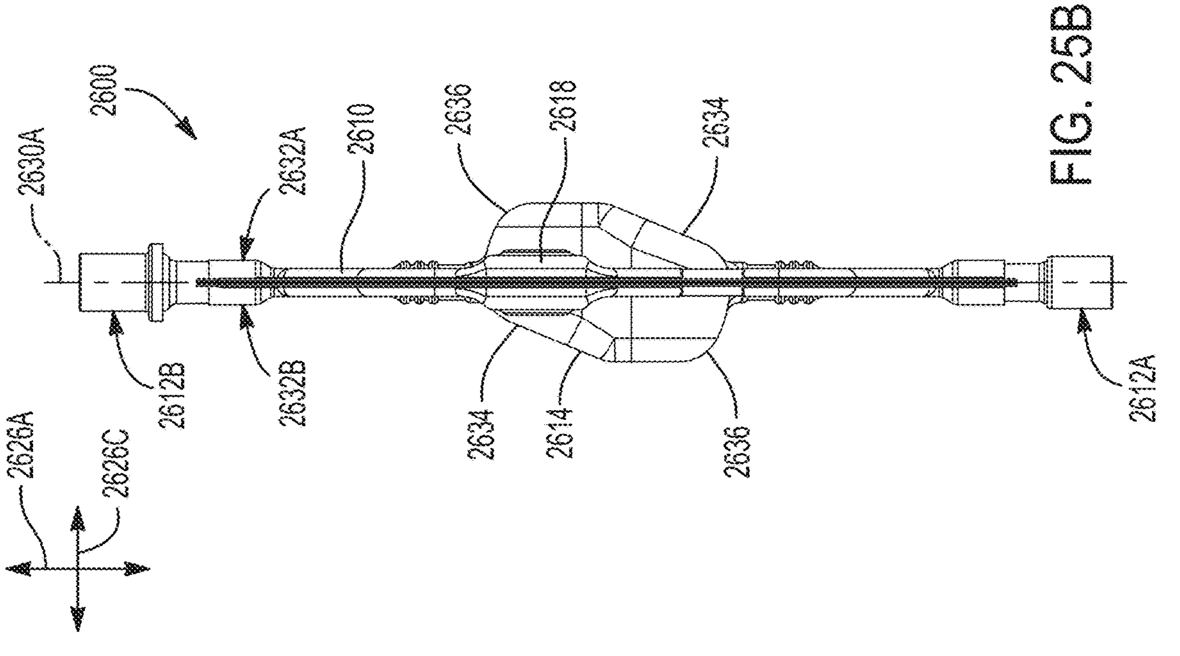
FIG. 25B is a side elevation view of the soft cassette of FIG. 25A in accordance with at least one example embodiment of the present disclosure.

FIG. 25B is a side elevation view of the soft cassette of FIG. 25A according to at least one example embodiment.

In at least one example embodiment, as shown in FIG. 25B, the body 2602 extends along or defines a first center plane 2630A. The first center plane 2630A is defined by the vertical axis 2626A and the horizontal axis 2626B (shown in FIG. 3A). The body 2602 includes a first side or body portion 2632A on one side of the first center plane 2630A and a second side or body portion 2632B on the other side of the first center plane 2630A. As will be described in greater detail below, the first and second body portions 2632A, 2632B cooperate to at least partially define the first and second port apertures 2608A, 2608B (shown in FIG. 25A), the direct flow lumen 2610, the bypass flow lumen 2616 (shown in FIG. 25A), the first chamber 2614, the pressure sensing chamber 2618 (shown in FIG. 25A), and/or the compliant regions 2624 (shown in FIG. 25A).

In at least one example embodiment, the first chamber 2614 is reflection asymmetric about the first center plane 2630A. In at least one example embodiment, the first chamber 2614 may have two degrees of rotation symmetry about an axis parallel to the horizontal axis 2626B. In at least the example embodiment shown, the first chamber 2614 may include two ramped surfaces 2634 and two curved or convex surfaces 2636.

FIG. 25C is a front elevation view of the soft cassette of FIG. 25A according to at least one example embodiment.

In at least one example embodiment, as shown in FIG. 25C, the soft cassette 2600 extends along or defines a second center plane 2630B defined by the vertical axis 2626A and the depth axis 2626C (shown in FIG. 25A) and a third center plane 2630C defined by the horizontal axis 2626B and the depth axis 2626C. The second center plane 2630B may run through a center of the width of the body 2602 from the first cassette end 2602A to the second cassette end 2606B. The third center plane 2630C may run through a center of the height of the body 2602 between the first cassette end 2606A and the second cassette end 2606B. In at least one example embodiment, the soft cassette 2600 is asymmetric about the second center plane 2630B and/or the third center plane 2630C.

In at least one example embodiment, the body 2602 is asymmetric about the second center plane 2630B. At least a portion of the first chamber 2614 may be on one side of the second center plane 2630B and at least a portion of the pressure sensing chamber 2618 may be on the other side of the second center plane 2630B. In at least the example embodiment shown, a horizontal center of the first chamber 2614 is on one side of the second center plane 2630B and a horizontal center of the pressure sensing chamber 2618 is on the other side of the second center plane 2630B. In the example embodiment shown, the entire pressure sensing chamber 2618 is on the other side of the second center plane 2630B. The first chamber 2614 may be reflection asymmetry about the second center plane 2630B. Respective horizontal centers of the first chamber 2614 and the pressure sensing chamber 2618 may be offset from one another along the horizontal axis 2626B.

In at least one example embodiment, the body 2602 is asymmetric about the third center plane 2630C. At least a portion of the first chamber 2614 may be on one side of the third center plane 2630C and at least a portion of the pressure sensing chamber 2618 may be on the other side of the third center plane 2630C. In at least the example embodiment shown, the first chamber 2614 is vertically centered on the third center plane 2630C and a vertical center of the pressure sensing chamber 2618 is on one side of the third center plane 2630C. In the example embodiment shown, the entire pressure sensing chamber 2618 is on one side of the third center plane 2630C. The first chamber 2614 may be reflection asymmetric about the third center plane 2630C. Respective vertical centers of the first chamber 2614 and the pressure sensing chamber 2618 may be offset from one another along the vertical axis 2626A.

Figure 25D:
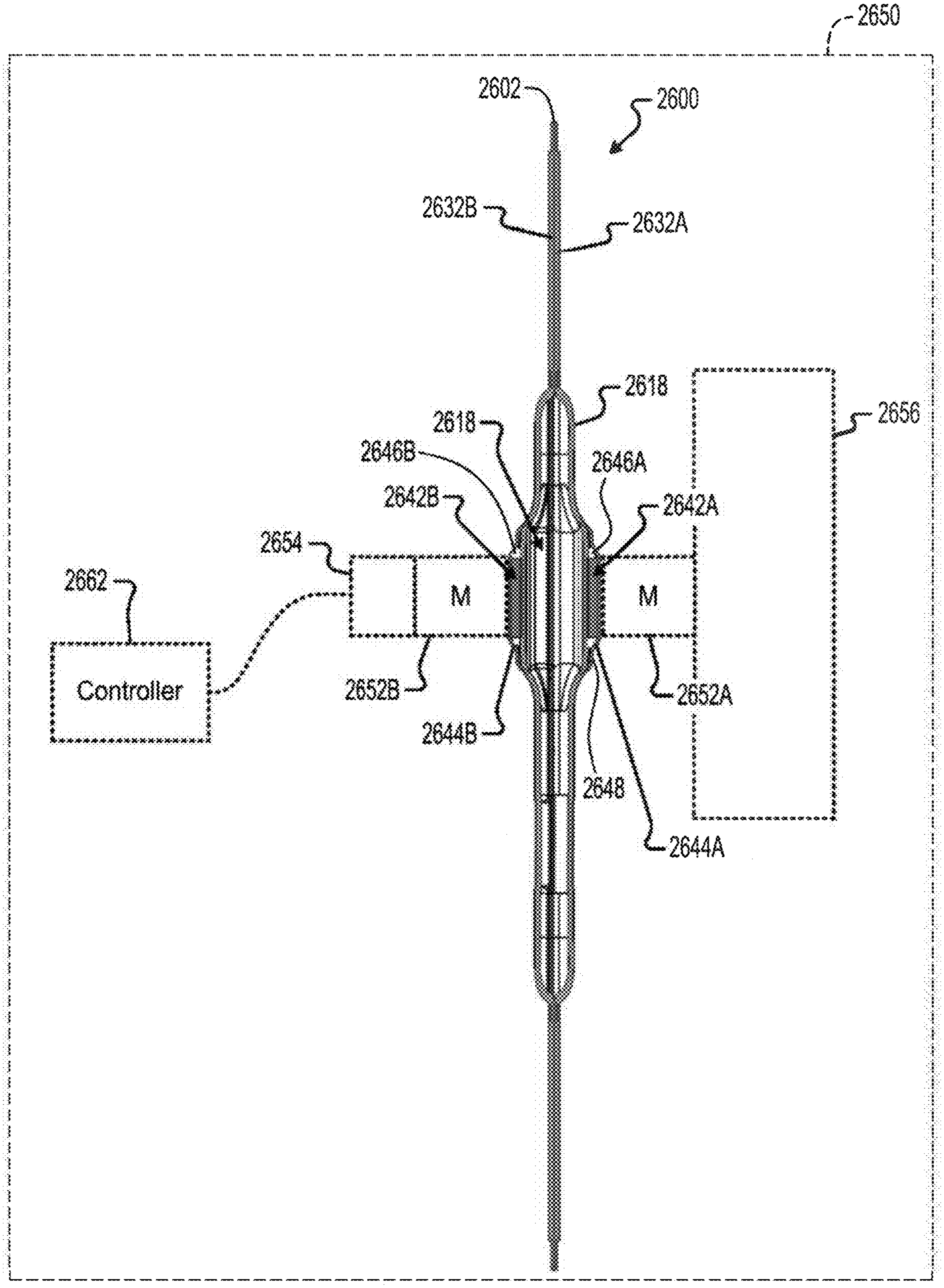
FIG. 25D is a schematic sectional view of a soft cassette assembly including the soft cassette of FIG. 25A in accordance with at least one example embodiment of the present disclosure.
Figure 25E:
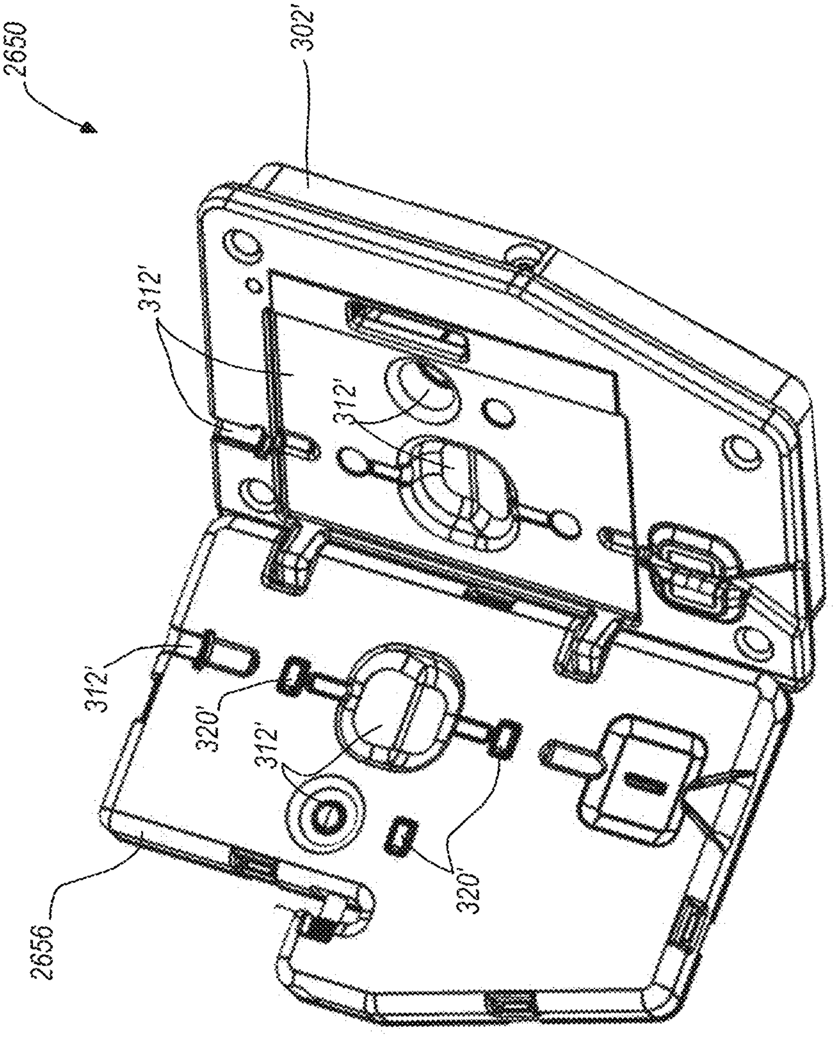
FIG. 25E is a perspective view of the soft cassette assembly of FIG. 25D in an open state in accordance with at least one example embodiment of the present disclosure.

The asymmetry may, in at least one example embodiment, facilitate proper positioning and/or orientation of the soft cassette 2600 in a soft cassette assembly (see, e.g., the soft cassette assembly 300 of FIG. 3A or the soft cassette assembly 2650 of FIGS. 25D-25E). Accordingly, the asymmetric arrangement may reduce or prevent inadvertent improper loading of the soft cassette 2600 in the soft cassette assembly, thereby increasing safety of use and east of operation of a blood component collection set (see, e.g., blood component collection set 500) including the soft cassette 2600. In at least one example embodiment, a base plate and a cassette access door of the soft cassette assembly may define receiving spaces that mate with the protruding portions of the soft cassette 2600. Because features of the soft cassette 2600 are asymmetrically arranged, the soft cassette 2600 can only be loaded in the soft cassette assembly 300 in one position and orientation FIG. 25D is a schematic sectional view of a soft cassette assembly of the soft cassette of FIG. 25A according to at least one example embodiment.

In at least one example embodiment, as shown in FIG. 25D, the pressure sensing chamber 2618 is unobstructed. In at least one example embodiment, a first component or first pressure sensor disk 2642A is disposed on a first side of the pressure sensing chamber 2618 and a second component or second pressure sensor disk 2642B is disposed on a second side of the pressure sensing chamber 2618. In at least one example embodiment, the pressure sensor disks 2642A, 2642B may be or include circular disks made from a material that is capable of engaging and/or interacting with a magnet, such as a ferromagnetic metal. The ferromagnetic metal may include iron, steel, or other material that is capable of being attracted by a magnet. The pressure sensor disks 2642A, 2642B may consist essentially of the ferromagnetic metal and/or have a coating including the ferromagnetic metal. In at least one other example embodiment, the pressure sensor disks 2642A, 2642B may include magnets, such as rare earth magnets, permanent magnets, and/or the like.

In at least one example embodiment, the soft cassette 2600 includes a first disk cover 2644A and a second disk cover 2644B. The first and second disk covers 2644A, 2644B may be substantially circular and have a diameter that is larger than that of the respective pressure sensor disk 2642A, 2642B. The first and second disk covers 2644A, 2644B may include the same material as the body 2602 or a different material than the body 2602 (e.g., vinyl, plastic, etc.). The first disk cover 2644A may cooperate with the body 2602 to at least partially define a first pocket 2646A. The first pressure sensor disk 2642A may be in the first pocket 2646A. The second disk cover 2644B may cooperate with the body 2602 to at least partially define a second pocket 2646B. The second pressure sensor disk 2644B may be in the second pocket 2646B. In at least one example embodiment, the first and second pockets 2646A, 2646B are fully enclosed.

In at least one example embodiment, the soft cassette 2600 may further include one or more cover welds 2648. Each of the cover welds 2648 may seal or trap one of the pressure sensor disks 2642A, 2642B in a respective one of the pockets 2646A, 2646B. The welds 2648 may extend around respective peripheries of the respective disk covers 2644A, 2644B.

In at least one example embodiment, a soft cassette assembly 2650 may include a first magnet 2652A and a second magnet 2652B. The second magnet 2652B may be operatively connected to a pressure sensor 2654 of an apheresis system (e.g., the apheresis system 200 of FIG. 1A). In at least one example embodiment, the pressure sensor 2654 is the same as or similar to the pressure sensors 808, 806 of FIG. 8. The second magnet 2652B may be disposed in a portion of a base plate of the soft cassette assembly 2650 and arranged to magnetically couple to the second pressure sensor disk 2642B of the soft cassette 2600 when the soft cassette 2600 is engaged with the soft cassette assembly 2650. In at least one example embodiment, such as when the second pressure sensor disk 2642B is a magnet, the soft cassette assembly may alternatively include a ferromagnetic metal component (e.g., a distinct component and/or an integral portion of the assembly).

In at least one example embodiment, a cassette access door 2656 of the soft cassette assembly 2650 may include the first magnet 2652A embedded in and/or attached to a portion (e.g., body, etc.) of the cassette access door 2656. When the cassette access door 2656 of the soft cassette assembly 2650 is closed (e.g., as shown in FIG. 3A), the first magnet 2652A of the cassette access door 2656 may magnetically couple to the first pressure sensor disk 2642A of the soft cassette 2600. In at least one example embodiment, this dual magnetic coupling (e.g., between the first magnet 2652A of the pressure sensor 2654 and the opposing second magnet 2652B of the cassette access door 2656 may hold the first pressure sensor disk 2642A and the second pressure sensor disk 2642B apart at the pressure sensing chamber 2618.

FIG. 25E is a perspective view of the soft cassette assembly of FIG. 25D in an open state in accordance with at least one example embodiment.

In at least one example embodiment, as shown in FIG. 25E, the soft cassette assembly 2650 may be similar to the soft cassette assembly 300 of FIG. 3A. The soft cassette assembly 2650 may include a base plate 302' and the door 2656. The base plate 302' and/or the door 2656 may define one or more receiving features 312'. The receiving features 312' may be depressions that are sized and shaped to receive at least a portion of the soft cassette 2600 (shown in FIG. 25A), such as the chambers 2614, 2618 and ports 2612A, 2612B (shown in FIG. 25A). The soft cassette assembly 2650 may further include fluid control valves 320'. The first magnet 2652A (shown in FIG. 25D) may be in the door 2656 and the second magnet 2652B and the pressure sensor 2654 may be in the base plate 302'

Figure 25F:
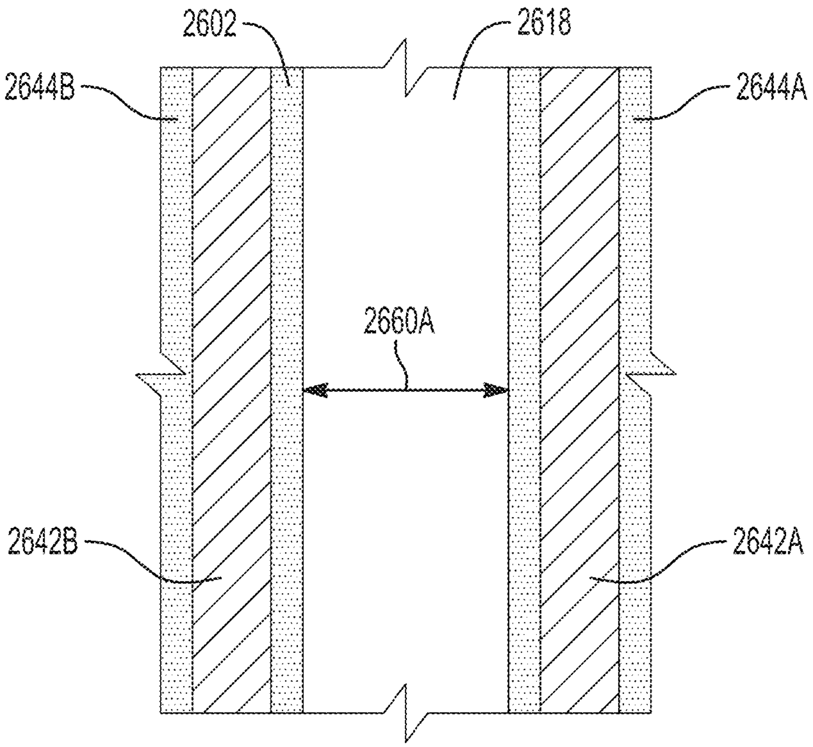
FIG. 25F is a partial sectional view of the soft cassette of FIG. 25A in a first pressure state in accordance with at least one example embodiment of the present disclosure.
Figure 25G:
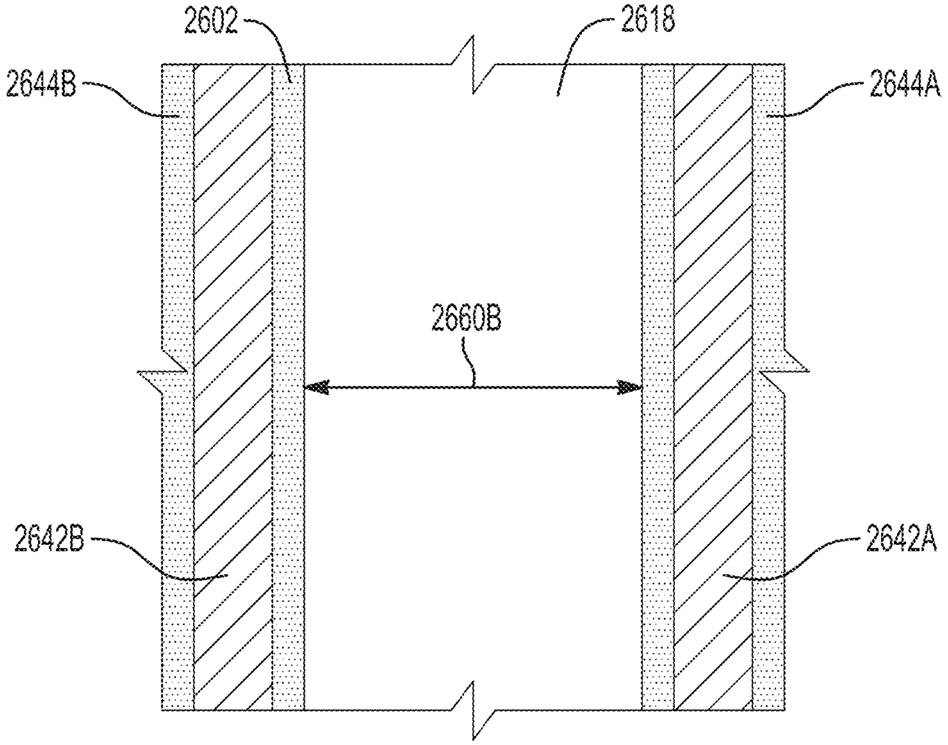
FIG. 25G is a partial sectional view of the soft cassette of FIG. 25A in a second pressure state in accordance with at least one example embodiment of the present disclosure.

FIG. 25F is a partial sectional view of the soft cassette of FIG. 25A in a first pressure state according to at least one example embodiment. FIG. 25G is a partial sectional view of the soft cassette of FIG. 25A in a second pressure state according to at least one example embodiment.

In at least one example embodiment, as the pressure changes inside the pressure sensing chamber 2618 of the soft cassette 2600 (e.g., during draw cycles, separation operations, fluid movement through the fluid pressure chamber 2624, etc.), a distance between the first pressure sensor disk 2642A and the second pressure sensor disk 2642B may change. In at least the example embodiment shown in FIG. 25F, a first pressure inside the fluid pressure sensing chamber 2618 may cause the second pressure sensor disk 2642B to move relative to the first pressure sensor disk 2642A. This movement and associated pressure may be detected as a first pressure and corresponding internal pressure of the pressure sensing chamber 2618 by the pressure sensor 2654. The first pressure may correspond to a first dimension 2660A between the pressure sensor disks 2642A, 2642B.

With reference to FIG. 25G, a second pressure greater than the first pressure inside the pressure sensing chamber 2618 may cause the second pressure sensor disk 2642B to move relative to the first pressure sensor disk 2642A at an increased movement and/or associated pressure. This increased movement and/or associated pressure may be detected as a second pressure and a corresponding second internal pressure of the pressure sensing chamber 2618 by the pressure sensor 2654. The second pressure may correspond to a second dimension 2660B between the pressure sensor disks 2642A, 2642B. The second dimension 2660B may be larger than the first dimension 2660A. Based on the pressures detected by the pressure sensor 2654, a controller 2662 (shown in FIG. 25D) (e.g., controller 1004, 1104, etc.) may control operations of the apheresis system as described herein.

Figure 25H:
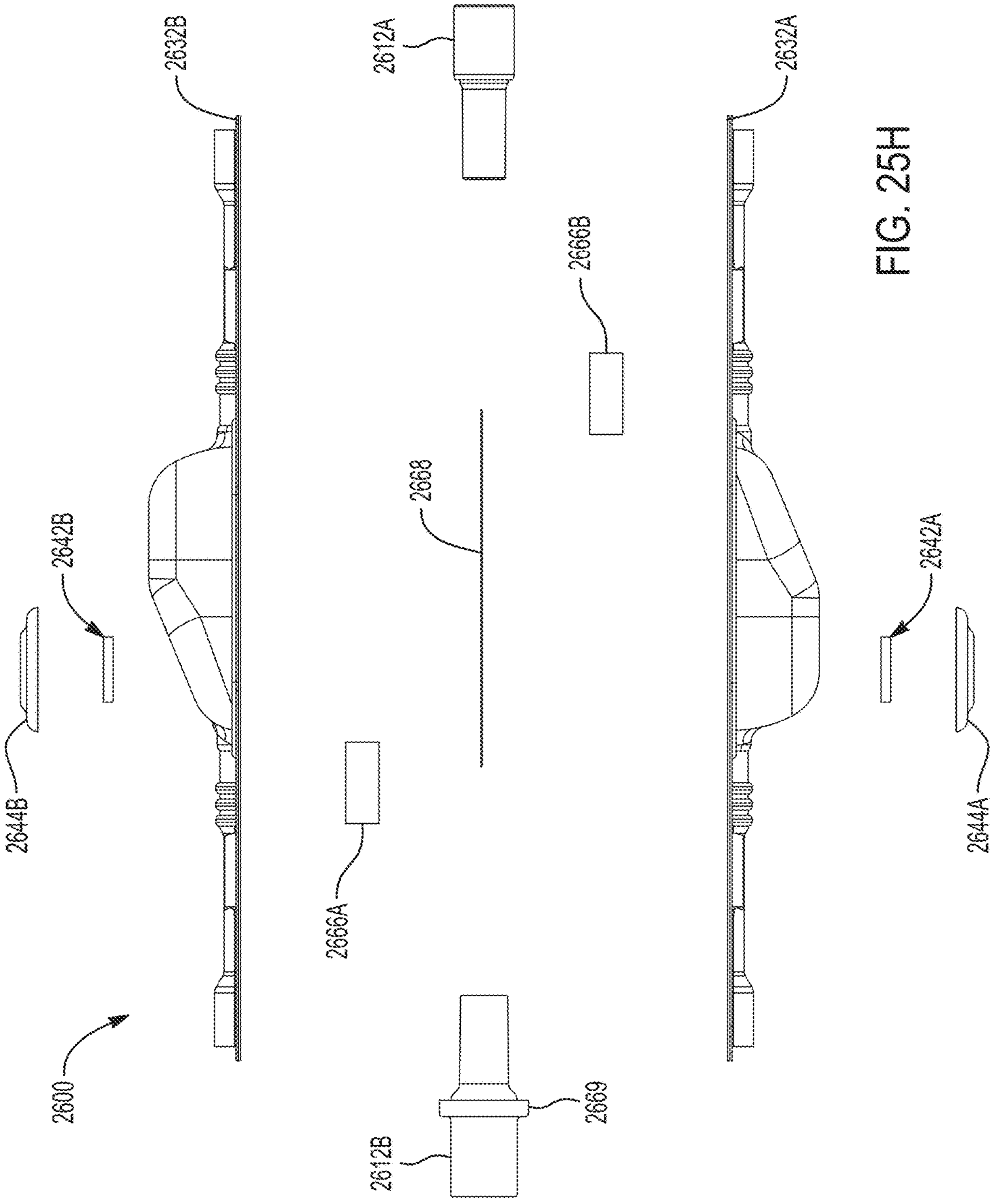
FIG. 25H is an exploded view of the soft cassette of FIG. 25A in accordance with at least one example embodiment of the present disclosure.
Figure 25I:
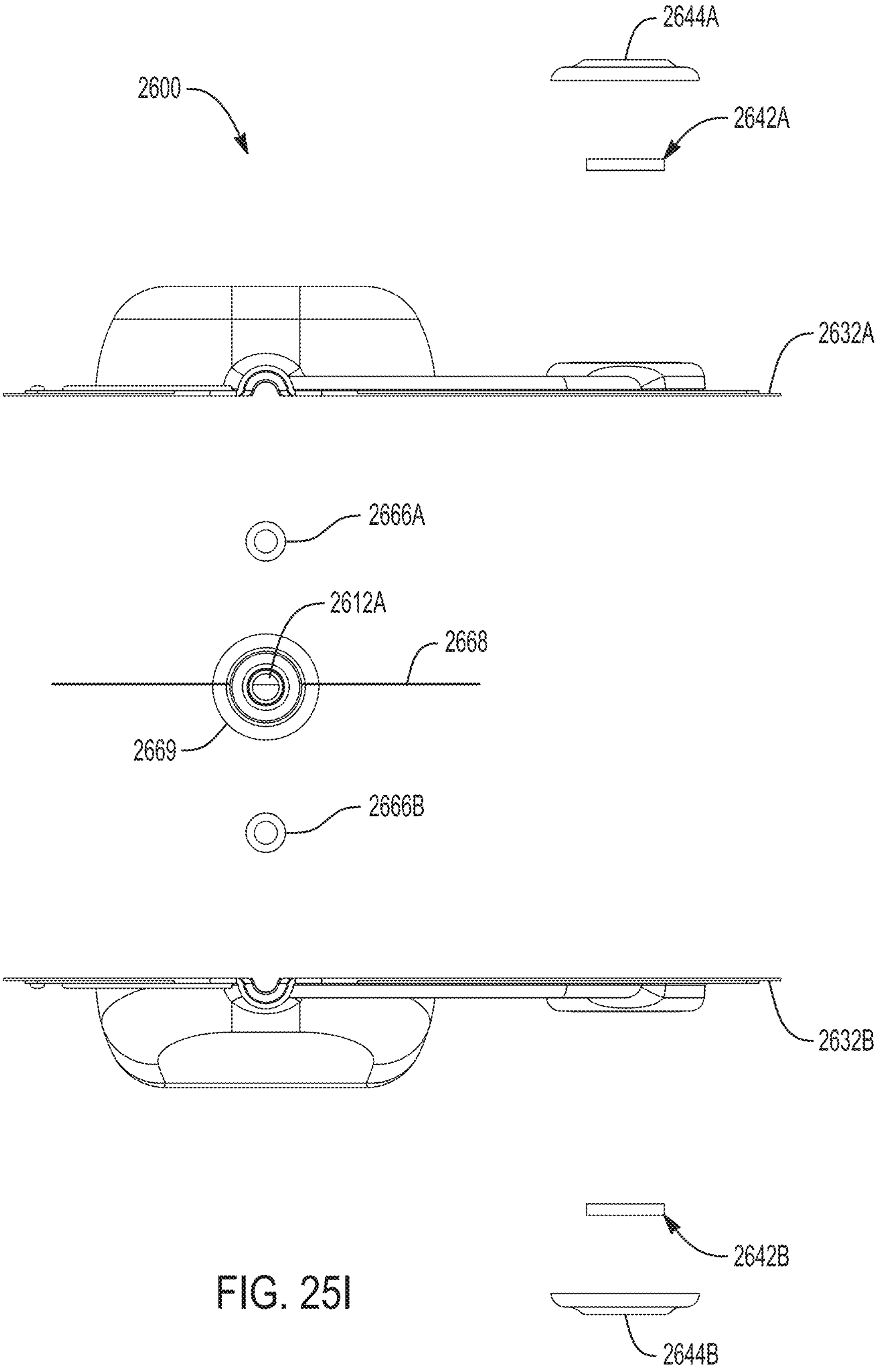
FIG. 25I is another exploded view of the soft cassette of FIG. 25A in accordance with at least one example embodiment of the present disclosure.

FIG. 25H is an exploded view of the soft cassette of FIG. 25A according to at least one example embodiment. FIG. 25I is another exploded view of the soft cassette of FIG. 25A according to at least one example embodiment.

In at least one example embodiment, as shown in FIGS. 25H-25I, the body 2602 of the soft cassette 2600 includes the first body portion 2632A and the second body portion 2632B. The soft cassette 2600 may further include the ports 2612A, 2612B, first and second tubes 2666A, 2666B, a filter 2668, first and second pressure sensor disks 2642A, 2642B, and first and second disk covers 2644A, 2644B.

The ports 2612A, 2612B may be each be at least partially between the first and second body portions 2632A, 2632B. In at least one example embodiments, the ports 2612A, 2612B have different colors and/or geometries. In at least the example embodiment shown, the second port 2612B includes a radially-extending flange 2669 that is not present on the second port 2612B. The flange (and/or different colors) may facilitate proper positioning and/or orientation of the soft cassette 2600 in a soft cassette assembly (e.g., the soft cassette assembly 300 of FIG. 3A).

The first pressure sensor disk 2642A may be between the first body portion 2632A and the first disk cover 2644A. The second pressure sensor disk 2642B may be between the second body portion 2632B and the second disk cover 2644B.

In at least one example embodiment, the tubes 2666A, 2666B may be within the direct flow lumen 2610 (shown in FIG. 25A) on opposing sides of the first chamber 2614 and adjacent to inlet and outlets to the first chamber 2614. The tubes 2666A, 2666B may be retained between the first and second cassette body portions 2632A, 2632B. The first tube 2666A may be between the first junction 2620A and the first chamber 2614. The second tube 2666B may be between the second junction 2620B and the first chamber 2614. In at least one example embodiment, the tubes 2666A, 2666B may reduce or prevent collapsing of the direct flow lumen 2610 to permit fluid within the direct flow lumen 2610 to freely enter and exit the first chamber 2614.

In at least one example embodiment, the filter 2668 is within the first chamber 2614. The filter 2668 is retained between the first and second cassette body portions 2632A, 2632B. The filter 2668 may be arranged such that all fluid passing through the first chamber 2614 passes through the filter 2668. In at least one example embodiment, the filter 2668 is configured to reduce or prevent unwanted components in the fluid (e.g., blood) from being exchanged between the donor 102 (shown in FIG. 1A) and the apheresis system 200 (shown in FIG. 1A). The filter 2668 may be or include a screen material (e.g., a 200 micron filter, etc.) that is between the first and second cassette body portions 2632A, 2632B. The screen material may be disposed in a flow path between the cassette inlet tubing 108A (shown in FIG. 1A) and the loop inlet tubing 108B of the extracorporeal tubing circuit. The filter 2668 may separate an inner chamber volume of the first chamber 2614 into a first side associated with the cassette inlet tubing 108A and a second side associated with the loop inlet tubing 108B. Accordingly, blood components flowing through the cassette inlet tubing 108A (e.g., in the direction of the drip chamber 2416) may enter the inner chamber volume on the first side of the filter 2668 and pass through the filter 2668 to the second side and into the loop inlet tubing 108B.

Figure 25J:
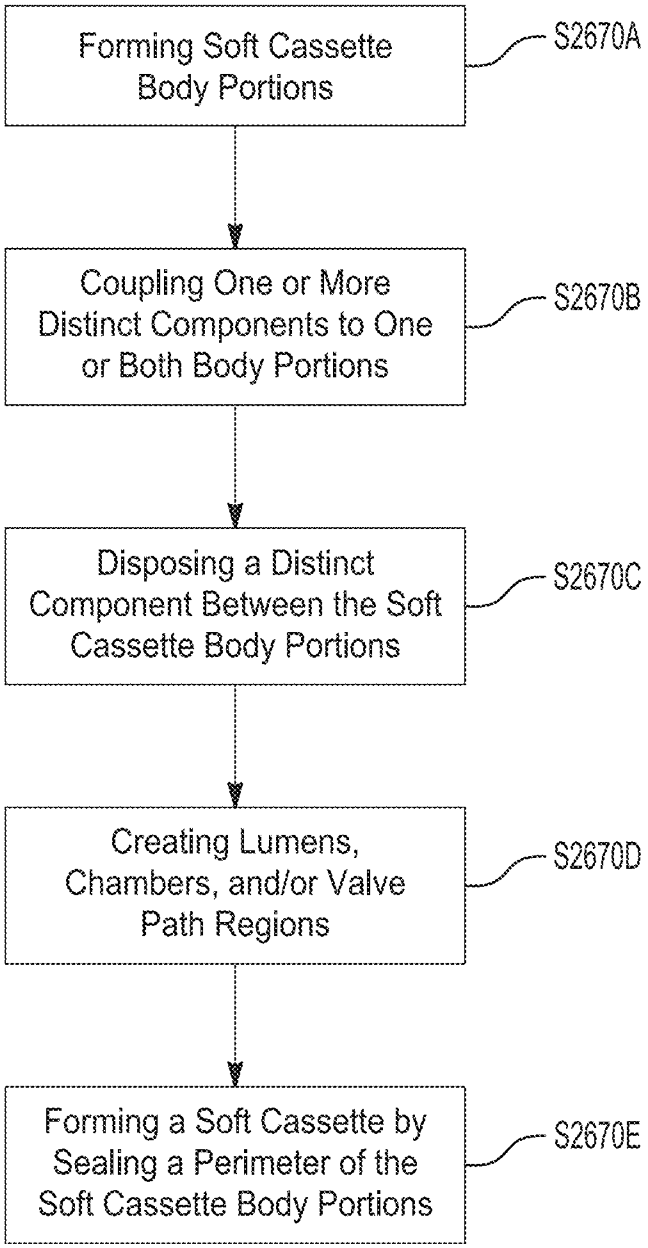
FIG. 25J is a flowchart depicting a method of manufacturing the soft cassette of FIG. 25A in accordance with at least one example embodiment of the present disclosure.

FIG. 25J is a flowchart depicting a method of manufacturing a soft cassette according to at least one example embodiment.

In at least one example embodiment, as shown in FIG. 25J, a method of manufacturing a soft cassette is provided. The method generally includes forming soft cassette body portions at S2670A; coupling one or more distinct components to one or both body portions at S2670B; disposing one or more distinct components (e.g., a filter, a pump) between the soft cassette body portions at S2670C; creating lumens, chambers, and/or valve paths in the soft cassette body portions at S2670D; and forming the soft cassette by sealing a perimeter of the soft cassette body portions at 2670E. The method will be described in the context of the soft cassette 2600 of FIGS. 25A-25H; however, it should be appreciated that the same or a similar method may be used to form other soft cassettes (e.g., the soft cassette 314 of FIGS. 3A-3D). Each of these steps is described in greater detail below.

At 2670A, the method includes forming first and second body portions 2632A, 2632B. In at least one example embodiment, the first and second body portions 2632A, 2632B are formed concurrently, such as from a single sheet of material or multiple sheets of material. After forming, the single sheet of material may be subdivided to separate the first and second body portions 2632A, 2632B. Alternatively, the first and second body portions 2632A, 2632B may remain part of the single sheet, which may be folded onto itself prior to performing subsequent method steps.

In at least one example embodiment, forming the first and second body portions 2632A, 2632B includes radio frequency ("RF") forming. The material sheet(s) may be placed between a pair of dies and subjected to heat and/or pressure to achieve desired shapes and thicknesses in the first and second body portions 2632A, 2632B. In at least one example embodiment, each of the first and second body portions 2632A, 2632B includes a half or portion of the respective features to be formed, such as the lumens 2610, 2616, chambers 2614, 2618, and compliant regions 2624A, 2624B, 2624C. In at least one example embodiment, S2670A includes forming the valve pads 2625. The valve pads 2625 may be formed concurrently with the lumens 2610, 2616 and the chambers 2614, 2618.

Figure 25K:
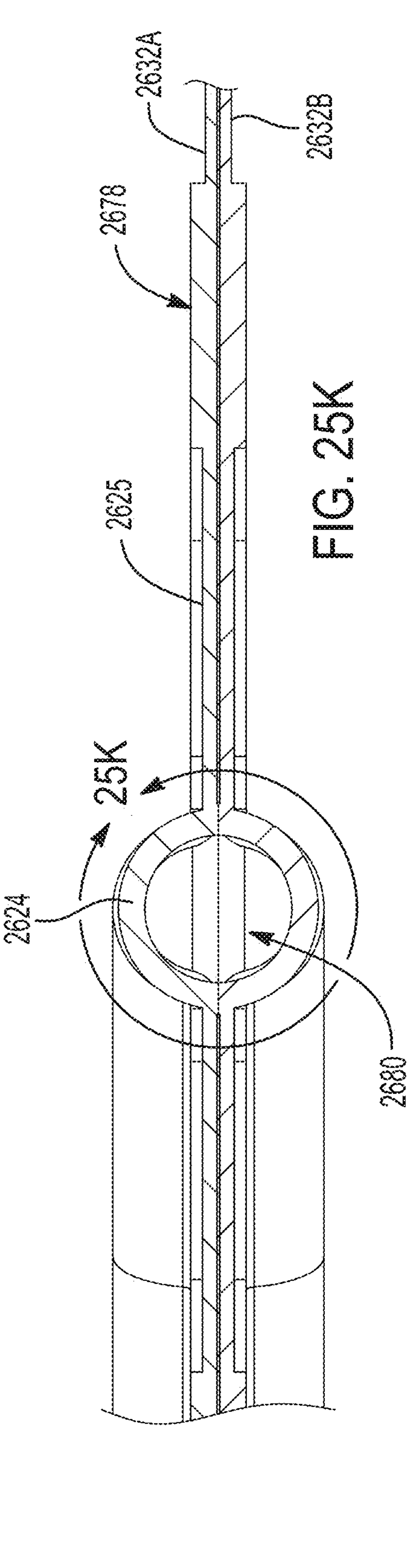
FIG. 25K is a partial sectional view of the soft cassette of FIG. 25A showing a valve region in accordance with at least one example embodiment of the present disclosure.
Figure 25L:
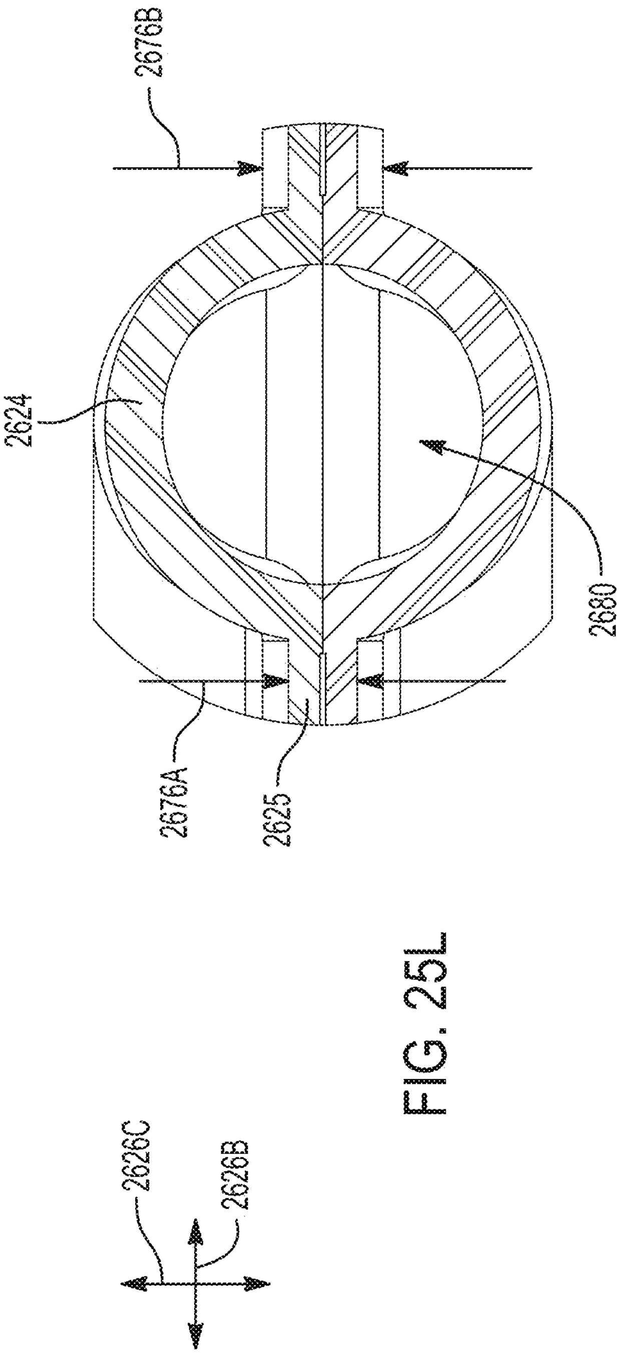
FIG. 25L is a detail sectional view of the valve region of FIG. 25K in accordance with at least one example embodiment of the present disclosure.

FIG. 25K is a partial sectional view of the soft cassette of FIG. 25A showing a valve region. FIG. 25L is a detailed sectional view of the valve region of FIG. 25K according to at least one example embodiment.

In at least one example embodiment, as shown in FIGS. 25K-25L, the body 2602 defines a thickness parallel to the depth axis 2626C. Each of the valve pads 2625 may define a first thickness 2676A. Other body regions 2678, such as those adjacent to the valve pads 2625, may define a second thickness 2676B. The first thickness 2676A may be less than the second thickness 2676B. The forming at S2670A may, in some example embodiments, include forming the first and second body portions 2632A, 2632B such that the valve pads 2625 have a desired thickness (i.e., half of the first thickness 2676A).

Forming the valve pads 2625 to have the desired thickness may be performed concurrently with the formation of other features in the first and second body portions 2632A, 2632B, such as the halves of the lumens 2610, 2616 and chambers 2614, 2618 (shown in FIG. 25A). In at least one example embodiment, the dies are sized and shaped to achieve the desired thickness. The reduced thickness at the valve pads 2625 facilitates a reduction or prevention of material entering a flow region 2680 during subsequent forming steps (e.g., 52676D).

Returning to FIG. 25J, at S2676B, in at least one example embodiment, the method may include coupling one or more first distinct components to one or both of the first and second body portions 2632A, 2632B. The first distinct components may include the pressure sensor disks 2642A, 2642B. The coupling may include disposing the first pressure sensor disk 2642A between the first body portion 2632A and the first disk cover 2644A. The coupling may further include disposing the second pressure sensor disk 2642B between the second body portion 2632B and the second disk cover 2644B. The coupling may further include bonding the first and second body portions 2632A, 2632B to respective first and second disk covers 2644A, 2644B to trap the respective pressure sensor disks 2642A, 2642B therebetween, such as by forming the cover welds 2648.

With continued reference to FIG. 25J, at S2676C, in at least one example embodiment, the method includes disposing one or more second distinct components at least partially between the first and second body portions 2632A, 2632B. The second distinct component may include the ports 2612A, 2612B, the tubes 2666A, 2666B, the filter 2668, and/or any other desired component (e.g., those described in the discussion accompanying FIG. 25M, below).

In at least one other example embodiment, additionally or alternatively to disposing the ports 2612A, 2612B at least partially between the first and second body portions 2632A, 2632B, the method may include disposing the cassette inlet tubing 108A and the loop inlet tubing 108B (shown in FIG. 5A) at least partially between the first and second body portions 2632A, 2632B. The cassette inlet tubing 108A may be disposed on the first side of the filter 2668 and the loop inlet tubing 108B may be arranged on the second side of the filter 2668.

In at least one example embodiment, the method may include temporarily disposing a third distinct component between the first and second body portions 2632A, 2632B. In at least one example embodiment, the method includes disposing one or more mandrels between the first and second body portions 2632A, 2632B. The mandrels may be positioned within the flow regions 2680 (shown, for example, in FIG. 25L). The mandrels may be sized and shaped to achieve a desired size and shape of the flow regions 2680. In at least one example embodiment, the mandrels are a cylindrical mandrels having a diameter corresponding to a desired diameter of the flow region 2680. The mandrels may be formed from a material that will maintain its integrity during subsequent forming manufacturing steps. In at least one example embodiment, the mandrels are formed from brass, copper, or any other suitable material.

In at least one example embodiment, at S2670D, the method includes creating the lumens 2610, 2616, the chambers 2614, 2618, and the valve paths 2624. The method may include aligning the first and second body portions 2632A, 2632B such that a first portion/half of each feature opposes a second portion/half of each feature. After aligning, the method may include bonding or otherwise attaching the first and second body portions 2632A, 2632B. In at least one example embodiment, the bonding includes RF welding a periphery of each feature, such as by forming the feature welds 2623B. Accordingly, distinct components that were placed in S2670B may be retained or trapped between the first and second body portions 2632A, 2632B.

Forming the valve paths 2624 may include applying energy (e.g., RF energy) at the valve pads 2625 while the mandrel is between the first and second body portions 2632A, 2632B. The presence of the mandrel facilitates formation of a flow region 2680 having a desired size and shape, such as cylindrical or substantially cylindrical. Moreover, in at least one example embodiment, the reduced thickness at the valve pads 2625 reduces or prevents softened material from the first and second body portions 2632A, 2632B from flowing into the flow region 2680 during S2670D. In contrast, other forming and welding techniques may cause the cross-sectional shape of a flow region to have a non-circular shape. Specifically, the cross-sectional shape may include gaps between the first and second body portions 2632A, 2632B when attached to one another. This gapped welding may result in a cross-sectional geometry that is difficult, if not impossible, to reliably seal or close using valves (e.g., valves 320A, 320B, 320C of FIG. 3A). In at least one example embodiment, by providing a circular cross-sectional joint between the layers of the soft cassette 2600, as described herein, the valve path regions 2624 can be reliably and repeatably closed and opened during use.

In at least one example embodiment, the method further includes, after 52670C, removing third distinct components, such as the mandrels.

In at least one example embodiment, at S2670E, the method further includes forming the soft cassette 2600. The soft cassette may be formed by sealing a perimeter of the first and second body portions 2632A, 2632B to form the perimeter weld 2623A. The sealing may be performed by welding (e.g., RF welding), bonding, or otherwise affixing the first and second body portions 2632A, 2632B to one another.

In at least one example embodiment, a soft cassette may include different or additional features and/or components. The additional features and/or components may be manufactured as described above, and/or overwelded or overmolded into the soft cassette. Examples of components/features include sensor wires, pumps, and/or optical sensing regions.

In at least one example embodiment, wires may be incorporated for sensing or detecting of inductive properties in a flow path. These measurements may be used to determine a type of fluid in the flow path (e.g., AC, plasma, red blood cell content, etc.). In at least one example embodiment, optical sensing regions may include one or more smoothed regions (e.g., that are non-opaque, translucent, transparent, and/or light transmissive, etc.) where an optical sensor may measure a color of a fluid in, or passing through, the soft cassette.

Figure 25M:
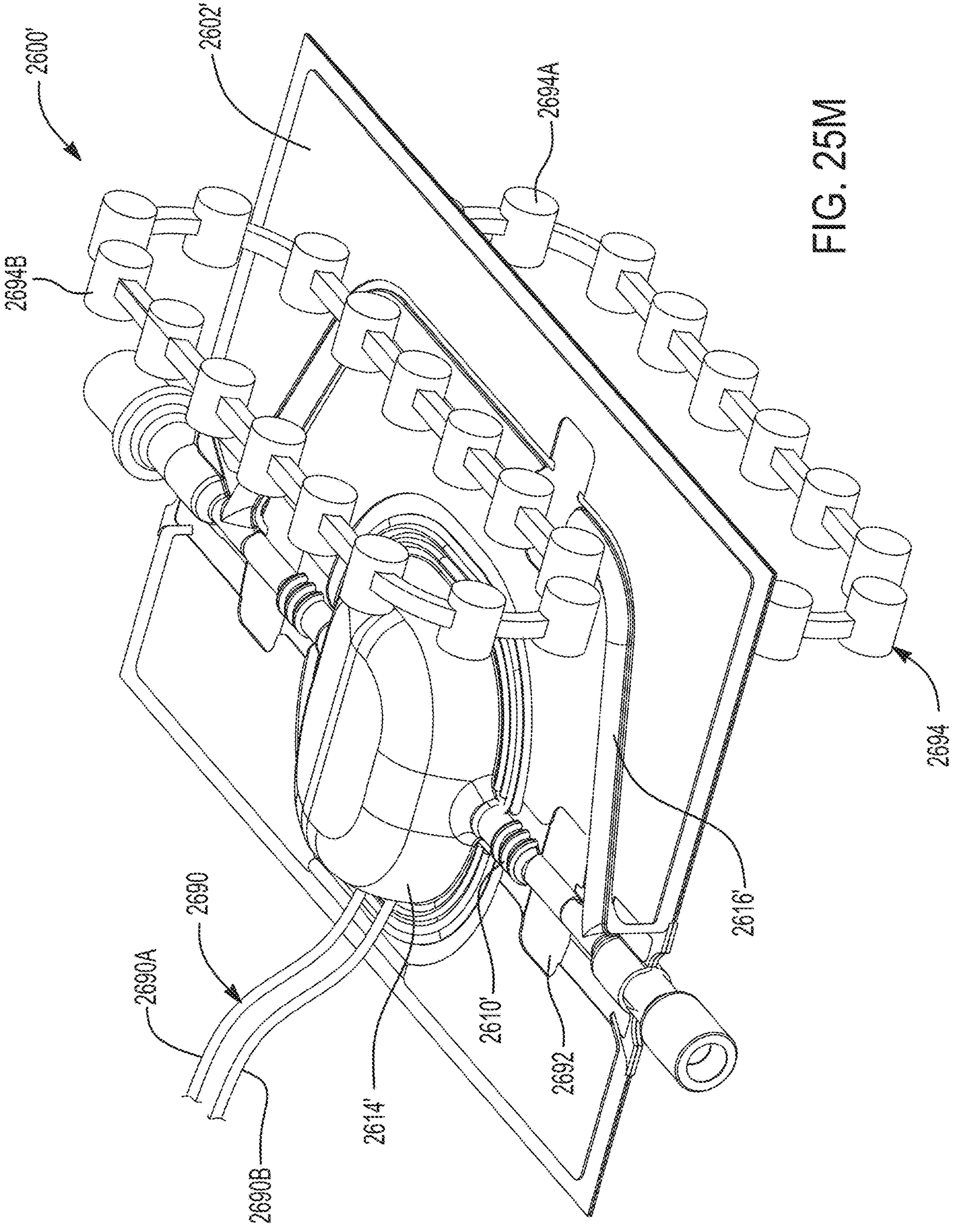
FIG. 25M is a schematic view of another soft cassette in accordance with at least one example embodiment of the present disclosure.

FIG. 25M is a perspective view of another soft cassette according to at least one example embodiment.

In at least one example embodiment, as shown in FIG. 25M, a soft cassette 2600' is provided. The soft cassette 2600' is the same as the soft cassette 2600 of FIGS. 25A-25H, except that it further includes an inductive sensor 2690, an optical sensor region 2692, and a pump 2694. Features of the soft cassette 2600' that are the same as features of the soft cassette 2600 use the same reference number followed by the prime symbol. In at least one example embodiment, the soft cassette 2600' includes a body 2602', a direct flow lumen 2610', a chamber 2614', and a bypass flow lumen 2616'.

In at least the example embodiment shown, the inductive sensor 2690 is operatively connected to the chamber 2614'. The inductive sensor 2690 may include first and second sensor leads 2690A, 2690B. In at least the example embodiment shown, the optical sensor region 2692 is operatively connected to the direct flow lumen 2610'. In at least the example embodiment shown, the pump 2694 is a roller pump including a first portion 2694A and a second 2694B. The pump 294 may be operatively connected to the bypass flow lumen 2616'.

The soft cassette 2600 is shown in a particular configuration (or shown to have a particular shape/design), but it should be appreciated that this is one of many possible configurations/shapes/designs.

Exemplary aspects are directed to a soft cassette, comprising: a body; a first cassette port disposed in the body; a second cassette port disposed in the body; a direct flow lumen disposed in the body and fluidly connected to the first cassette port and the second cassette port; a drip chamber disposed in the direct flow lumen such that fluid passing through the direct flow lumen passes through the drip chamber; a fluid flow bypass path disposed both fluidly connected to the direct flow lumen adjacent the first cassette port and between the first cassette port and the drip chamber and fluidly connected to the direct flow lumen adjacent the second cassette port and between the second cassette port and the drip chamber, such that fluid flowing through the fluid flow bypass path bypasses the drip chamber; and a fluid pressure chamber disposed in the body along a length of the fluid flow bypass path, wherein the fluid pressure chamber comprises a first side and a second side disposed opposite the first side, wherein a first magnetic disk is arranged on the first side of the fluid pressure chamber, wherein a second magnetic disk is arranged on the second side of the fluid pressure chamber, and wherein a space comprising a portion of the fluid flow bypass path is disposed in the fluid pressure chamber between the first side and the second side.

Any one or more of the above aspects wherein the body further comprises: a first sheet arranged on a first side of the body; and a second sheet arranged on a second side of the body disposed opposite the first side of the body; wherein a first half of the direct flow lumen, a first half of the drip chamber, and a first half of the fluid pressure chamber are formed in the first sheet, wherein a second half of the direct flow lumen, a second half of the drip chamber, and a second half of the fluid pressure chamber are formed in the second sheet, and wherein the first sheet is attached to the second sheet such that the first half of the direct flow lumen opposes the second half of the direct flow lumen, the first half of the drip chamber opposes the second half of the direct flow lumen, and the first half of the fluid pressure chamber opposes the second half of the fluid pressure chamber. Any one or more of the above aspects wherein the first magnetic disk is arranged on an outside of the fluid pressure chamber and the first sheet at the first side of the fluid pressure chamber, wherein the second magnetic disk is arranged on an outside of the fluid pressure chamber and the second sheet at the second side of the fluid pressure chamber. Any one or more of the above aspects further comprising: a first disk cover sheet attached to the first sheet over the first magnetic disk at the first side of the fluid pressure chamber trapping the first magnetic disk between the first sheet and the first disk cover. Any one or more of the above aspects further comprising: a second disk cover sheet attached to the first sheet over the second magnetic disk at the second side of the fluid pressure chamber trapping the second magnetic disk between the second sheet and the second disk cover. Any one or more of the above aspects wherein the first magnetic disk comprises a metal that is capable of being magnetized. Any one or more of the above aspects wherein the space is unobstructed between the first side of the fluid pressure chamber and the second side of the fluid pressure chamber, and wherein at least one of the first side of the fluid pressure chamber and the second side of the fluid pressure chamber is moveable between a first state and a second state based on a pressure inside the fluid pressure chamber. Any one or more of the above aspects wherein, in the first state, a first dimension is defined between the first magnetic disk and the second magnetic disk, wherein, in the second state, a second dimension is defined between the first magnetic disk and the second magnetic disk, and wherein the second dimension is larger than the first dimension. Any one or more of the above aspects wherein, in the first state, a first pressure is defined in the fluid pressure chamber, wherein, in the second state, a second pressure is defined in the fluid pressure chamber, and wherein the second pressure is greater than the first pressure.

Exemplary aspects are directed to a soft cassette assembly, comprising: a base plate having a plurality of receiving spaces formed therein; a pressure sensor arranged adjacent the base plate; a first magnet arranged in contact with the pressure sensor and disposed in a first receiving space of the plurality of receiving spaces; an access door pivotally attached to the base plate; a second magnet disposed in the access door, wherein, when the access door is closed relative to the base plate, the first magnet and the second magnet are offset from and opposing one another; and a soft cassette attached to the base plate, the soft cassette comprising: a body comprising a first sheet arranged on a first side of the body and a second sheet arranged on a second side of the body disposed opposite the first side of the body; a fluid pressure chamber disposed in the body, wherein the fluid pressure chamber comprises a first side and a second side disposed opposite the first side, wherein a first magnetic disk is arranged on the first side of the fluid pressure chamber, wherein a second magnetic disk is arranged on the second side of the fluid pressure chamber, and wherein a space is disposed in the fluid pressure chamber between the first side and the second side; wherein the second magnetic disk is magnetically coupled to the first magnet, and wherein the first magnetic disk is magnetically coupled to the second magnet when the access door is closed.

Example Blood Component Collection Set with Integrated Safety Features

FIG. 26A is a perspective view of a separation set in a packaged state according to at least one example embodiment. FIG. 26B is an elevation view of the separation set of FIG. 26A in the packaged configuration according to at least one example embodiment.

In at least one example embodiment, as shown in FIGS. 26A-26B, a separation set 2700 or component collection set includes one or more features to facilitate correct and/or safe use of the separation set 2700 in an apheresis system (see, e.g., apheresis system 200 of FIG. 1A). The separation set 2700 may be the same as or similar to the collection set 500 (shown in FIG. 5A). In a packaged configuration, the separation set 2700 may be folded and/or coiled and secured with one or more bands or tapes 2702.

FIG. 26C is a schematic view of a separation assembly including the separation set of FIG. 26A according to at least one example embodiment.

In at least one example embodiment, a separation assembly 2710 includes the separation set 2700, a first media or anticoagulant (AC) bag 2712, a second media or saline bag 2714, and a collection vessel or plasma bottle 2716. The separation set 2700 includes a soft cassette 2718, a bladder 2720, first or AC tubing 2724, cassette inlet tubing 2726, loop inlet tubing 2728, a component collection loop 2730, loop exit tubing 2732, second or saline tubing 2734, and third or plasma tubing 2736.

The separation set 2700 may further include a first connector 2738, a second connector 2740, and a third connector 2742. The first connector 2738 may fluidly connect the AC tubing 2724 and the cassette inlet tubing 2726 to feed tubing (not shown). The second connector 2740 may fluidly connector the component collection loop 2730, the loop exit tubing 2732, and the loop inlet tubing 2728. The third connector 2742 may fluidly connect the loop exit tubing 2732, the saline tubing 2734, and the plasma tubing 2736.

In at least one example embodiment, the separation set 2700 further includes a first or AC tube fitting, spike, or connector 2744A, a second or saline tube fitting, spike, or connector 2746A, and a third or plasma tube fitting, spike, or connector 2748A. The AC tube fitting 2744A is configured to engage a mating first receptacle 2744B of the AC bag 2712. The saline tube fitting 2746A is configured to engage a mating second receptacle 2746B of the saline bag 2714. The plasma tube fitting 2748A is configured to engage a mating third receptacle 2748B of the plasma bottle 2716.

FIG. 26D is a schematic view of an apheresis system including a properly installed component collection assembly according to at least one example embodiment. FIG. 26E is a partial perspective view of a valve housing of the apheresis system of FIG. 26D according to at least one example embodiment.

In at least one example embodiment, as shown in FIG. 26D, an apheresis system 2750 includes a housing 2752, a soft cassette assembly 2754, an access panel 2756 configured to provide access to a centrifuge in the housing 2752, an AC pump 2758, a draw pump 2760, a return pump 2762, and a fluid valve control system 2764. The housing 2752, the soft cassette assembly 2754, the access panel 2756, the AC pump 2758, the draw pump 2760, the return pump 2762, and the fluid valve control system 2764 may be similar to or the same as the housing 204, the soft cassette assembly 300, the access panel 224, the AC pump 216, the draw pump 208, the return pump 212, and the fluid valve control system 228 of FIG. 2A.

In at least one example embodiment, in an installed state, the soft cassette 2718 is in the soft cassette assembly 2754, the bladder 2720 (shown in FIG. 26C) is in the centrifuge, and the third connector 2742 is in the fluid valve control assembly 2764. In at least one example embodiment, as shown in FIG. 26E, the fluid valve control assembly 2746 includes a valve housing 2766. The valve housing 2766 may at least partially define a connector receptacle. The connector receptacle may be configured to receive the third connector 2742. In at least one example embodiment, the connector receptacle is configured to receive the third connector 2742 in only a predetermined (or alternatively, desired) orientation. In the predetermined orientation, the saline tubing 2734 is orientated toward the saline bag 2714 and closer to the saline bag 2714 than the plasma bottle 2716. In the predetermined orientation, the plasma tubing 2736 is oriented toward the plasma bottle 2716 and closer to the plasma bottle 2716 than the saline bag 2714. Accordingly, the connector receptacle may facilitate proper orientation of the separation set 2700 in the apheresis system 2750.

Returning to FIG. 26D, in at least one example embodiment, when the separation set 2700 is in the installed state, the AC and saline tubing 2724, 2734 may be configured to reach only the desired respective media bag 2712, 2714. The AC tubing 2724 may be configured to reach the first receptacle 2744B of the AC bag, but not the second receptacle 2746B of the saline bag 2714. The saline tubing 2734 may be configured to reach the second receptacle 2746B of the saline bag 2714, but not the first receptacle 2744B of the AC bag. In at least one example embodiment, the AC tubing 2724 may define a first length and the saline tubing 2734 may define a second length. The first and second lengths may be different. In at least one example embodiment, the first length is longer than the second length.

FIG. 26D is a schematic view of an apheresis system including a properly installed component collection assembly according to at least one example embodiment. FIG. 26E is a partial perspective view of a valve housing of the apheresis system of FIG. 26D according to at least one example embodiment.

With reference to FIG. 26E, in at least one example embodiment, when the soft cassette 2718 is in the soft cassette assembly 2754, the bladder 2720 (shown in FIG. 26C) is in the centrifuge, and/or the third connector 2742 is in the fluid valve control assembly 2764, the first and second lengths of the AC and saline tubing 2724, 2734, respectively, may reduce or prevent the occurrence of incorrectly connecting the tubes to the media bags 2712, 2714. As shown, the AC tubing 2724 is not long enough to reach the second receptacle 2746B of the saline bag 2714 and the saline tubing 2734 is not long enough to reach the first receptacle 2744B of the AC bag 2712. In at least one example embodiment, the above features may reduce or prevent misconnection of the tubing 2724, 2734 when installed in the apheresis system 2750. Accordingly, the features may reduce or prevent excessive citrate reactions in a donor, which could cause hypocalcemia, cardiac arrhythmia, and/or other health issues in the donor.

Returning to FIG. 26C, the tube fittings 2744A, 2746A and the respective receptacles 2744B, 2746B may be configured to reduce or prevent connection to the incorrect bags 2714, 2712. In at least one example embodiment the tube fittings 2744A, 2746A may be color coded to provide visual indicia of proper connectivity. For example, a first color of the AC tube fitting 2744A may be the same as or similar to a color of the first receptacle 2744B and/or at least a portion of the AC bag 2712 (e.g., graphics and/or lettering on the AC bag 2712). A second color of the saline tube fitting 2746A may be the same as or similar to a color of the second receptacle 2746B and/or at least a portion of the saline bag 2714 (e.g., graphics and/or lettering on the saline bag 2714). The first and second colors may be different. In at least one example embodiment, the first color is red and the second color is white.

In at least one other example embodiment, the tube fittings 2744A, 2746A are shaped and/or keyed to reduce or prevent connection to incorrect media bags 2714, 2712. The first tube fitting 2744A may be shaped and/or keyed to engage the first receptacle 2744B, but not the second receptacle 2746B of the saline bag 2714. The second tube fitting 2746A may be shaped and/or keyed to engage the second receptacle 2746B, but not the first receptacle 2744B. that is, the tube fittings 2744A, 2746A may be physically incapable of fitting into the incorrect receptacle 2746B, 2744B. In at least one example embodiment, the second tube fitting 2746A is a spike and the first tube fitting 2744A is an ISO18250-8 connector.

Figure 26H:
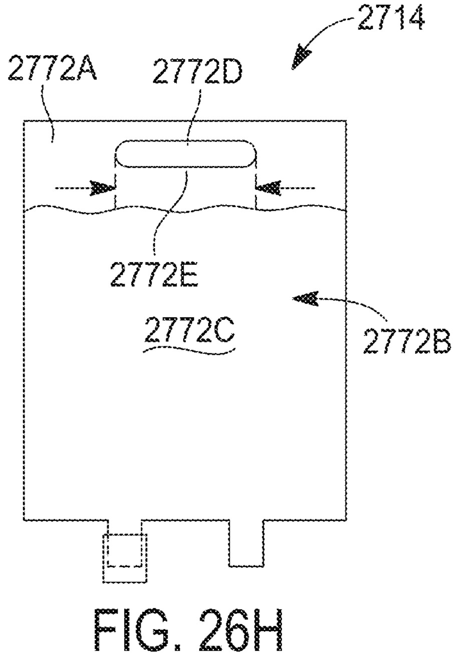
FIG. 26H is a schematic view of a saline bag of the separation assembly of FIG. 26C in accordance with at least one example embodiment of the present disclosure.

FIG. 26G is a schematic view of an AC bag of the separation assembly of FIG. 26C according to at least one example embodiment. FIG. 26H is a schematic view of a saline bag of the separation assembly of FIG. 26C according to at least one example embodiment.

In at least one example embodiment, as shown in FIG. 26G, the AC bag 2712 includes a first body 2770A that at least partially defines a first interior region 2770B. The first interior region 2770B may contain AC media 2770C. The first body 2770A may further define a first hanger aperture 2770D. The first hanger aperture 2770D may have a first size, a first shape, and a first dimension, such as a first length 2770E. The first body 2770A may be coupled to the first receptacle 2744B.

In at least one example embodiment, as shown in FIG. 26H, the saline bag 2714 includes a second body 2772A that at least partially defines a second interior region 2772B. The second interior region 2772B may contain saline media 2772C. The second body 2772A may further define a second hanger aperture 2772D. The second hanger aperture 2772D may have a second size, a second shape, and a second dimension, such as a second length 2772E. The second body 2772A may be coupled to the second receptacle 2746B.

In at least one example embodiment, as described above in the discussion accompanying FIGS. 21A-21E, the bags 2712, 2714 may be configured with visual and/or physical features to facilitate hanging on the correct stand. Accordingly, the first and second hanger apertures 2770D, 2772D may differ in terms of size, shape, and/or dimension(s). In at least the example embodiment shown, the second hanger aperture is larger than the first hanger aperture. The second length is longer than the first length. In at least one example embodiment, if an operator of the apheresis system 2750 attempts to hang the AC bag 2712 on a saline hanger, the saline hanger would be too large to fit through the first aperture 2770D. If the operator attempts to hang the saline bag 2714 on an AC hanger, the second hanger aperture 2772D would be much larger than the AC hanger and should provide a visual indication that the installation is incorrect.

Figure 26I:
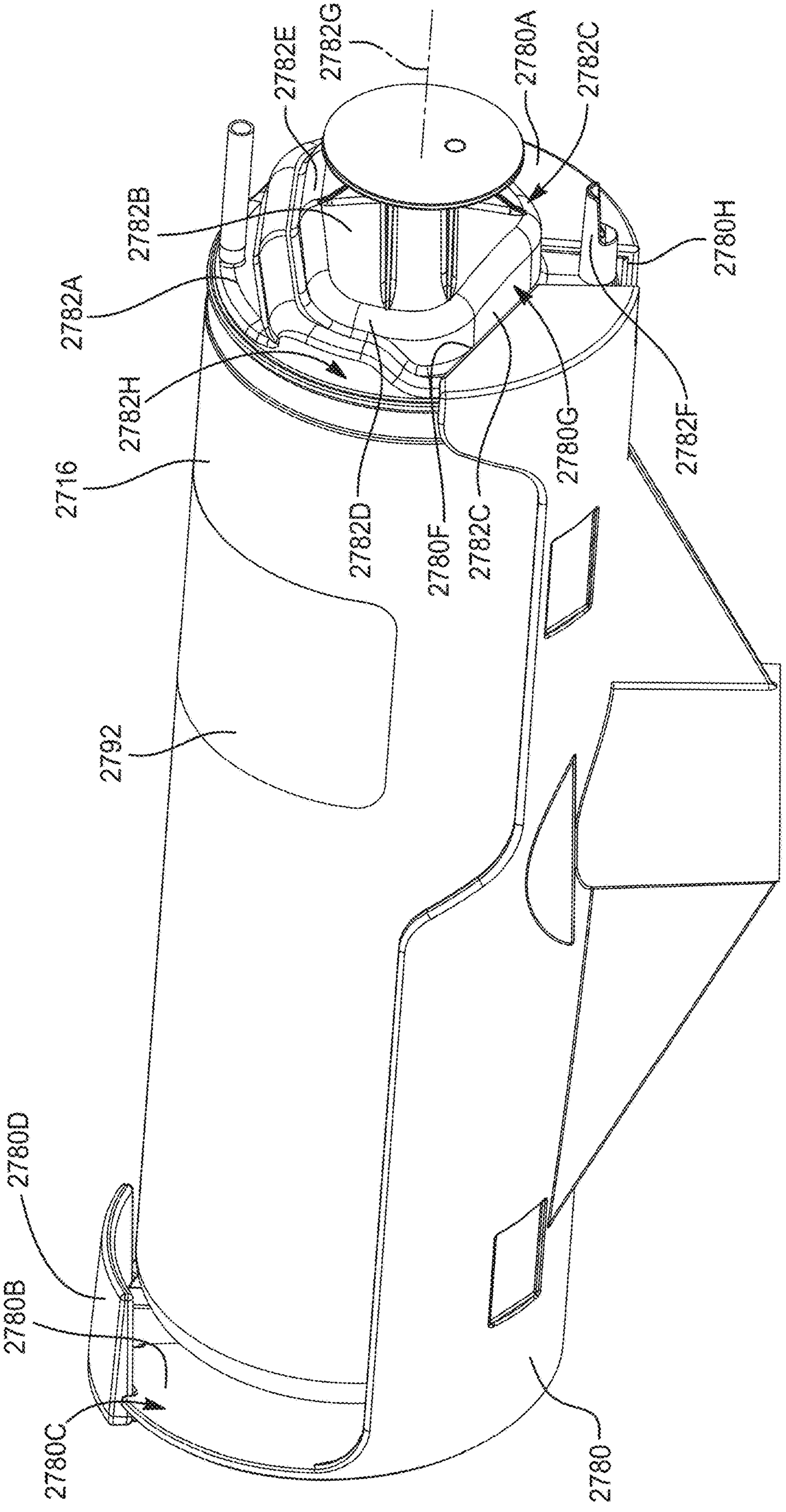
FIG. 26I is perspective view of a vessel in a cradle of the apheresis system of FIG. 26D in accordance with at least one example embodiment of the present disclosure.
Figure 26J:
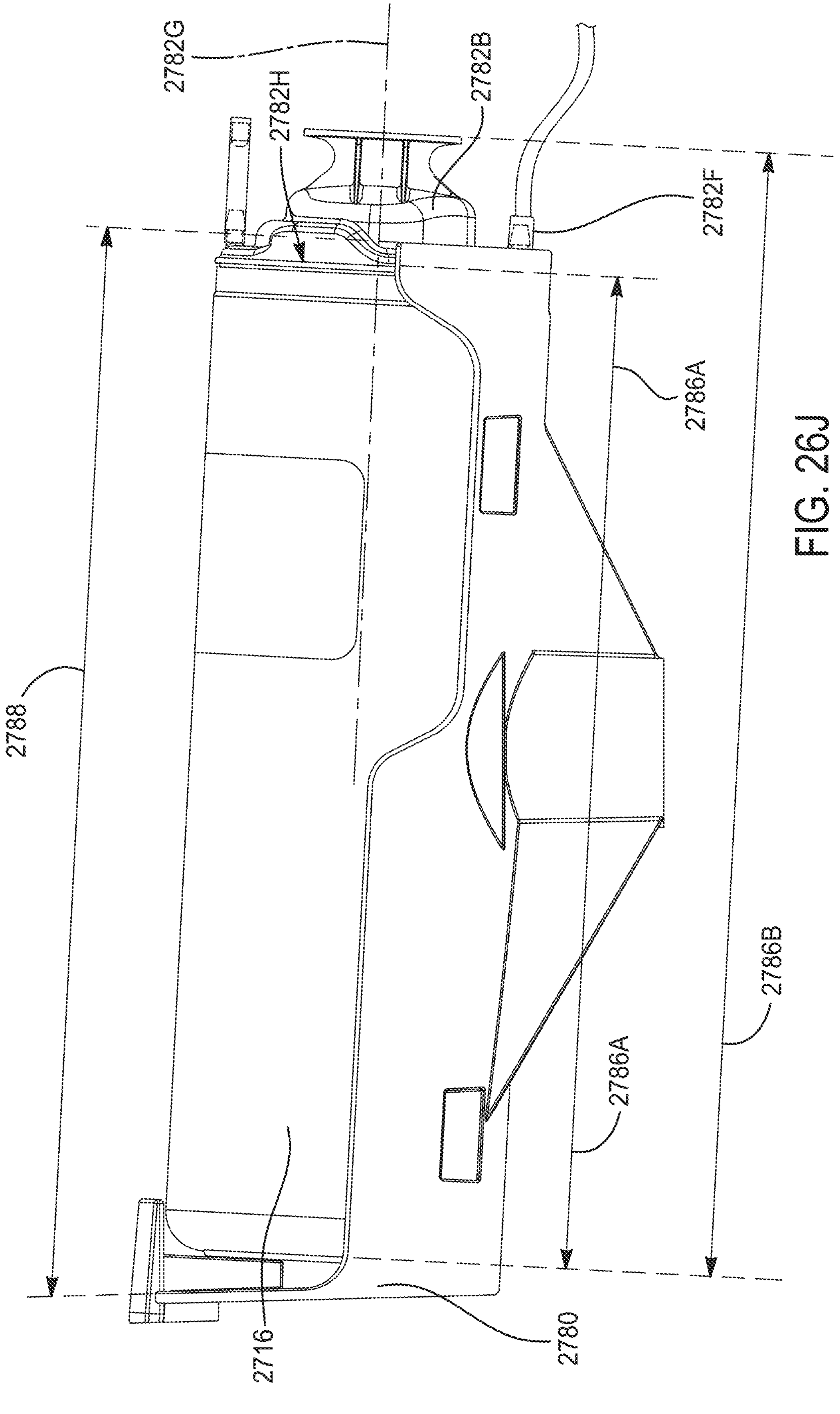
FIG. 26J is a side elevation view of the vessel and cradle of FIG. 26I in accordance with at least one example embodiment of the present disclosure.

FIG. 26I is perspective view of a vessel in a cradle of the apheresis system of FIG. 26D according to at least one example embodiment. FIG. 26J is a side elevation view of the vessel and cradle of FIG. 26I.

In at least one example embodiment, the apheresis system 2750 (shown in FIG. 26D) includes a cradle 2780 for retaining the plasma bottle 2716 in a desired orientation. The plasma bottle 2780 may be similar to or the same as the bottle 1900 of FIG. 19A. The cradle 2780 may the similar to or the same as the cradle 1516 of FIGS. 15K-15M. Accordingly, the cradle 2780 may include a first end wall 2780A, a second end wall 2780B, a vessel region 2780C, a cradle cap 2780D, alignment surfaces 2780E, an alignment region 2780F, and a slot 2780H.

In at least one example embodiment, the bottle 2716 includes a cap 2782A. The cap 2782A may include a protrusion 2782B including a pair of bottle alignment surfaces 2782C, a pair of side surfaces 2782D, and an opposing surfaces 2782E. The cap 2782A may further include a port 2782F. The bottle 2716 may extend along a longitudinal axis 2782G.

In at least one example embodiment, when the bottle 2716 is properly oriented in the cradle 2780, the protrusion 2782B is at least partially within the alignment region 2780F. The alignment surfaces 2780E of the cradle 2780 engage (e.g., are in direct contact with) the vessel alignment surfaces 2782C and the port 2782F is at least partially within the slot 2780H. In at least one example embodiment, the bottle alignment surfaces 2780F are configured to engage the vessel alignment surfaces 2780F to reduce or prevent rotation of the bottle 2716 about the longitudinal axis 2782G. Accordingly, the cradle 2780 is configured to retain the bottle 2716 in a desired angular orientation. When the bottle 2716 is in an improper orientation within the cradle 2780, the opposing surface 2782E of the cap 2782A may engage one or both of the cradle alignment surfaces 2780F, thereby preventing the protrusion 2782B from being in the alignment region 2780G.

In at least one example embodiment, the cap 2782A further defines a planar region 2782H. The planar region 2782H may be concentrically around and/or radially outside of the protrusion 2782A. As shown in FIG. 26J, the bottle 2716 defines a first length 2786A parallel to the longitudinal axis 2782G at a first radial location and/or intersecting the planar region 2782H. The bottle 2716 defines a second length 2786B at a second radial location different from the first radial location and/or intersecting the protrusion 2782B. An interior region of the cradle 2780 defines a third length 2788. The third length 2788 is longer than the first length 2786A, but shorter than the second length 2786B. Accordingly, the bottle 2716 only fits in the cradle 2780 in the orientation shown, with the cap 2782A of the bottle 2716 adjacent to and/or engaging the first end wall 2780A of the cradle 2780 and the protrusion 2782B of the bottle 2716 at least partially in the alignment region 2780G of the cradle 2780. In contrast, if the cap 2782A were placed adjacent to the second end wall 2780B, the bottle 2716 would be too long to sit fully within the cradle 2780 because the second length 2786B is greater than the third length 2788.

In at least one example embodiment, the bottle 2716 includes an indicum, such as a label 2792. The bottle 2716 may be determined to be in a correct orientation when the indicum is in a predetermined (or alternatively, desired) orientation. In at least the example embodiment shown, the bottle 2716 is correctly angularly oriented within the cradle 2780 when the label 2792 faces upward.

Embodiments include a system for separating a component from a multi-component fluid comprising: a housing comprising an access door and a top cover, the access door providing access to a chamber; a centrifuge housed in the chamber and configured to receive the multi-component fluid, the centrifuge configured to rotate to separate the component the multi-component fluid; a first fluid bag and a second fluid bag; and a first hook configured to support the first fluid bag and a second hook configured to support the second fluid bag, wherein the first hook is shaped to receive the first fluid bag and the second hook is shaped to receive the second fluid bag.

Aspects of the system further comprise a first tubing configured to couple to the first fluid bag and a second tubing configured to couple to the second fluid bag, wherein the first tubing has a first length and the second tubing has a second length different than the first length, and wherein the first tubing reaches the first fluid bag and not the second fluid bag and the second tubing reaches the second fluid bag and not the first fluid bag. Aspects of the system include the first tubing comprising a first connector and the second tubing comprising a second connector, wherein the first connector is a first color and the second connector is a second color different from the first color. Aspects of the system include the first fluid bag comprising a first receiver configured to receive the first connector and the second fluid bag comprising a second receiver configured to receive the second connector, wherein the first receiver is shaped to receive the first connector and the second receiver is shaped to receive the second connector. Aspects of the system further comprise a third tubing, wherein the second tubing and the third tubing are connected via a y-connector. Aspects of the system include the housing further comprising a valve housing disposed on the top cover, and wherein the valve housing is configured to receive the y-connector. Aspects of the system further comprise a plasma collection bottle and a holder configured to receive the plasma collection bottle, wherein the holder is disposed on the top cover. Aspects of the system include the plasma collection bottle being asymmetrical and the holder is shaped to receive the plasma collection bottle in a specific configuration. Aspects of the system include the plasma collection bottle comprising an indicator, wherein the indicator faces a predetermined direction when the plasma collection bottle is properly loaded in the holder. Aspects of the system include the first tubing configured to transport anticoagulant fluid, the second tubing configured to transport saline, and the third tubing configured to transport plasma.

The exemplary systems and methods of this disclosure have been described in relation to apheresis methods and systems. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as the cassette node 904 and the centrifuge node 908, or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular serviceability sled for an apparatus, the modular serviceability sled comprising:

a frame;

a first subassembly attached to the frame;

a first sled interconnection operatively connected to the first subassembly, the first sled interconnection including an electrical connection, a pneumatic connection, a hydraulic connection, or any combination thereof;

a gasket configured to engage the frame and a base assembly of the apparatus; and a shielding component configured to contact the frame and the base assembly of the apparatus, the shielding component including an electromagnetic interference shielding component, a radio frequency interference shielding component, or both the electromagnetic interference shielding component and the radio frequency interference shielding component, wherein the modular serviceability sled is configured to be moved between an engaged state and a disengaged state, in the engaged state, the modular serviceability sled is at least partially within a receiving space of the apparatus, the gasket engages the frame and the base assembly, the shielding component contacts the frame and the base assembly, and the first sled interconnection is operatively connected to a first machine interconnection of the apparatus, and in the disengaged state, the first sled interconnection is disconnected from the first machine interconnection and the modular serviceability sled is configured to be freely moved with respect to the base assembly.

2. The modular serviceability sled of claim 1, wherein the first subassembly includes an electrical component, a pneumatic component, a mechanical component, or any combination thereof.

3. The modular serviceability sled of claim 2, wherein the first subassembly includes the electrical component, and the electrical component includes a microcontroller, sensor, a relay, a printed circuit board, a transformer, or any combination thereof.

4. The modular serviceability sled of claim 2, wherein the first subassembly includes the pneumatic component, and the pneumatic component includes a fluid reservoir, a compressor, a solenoid valve, an air valve, a plenum, a manifold, or any combination thereof.

5. The modular serviceability sled of claim 2, wherein the first subassembly includes the mechanical component, and the mechanical component includes a linear actuator, a load cell, a strain gauge, a pneumatic cylinder, a bladder, a balloon, an air cylinder, a motor, or any combination thereof.

6. The modular serviceability sled of claim 1, wherein the first subassembly includes a pump.

7. The modular serviceability sled of claim 1, further comprising:

a plurality of sled interconnections including the first sled interconnection, wherein each of the plurality of sled interconnections is independently selected from an electrical connection, a pneumatic connection, a hydraulic connection, or any combination thereof.

8. The modular serviceability sled of claim 1, wherein the first sled interconnection includes the electrical connection, and the first sled interconnection includes a power connection, a communications connection, or both a power connection and a communications connection.

9. The modular serviceability sled of claim 1, further comprising:

a second subassembly attached to the frame; and a second sled interconnection operatively connected to the second subassembly, the first sled interconnection including an electrical connection, a pneumatic connection, a hydraulic connection, or any combination thereof.

10. The modular serviceability sled of claim 1, wherein the shielding component includes a conductive gasket.

11. The modular serviceability sled of claim 1, wherein the gasket includes an O-ring.

12. The modular serviceability sled of claim 1, wherein the frame defines a junction, a communication path operatively connects the first subassembly to the first sled interconnection via the junction.

13. The modular serviceability sled of claim 12, wherein the junction includes an aperture, an electrical via, or both an aperture and an electrical via.

14. The modular serviceability sled of claim 12, wherein the junction is hermetically sealed.

15. An apheresis system comprising:

a base assembly defining a first receiving space; and a first modular serviceability sled including, a sled frame, a subassembly attached to the sled frame, a sled interconnection operatively connected to the subassembly, the sled interconnection including an electrical connection, a pneumatic connection, a hydraulic connection, or any combination thereof, a gasket configured to engage the sled frame and a base assembly, and a shielding component configured to contact the sled frame and the base assembly, the shielding component including an electromagnetic interference shielding component, a radio frequency interference shielding component, or both the electromagnetic interference shielding component and the radio frequency interference shielding component, wherein the first modular serviceability sled is configured to be moved between an engaged state and a disengaged state, in the engaged state, the first modular serviceability sled is at least partially within the first receiving space, the gasket engages the sled frame and the base assembly, the shielding component contacts the sled frame and the base assembly, and the sled interconnection is operatively connected to a machine interconnection of the apheresis system, and in the disengaged state, the sled interconnection is disconnected from the machine interconnection and the first modular serviceability sled is configured to be freely moved with respect to the base assembly.

16. The apheresis system of claim 15, further comprising:

a plurality of modular serviceability sleds including the first modular serviceability sled, wherein the base assembly defines a plurality of receiving spaces including the first receiving space, and each of the plurality of modular serviceability sleds is configured to be at least partially in a respective one of the plurality of receiving spaces.

17. The apheresis system of claim 16, wherein each of the plurality of modular serviceability sleds is configured operate independently of the other of the modular serviceability sleds.

18. The apheresis system of claim 16, wherein each of the plurality of modular serviceability sleds includes a respective memory including a unique identifier, and the apheresis system is configured to identify each of the modular serviceability sleds based on the unique identifier.

19. The apheresis system of claim 15, wherein the base assembly includes a base frame and a base housing, the base frame comprises a metal, the base housing comprises a plastic, and in the engaged state, the gasket engages the sled frame and the base housing, and the shielding component engages the sled frame and the base frame.

20. The apheresis system of claim 19, wherein the base housing defines a sloped region adjacent to a periphery of the first receiving space.

21. A method of servicing a modular serviceability sled of an apheresis system, the method comprising:

detaching the modular serviceability sled from a base assembly of the apheresis system, the modular serviceability sled including a frame, a subassembly attached to the frame, a sled interconnection operatively connected to the subassembly, a gasket, and a shielding component configured to contact the frame and the base assembly, the shielding component including an electromagnetic interference shielding component, a radio frequency interference shielding component, or both the electromagnetic interference shielding component and the radio frequency interference shielding component, and the sled interconnection including an electrical connection, a pneumatic connection, a hydraulic connection, or any combination thereof;

disconnecting the sled interconnection from a machine interconnection;

at least partially removing the modular serviceability sled from a receiving space defined in the base assembly; and servicing the modular serviceability sled.

22. The method of claim 21, wherein the servicing includes maintaining the modular serviceability sled, repairing the modular serviceability sled, replacing the modular serviceability sled, or any combination thereof.

23. The method of claim 21, further comprising:

after the servicing, connecting the sled interconnection with the machine interconnection; and attaching the modular serviceability sled to the base assembly such that the gasket engages the base assembly and the housing and the shielding component contacts the frame and the base assembly.

* * * * *